United States Patent
Stenkamp et al.

(10) Patent No.: US 8,067,590 B2
(45) Date of Patent: Nov. 29, 2011

(54) PYRIDONE DERIVATES WITH MCH ANTAGONISTIC ACTIVITY AND MEDICAMENTS COMPRISING THESE COMPOUNDS

(75) Inventors: Dirk Stenkamp, Biberach (DE); Stephan Georg Mueller, Warthausen (DE); Gerald Juergen Roth, Biberach (DE); Joerg Kley, Mittelbiberach (DE); Klaus Rudolf, Warthausen (DE); Armin Heckel, Biberach (DE); Marcus Schindler, Biberach (DE); Ralf Lotz, Schemmerhofen (DE); Thorsten Lehmann-Lintz, Ochsenhausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 931 days.

(21) Appl. No.: 11/844,842

(22) Filed: Aug. 24, 2007

(65) Prior Publication Data
US 2008/0255083 A1 Oct. 16, 2008

(30) Foreign Application Priority Data
Aug. 25, 2006 (EP) ..................... 06119523

(51) Int. Cl.
*C07D 237/04* (2006.01)
*A61K 31/50* (2006.01)
*A61K 31/501* (2006.01)
(52) U.S. Cl. .... 544/238; 544/239; 514/247; 514/252.01
(58) Field of Classification Search .................. 544/238, 544/239; 514/247, 252.01
See application file for complete search history.

(56) References Cited

FOREIGN PATENT DOCUMENTS

| | | |
|---|---|---|
| CA | 2 558 272 A1 | 9/2005 |
| CA | 2 618 112 A1 | 2/2007 |
| WO | 2005/085200 A1 | 9/2005 |
| WO | 2007/018248 A1 | 2/2007 |

OTHER PUBLICATIONS

Guo et. al. "Discovery and SAR of biaryl piperidine MCH1 receptor antagonists through solid-phase encoded combinatorial synthesis" Bioorganic & Medicinal Chemistry Letters 2005, 15, 3696-3700.*
International Search Report and Written Opinion for PCT/EP2007/058601 mailed Feb. 6, 2008.
Hazel J. Dyke, et al; Recent Developments in the Discovery of MCH-1R Antagonists for the Treatment of Obesity—an Update; Expert Opinion on Therapeutic Patents (2005) vol. 15, No. 10 pp. 1303-1313.

* cited by examiner

*Primary Examiner* — David K. O'Dell
(74) *Attorney, Agent, or Firm* — Michael P. Morris; Mary-Ellen M. Devlin

(57) ABSTRACT

The present invention relates to compounds of general formula I

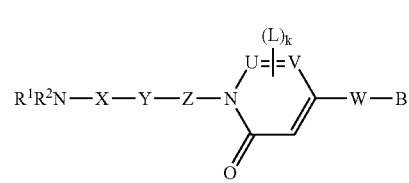

wherein the groups and radicals B, k, L, U, V, W, X, Y, Z, $R^1$, $R^2$, have the meanings given in claim 1. Moreover the invention relates to pharmaceutical compositions containing at least one compound according to the invention. By virtue of their MCH-receptor antagonistic activity the pharmaceutical compositions according to the invention are suitable for the treatment of metabolic disorders and/or eating disorders, particularly obesity, bulimia, anorexia, hyperphagia and diabetes.

12 Claims, No Drawings

PYRIDONE DERIVATES WITH MCH ANTAGONISTIC ACTIVITY AND MEDICAMENTS COMPRISING THESE COMPOUNDS

The present invention relates to new pyridone derivatives, the physiologically acceptable salts thereof as well as their use as MCH antagonists and their use in preparing a pharmaceutical preparation which is suitable for the prevention and/or treatment of symptoms and/or diseases caused by MCH or causally connected with MCH in some other way. The invention also relates to the use of a compound according to the invention for influencing eating behaviour and for reducing body weight and/or for preventing any increase in body weight in a mammal. It further relates to compositions and medicaments containing a compound according to the invention and processes for preparing them. Other aspects of this invention relate to processes for preparing the compounds according to the invention.

BACKGROUND TO THE INVENTION

The intake of food and its conversion in the body is an essential part of life for all living creatures. Therefore, deviations in the intake and conversion of food generally lead to problems and also illness. The changes in the lifestyle and nutrition of humans, particularly in industrialised countries, have promoted morbid overweight (also known as corpulence or obesity) in recent decades. In affected people, obesity leads directly to restricted mobility and a reduction in the quality of life. There is the additional factor that obesity often leads to other diseases such as, for example, diabetes, dyslipidaemia, high blood pressure, arteriosclerosis and coronary heart disease. Moreover, high body weight alone puts an increased strain on the support and mobility apparatus, which can lead to chronic pain and diseases such as arthritis or osteoarthritis. Thus, obesity is a serious health problem for society.

The term obesity means an excess of adipose tissue in the body. In this connection, obesity is fundamentally to be seen as the increased level of fatness which leads to a health risk. There is no sharp distinction between normal individuals and those suffering from obesity, but the health risk accompanying obesity is presumed to rise continuously as the level of fatness increases. For simplicity's sake, in the present invention, individuals with a Body Mass Index (BMI), which is defined as the body weight measured in kilograms divided by the height (in metres) squared, above a value of 25 and more particularly above 30, are preferably regarded as suffering from obesity.

Apart from physical activity and a change in nutrition, there is currently no convincing treatment option for effectively reducing body weight. However, as obesity is a major risk factor in the development of serious and even life-threatening diseases, it is all the more important to have access to pharmaceutical active substances for the prevention and/or treatment of obesity. One approach which has been proposed very recently is the therapeutic use of MCH antagonists (cf. inter alia WO 01/21577, WO 01/82925).

Melanin-concentrating hormone (MCH) is a cyclic neuropeptide consisting of 19 amino acids. It is synthesised predominantly in the hypothalamus in mammals and from there travels to other parts of the brain by the projections of hypothalamic neurones. Its biological activity is mediated in humans through two different G-protein-coupled receptors (GPCRs) from the family of rhodopsin-related GPCRs, namely the MCH receptors 1 and 2 (MCH-1R, MCH-2R).

Investigations into the function of MCH in animal models have provided good indications for a role of the peptide in regulating the energy balance, i.e. changing metabolic activity and food intake [1,2]. For example, after intraventricular administration of MCH in rats, food intake was increased compared with control animals. Additionally, transgenic rats which produce more MCH than control animals, when given a high-fat diet, responded by gaining significantly more weight than animals without an experimentally altered MCH level. It was also found that there is a positive correlation between phases of increased desire for food and the quantity of MCH mRNA in the hypothalamus of rats. However, experiments with MCH knock-out mice are particularly important in showing the function of MCH. Loss of the neuropeptide results in lean animals with a reduced fat mass, which take in significantly less food than control animals.

The anorectic effects of MCH are presumably mediated in rodents through the $G_{\alpha s}$-coupled MCH-1R [3-6], as, unlike primates, ferrets and dogs, no second MCH receptor subtype has hitherto been found in rodents. After losing the MCH-1R, knock-out mice have a lower fat mass, an increased energy conversion and, when fed on a high fat diet, do not put on weight, compared with control animals. Another indication of the importance of the MCH system in regulating the energy balance results from experiments with a receptor antagonist (SNAP-7941) [3]. In long term trials the animals treated with the antagonist lose significant amounts of weight.

In addition to its anorectic effect, the MCH-1R antagonist SNAP-7941 also achieves additional anxiolytic and antidepressant effects in behavioural experiments on rats [3]. Thus, there are clear indications that the MCH-MCH-1R system is involved not only in regulating the energy balance but also in affectivity.

LITERATURE

1. Qu, D., et al., *A role for melanin-concentrating hormone in the central regulation of feeding behaviour* Nature, 1996. 380 (6571): p. 243-7.
2. Shimada, M., et al., *Mice lacking melanin-concentrating hormone are hypophagic and lean*. Nature, 1998. 396 (6712): p. 670-4.
3. Borowsky, B., et al., *Antidepressant, anxiolytic and anorectic effects of a melanin-concentrating hormone*-1 *receptor antagonist* Nat Med. 2002. 8 (8): p. 825-30.
4. Chen, Y., et al., *Targeted disruption of the melanin-concentrating hormone receptor*-1 *results in hyperphagia and resistance to diet-induced obesity*. Endocrinology, 2002. 143 (7): p. 2469-77.
5. Marsh, D. J., et al., *Melanin-concentrating hormone 1 receptor-deficient mice are lean, hyperactive, and hyperphagic and have altered metabolism*. Proc Natl Acad Sci USA, 2002. 99 (5): p. 3240-5.
6. Takekawa, S., et al., T-226296: *A novel, orally active and selective melanin-concentrating hormone receptor antagonist*. Eur J Pharmacol, 2002. 438 (3): p. 129-35.

In the patent literature (WO 01/21577, WO 01/82925) amine compounds of the general formula formula

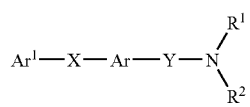

are proposed as MCH antagonists for the treatment of obesity.

Further patent publication related to amine compounds with MCH antagonistic activity are for example: WO 04/024702, WO 04/039780, WO 04/039764, WO 05/063239, WO 05/085221, WO 05/103031, WO 05/103032, WO 05/103029, WO 05/100285, WO 05/103002, WO 05/85200, WO 2007/048802.

In the WO 03/068230, WO 2005/018557 (Pharmacia Corp.) substituted pyridinones are described. The WO 2004/087677 (Pharmacia Corp.) is related to pyrimidone derivatives and the WO 03/059891 as well as the WO 2005/007632 (Pharmacia Corp.) refer to pyridazinone derivatives. These compounds are described as modulators of p38 MAP kinase.

In the WO 2007/18248 (Banyu Pharmaceuticals), which was published after the priority date claimed by the present application, pyridone derivatives of the formula

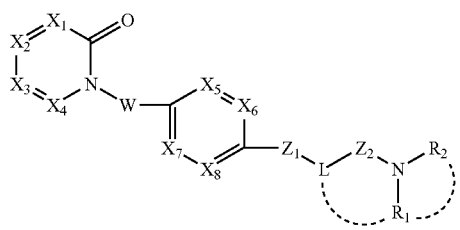

are proposed as MCH receptor antagonists.

In the WO 2007/029847 (Banyu Pharmaceuticals) pyridone derivatives of the formula

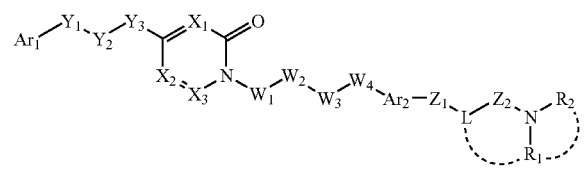

are described which contain a bicyclic aromatic group $Ar_2$. These compounds are proposed as MCH receptor antagonists.

Furthermore in the WO 2007/024004 (Banyu Pharmaceuticals) phenylpyridone derivatives are proposed as MCH receptor antagonists.

AIM OF THE INVENTION

The aim of the present invention is to identify compounds which are especially effective as MCH antagonists. Another aim of this invention is to provide compounds which are effective as MCH antagonists and which possess advantageous pharmacokinetic properties. The invention also sets out to provide compounds which can be used to influence the eating habits of mammals and achieve a reduction in body weight, particularly in mammals, and/or prevent an increase in body weight.

The present invention further sets out to provide new pharmaceutical compositions which are suitable for the prevention and/or treatment of symptoms and/or diseases caused by MCH or otherwise causally connected to MCH. In particular, the aim of this invention is to provide pharmaceutical compositions for the treatment of metabolic disorders such as obesity and/or diabetes as well as diseases and/or disorders which are associated with obesity and diabetes. Other objectives of the present invention are concerned with demonstrating advantageous uses of the compounds according to the invention. The invention also sets out to provide a process for preparing the compounds according to the invention. Other aims of the present invention will be immediately apparent to the skilled man from the foregoing remarks and those that follow.

OBJECT OF THE INVENTION

In a first aspect the present invention relates to pyridone derivatives of general formula I

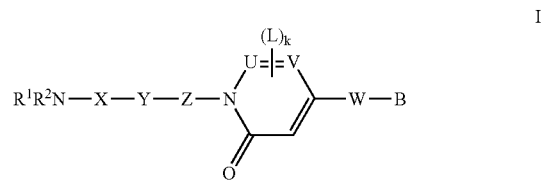

wherein $R^1$, $R^2$ independently of one another denote H, $C_{1-8}$-alkyl or $C_{3-7}$-cycloalkyl, while the alkyl or cycloalkyl group may be mono- or polysubstituted by identical or different groups $R^{11}$, and a —$CH_2$— group in position 3 or 4 of a 5-, 6- or 7-membered cycloalkyl group may be replaced by —O—, —S— or —$NR^{13}$—; or $R^2$ denotes a $C_{1-3}$-alkylene bridge which is linked to the group Y, wherein the alkylene bridge may be substituted with one or more $C_{1-3}$-alkyl-groups, and $R^1$ is defined as hereinbefore or denotes a group selected from $C_{1-4}$-alkyl-CO—, $C_{1-4}$-alkyl-O—CO—, ($C_{1-4}$-alkyl)NH—CO— and ($C_{1-4}$-alkyl)$_2$N—CO— wherein alkyl-groups may be mono- or polyfluorinated; or $R^1$ and $R^2$ form a $C_{3-8}$-alkylene bridge, wherein a —$CH_2$— group not adjacent to the N atom of the $R^1R^2N$— group may be replaced by —CH═N—, —CH═CH—, —O—, —S—, —SO—, —(SO$_2$)—, —CO—, —C(═CH$_2$)—, —C(═N—OH)—, —C(═N—($C_{1-4}$-alkyl))— or —$NR^{13}$— while in the case when $R^1$ and $R^2$ form an alkylene bridge in the alkylene bridge one or more H atoms may be replaced by identical or different groups $R^{14}$, and the alkylene bridge defined hereinbefore may be substituted by one or two identical or different carbo- or heterocyclic groups Cy in such a way that the bond between the alkylene bridge and the group Cy is made
  via a single or double bond,
  via a common C atom forming a spirocyclic ring system,
  via two common adjacent C and/or N atoms forming a fused bicyclic ring system or
  via three or more C and/or N atoms forming a bridged ring system;

x denotes a $C_{1-3}$-alkylene bridge, which may comprise one, two or three identical or different $C_{1-4}$-alkyl substituents, while two alkyl groups may be joined together forming a 3 to 7-membered cyclic group, and while in a $C_{2-3}$-alkylene bridge one or two C atoms may be monosubstituted by $R^{10}$; and $R^{10}$ is selected from the group consisting of hydroxy, hydroxy-$C_{1-3}$-alkyl, $C_{1-4}$-alkoxy or $C_{1-4}$-alkoxy-$C_{1-3}$-alkyl; and Y denotes a 5- to 6-membered aromatic carbocyclic group, which may contain 1, 2 or 3 heteroatoms independently selected from N, O and/or S; which cyclic group may be mono- or polysubstituted by identical or different substituents $R^{20}$;

Z denotes —CH$_2$—CH$_2$—, —C(=O)—CH$_2$—, —C(=CH$_2$)—CH$_2$— or —C(OH)H—CH$_2$— all of which may be mono- or polysubstituted with substituents independently from each other selected from C$_{1-3}$-alkyl;

U, V both denote CH or one of the groups U, V denotes N and the other of U, V denotes CH, wherein CH may be substituted with L; and L independently of each other denotes halogen, cyano or C$_{1-3}$-alkyl; and k denotes 0, 1 or 2;

W is selected from the group consisting of —CH$_2$—CH$_2$—, —CH$_2$—O—, —O—CH$_2$—, —CH=CH—, —CH$_2$—NR$^N$—, —NR$^N$—CH$_2$—, —CH$_2$—, —O—, —S— and —NR$^N$—;

R$^N$ denotes H, C$_{1-4}$-alkyl, formyl, C$_{1-3}$-alkylcarbonyl or C$_{1-3}$-alkylsulfonyl; and in case the group W denotes —NR$^N$—CH$_2$— the group R$^N$ may denote a —CH$_2$— or —CH$_2$—CH$_2$— bridge being linked to the cylic group B; and B is a 5- or 6-membered unsaturated or aromatic carbocyclic group which may contain 1, 2, 3 or 4 heteroatoms independently selected from N, O and/or S; which cyclic group may be mono- or polysubstituted by identical or different substituents R$^{20}$; and Cy denotes a carbo- or heterocyclic group selected from one of the following meanings
  a saturated 3- to 7-membered carbocyclic group,
  an unsaturated 4- to 7-membered carbocyclic group,
  a phenyl group,
  a saturated 4- to 7-membered or unsaturated 5- to 7-membered heterocyclic group with an N, O or S atom as heteroatom,
  a saturated or unsaturated 5- to 7-membered heterocyclic group with two or more N atoms or with one or two N atoms and an O or S atom as heteroatoms,
  an aromatic heterocyclic 5- or 6-membered group with one or more identical or different heteroatoms selected from N, O and/or S.
  while the above-mentioned saturated 6- or 7-membered groups may also be present as bridged ring systems with an imino, (C$_{1-4}$-alkyl)-imino, methylene, ethylene, (C$_{1-4}$-alkyl)-methylene or di-(C$_{1-4}$-alkyl)-methylene bridge, and
  while the above-mentioned cyclic groups may be mono- or polysubstituted at one or more C atoms by identical or different groups R$^{20}$, or in the case of a phenyl group may also additionally be monosubstituted by nitro, and/or one or more NH groups may be substituted by R$^{21}$; and
  while in the above-mentioned saturated or unsaturated carbo- or heterocyclic groups a —CH$_2$-group may be replaced by a —C(=O)— group;

R$^{11}$ denotes halogen, C$_{1-6}$-alkyl, C$_{2-6}$-alkenyl, C$_{2-6}$-alkynyl, R$^{15}$—O—, R$^{15}$—O—CO—, R$^{15}$—CO—O—, cyano, R$^{16}$R$^{17}$N—, R$^{18}$R$^{19}$N—CO— or Cy, while in the above-mentioned groups one or more C atoms may be substituted independently of one another by substituents selected from halogen, OH, CN, CF$_3$, C$_{1-3}$-alkyl, C$_{1-3}$-alkoxy, hydroxy-C$_{1-3}$-alkyl;

R$^{13}$ has one of the meanings given for R$^{17}$ or denotes formyl;

R$^{14}$ denotes halogen, cyano, C$_{1-6}$-alkyl, C$_{2-6}$-alkenyl, C$_{2-6}$-alkynyl, R$^{15}$—O—R$^{15}$—O—CO—R$^{15}$—CO—, R$^{15}$—CO—O—R$^{16}$R$^{17}$N—, HCO—NR$^{15}$— R$^{18}$R$^{19}$N—CO—, R$^{18}$R$^{19}$N—CO—NH—, R$^{15}$—O—C$_{1-3}$-alkyl, R$^{15}$—O—CO—C$_{1-3}$-alkyl-, R$^{15}$—SO$_2$—NH—, R$^{15}$—SO$_2$—N(C$_{1-3}$-alkyl)-, R$^{15}$—O—CO—NH—C$_{1-3}$-alkyl, R$^{15}$—SO$_2$—NH—C$_{1-3}$-alkyl-, R$^{15}$—CO—O—C$_{1-3}$-alkyl-, R$^{15}$—CO—O—C$_{1-3}$-alkyl-, R$^{16}$R$^{17}$N—C$_{1-3}$-alkyl-, R$^{18}$R$^{19}$N—CO—C$_{1-3}$-alkyl- or Cy-C$_{1-3}$-alkyl-, R$^{15}$ denotes H, C$_{1-4}$-alkyl, C$_{3-7}$-cycloalkyl, C$_{3-7}$-cycloalkyl-C$_{1-3}$-alkyl, phenyl, phenyl-C$_{1-3}$-alkyl, pyridinyl or pyridinyl-C$_{1-3}$-alkyl, R$^{16}$ denotes H, C$_{1-6}$-alkyl, C$_{3-7}$-cycloalkyl, C$_{3-7}$-cycloalkyl-C$_{1-3}$-alkyl, C$_{4-7}$-cycloalkenyl, C$_{4-7}$-cycloalkenyl-C$_{1-3}$-alkyl, ω-hydroxy-C$_{2-3}$-alkyl, ω-(C$_{1-4}$-alkoxy)-C$_{2-3}$-alkyl, amino-C$_{2-6}$-alkyl, C$_{1-4}$-alkyl-amino-C$_{2-6}$-alkyl, di-(C$_{1-4}$-alkyl)-amino-C$_{2-6}$-alkyl or cyclo-C$_{3-6}$-alkyleneimino-C$_{2-6}$-alkyl, R$^{17}$ has one of the meanings given for R$^{16}$ or denotes phenyl, phenyl-C$_{1-3}$-alkyl, pyridinyl, C$_{1-4}$-alkylcarbonyl, C$_{3-7}$-cycloalkylcarbonyl, hydroxycarbonyl-C$_{1-3}$-alkyl, C$_{1-4}$-alkoxycarbonyl, C$_{1-4}$-alkoxycarbonyl-C$_{1-3}$-alkyl, C$_{1-4}$-alkylcarbonylamino-C$_{2-3}$-alkyl, N—(C$_{1-4}$-alkylcarbonyl)-N—(C$_{1-4}$-alkyl)-amino-C$_{2-3}$-alkyl, C$_{1-4}$-alkylaminocarbonyl, C$_{1-4}$-alkylsulphonyl, C$_{1-4}$-alkylsulphonylamino-C$_{2-3}$-alkyl or N—(C$_{1-4}$-alkylsulphonyl)-N—(C$_{1-4}$-alkyl)-amino-C$_{2-3}$-alkyl;

R$^{18}$, R$^{19}$ independently of one another denote H or C$_{1-6}$-alkyl wherein R$^{18}$, R$^{19}$ may be linked to form a C$_{3-6}$-alkylene bridge, wherein a —CH$_2$— group not adjacent to an N atom may be replaced by —O—, —S—, —SO—, —(SO$_2$)—, —CO—, —C(=CH$_2$)— or —NR$^{13}$—;

R$^{20}$ denotes halogen, hydroxy, cyano, nitro, C$_{1-6}$-alkyl, C$_{2-6}$-alkenyl, C$_{2-6}$-alkynyl, C$_{3-7}$-cycloalkyl, C$_{3-7}$-cycloalkyl-C$_{1-3}$-alkyl, hydroxy-C$_{1-3}$-alkyl, R$^{22}$—C$_{1-3}$-alkyl or has one of the meanings given for R$^{22}$; and R$^{21}$ denotes C$_{1-4}$-alkyl, ω-hydroxy-C$_{2-6}$-alkyl, ω-C$_{1-4}$-alkoxy-C$_{2-6}$-alkyl, ω-C$_{1-4}$-alkyl-amino-C$_{2-6}$-alkyl, ω-di-(C$_{1-4}$-alkyl)-amino-C$_{2-6}$-alkyl, ω-cyclo-C$_{3-6}$-alkylene-imino-C$_{2-6}$-alkyl, phenyl, phenyl-C$_{1-3}$-alkyl, C$_{1-4}$-alkylcarbonyl, C$_{1-4}$-alkoxy-carbonyl, C$_{1-4}$-alkylsulphonyl, aminosulphonyl, C$_{1-4}$-alkylaminosulphonyl, di-C$_{1-4}$-alkylaminosulphonyl or cyclo-C$_{3-6}$-alkylene-imino-sulphonyl, R$^{22}$ denotes pyridinyl, phenyl, phenyl-C$_{1-3}$-alkoxy, cyclo-C$_{3-6}$-alkyleneimino-C$_{2-4}$-alkoxy, OHC—, HO—N=HC—, C$_{1-4}$-alkoxy-N=HC—, C$_{1-4}$-alkoxy, C$_{1-4}$-alkylthio, carboxy, C$_{1-4}$-alkylcarbonyl, C$_{1-4}$-alkoxycarbonyl, aminocarbonyl, C$_{1-4}$-alkylamino-carbonyl, di-(C$_{1-4}$-alkyl)-aminocarbonyl, cyclo-C$_{3-6}$-alkyl-amino-carbonyl, cyclo-C$_{3-6}$-alkyleneimino-carbonyl, phenylaminocarbonyl, cyclo-C$_{3-6}$-alkyleneimino-C$_{2-4}$-alkyl-aminocarbonyl, C$_{1-4}$-alkyl-sulphonyl, C$_{1-4}$-alkylsulphinyl, C$_{1-4}$-alkyl-sulphonylamino, C$_{1-4}$-alkyl-sulphonyl-N—(C$_{1-4}$-alkyl)amino, amino, C$_{1-4}$-alkyl-amino, di-(C$_{1-4}$-alkyl)-amino, C$_{1-4}$-alkyl-carbonyl-amino, C$_{1-4}$-alkyl-carbonyl-N—(C$_{1-4}$-alkyl)-amino, cyclo-C$_{3-6}$-alkyleneimino, phenyl-C$_{1-3}$-alkylamino, N—(C$_{1-4}$-alkyl)-phenyl-C$_{1-3}$-alkylamino, acetylamino, propionylamino, phenylcarbonyl, phenylcarbonylamino, phenylcarbonylmethylamino, hydroxy-C$_{2-3}$-alkyl-aminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, aminocarbonylamino or C$_{1-4}$-alkylaminocarbonylamino, while in the above-mentioned groups and radicals, particularly in L, W, X, Z, R$^N$, R$^{10}$, R$^{11}$, R$^{13}$ to R$^{22}$, in each case one or more C atoms may additionally be mono- or polysubstituted by F and/or in each case one or two C atoms independently of one another may additionally be monosubstituted by Cl or Br and/or in each case one or more phenyl rings may additionally comprise independently of one another one, two or three substituents selected from the group F, Cl, Br, I, cyano, C$_{1-4}$-alkyl, C$_{1-4}$-alkoxy, difluoromethyl, trifluoromethyl, hydroxy, amino, C$_{1-3}$-alkylamino, di-(C$_{1-3}$-alkyl)-amino, acetylamino, aminocarbonyl, difluoromethoxy, trifluoromethoxy, amino-$C_{1-3}$-alkyl, $C_{1-3}$-alkylamino-$C_{1-3}$-alkyl- and di-($C_{1-3}$-alkyl)-amino-$C_{1-3}$-alkyl and/or may be monosubstituted by nitro, and the H atom of any carboxy group present or an H atom bound to an N atom may in each case be replaced by a group which can be cleaved in vivo, the tautomers, the diastereomers, the enantiomers, the mixtures thereof and the salts thereof.

The invention also relates to the compounds in the form of the individual optical isomers, mixtures of the individual enantiomers or racemates, in the form of the tautomers and in the form of the free bases or corresponding acid addition salts with pharmacologically acceptable acids. The subject of the invention also includes the compounds according to the invention, including their salts, wherein one or more hydrogen atoms are replaced by deuterium.

This invention also includes the physiologically acceptable salts of the compounds according to the invention as described above and hereinafter.

Also covered by this invention are compositions containing at least one compound according to the invention and/or a salt according to the invention optionally together with one or more physiologically acceptable excipients.

Also covered by this invention are pharmaceutical compositions containing at least one compound according to the invention and/or a salt according to the invention optionally together with one or more inert carriers and/or diluents.

This invention also relates to the use of at least one compound according to the invention and/or a salt according to the invention, for influencing the eating behaviour of a mammal.

The invention further relates to the use of at least one compound according to the invention and/or a salt according to the invention, for reducing the body weight and/or for preventing an increase in the body weight of a mammal.

The invention also relates to the use of at least one compound according to the invention and/or a salt according to the invention, for preparing a pharmaceutical composition with an MCH receptor-antagonistic activity, particularly with an MCH-1 receptor-antagonistic activity.

This invention also relates to the use of at least one compound according to the invention and/or a salt according to the invention, for preparing a pharmaceutical composition which is suitable for the prevention and/or treatment of symptoms and/or diseases which are caused by MCH or are otherwise causally connected with MCH.

A further object of this invention is the use of at least one compound according to the invention and/or a salt according to the invention, for preparing a pharmaceutical composition which is suitable for the prevention and/or treatment of metabolic disorders and/or eating disorders, particularly obesity, bulimia, bulimia nervosa, cachexia, anorexia, anorexia nervosa and hyperphagia.

The invention also relates to the use of at least one compound according to the invention and/or a salt according to the invention, for preparing a pharmaceutical composition which is suitable for the prevention and/or treatment of diseases and/or disorders associated with obesity, particularly diabetes, especially type II diabetes, complications of diabetes including diabetic retinopathy, diabetic neuropathy, diabetic nephropathy, insulin resistance, pathological glucose tolerance, encephalorrhagia, cardiac insufficiency, cardiovascular diseases, particularly arteriosclerosis and high blood pressure, arthritis and gonitis.

In addition the present invention relates to the use of at least one compound according to the invention and/or a salt according to the invention, for preparing a pharmaceutical composition which is suitable for the prevention and/or treatment of hyperlipidaemia, cellulitis, fat accumulation, malignant mastocytosis, systemic mastocytosis, emotional disorders, affective disorders, depression, anxiety, sleep disorders, reproductive disorders, sexual disorders, memory disorders, epilepsy, forms of dementia and hormonal disorders.

The invention also relates to the use of at least one compound according to the invention and/or a salt according to the invention, for preparing a pharmaceutical composition which is suitable for the prevention and/or treatment of urinary problems, such as for example urinary incontinence, overactive bladder, urgency, nycturia and enuresis.

The invention further relates to the use of at least one compound according to the invention and/or a salt according to the invention, for preparing a pharmaceutical composition which is suitable for the prevention and/or treatment of dependencies and/or withdrawal symptoms.

The invention also relates to a pharmaceutical composition containing a first active substance which is selected from the compounds according to the invention and/or the corresponding salts, as well as a second active substance which is selected from the group consisting of active substances for the treatment of diabetes, active substances for the treatment of diabetic complications, active substances for the treatment of obesity, preferably other than MCH antagonists, active substances for the treatment of high blood pressure, active substances for the treatment of dyslipidaemia or hyperlipidaemia, including arteriosclerosis, active substances for the treatment of arthritis, active substances for the treatment of anxiety states and active substances for the treatment of depression, optionally together with one or more inert carriers and/or diluents.

Moreover the invention relates to processes for preparing compounds of formula I as described hereinafter.

The starting materials and intermediate products used in the synthesis according to the invention are also a subject of this invention.

DETAILED DESCRIPTION OF THE INVENTION

Unless otherwise specified, the groups, residues and substituents, particularly B, k, L, U, V, W, X, Y, Z, Cy, $R^1$, $R^2$, $R^{10}$, $R^{11}$, $R^{13}$ to $R^{22}$, $R^N$, have the meanings given hereinbefore.

If groups, residues and/or substituents occur more than once in a compound, they may have the same or different meanings in each case.

If $R^1$ and $R^2$ are not joined together via an alkylene bridge, $R^1$ and $R^2$ independently of one another preferably denote a $C_{1-8}$-alkyl or $C_{3-7}$-cycloalkyl group which may be mono- or polysubstituted by identical or different groups $R^{11}$, while a —$CH_2$— group in position 3 or 4 of a 5-, 6- or 7-membered cycloalkyl group may be replaced by —O—, —S— or —$NR^{13}$—, while one or both of the groups $R^1$ and $R^2$ may also represent H.

Preferred meanings of the group $R^{11}$ are F, $C_{1-6}$-alkyl, $C_{2-6}$-alkenyl, $C_{2-6}$-alkynyl, $R^{15}$—O—, cyano, $R^{16}R^{17}N$, $C_{3-7}$-cycloalkyl, cyclo-$C_{3-6}$-alkyleneimino, pyrrolidinyl, N—($C_{1-4}$-alkyl)-pyrrolidinyl, piperidinyl, N—($C_{1-4}$-alkyl)-piperidinyl, phenyl, pyridyl, pyrazolyl, thiazolyl, imidazolyl, while in the above-mentioned groups and radicals one or more C atoms may be mono- or polysubstituted independently of one another by F, $C_{1-3}$-alkyl, $C_{1-3}$-alkoxy or hydroxy-$C_{1-3}$-alkyl, and/or one or two C atoms may be monosubstituted independently of one another by Cl, Br, OH, $CF_3$ or CN, and the above-mentioned cyclic groups may be mono- or polysubstituted at one or more C atoms by identical or different radicals $R^{20}$, or in the case of a phenyl group may also additionally be monosubstituted by nitro, and/or one or more NH groups may be substituted by $R^{21}$. If $R^{11}$ has one of the meanings $R^{15}$—O—, cyano, $R^{16}R^{17}$N or cyclo-$C_{3-6}$-alkyleneimino the C atom of the alkyl or cycloalkyl group substituted by $R^{11}$ is preferably not directly connected to a heteroatom, such as for example to the group —N—X—.

Preferably the groups $R^1$, $R^2$ independently of one another represent H, $C_{1-6}$-alkyl, $C_{3-5}$-alkenyl, $C_{3-5}$-alkynyl, $C_{3-7}$-cycloalkyl, hydroxy-$C_{3-7}$-cycloalkyl, $C_{3-7}$-cycloalkyl-$C_{1-3}$-alkyl, (hydroxy-$C_{3-7}$-cycloalkyl)-$C_{1-3}$-alkyl, hydroxy-$C_{2-4}$-alkyl, $\omega$-NC—$C_{2-3}$-alkyl, $C_{1-4}$-alkoxy-$C_{2-4}$-alkyl, hydroxy-$C_{1-4}$-alkoxy-$C_{2-4}$-alkyl, $C_{1-4}$-alkoxy-carbonyl-$C_{1-4}$-alkyl, carboxyl-$C_{1-4}$-alkyl, amino-$C_{2-4}$-alkyl, $C_{1-4}$-alkyl-amino-$C_{2-4}$-alkyl, di-($C_{1-4}$-alkyl)-amino-$C_{2-4}$-alkyl, cyclo-$C_{3-6}$-alkyleneimino-$C_{2-4}$-alkyl, pyrrolidin-3-yl, N—($C_{1-4}$-alkyl)-pyrrolidin-3-yl, pyrrolidinyl-$C_{1-3}$-alkyl, N—($C_{1-4}$-alkyl)-pyrrolidinyl-$C_{1-3}$-alkyl, piperidin-3-yl, piperidin-4-yl, N—($C_{1-4}$-alkyl)-piperidin-3-yl, N—($C_{1-4}$-alkyl)-piperidin-4-yl, piperidinyl-$C_{1-3}$-alkyl, N—($C_{1-4}$-alkyl)-piperidinyl-$C_{1-3}$-alkyl, tetrahydropyran-3-yl, tetrahydropyran-4-yl, tetrahydrofuran-2-ylmethyl, tetrahydrofuran-3-ylmethyl, phenyl-$C_{1-3}$-alkyl, pyridyl-$C_{1-3}$-alkyl, pyrazolyl-$C_{1-3}$-alkyl, thiazolyl-$C_{1-3}$-alkyl or imidazolyl-$C_{1-3}$-alkyl, while in the above-mentioned groups and radicals one or more C atoms independently of one another may be mono- or polysubstituted by F, $C_{1-3}$-alkyl or hydroxy-$C_{1-3}$-alkyl, and/or one or two C atoms independently of one another may be monosubstituted by Cl, Br, OH, $CF_3$ or CN, and the above-mentioned cyclic groups may be mono- or polysubstituted at one or more C atoms by identical or different radicals $R^{20}$, in the case of a phenyl group may also additionally be monosubstituted by nitro, and/or one or more NH groups may be substituted by $R^{21}$. Preferred substituents of the above-mentioned phenyl or pyridyl groups are selected from the group F, Cl, Br, I, cyano, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)-amino, acetylamino, aminocarbonyl, difluoromethoxy, trifluoromethoxy, amino-$C_{1-3}$-alkyl, $C_{1-3}$-alkylamino-$C_{1-3}$-alkyl and di-($C_{1-3}$-alkyl)-amino-$C_{1-3}$-alkyl, while a phenyl group may also be monosubstituted by nitro.

Particularly preferred definitions of the groups $R^1$ and/or $R^2$ are selected from the group consisting of H, $C_{1-4}$-alkyl, hydroxy-$C_{1-4}$-alkyl, $C_{3-5}$-alkenyl, $C_{3-5}$-alkynyl, $C_{3-7}$-cycloalkyl, hydroxy-$C_{3-7}$-cycloalkyl, dihydroxy-$C_{3-6}$-alkyl, $C_{3-7}$-cycloalkyl-$C_{1-3}$-alkyl, tetrahydropyran-3-yl, tetrahydropyran-4-yl, tetrahydrofuran-2-ylmethyl, tetrahydrofuran-3-yl methyl, (hydroxy-$C_{3-7}$-cycloalkyl)-$C_{1-3}$-alkyl, $C_{1-4}$-alkoxy-$C_{2-3}$-alkyl, hydroxy-$C_{1-4}$-alkoxy-$C_{2-3}$-alkyl, $C_{1-4}$-alkoxy-$C_{1-4}$-alkoxy-$C_{2-3}$-alkyl, di-($C_{1-3}$-alkyl)amino-$C_{2-3}$-alkyl, pyrrolidin-N-yl-$C_{2-3}$-alkyl, piperidin-N-yl-$C_{2-3}$-alkyl, pyridylmethyl, pyrazolylmethyl, thiazolylmethyl and imidazolylmethyl, while an alkyl, cycloalkyl or cycloalkyl-alkyl group may additionally be mono- or disubstituted by hydroxy and/or hydroxy-$C_{1-3}$-alkyl, and/or mono- or polysubstituted by F or $C_{1-3}$-alkyl and/or monosubstituted by $CF_3$, Br, Cl or CN.

Most particularly preferred groups $R^1$ and/or $R^2$ are selected from the group consisting of H, methyl, ethyl, n-propyl, i-propyl, prop-2-enyl, but-2-enyl, prop-2-ynyl, but-2-ynyl, 2-methoxyethyl, cyclopropyl, cyclopentyl, cyclohexyl, cyclopropylmethyl, cyclopentylmethyl, hydroxy-$C_{3-7}$-cycloalkyl, (hydroxy-$C_{1-3}$-alkyl)-hydroxy-$C_{3-7}$-cycloalkyl, dihydroxy-$C_{3-5}$-alkyl, 2-hydroxy-1-(hydroxymethyl)-ethyl, 1,1-di(hydroxymethyl)-ethyl, (1-hydroxy-$C_{3-6}$-cycloalkyl)-methyl, tetrahydropyran-3-yl, tetrahydropyran-4-yl, tetrahydrofuran-2-ylmethyl, tetrahydrofuran-3-ylmethyl, 2-hydroxyethyl, 3-hydroxypropyl, 2-hydroxy-2-methyl-propyl, di-($C_{1-3}$-alkyl)aminoethyl, pyrrolidin-N-yl-ethyl and piperidin-N-ylethyl, while the above-mentioned groups may be mono- or polysubstituted by F and/or $C_{1-3}$-alkyl.

Examples of most particularly preferred groups $R^1$ and/or $R^2$ are therefore H, methyl, ethyl, n-propyl, i-propyl, prop-2-enyl, prop-2-ynyl, 2-methoxyethyl, cyclopropyl, cyclopentyl, cyclohexyl, cyclopropylmethyl, cyclopentylmethyl, hydroxy-cyclopentyl, hydroxy-cyclohexyl, (hydroxymethyl)-hydroxy-cyclopentyl, (hydroxymethyl)-hydroxy-cyclohexyl, 2,3-dihydroxypropyl, (1-hydroxy-cyclopropyl)-methyl, tetrahydropyran-3-yl, tetrahydropyran-4-yl, tetrahydrofuran-2-ylmethyl, tetrahydrofuran-3-ylmethyl, 2-hydroxyethyl, 3-hydroxypropyl and 2-hydroxy-2-methylpropyl.

Particularly preferably, at least one of the groups $R^1$, $R^2$ has a meaning other than H.

In case the group $R^2$ denotes a $C_{1-3}$-alkylen bridge which is linked to the group Y, preferably the definition of $R^1$ is in accordance with a preferred definition as described hereinbefore or $R^1$ denotes a group selected from $C_{1-4}$-alkyl-CO—, $C_{1-4}$-alkyl-O—CO—, ($C_{1-4}$-alkyl)NH—CO— or ($C_{1-4}$-alkyl)$_2$N—CO— wherein alkyl-groups may be mono- or polyfluorinated. In case $R^2$ is linked to the group Y, then $R^2$ preferably denotes —$CH_2$— or —$CH_2$—$CH_2$—, wherein the alkylene bridge may be substituted with one or more $C_{1-3}$-alkyl-groups. In case $R^2$ is linked to the group Y, then $R^1$ preferably denotes H, $C_{1-4}$-alkyl or $C_{1-4}$-alkyl-carbonyl, wherein alkyl may be mono- or polyfluorinated, even more preferably H, methylcarbonyl or $C_{1-3}$-alkyl which may be mono- or polyfluorinated. Preferred examples of $R^1$ in this case are H, methyl, ethyl, n-propyl, i-propyl, trifluoromethyl, methylcarbonyl or trifluoromethylcarbonyl.

In case the groups $R^1$ and $R^2$ form an alkylene bridge, this is preferably a $C_{3-7}$-alkylene bridge or a $C_{3-7}$-alkylene bridge, wherein a —$CH_2$— group not adjacent to the N atom of the $R^1R^2N$ group is replaced by —CH=N—, —CH=CH—, —O—, —S—, —($SO_2$)—, —CO—, —C(=N—OH)—, —C(=N—($C_{1-4}$-alkyl))- or —$NR^{13}$—, while in the alkylene bridge defined hereinbefore one or more H atoms may be replaced by identical or different groups $R^{14}$, and the alkylene bridge defined hereinbefore may be substituted with a carbo- or heterocyclic group cy in such a way that the bond between the alkylene bridge and the group Cy is made
 via a single or double bond,
 via a common C atom forming a spirocyclic ring system,
 via two common adjacent C— and/or N atoms forming a fused bicyclic ring system or
 via three or more C— and/or N atoms forming a bridged ring system.

Preferably also, $R^1$ and $R^2$ form an alkylene bridge such that $R^1R^2N$— denotes a group which is selected from azetidine, pyrrolidine, piperidine, azepan, 2,5-dihydro-1H-pyrrole, 1,2,3,6-tetrahydro-pyridine, 2,3,4,7-tetrahydro-1H-azepine, 2,3,6,7-tetrahydro-1H-azepine, piperazine in which the free imine function is substituted by $R^{13}$, piperidin-4-one morpholine thiomorpholine 4-$C_{1-4}$-alkoxy-imino-piperidin-1-yl and 4-hydroxyimino-piperidin-1-yl; or a group which is particularly preferably selected from azetidine, pyrrolidine, piperidine, piperazine in which the free imine function is substituted by $R^{13}$, and morpholine, while according to the general definition of $R^1$ and $R^2$ one or more H atoms may be replaced by identical or different groups $R^{14}$, and/or the above-mentioned groups may be substituted by one or two identical or different carbo- or heterocyclic groups Cy in a manner specified according to the general definition of $R^1$ and $R^2$, while the group Cy may be mono- or polysubstituted by $R^{20}$.

Particularly preferred groups Cy are $C_{3-7}$-cycloalkyl, aza-$C_{4-7}$-cycloalkyl, particularly cyclo-$C_{3-6}$-alkyleneimino, as well as 1-$C_{1-4}$-alkyl-aza-$C_{4-7}$-cycloalkyl, while the group Cy may be mono- or polysubstituted by $R^{20}$.

The $C_{3-8}$-alkylene bridge formed by $R^1$ and $R^2$, wherein —$CH_2$— groups may be replaced as specified, may be substituted, as described, by one or two identical or different carbo- or heterocyclic groups Cy, which may be substituted as specified hereinbefore.

In the event that the alkylene bridge is linked to a group Cy through a single bond, Cy is preferably selected from the group consisting of $C_{3-7}$-cycloalkyl, cyclo-$C_{3-6}$-alkyleneimino, imidazol, triazol, thienyl and phenyl.

In the event that the alkylene bridge is linked to a group Cy via a common C atom forming a spirocyclic ring system, Cy is preferably selected from the group consisting of $C_{3-7}$-cycloalkyl, aza-$C_{4-8}$-cycloalkyl, oxa-$C_{4-8}$-cycloalkyl, 2,3-dihydro-1H-quinazolin-4-one.

In the event that the alkylene bridge is linked to a group Cy via two common adjacent C and/or N atoms forming a fused bicyclic ring system, Cy is preferably selected from the group consisting of $C_{4-7}$-cycloalkyl, phenyl, thienyl.

In the event that the alkylene bridge is linked to a group Cy via three or more C and/or N atoms forming a bridged ring system, Cy preferably denotes $C_{4-8}$-cycloalkyl or aza-$C_{4-8}$-cycloalkyl.

In the event that the heterocyclic group $R^1R^2N$— is substituted by a group Cy, the group Cy is preferably linked to the group $R^1R^2N$— through a single bond, while Cy is preferably selected from the group consisting of $C_{3-7}$-cycloalkyl, cyclo-$C_{3-6}$-alkyleneimino, imidazol and triazol, while these groups may be substituted as specified, preferably by fluorine, $C_{1-3}$-alkyl, hydroxy-$C_{1-3}$-alkyl and hydroxy.

Particularly preferably the group

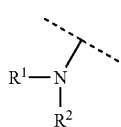

is defined according to one of the following partial formulae

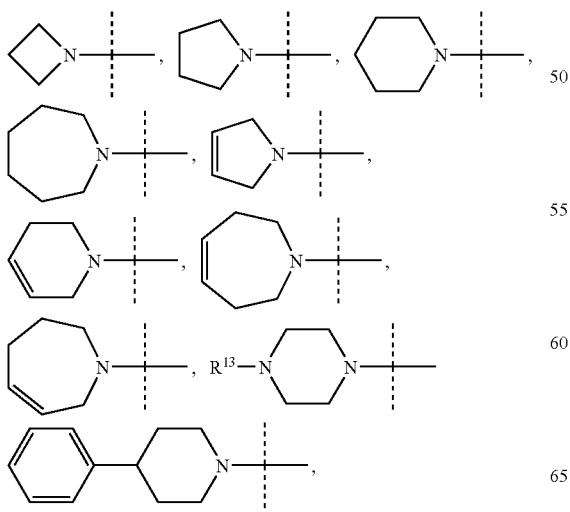

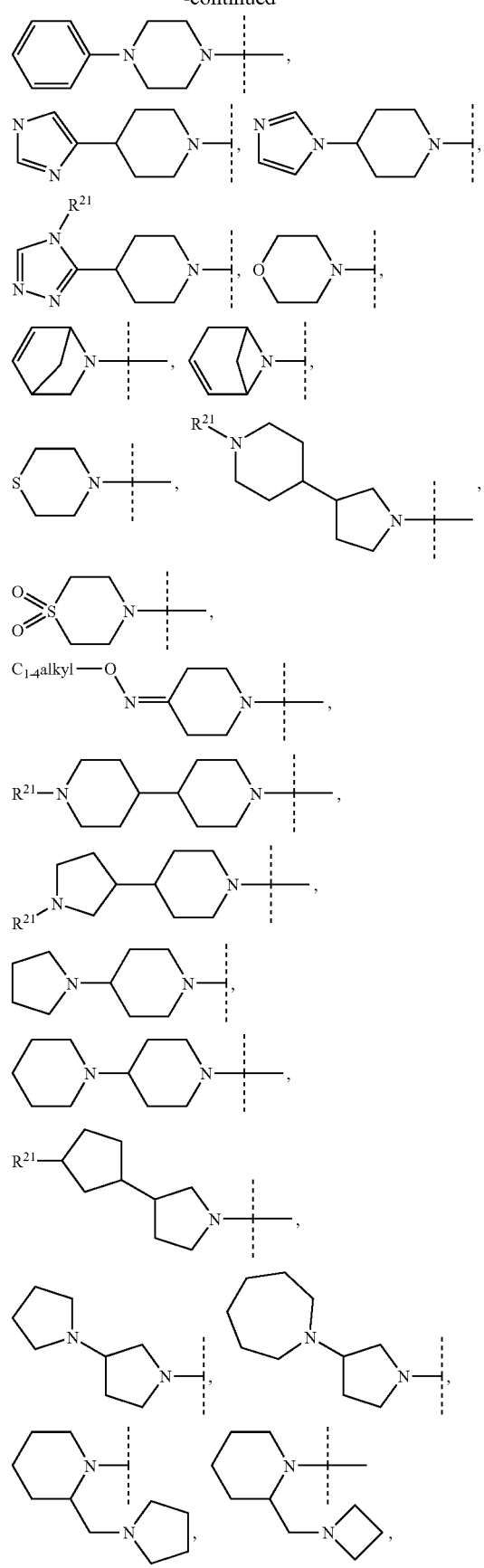

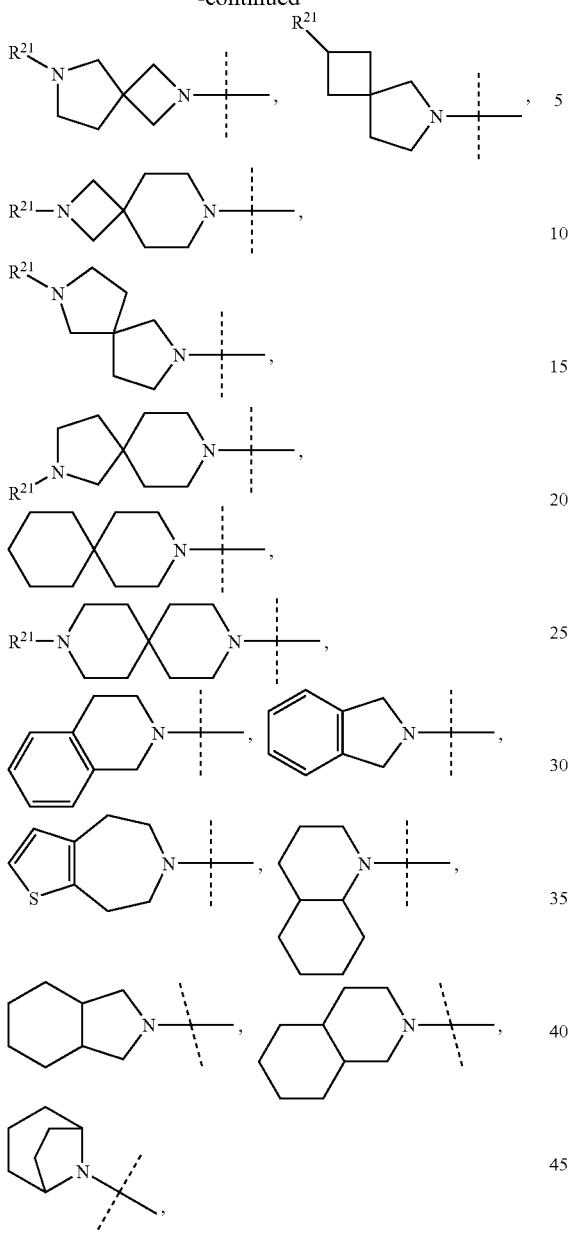

wherein one or more H atoms of the heterocycle formed by the group $R^1R^2N$— may be replaced by identical or different groups $R^{14}$, and
the heterocycle formed by the group $R^1R^2N$— may be substituted by one or two, preferably one group Cy, particularly preferably by a $C_{3-7}$-cycloalkyl group, while the cycloalkyl group may be mono- or polysubstituted by $R^{20}$, and
the ring attached to the heterocycle formed by the group $R^1R^2N$— may be mono- or polysubstituted at one or more C atoms by $R^{20}$, or in the case of a phenyl ring may also additionally be monosubstituted by nitro and
wherein $R^{13}$, $R^{14}$, $R^{20}$, $R^{21}$ have the meanings given hereinbefore and hereinafter.

If the heterocycle formed by the group $R^1R^2N$— is substituted as specified by one or two cycloalkyl groups mono- or polysubstituted by $R^{20}$, the substituents $R^{20}$ independently of one another preferably denote $C_{1-4}$-alkyl, $C_{1-4}$-alkoxy-$C_{1-3}$-alkyl, hydroxy-$C_{1-3}$-alkyl, hydroxy, fluorine, chlorine, bromine or $CF_3$, particularly hydroxy.

Most particularly preferably the group

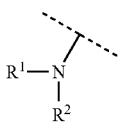

is defined according to one of the following partial formulae

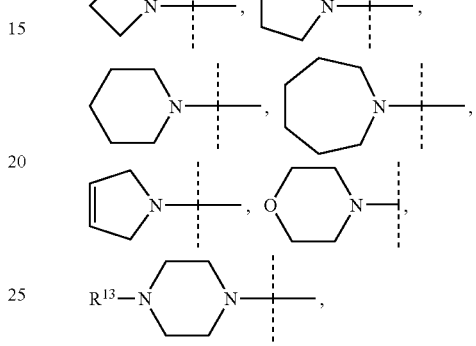

where $R^{13}$ has the meanings given above and hereinafter, and the heterocycle formed by the group $R^1R^2N$— may be substituted by a group Cy, preferably by $C_{3-6}$-cycloalkyl, hydroxy-$C_{3-6}$-cycloalkyl or (hydroxy-$C_{3-6}$-cycloalkyl)-$C_{1-3}$-alkyl, and
the heterocycle formed by the group $R^1R^2N$— may be mono-, di- or trisubstituted by identical or different groups $R^{14}$.

The following partial formulae are most particularly preferred definitions of the heterocyclic group

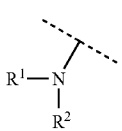

specified above:

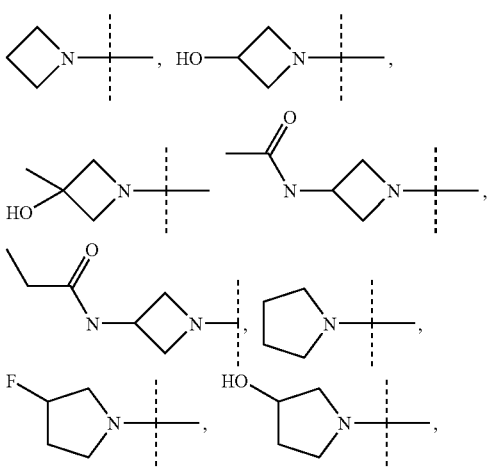

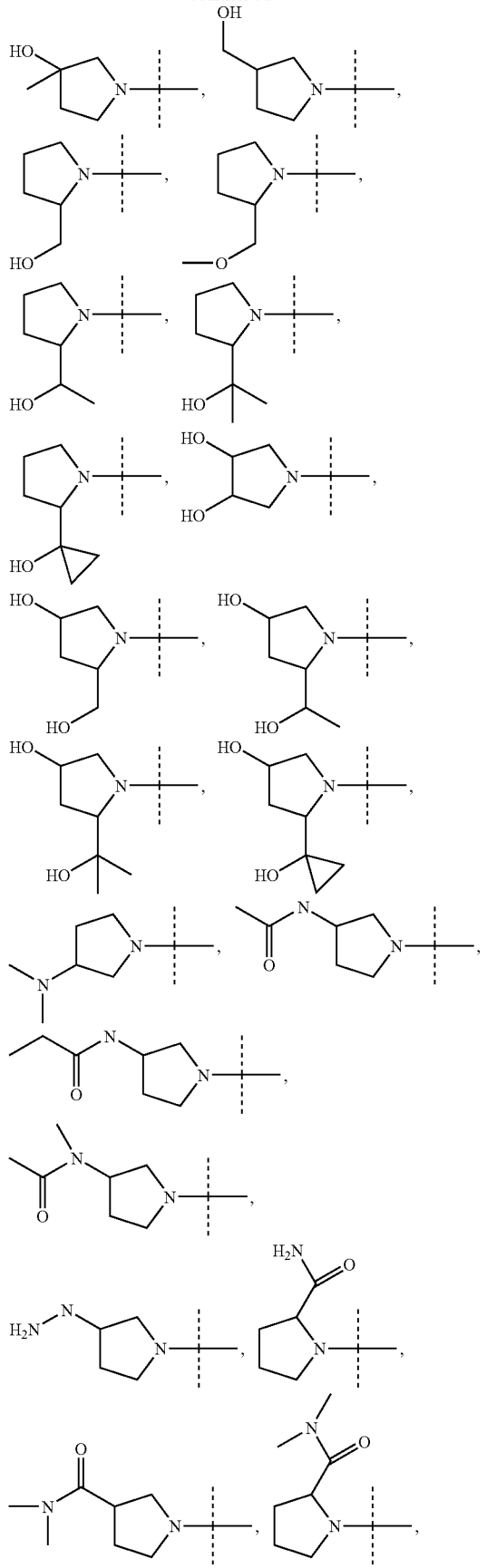
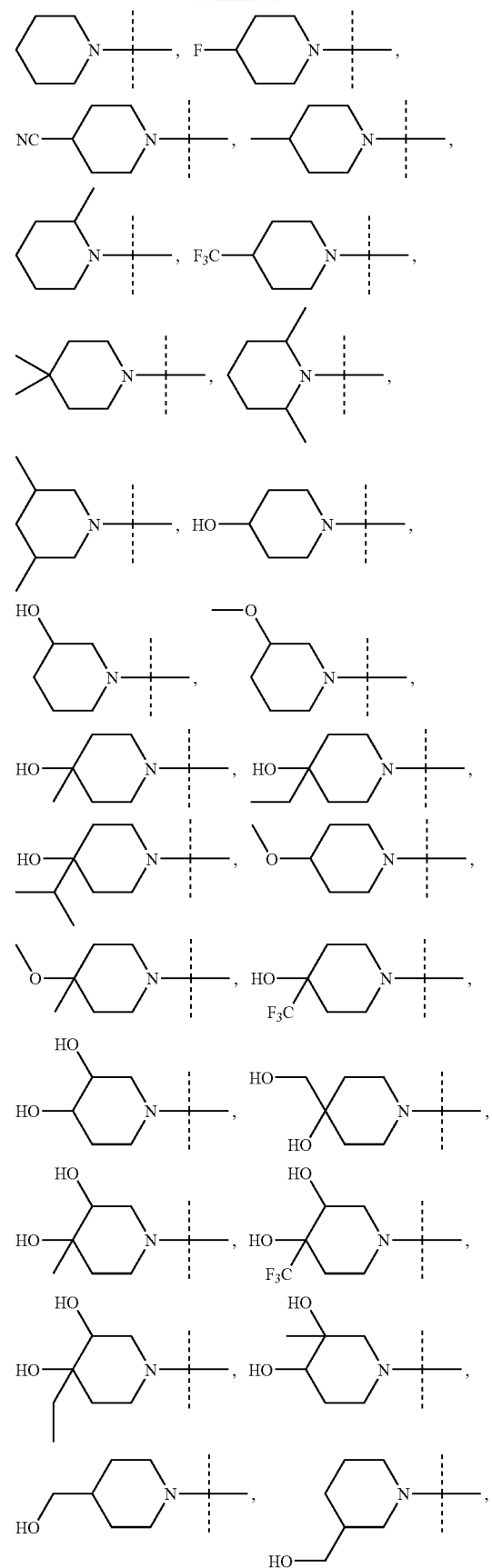

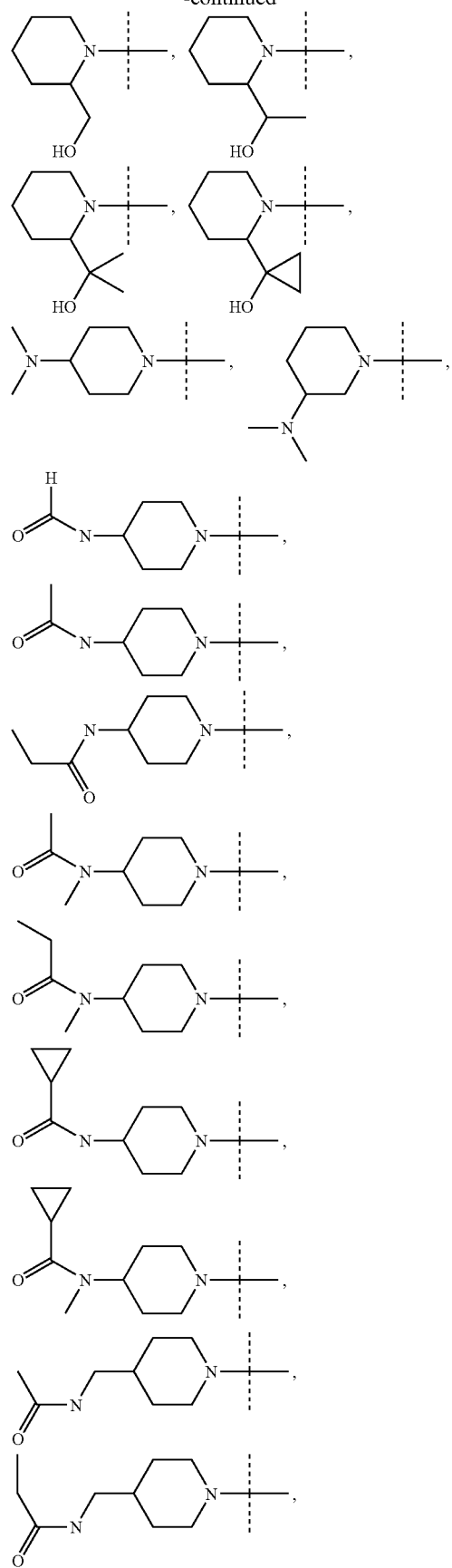
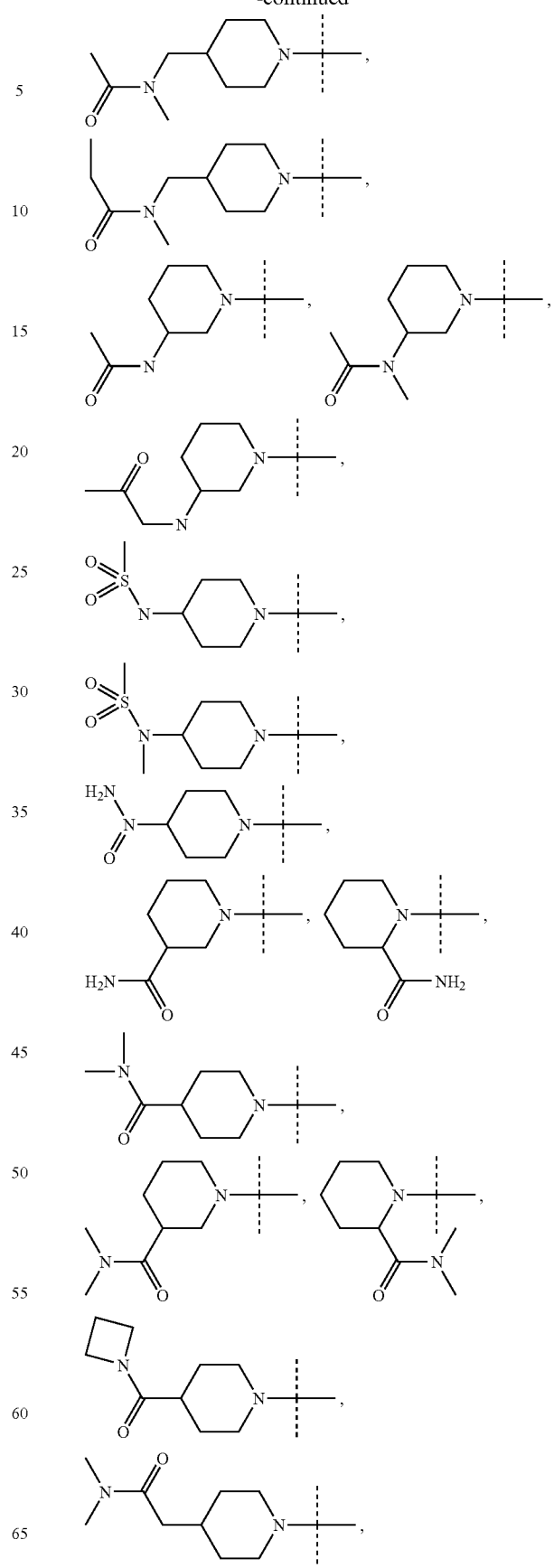

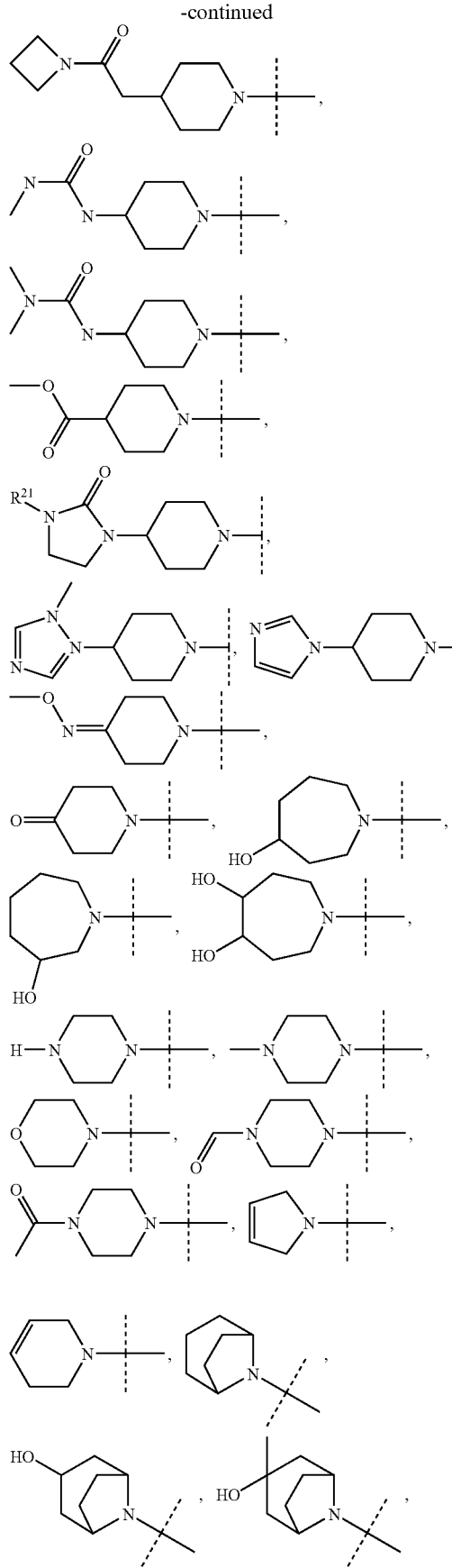

wherein the groups mentioned are not further substituted, or wherein methyl or ethyl groups may be mono-, di- or trisubstituted by fluorine, and wherein one or more H atoms of the heterocycle formed by the group $R^1R^2N$— which are bound to carbon may be substituted independently of one another by fluorine, chlorine, CN, $CF_3$, $C_{1-3}$-alkyl, hydroxy-$C_{1-3}$-alkyl, particularly $C_{1-3}$-alkyl or $CF_3$, preferably methyl, ethyl, $CF_3$.

From the above listed preferred partial formulae the following definitions of the heterocyclic group

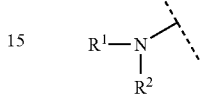

are particularly preferred:

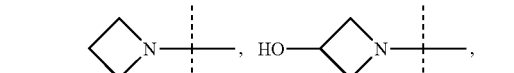
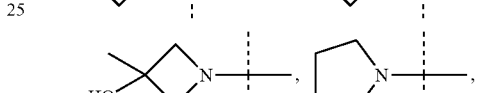
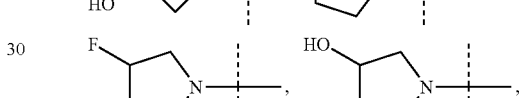
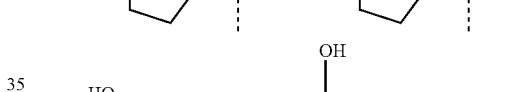
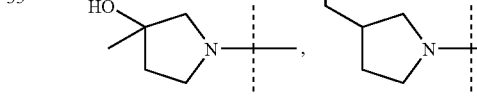
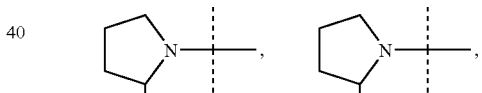
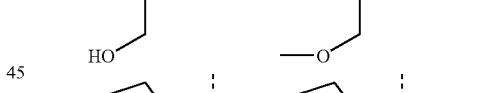
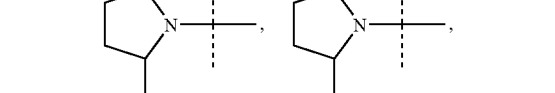
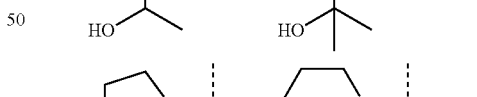

-continued

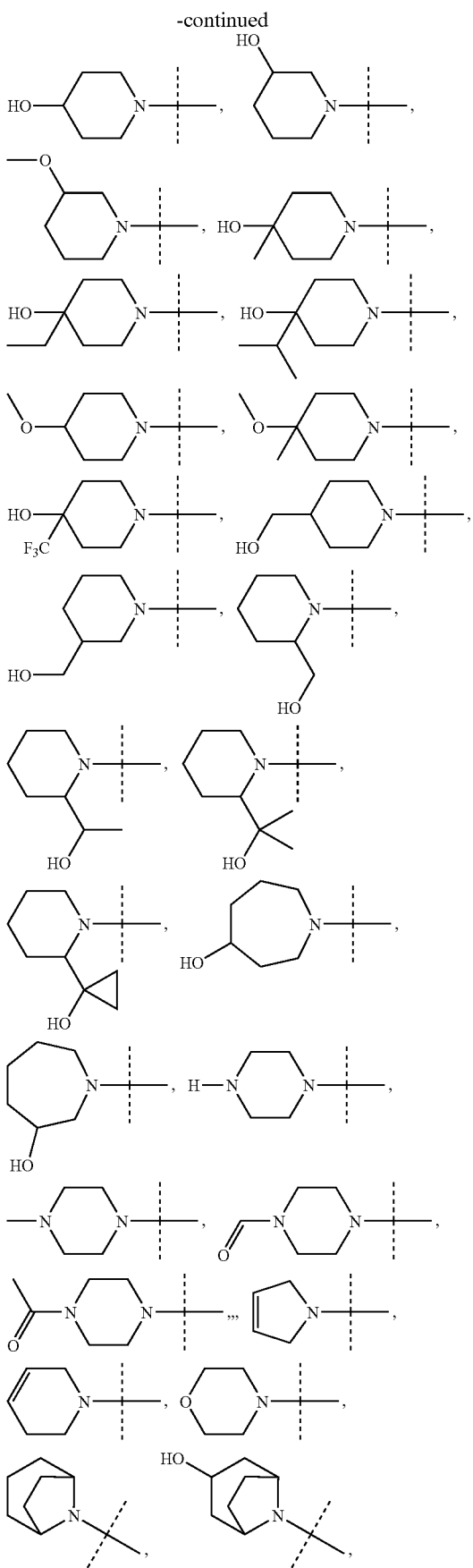

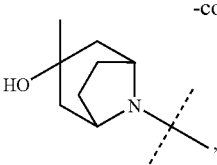

wherein the groups mentioned are not further substituted, or wherein methyl or ethyl groups may be mono-, di- or trisubstituted by fluorine, and wherein one or more H atoms of the heterocycle formed by the group $R^1R^2N$— which are bound to carbon may be substituted independently of one another by fluorine, chlorine, CN, $CF_3$, $C_{1-3}$-alkyl, hydroxy-$C_{1-3}$-alkyl, particularly $C_{1-3}$-alkyl or $CF_3$, preferably methyl, ethyl, $CF_3$.

Among the above-mentioned preferred and particularly preferred meanings of $R^1R^2N$, the following definitions of the substituent $R^{14}$ are preferred:

F, Cl, Br, cyano,
$C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$-alkyl,
hydroxy, hydroxy-$C_{1-3}$-alkyl, $C_{1-4}$-alkoxy, ω-($C_{1-4}$-alkoxy)-$C_{1-3}$-alkyl,
$C_{1-4}$-alkyl-carbonyl, carboxy, $C_{1-4}$-alkoxycarbonyl, hydroxy-carbonyl-$C_{1-3}$-alkyl, $C_{1-4}$-alkoxycarbonyl-$C_{1-3}$-alkyl,
formylamino, N-formyl-N($C_{1-4}$-alkyl)-amino, formylamino-$C_{1-3}$-alkyl, formyl-N($C_{1-4}$-alkyl)amino-$C_{1-3}$-alkyl, $C_{1-4}$-alkyl-carbonylamino, $C_{1-4}$-alkyl-carbonyl-N—($C_{1-4}$-alkyl)-amino, $C_{1-4}$-alkyl-carbonylamino-$C_{1-3}$-alkyl, $C_{1-4}$-alkyl-carbonyl-N—($C_{1-4}$-alkyl)-amino-$C_{1-3}$-alkyl,
$C_{1-4}$-alkoxy-carbonylamino, $C_{1-4}$-alkoxy-carbonylamino-$C_{1-3}$-alkyl,
amino, $C_{1-4}$-alkyl-amino, $C_{3-7}$-cycloalkyl-amino, $C_{3-7}$-cycloalkyl-N—($C_{1-4}$-alkyl)-amino, di-($C_{1-4}$-alkyl)-amino, cyclo-$C_{3-6}$-alkyleneimino, amino-$C_{1-3}$-alkyl, $C_{1-4}$-alkyl-amino-$C_{1-3}$-alkyl, $C_{3-7}$-cycloalkyl-amino-$C_{1-3}$-alkyl, $C_{3-7}$-cycloalkyl-N—($C_{1-4}$-alkyl)-amino-$C_{1-3}$-alkyl, di-($C_{1-4}$-alkyl)amino-$C_{1-3}$-alkyl, cyclo-$C_{3-6}$-alkyleneimino-$C_{1-3}$-alkyl,
aminocarbonyl, $C_{1-4}$-alkyl-amino-carbonyl, $C_{3-7}$-cycloalkyl-amino-carbonyl, $C_{3-7}$-cycloalkyl-N—($C_{1-4}$-alkyl)-amino-carbonyl, di-($C_{1-4}$-alkyl)-amino-carbonyl, (aza-$C_{4-6}$-cycloalkyl)-carbonyl, aminocarbonyl-$C_{1-3}$-alkyl, $C_{1-4}$-alkyl-amino-carbonyl-$C_{1-3}$-alkyl, $C_{3-7}$-cycloalkyl-aminocarbonyl-$C_{1-3}$-alkyl, $C_{3-7}$-cycloalkyl-N—($C_{1-4}$-alkyl)-amino-carbonyl-$C_{1-3}$-alkyl, di-($C_{1-4}$-alkyl)amino-carbonyl-$C_{1-3}$-alkyl, (aza-$C_{4-6}$-cycloalkyl)-carbonyl-$C_{1-3}$-alkyl,
$C_{1-4}$-alkyl-amino-carbonyl-amino-, di-($C_{1-4}$-alkyl)-amino-carbonyl-amino-.

Particularly preferred meanings of the substituent $R^{14}$ are selected from:
F, Cl, Br, cyano,
$C_{1-4}$-alkyl,
hydroxy, hydroxy-$C_{1-3}$-alkyl, $C_{1-4}$-alkoxy, ω-($C_{1-4}$-alkoxy)-$C_{1-3}$-alkyl,
formylamino, formyl-N($C_{1-4}$-alkyl)-amino, $C_{1-4}$-alkyl-carbonylamino, $C_{1-4}$-alkyl-carbonyl-N—($C_{1-4}$-alkyl)-amino, $C_{1-4}$-alkyl-carbonylamino-$C_{1-3}$-alkyl, $C_{1-4}$-alkyl-carbonyl-N—($C_{1-4}$-alkyl)-amino$C_{1-3}$-alkyl,
di-($C_{1-4}$-alkyl)-amino, amino-$C_{1-3}$-alkyl, $C_{1-4}$-alkyl-amino-$C_{1-3}$-alkyl, $C_{3-7}$-cycloalkyl-amino$C_{1-3}$-alkyl, $C_{3-7}$-cycloalkyl-N—($C_{1-4}$-alkyl)-amino-$C_{1-3}$-alkyl, di-($C_{1-4}$-alkyl)-amino-$C_{1-3}$-alkyl, cyclo-$C_{3-6}$-alkylene-imino-$C_{1-3}$-alkyl, aminocarbonyl, $C_{1-4}$-alkyl-amino-carbonyl, di-($C_{1-4}$-alkyl)-amino-carbonyl, (aza-$C_{4-6}$-cycloalkyl)-carbonyl, di-($C_{1-4}$-alkyl)-amino-carbonyl-$C_{1-3}$-alkyl, (aza-$C_{4-6}$-cycloalkyl)-carbonyl$C_{1-3}$-alkyl.

Most particularly preferred meanings of the substituent $R^{14}$ are $C_{1-3}$-alkyl, hydroxy-$C_{1-3}$-alkyl, methoxymethyl, hydroxy, aminocarbonyl, di($C_{1-3}$-alkyl)amino, formylamino, formyl-N($C_{1-3}$-alkyl)amino, $C_{1-3}$-alkylcarbonylamino, $C_{1-3}$-alkyl-carbonyl-N—($C_{1-3}$-alkyl)-amino, $C_{1-3}$-alkylcarbonylamino-methyl, $C_{1-3}$-alkyl-carbonyl-N—($C_{1-3}$-alkyl)-amino-methyl, $C_{1-3}$-alkyl-aminocarbonyl, di-($C_{1-3}$-alkyl)-amino-carbonyl, $C_{1-3}$-alkyl-amino-carbonyl-methyl, di-($C_{1-3}$-alkyl)-aminocarbonyl-methyl.

In the above-mentioned preferred meanings of $R^{14}$ in each case one or more C atoms may additionally be mono- or polysubstituted by F and/or in each case one or two C atoms may independently of one another additionally be monosubstituted by Cl or Br. Thus, preferred meanings of $R^{14}$ also include, for example, —$CF_3$, —$OCF_3$, $CF_3$—CO— and $CF_3$—CHOH—.

Examples of most preferred meanings of $R^{14}$ are hydroxy, methyl, ethyl, $CF_3$, hydroxymethyl, 2-hydroxyethyl, dimethylamino, formylamino, methylaminocarbonyl, methylaminocarbonylmethyl, dimethylaminocarbonyl, dimethylaminocarbonylmethyl, methylcarbonylamino, methylcarbonylaminomethyl, ethylcarbonylamino, ethylcarbonylaminomethyl, methylcarbonyl-N-(methyl)-amino, methylcarbonyl-N-(methyl)-aminomethyl, ethylcarbonyl-N-(methyl)-amino, ethylcarbonyl-N-(methyl)-aminomethyl.

Preferably the group X denotes —$CH_2$—, —$CH_2$—$CH_2$— or —$CH_2$—$CH_2$—$CH_2$—; most preferably —$CH_2$—. The group X may be mono- or disubstituted with $C_{1-3}$-alkyl, in particular with methyl. Therefore most preferred meaning of X are —$CH_2$— and —$CH(CH_3)$—.

In case the substituent $R^2$ denotes an alkylene bridge which is linked to the group Y, then the group X preferably denotes —$CH_2$— or —$CH_2$—$CH_2$—.

The group Y is preferably selected from the group consisting of phenyl, pyridyl, pyridazinyl, pyrimidinyl, pyrazinyl, furyl, thiophenyl and thiazolyl all of which may be mono- or polysubstituted by identical or different substituents $R^{20}$.

More preferably the group Y denotes a phenyl, pyridyl, thiophenyl, pyridazinyl, pyrimidinyl, pyrazinyl or thiazolyl group which may be mono- or polysubstituted by identical or different substituents $R^{20}$.

Even more preferably the group Y denotes phenyl, thiophenyl, pyridyl or pyridazinyl, which may be mono- or polysubstituted, in particular mono- or disubstituted by identical or different substituents $R^{20}$.

Most preferably the group Y denotes a group characterized by a subformula selected from

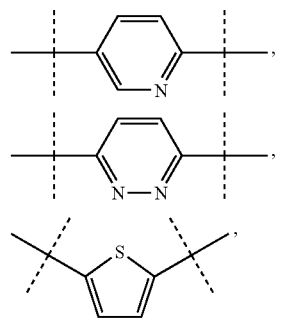

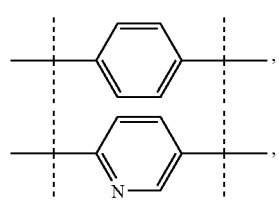

which may be mono- or disubstituted by identical or different substituents $R^{20}$.

According to an alternative embodiment according to the present invention the substituent $R^2$ denotes an alkylene bridge which is linked to the group Y, wherein the group X preferably denotes —$CH_2$— or —$CH_2$—$CH_2$— and the group $R^2$ preferably denotes —$CH_2$— or —$CH_2$—$CH_2$—. A preferred meaning of the group Y is phenyl, pyridyl or thiophenyl.

In this case the subformula

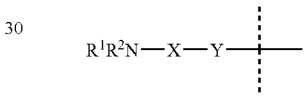

is preferably selected from the group consisting of

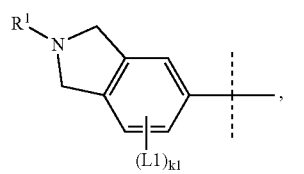

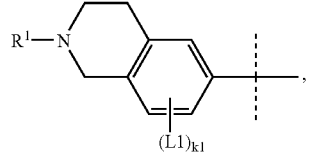

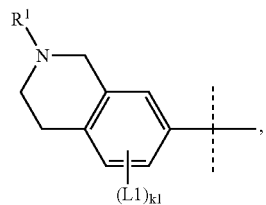

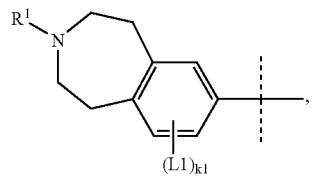

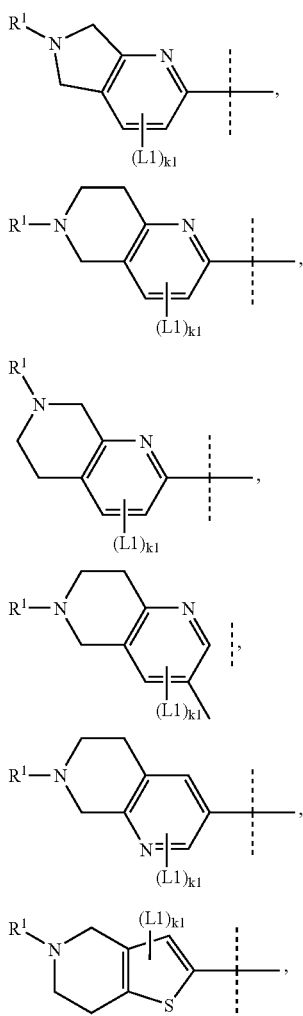

wherein R¹ is defined as hereinbefore, L1 is defined as $R^{20}$ and k1 denotes 0, 1 or 2. Preferably R¹ denotes H, $C_{1-4}$-alkyl or $C_{1-4}$-alkyl-carbonyl, wherein alkyl may be mono- or polyfluorinated. Most preferably R¹ denotes H, methyl, ethyl, n-propyl, i-propyl, trifluoromethyl, methylcarbonyl or trifluoromethylcarbonyl. Preferably k1 denotes 0 or 1.

Preferred substituents $R^{20}$ of the group Y are selected from halogen, $C_{1-3}$-alkyl, $C_{1-3}$-alkoxy, hydroxy and $CF_3$; in particular fluorine, chlorine, bromine or methyl.

The group Z preferably denotes a group selected from —$CH_2$—$CH_2$—, —C(=O)—$CH_2$—, —C(=$CH_2$)—$CH_2$—, —CH($CH_3$)—$CH_2$— and —C(OH)H—$CH_2$—. Even more preferably the group Z denotes —$CH_2$—$CH_2$—, —C(=O)—$CH_2$— or —C(=$CH_2$)—$CH_2$—. The group Z may be mono- or polyfluorinated. Examples of most preferred groups Z are —$CH_2$—$CH_2$—, —CFH—$CH_2$— and —C(=O)—$CH_2$—, in particular —C(=O)—$CH_2$—.

Compounds according to the invention, in particular wherein Z is —C(=O)—$CH_2$—, possess advantageous pharmacokinetic properties, e.g. metabolic stability in liver microsomes and/or plasma levels.

The groups U, V both denote CH; or one of the groups U, V denotes N and the other of U, V denotes CH.

Therefore, the group

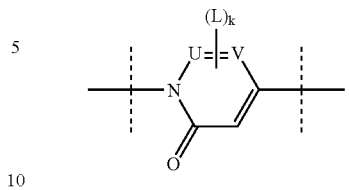

is preferably selected from the groups

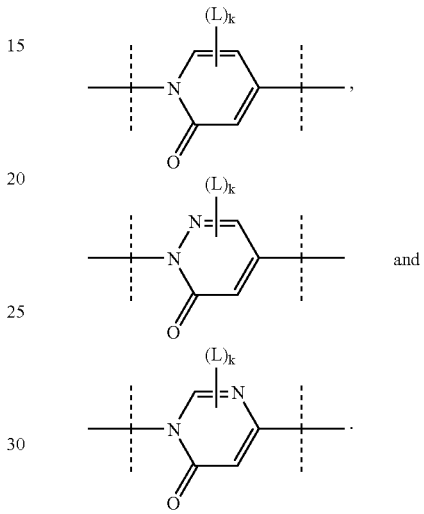

The substituent L is preferably selected from fluorine, chlorine, bromine, methyl, ethyl and trifluoromethyl.

The index k preferably denotes 0 or 1; most preferably 0.

The group W is preferably selected from the group consisting of —$CH_2$—O—, —O—$CH_2$— and —$NR^N$—$CH_2$—. Most preferably the group W denotes —O—$CH_2$—.

The groups $R^N$ independently of each other preferably denotes H, methyl, ethyl or formyl; most preferably H or methyl.

In case the group W denotes —$NR^N$—$CH_2$— the group $R^N$ may denote a —$CH_2$— or —$CH_2$—$CH_2$— bridge being linked to the cyclic group B. According to this embodiment the subformula —W—B preferably denotes

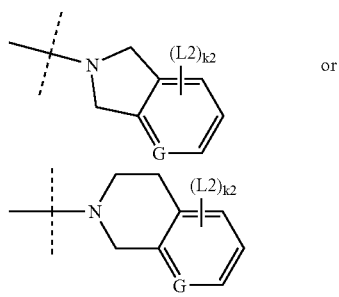

wherein
G denotes CH or N, wherein CH may be substituted with L2; and
L2 are independently of one another selected from the meanings of $R^{20}$ as defined hereinafter, in particular of the meanings of $R^{20}$ as a substituent of the group B as defined hereinafter; and
k2 denotes 0, 1 or 2.

The group B is preferably selected from the group consisting of phenyl and 5- to 6-membered unsaturated or aromatic heterocyclic groups which contain 1 to 4 heteroatoms selected from N, O and S wherein the phenyl or heterocyclic group may be mono- or polysubstituted by identical or different substituents $R^{20}$.

More preferably the group B is selected from the group consisting of phenyl, pyridyl, pyridazinyl, pyrazinyl, pyrimidinyl, pyrrolyl, pyrazolyl, imidazolyl, triazolyl, tetrazolyl, furyl, thiophenyl and thiazolyl; in particular selected from phenyl, pyridyl, furyl and thiophenyl; even more preferably phenyl and pyridyl; wherein said group B may be mono- or polysubstituted, preferably mono- or disubstituted by identical or different substituents $R^{20}$.

Most preferably the group B denotes a group characterized by a subformula selected from

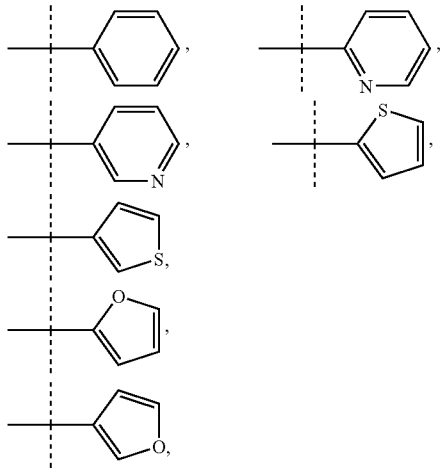

which may be mono- or polysubstituted, particularly mono- or disubstituted by identical or different substituents $R^{20}$.

According to the above listed definitions for the group B the following selected are particularly preferred:

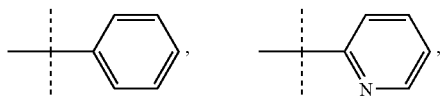

which may be mono- or polysubstituted, particularly mono- or disubstituted by identical or different substituents $R^{20}$.

Alternatively the following listed definitions for the group B are particularly preferred:

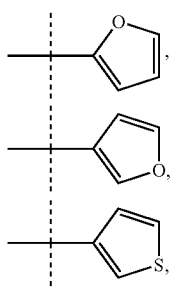

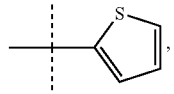

which may be mono- or polysubstituted, particularly mono- or disubstituted by identical or different substituents $R^{20}$.

In case the group B is a 6-membered ring, in particular a phenyl or pyridyl group, it is preferably unsubstituted or mono- or disubstituted by identical or different groups $R^{20}$, wherein the preferred position of a substituent is para with respect to the group W.

Preferred substituents $R^{20}$ of the group B are selected from halogen, hydroxy, nitro, $C_{1-3}$-alkyl, $C_{1-3}$-alkoxy, ($C_{1-3}$-alkyl)-carbonyl-, di-($C_{1-3}$-alkyl)amino, aminocarbonyl, ($C_{1-3}$-alkyl)carbonylamino and ($C_{1-3}$-alkyl)-sulfonylamino, wherein in each case one or more C atoms may additionally be mono- or polysubstituted by F. Preferred examples of fluorinated groups $R^{20}$ are $CF_3$ and —O—$CF_3$. Particularly preferred meanings of $R^{20}$ are fluorine, chlorine, bromine, methyl and methoxy.

The following are preferred definitions of other substituents according to the invention:

Preferably the substituent $R^{13}$ has one of the meanings given for $R^{16}$ or formyl. Particularly preferably $R^{13}$ denotes H, $C_{1-4}$-alkyl, $C_{3-7}$-cycloalkyl, $C_{3-7}$-cycloalkyl-$C_{1-3}$-alkyl, ω-hydroxy-$C_{2-3}$-alkyl, ω-($C_{1-4}$-alkoxy)-$C_{2-3}$-alkyl, formyl or ($C_{1-4}$-alkyl)-carbonyl. Most particularly preferably $R^{13}$ denotes H, $C_{1-4}$-alkyl, formyl, methylcarbonyl or ethylcarbonyl. The alkyl groups mentioned hereinbefore may be monosubstituted by Cl or mono- or polysubstituted by F.

Preferred meanings of the substituent $R^{15}$ are H, $C_{1-4}$-alkyl, $C_{3-7}$-cycloalkyl, $C_{3-7}$-cycloalkyl-$C_{1-3}$-alkyl, while, as defined hereinbefore, in each case one or more C atoms may additionally be mono- or polysubstituted by F and/or in each case one or two C atoms independently of one another may additionally be monosubstituted by Cl or Br. Particularly preferably $R^{15}$ denotes H, $CF_3$, methyl, ethyl, propyl or butyl.

The substituent $R^{16}$ preferably denotes H, $C_{1-4}$-alkyl, $C_{3-7}$-cycloalkyl, $C_{3-7}$-cycloalkyl-$C_{1-3}$-alkyl, ω-hydroxy-$C_{2-3}$-alkyl or ω-($C_{1-4}$-alkoxy)-$C_{2-3}$-alkyl, while, as hereinbefore defined, in each case one or more C atoms may additionally be mono- or polysubstituted by F and/or in each case one or two C atoms independently of one another may additionally be monosubstituted by Cl or Br. More preferably $R^{16}$ denotes H, $CF_3$, $C_{1-4}$-alkyl, $C_{3-6}$-cycloalkyl or $C_{3-6}$-cycloalkyl-$C_{1-3}$-alkyl; in particular H, methyl, ethyl, n-propyl and i-propyl.

Preferably the substituent $R^{17}$ has one of the meanings given for $R^{16}$ as being preferred or denotes $C_{1-4}$-alkylcarbonyl. Particularly preferably $R^{17}$ denotes H, $C_{1-3}$-alkyl or $C_{1-3}$-alkyl-carbonyl.

Preferably one or both of the substituents $R^{18}$ and $R^{19}$ independently of one another denotes hydrogen or $C_{1-4}$-alkyl, particularly hydrogen or methyl.

In general the substituent $R^{20}$ preferably denotes halogen, hydroxy, cyano, nitro, $C_{1-4}$-alkyl, $C_{1-4}$-alkoxy, hydroxy-$C_{1-4}$-alkyl, ($C_{1-3}$-alkyl)-carbonyl-, di-($C_{1-3}$-alkyl)amino, aminocarbonyl, ($C_{1-3}$-alkyl)carbonylamino, ($C_{1-3}$-alkyl)-sulfonylamino or $R^{22}$—$C_{1-3}$-alkyl, while, as hereinbefore defined, in each case one or more C atoms may additionally be mono- or polysubstituted by F and/or in each case one or two C atoms independently of one another may additionally be monosubstituted by Cl or Br.

The substituent $R^{22}$ preferably denotes $C_{1-4}$-alkoxy, $C_{1-4}$-alkylthio, carboxy, $C_{1-4}$-alkyl-carbonyl, $C_{1-4}$-alkoxycarbonyl, aminocarbonyl, $C_{1-4}$-alkylaminocarbonyl, di-($C_{1-4}$- alkyl)-aminocarbonyl, amino, $C_{1-4}$-alkylamino, di-($C_{1-4}$-alkyl)-amino, $C_{1-4}$-alkyl-carbonyl-amino, aminocarbonylamino or $C_{1-4}$-alkylaminocarbonyl-amino, while, as hereinbefore defined, in each case one or more C atoms may additionally be mono- or polysubstituted by F and/or in each case one or two C atoms independently of one another may additionally be monosubstituted by Cl or Br. Most particularly preferred meanings for $R^{22}$ are $C_{1-4}$-alkoxy, $C_{1-4}$-alkylcarbonyl, amino, $C_{1-4}$-alkylamino, di-($C_{1-4}$-alkyl)-amino, wherein one or more H atoms may be replaced by fluorine.

Preferred definitions of the group $R^{21}$ are $C_{1-4}$-alkyl, $C_{1-4}$-alkylcarbonyl, $C_{1-4}$-alkylsulphonyl, —$SO_2$—$NH_2$, —$SO_2$—NH—$C_{1-3}$-alkyl, —$SO_2$—N($C_{1-3}$-alkyl)$_2$ and cyclo-$C_{3-6}$-alkyleneimino-sulphonyl, while, as hereinbefore defined, in each case one or more C atoms may additionally be mono- or polysubstituted by F and/or in each case one or two C atoms independently of one another may additionally be monosubstituted by Cl or Br. Most particularly preferably $R^{21}$ denotes $C_{1-4}$-alkyl or $CF_3$.

Cy preferably denotes a $C_{3-7}$-cycloalkyl, particularly a $C_{3-6}$-cycloalkyl group, a $C_{5-7}$-cycloalkenyl group, pyrrolidinyl, piperidinyl, piperazinyl, morpholinyl, thiomorpholinyl, aryl or heteroaryl, and the above-mentioned cyclic groups may be mono- or polysubstituted at one or more C atoms by identical or different groups $R^{20}$, or in the case of a phenyl group may also additionally be monosubstituted by nitro, and/or one or more NH groups may be substituted by $R^{21}$. Most particularly preferred definitions of the group Cy are $C_{3-6}$-cycloalkyl, pyrrolidinyl and piperidin-yl, which may be substituted as specified.

The term aryl preferably denotes phenyl or naphthyl, particularly phenyl.

The term heteroaryl preferably comprises pyridyl, pyridazinyl, thiophenyl, thiazolyl or furyl.

Preferred compounds according to the invention are those wherein one or more of the groups, radicals, substituents and/or indices have one of the meanings given hereinbefore as being preferred.

Preferred compounds according to the invention may be described by a general formula IIa to IIf, in particular by the formula IId, IIe and IIf:

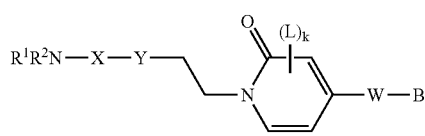

IIa

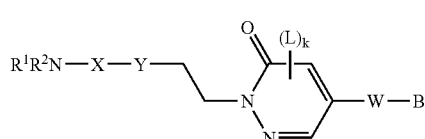

IIb

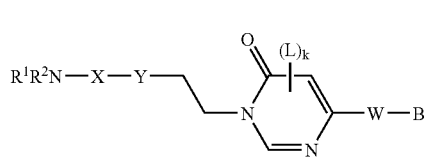

IIc

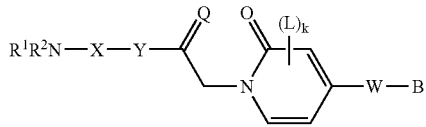

IId

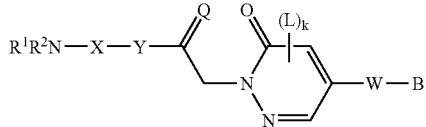

IIe

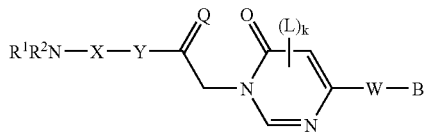

IIf wherein Q denotes O or $CH_2$; and wherein the —$CH_2$—$CH_2$— and —C(=O)—$CH_2$— bridge linked to the group Y and to the pyridinone, pyridazinone or pyrimidinone group may be mono- or polysubstituted with substituents independently from each other selected from $C_{1-3}$-alkyl; and wherein in the —$CH_2$—$CH_2$— bridge linked to the group Y and to the pyridinone, pyridazinone or pyrimidinone group the —C-atom linked to the group Y may be mono-substituted with hydroxy or fluorine; and wherein the groups k, L, $R^1$, $R^2$, X, Y, W and B are defined as hereinbefore and hereinafter; including the tautomers, the diastereomers, the enantiomers, the mixtures thereof and the salts thereof.

Preferred compounds according to the invention may be described by the following general formulae, even more preferably by the groups of formula selected from IIId to IIIL, IIIm to IIIo, IIIp to IIIx, IIIaa to IIIaf, IIIag to IIIaL, IIIba to IIIbc, IIIbd and IIIbf, IIIca to IIIcc, IIIcd and IIIcf:

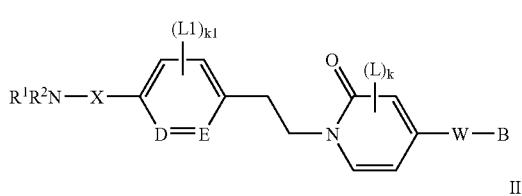

IIIa

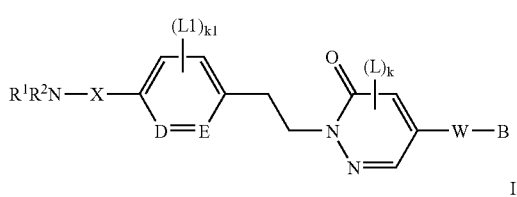

IIIb

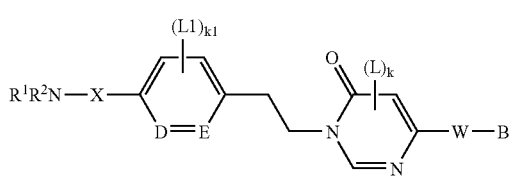

IIIc

-continued
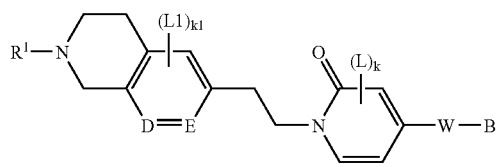
IIId
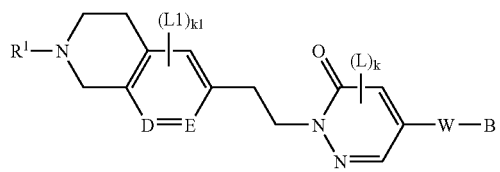
IIIe
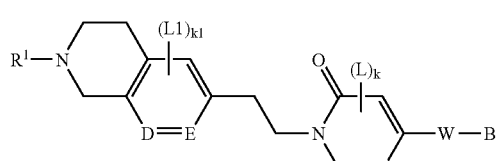
IIIf
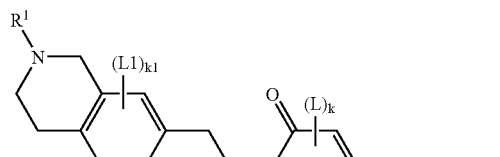
IIIg
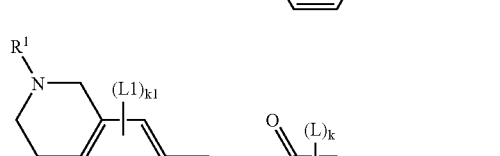
IIIh
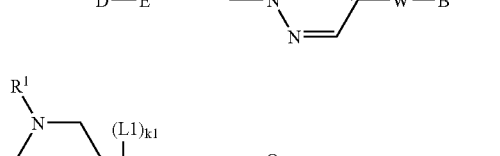
IIIi
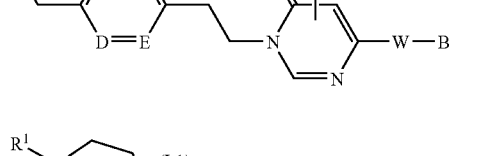
IIIj
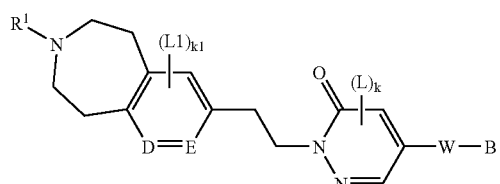
IIIk
-continued
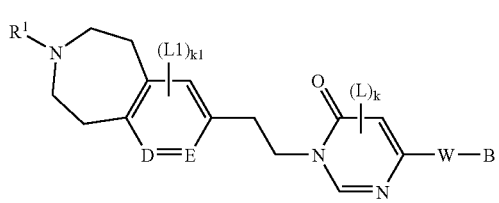
IIIL
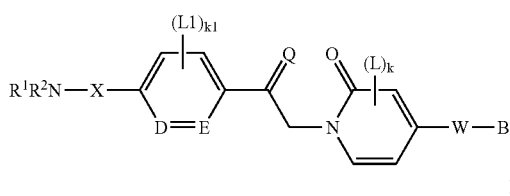
IIIm
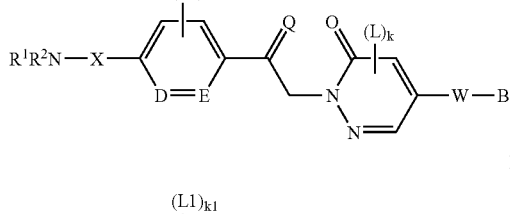
IIIn
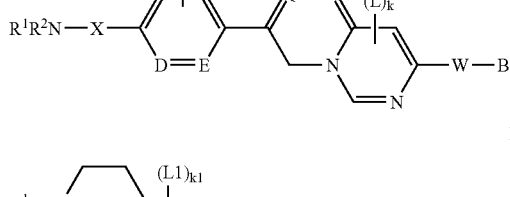
IIIo
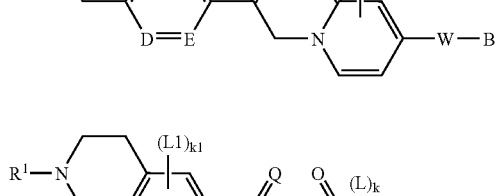
IIIp
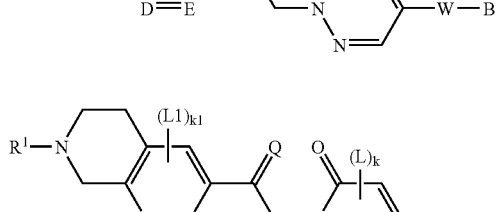
IIIq
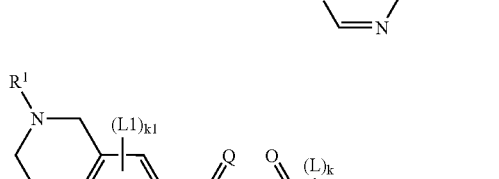
IIIr
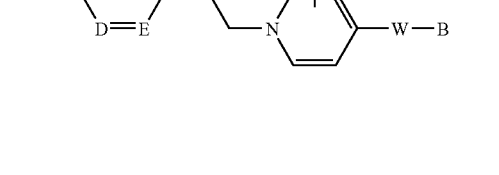
IIIs

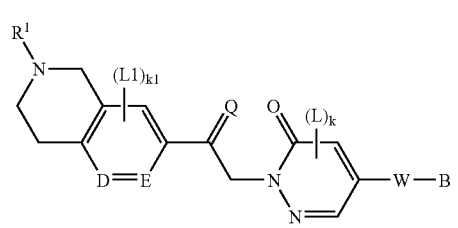 IIIt
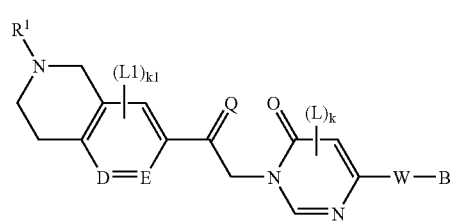 IIIu
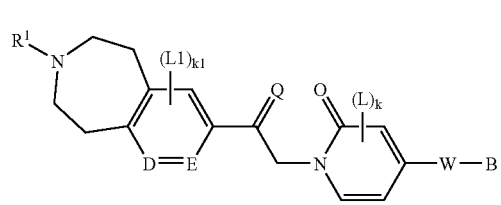 IIIv
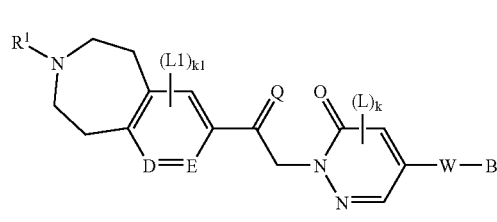 IIIw
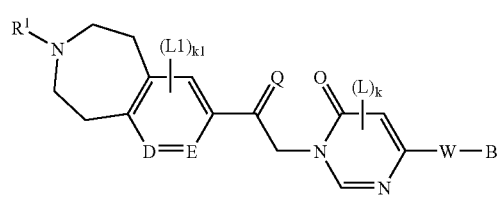 IIIx
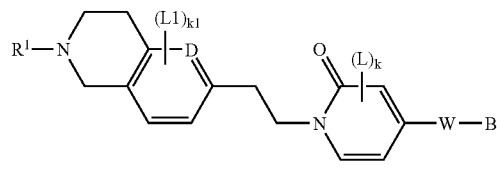 IIIaa
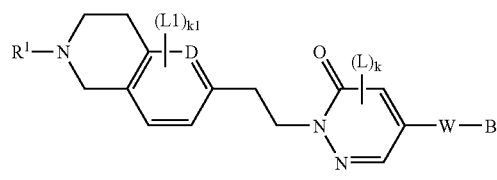 IIIab
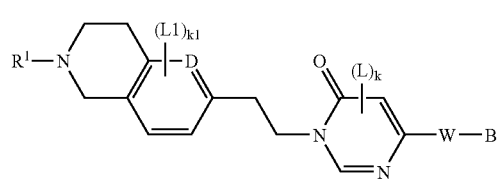 IIIac
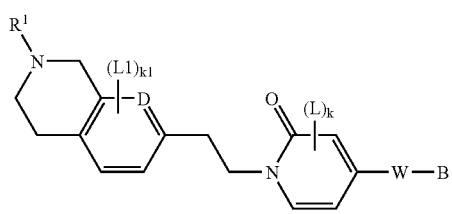 IIIad
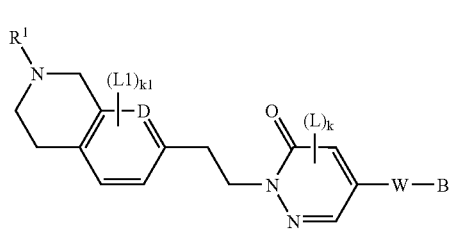 IIIae
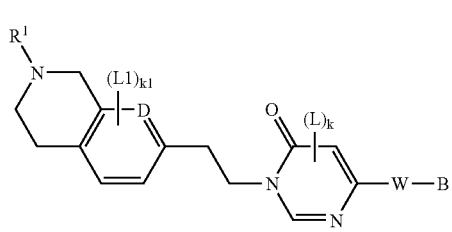 IIIaf
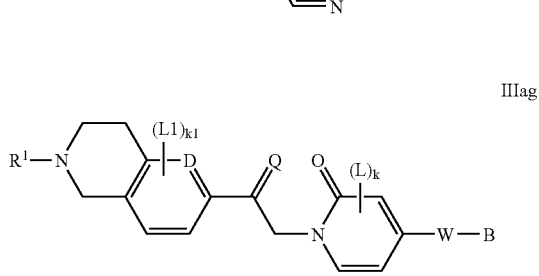 IIIag
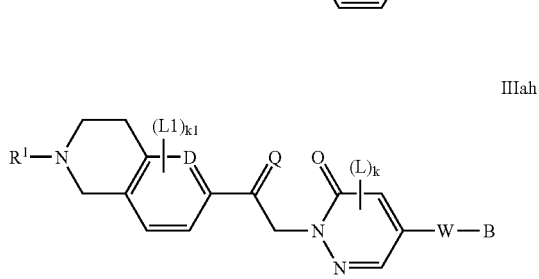 IIIah
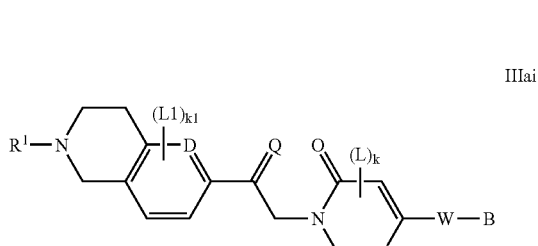 IIIai
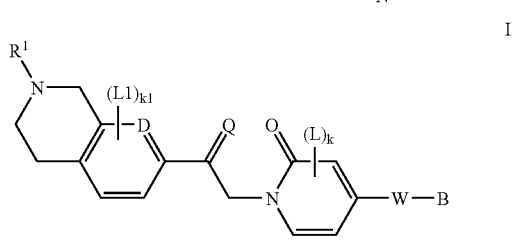 IIIaj wherein
D, E independently of each other denote CH or N, wherein CH may be substituted with L1; and L1 are independently of one another selected from the meanings of $R^{20}$ as defined hereinbefore, in particular of the meanings of $R^{20}$ as a substituent of the group Y as defined hereinbefore; and k1 denotes 0, 1 or 2; and Q denotes O or $CH_2$; and wherein the —$CH_2$—$CH_2$— and —C(=O)—$CH_2$— bridge linked to the group Y being

phenyl, pyridinyl or thiophenyl and to the pyridinone, pyridazinone or pyrimidinone group may be mono- or polysubstituted with substituents independently from each other selected from $C_{1-3}$-alkyl; and wherein in the —$CH_2$—$CH_2$— bridge linked to the group Y being

phenyl, pyridinyl or thiophenyl and to the pyridinone, pyridazinone or pyrimidinone group the —C-atom linked to the group Y may be mono-substituted with hydroxy or fluorine; and wherein the groups k, L, $R^1$, $R^2$, X, W and B are defined as hereinbefore and hereinafter; including the tautomers, the diastereomers, the enantiomers, the mixtures thereof and the salts thereof.

In the above formulae the group B preferably denotes phenyl, pyridyl, furyl or thiophenyl.

In the above formulae the group W preferably denotes —O—$CH_2$—.

Even more preferred compounds according to the invention may be described by a general formula IVa to IVf, in particular IVd, IVe and IVf:

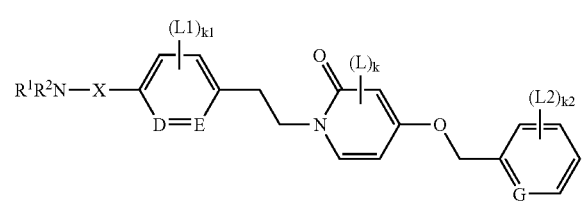

IVa

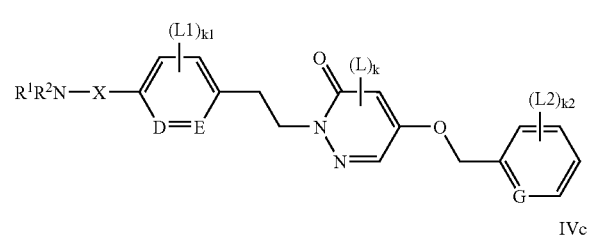

IVb

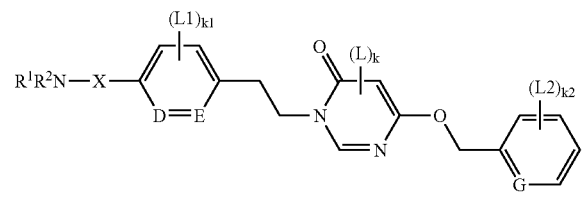

IVc

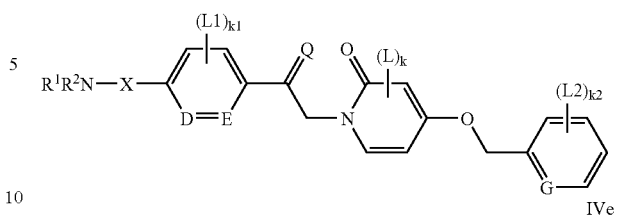

IVd

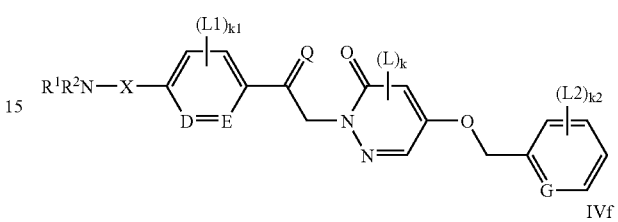

IVe

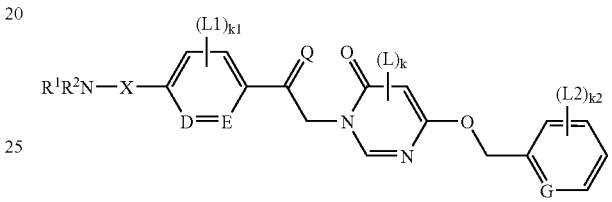

IVf wherein
Q denotes O or $CH_2$; and
D, E independently of each other denote CH or N, wherein CH may be substituted with L1; and
G denotes CH or N, wherein CH may be substituted with L2; and
L1 are independently of one another selected from the meanings of $R^{20}$ as defined hereinbefore, in particular of the meanings of $R^{20}$ as a substituent of the group Y as defined hereinbefore; and
k1 denotes 0, 1 or 2; and
L2 are independently of one another selected from the meanings of $R^{20}$ as defined hereinbefore, in particular of the meanings of $R^{20}$ as a substituent of the group B as defined hereinbefore; and
k2 denotes 0, 1 or 2; and
wherein the —$CH_2$—$CH_2$— and —C(=O)—$CH_2$— bridge linked to the group Y being

and to the pyridinone, pyridazinone or pyrimidinone group may be mono- or polysubstituted with substituents independently from each other selected from $C_{1-3}$-alkyl; and
wherein in the —$CH_2$—$CH_2$— bridge linked to the group Y being

and to the pyridinone, pyridazinone or pyrimidinone group the —C-atom linked to the group Y may be mono-substituted with hydroxy or fluorine; and wherein the groups k, L, $R^1$, $R^2$ and X are defined as hereinbefore and hereinafter; including the tautomers, the diastereomers, the enantiomers, the mixtures thereof and the salts thereof.
A group of most preferred compounds according to the invention may be described by the following general formulas:
Va
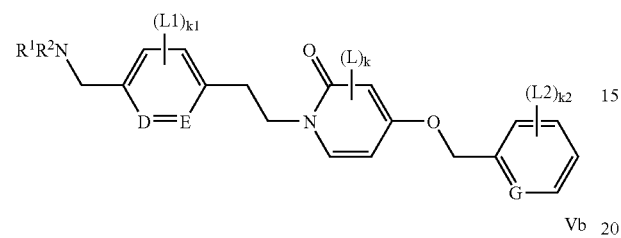
Vb
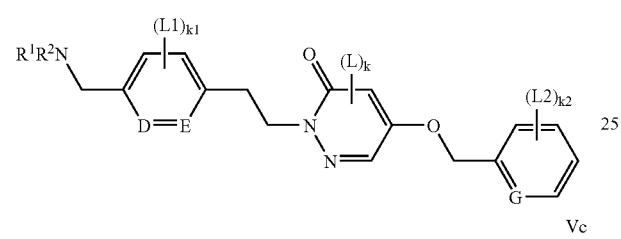
Vc
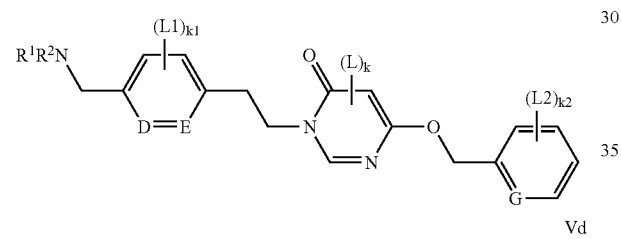
Vd
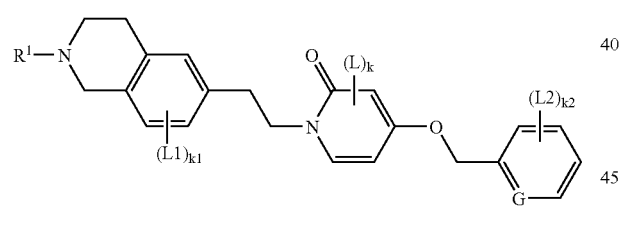
Ve
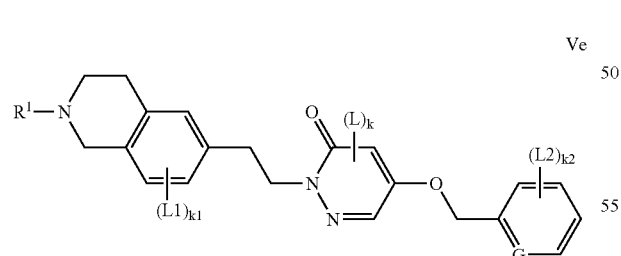
Vf

Vg
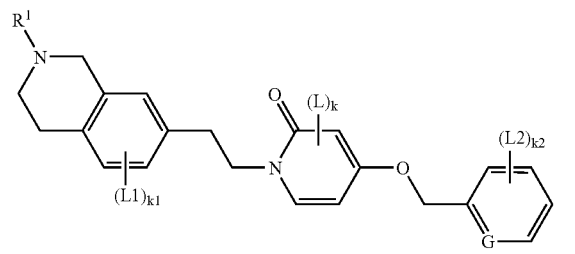
Vh
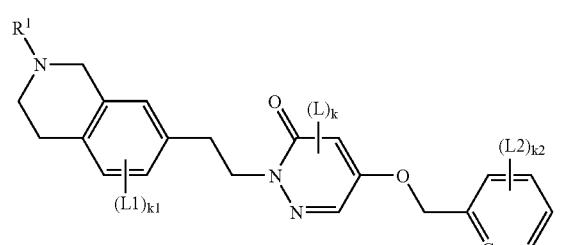
Vi
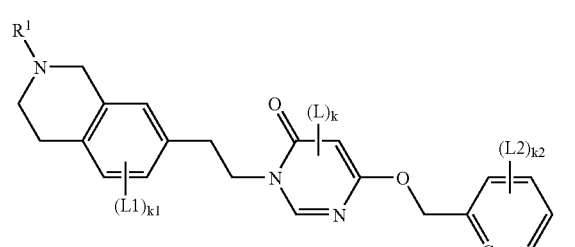
Vj
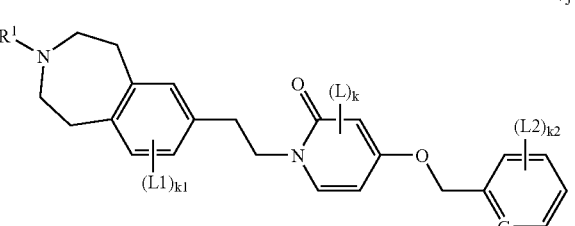
Vk
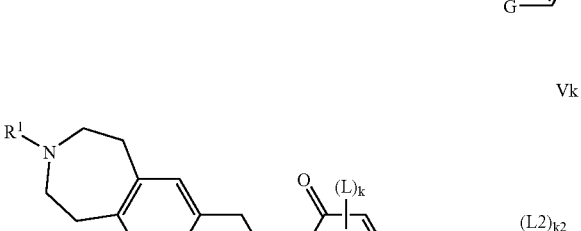
VL
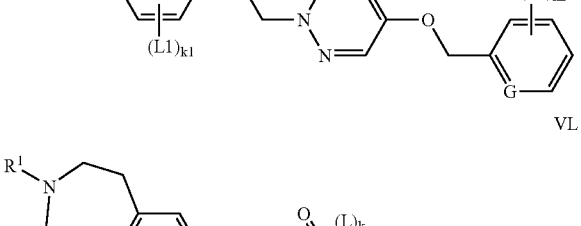

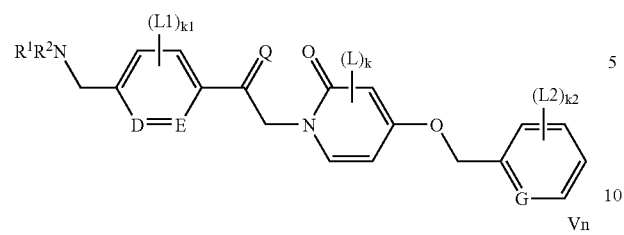 Vm
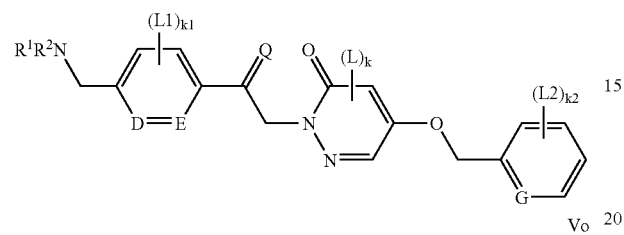 Vn
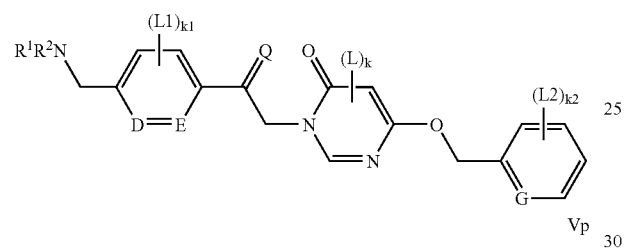 Vo
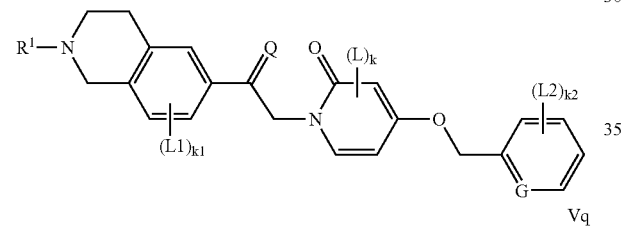 Vp
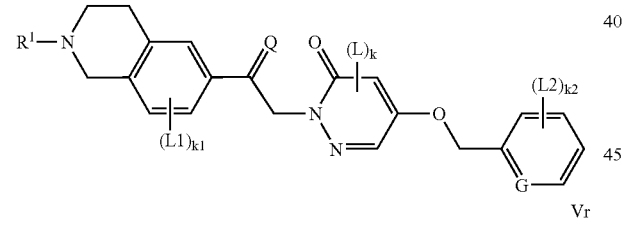 Vq
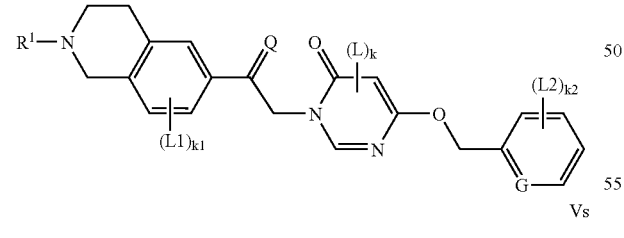 Vr
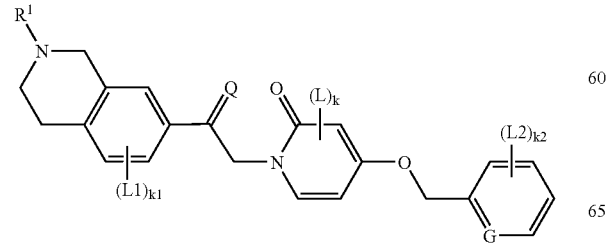 Vs
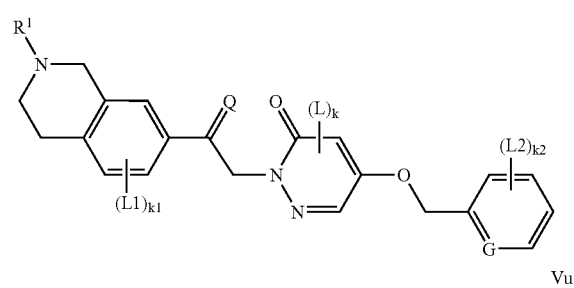 Vt
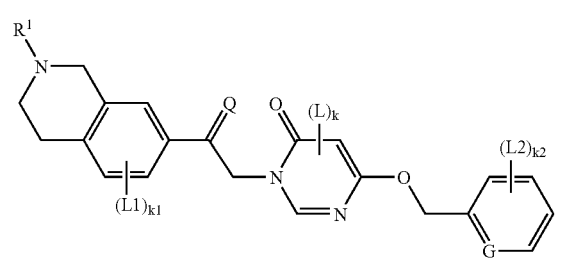 Vu
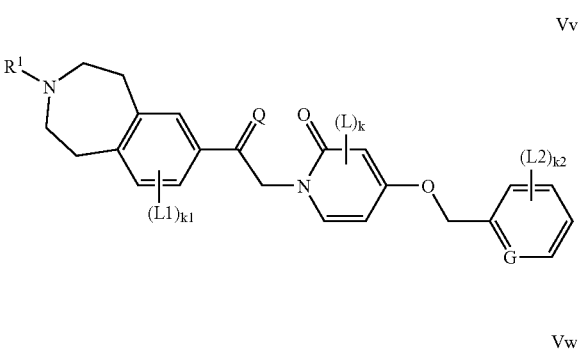 Vv
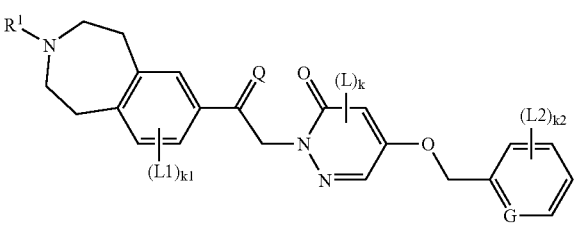 Vw
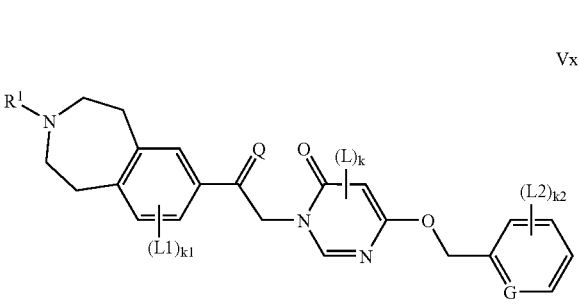 Vx
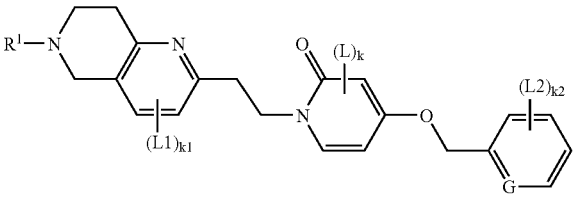 Vaa

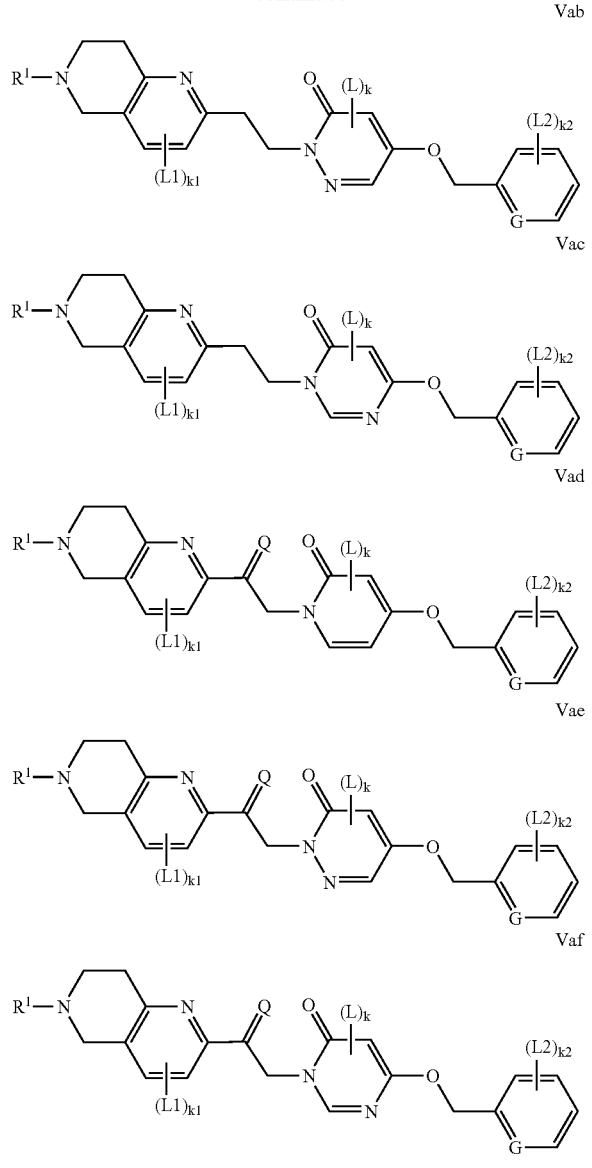

wherein

Q denotes O or CH₂; and

D, E independently of each other denote CH or N, wherein CH may be substituted with L1; and G denotes CH or N, wherein CH may be substituted with L2; and L1 are independently of one another selected from the meanings of $R^{20}$ as defined hereinbefore, in particular of the meanings of $R^{20}$ as a substituent of the group Y as defined hereinbefore; and k1 denotes 0, 1 or 2; and L2 are independently of one another selected from the meanings of $R^{20}$ as defined hereinbefore, in particular of the meanings of $R^{20}$ as a substituent of the group B as defined hereinbefore; and k2 denotes 0, 1 or 2; and wherein the —CH₂—CH₂— and —C(=O)—CH₂— bridge linked to the group Y being

or phenyl or pyridinyl and to the pyridinone, pyridazinone or pyrimidinone group may be mono- or polysubstituted with substituents independently from each other selected from $C_{1-3}$-alkyl; and wherein in the —CH₂—CH₂— bridge linked to the group Y being

or phenyl or pyridinyl and to the pyridinone, pyridazinone or pyrimidinone group the —C-atom linked to the group Y may be mono-substituted with hydroxy or fluorine; and wherein the groups k, L, $R^1$, $R^2$ are defined as hereinbefore and hereinafter; including the tautomers, the diastereomers, the enantiomers, the mixtures thereof and the salts thereof.

In the above formulae Va, Vb, Vc, Vm, Vn, Vo the group X being methylen may be mono- or di-substituted by methyl.

In particular in the formulae IIa to IIf, IIIa to IIIx, IIIaa to IIIaL, IIIba to IIIbf, IIIca to IIIcf, IVa to IVf and Va to Vx, Vaa to Vaf the following definitions are preferred:

$R^1$, $R^2$ independently of one another denote $C_{1-4}$-alkyl, hydroxy-$C_{1-4}$-alkyl, $C_{3-5}$-alkenyl, $C_{3-5}$-alkynyl, $C_{3-7}$-cycloalkyl, hydroxy-$C_{3-7}$-cycloalkyl, dihydroxy-$C_{3-6}$-alkyl, $C_{3-7}$-cycloalkyl$C_{1-3}$-alkyl, tetrahydropyran-3-yl, tetrahydropyran-4-yl, tetrahydrofuran-2-ylmethyl, tetrahydrofuran-3-ylmethyl, (hydroxy-$C_{3-7}$-cycloalkyl)-$C_{1-3}$-alkyl, $C_{1-4}$-alkoxy-$C_{2-3}$-alkyl, hydroxy-$C_{1-4}$-alkoxy-$C_{2-3}$-alkyl, $C_{1-4}$-alkoxy-$C_{1-4}$-alkoxy-$C_{2-3}$-alkyl, di-($C_{1-3}$-alkyl)amino$C_{2-3}$-alkyl, pyrrolidin-N-yl-$C_{2-3}$-alkyl, piperidin-N-yl-$C_{2-3}$-alkyl, pyridylmethyl, pyrazolylmethyl, thiazolylmethyl and imidazolylmethyl, while an alkyl, alkoxy, cycloalkyl or cycloalkyl-alkyl group may additionally be mono- or disubstituted by hydroxy and/or hydroxy-$C_{1-3}$-alkyl, and/or mono- or polysubstituted by F or $C_{1-3}$-alkyl and/or monosubstituted by CF₃, Br, Cl or CN; and one or both, preferably one of the groups $R^1$ and $R^2$ may also represent H; or $R^1$, $R^2$ are joined together and form together with the N atom to which they are bound a heterocyclic group which is selected from azetidine, pyrrolidine, piperidine, azepan, 2,5-dihydro-1H-pyrrole, 1,2,3,6-tetrahydro-pyridine, 2,3,4,7-tetrahydro-1H-azepine, 2,3,6,7-tetrahydro-1H-azepine, piperazine in which the free imine function is substituted by $R^{13}$ piperidin-4-one, morpholine, thiomorpholine, 4-$C_{1-4}$-alkoxy-iminopiperidin-1-yl and 4-hydroxyimino-piperidin-1-yl;

wherein one or more H atoms may be replaced by identical or different groups $R^{14}$ and the heterocyclic group defined hereinbefore may be substituted via a single bond by a carbo- or heterocyclic group Cy, while Cy is selected from the group comprising $C_{3-7}$-cycloalkyl, cyclo-$C_{3-6}$-alkyleneimino, imidazol, triazol, while Cy may be mono- or polysubstituted by identical or different groups $R^{20}$, where $R^{20}$ is as hereinbefore defined and is preferably selected from fluorine, CF₃, $C_{1-3}$-alkyl, hydroxy-$C_{1-3}$-alkyl and hydroxy, and $R^{14}$ is independently selected from F, Cl, Br, cyano, $C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$-alkyl, hydroxy, hydroxy-$C_{1-3}$-alkyl, $C_{1-4}$-alkoxy, ω-($C_{1-4}$-alkoxy)-$C_{1-3}$-alkyl, $C_{1-4}$-alkyl-carbonyl, formylamino, formyl-N($C_{1-4}$-alkyl)-amino, formylamino-$C_{1-3}$-alkyl, formyl-N($C_{1-4}$-alkyl)-amino-$C_{1-3}$-alkyl, $C_{1-4}$-alkyl-carbonylamino, $C_{1-4}$-alkyl-carbonyl-N—($C_{1-4}$-alkyl)amino, $C_{1-4}$-alkyl-carbonylamino-$C_{1-3}$-alkyl, $C_{1-4}$-alkyl-carbonyl-N—($C_{1-4}$-alkyl)-amino$C_{1-3}$-alkyl, $C_{1-4}$-alkoxy-carbonylamino, $C_{1-4}$-alkoxy-carbonylamino-$C_{1-3}$-alkyl, amino, $C_{1-4}$-alkyl-amino, $C_{3-7}$-cycloalkyl-amino, $C_{3-7}$-cycloalkyl-N—($C_{1-4}$-alkyl)-amino, di-($C_{1-4}$-alkyl)-amino, cyclo-$C_{3-6}$-alkyleneimino, amino-$C_{1-3}$-alkyl, $C_{1-4}$-alkyl-amino$C_{1-3}$-alkyl, $C_{3-7}$-cycloalkyl-amino-$C_{1-3}$-alkyl, $C_{3-7}$-cycloalkyl-N—($C_{1-4}$-alkyl)-amino $C_{1-3}$-alkyl, di-($C_{1-4}$-alkyl)-amino-$C_{1-3}$-alkyl, cyclo-$C_{3-6}$-alkyleneimino-$C_{1-3}$-alkyl, aminocarbonyl, $C_{1-4}$-alkyl-amino-carbonyl, $C_{3-7}$-cycloalkyl-amino-carbonyl, $C_{3-7}$-cycloalkyl-N—($C_{1-4}$-alkyl)-amino-carbonyl, di-($C_{1-4}$-alkyl)-amino-carbonyl, (aza-$C_{4-6}$-cycloalkyl)-carbonyl, aminocarbonyl-$C_{1-3}$-alkyl, $C_{1-4}$-alkyl-amino-carbonyl-$C_{1-3}$-alkyl, $C_{3-7}$-cycloalkyl-amino-carbonyl-$C_{1-3}$-alkyl, $C_{3-7}$-cycloalkyl-N—($C_{1-4}$-alkyl)-aminocarbonyl-$C_{1-3}$-alkyl, di-($C_{1-4}$-alkyl)-amino-carbonyl-$C_{1-3}$-alkyl, (aza-$C_{4-6}$-cycloalkyl)carbonyl-$C_{1-3}$-alkyl, $C_{1-4}$-alkyl-amino-carbonyl-amino-, di-($C_{1-4}$-alkyl)-amino-carbonyl-amino-;

while in the above-mentioned meanings in each case one or more C atoms may additionally be mono- or polysubstituted by F and/or in each case one or two C atoms independently of one another may additionally be monosubstituted by Cl or Br; and B denotes a group Cy, which is selected from the group consisting of phenyl, pyridyl, pyridazinyl, pyrazinyl, pyrimidinyl, pyrrolyl, pyrazolyl, imidazolyl, triazolyl, tetrazolyl, furyl, thiophenyl and thiazolyl; in particular selected from phenyl, pyridyl, furyl and thiophenyl, wherein the group B may be mono- or polysubstituted, preferably mono- or disubstituted by identical or different substituents $R^{20}$; and W denotes —CH$_2$—O—, —O—CH$_2$— and —NR$^N$—CH$_2$—; most preferably —O—CH$_2$—; and $R^{20}$ independently of one another denote halogen, hydroxy, nitro, $C_{1-3}$-alkyl, $C_{1-3}$-alkoxy, ($C_{1-3}$-alkyl)-carbonyl-, di-($C_{1-3}$-alkyl)amino, aminocarbonyl and ($C_{1-3}$-alkyl)carbonylamino, wherein in each case one or more C atoms may additionally be mono- or polysubstituted by F; and $R^N$ independently of each other denotes H, $C_{1-3}$-alkyl or formyl; more preferably H or methyl; and L fluorine, chlorine, bromine, methyl, ethyl and trifluoromethyl;

k is 0 or 1; and

L1 halogen, $C_{1-3}$-alkyl, $C_{1-3}$-alkoxy, hydroxy and CF$_3$; and k1 is 0 or 1; and L2 independently of each other halogen, hydroxy, nitro, $C_{1-3}$-alkyl, $C_{1-3}$-alkoxy, ($C_{1-3}$-alkyl)-carbonyl-, di-($C_{1-3}$-alkyl)amino, aminocarbonyl and ($C_{1-3}$-alkyl)-carbonylamino, wherein in each case one or more C atoms may additionally be mono- or polysubstituted by F; and k2 is 0, 1 or 2.

In addition a particularly preferred subset of compounds according to the invention is selected from one or more of the general formulas Vd to VL, Vm to Vx, Vaa to Vac and Vad to Vaf, in particular Vd, Vg, Vh, Vj, Vm, Vn, Vo, Vp, Vs, Vt, VU and VV as described above.

The compounds listed in the experimental section, including the tautomers, the diastereomers, the enantiomers, the mixtures thereof and the salts thereof, are preferred according to the invention.

Some expressions used hereinbefore and below to describe the compounds according to the invention will now be defined more fully.

The term halogen denotes an atom selected from among F, Cl, Br and I, particularly F, Cl and Br.

The term $C_{1-n}$-alkyl, where n has a value of 3 to 8, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{1-n}$-alkylene, where n may have a value of 1 to 8, denotes a saturated, branched or unbranched hydrocarbon bridge with 1 to n C atoms. Examples of such groups include methylene (—CH$_2$—), ethylene (—CH$_2$—CH$_2$—), 1-methyl-ethylene (—CH(CH$_3$)—CH$_2$—), 1,1-dimethylethylene (—C(CH$_3$)$_2$—CH$_2$—), n-prop-1,3-ylene (—CH$_2$—CH$_2$—CH$_2$—), 1-methylprop-1,3-ylene (—CH(CH$_3$)—CH$_2$—CH$_2$—), 2-methylprop-1,3-ylene (—CH$_2$—CH(CH$_3$)—CH$_2$—), etc., as well as the corresponding mirror-symmetrical forms.

The term $C_{2-n}$-alkenyl, where n has a value of 3 to 6, denotes a branched or unbranched hydrocarbon group with 2 to n C atoms and at least one C=C-double bond. Examples of such groups include vinyl, 1-propenyl, 2-propenyl, iso-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl etc.

The term $C_{2-n}$-alkynyl, where n has a value of 3 to 6, denotes a branched or unbranched hydrocarbon group with 2 to n C atoms and a C≡C triple bond. Examples of such groups include ethynyl, 1-propynyl, 2-propynyl, iso-propynyl, 1-butynyl, 2-butynyl, 3-butynyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, 4-hexynyl, 5-hexynyl etc.

The term $C_{1-n}$-alkoxy denotes a $C_{1-n}$-alkyl-O— group, wherein $C_{1-n}$-alkyl is defined as above. Examples of such groups include methoxy, ethoxy, n-propoxy, iso-propoxy, n-butoxy, isobutoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylthio denotes a $C_{1-n}$-alkyl-S— group, wherein $C_{1-n}$-alkyl is defined as above. Examples of such groups include methylthio, ethylthio, n-propylthio, iso-propylthio, n-butylthio, iso-butylthio, sec-butylthio, tert-butylthio, n-pentylthio, iso-pentylthio, neo-pentylthio, tertpentylthio, n-hexylthio, iso-hexylthio, etc.

The term $C_{1-n}$-alkylcarbonyl denotes a $C_{1-n}$-alkyl —C(=O)— group, wherein $C_{1-n}$-alkyl is defined as above. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, npentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic, preferably monocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3,2,1]octyl, spiro[4,5]decyl, norpinyl, norbonyl, norcaryl, adamantyl, etc.

The term $C_{5-n}$-cycloalkenyl denotes a monounsaturated mono-, bi-, tri- or spirocarbocyclic, preferably monocarboxylic group with 5 to n C atoms. Examples of such groups include cyclopentenyl, cyclohexenyl, cycloheptenyl, cyclooctenyl, cyclononenyl, etc.

The term $C_{3-n}$-cycloalkylcarbonyl denotes a $C_{3-n}$-cycloalkyl-C(=O) group, wherein $C_{3-n}$-cycloalkyl is as hereinbefore defined.

The term aryl denotes a carbocyclic, aromatic ring system, such as for example phenyl, biphenyl, naphthyl, anthracenyl, phenanthrenyl, fluorenyl, indenyl, pentalenyl, azulenyl, biphenylenyl, etc. A particularly preferred meaning of "aryl" is phenyl.

The term cyclo-$C_{3-6}$-alkyleneimino denotes a 4- to 7-membered ring which comprises 3 to 6 methylene units as well as an imino group, while the bond to the residue of the molecule is made via the imino group.

The term cyclo-$C_{3-6}$-alkyleneimino-carbonyl denotes a cyclo-$C_{3-6}$-alkyleneimino ring as hereinbefore defined which is linked to a carbonyl group via the imino group.

The term heteroaryl used in this application denotes a heterocyclic, aromatic ring system which comprises in addition to at least one C atom one or more heteroatoms selected from N, O and/or S. Examples of such groups are furanyl, thiophenyl, pyrrolyl, oxazolyl, thiazolyl, imidazolyl, isoxazolyl, isothiazolyl, 1,2,3-triazolyl, 1,3,5-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indazolyl, benzimidazolyl, benzthiazolyl, benzisothiazolyl, benzoxazolyl, benzisoxazolyl, purinyl, quinazolinyl, quinozilinyl, quinolinyl, isoquinolinyl, quinoxalinyl, naphthyridinyl, pteridinyl, carbazolyl, azepinyl, diazepinyl, acridinyl, etc. The term heteroaryl also comprises the partially hydrogenated heterocyclic, aromatic ring systems, particularly those listed above. Examples of such partially hydrogenated ring systems are 2,3-dihydrobenzofuranyl, pyrrolinyl, pyrazolinyl, indolinyl, oxazolidinyl, oxazolinyl, oxazepinyl, etc. Particularly preferably heteroaryl denotes a heteroaromatic mono- or bicyclic ring system.

Terms such as $C_{3-7}$-cycloalkyl-$C_{1-n}$-alkyl, heteroaryl-$C_{1-n}$-alkyl, etc. refer to $C_{1-n}$-alkyl, as defined above, which is substituted with a $C_{3-7}$-cycloalkyl, aryl or heteroaryl group.

Many of the terms given above may be used repeatedly in the definition of a formula or group and in each case have one of the meanings given above, independently of one another. Thus, for example, in the group di-$C_{1-4}$-alkyl-amino, the two alkyl groups may have the same or different meanings.

The term "unsaturated", for example in "unsaturated carbocyclic group" or "unsaturated heterocyclic group", as used particularly in the definition of the group Cy, comprises in addition to the mono- or polyunsaturated groups, the corresponding, totally unsaturated groups, but particularly the mono- and diunsaturated groups.

The term "optionally substituted" used in this application indicates that the group thus designated is either unsubstituted or mono- or polysubstituted by the substituents specified. If the group in question is polysubstituted, the substituents may be identical or different.

The style used hereinbefore and hereinafter, according to which in a cyclic group a bond of a substituent is shown towards the centre of this cyclic group, indicates unless otherwise stated that this substituent may be bound to any free position of the cyclic group carrying an H atom.

Thus in the example

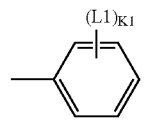

the substituent L1 where k1=1 may be bound to any of the free positions of the phenyl ring; where k1=2 selected substituents L1 may independently of one another be bound to different free positions of the phenyl ring.

The following signs

and →* are used interchangeably in subformulas to indicate the bond, or in the case of a spirocyclic group the atom, which is bonded to the rest of the molecule as defined.

The H atom of any carboxy group present or an H atom bound to an N atom (imino or amino group) may in each case be replaced by a group which can be cleaved in vivo. By a group which can be cleaved in vivo from an N atom is meant, for example, a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_eCO-O-(R_fCR_g)-O-CO-$ group wherein $R_e$ denotes a $C_{1-8}$-alkyl, $C_{5-7}$-cycloalkyl, phenyl or phenyl-$C_{1-3}$-alkyl group, $R_f$ denotes a hydrogen atom, a $C_{1-3}$-alkyl, $C_{5-7}$-cycloalkyl or phenyl group and $R_g$ denotes a hydrogen atom, a $C_{1-3}$-alkyl or $R_eCO-O-(R_fCR_h)-O$ group wherein $R_e$ and $R_f$ are as hereinbefore defined and $R_h$ is a hydrogen atom or a $C_{1-3}$-alkyl group, while the phthalimido group is an additional possibility for an amino group, and the above-mentioned ester groups may also be used as a group which can be converted in vivo into a carboxy group.

The residues and substituents described above may be mono- or polysubstituted by fluorine as described. Preferred fluorinated alkyl groups are fluoromethyl, difluoromethyl and trifluoromethyl. Preferred fluorinated alkoxy groups are fluoromethoxy, difluoromethoxy and trifluoromethoxy. Preferred fluorinated alkylsulphinyl and alkylsulphonyl groups are trifluoromethylsulphinyl and trifluoromethylsulphonyl.

The compounds of general formula I according to the invention may have acid groups, predominantly carboxyl groups, and/or basic groups such as e.g. amino functions. Compounds of general formula I may therefore be present as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali or alkaline earth metal hydroxides or carbonates, zinc or ammonium hydroxides or organic amines such as e.g. diethylamine, triethylamine, triethanolamine inter alia.

The compounds according to the invention may be obtained using methods of synthesis which are known to the one skilled in the art and described in the literature of organic synthesis. Preferably the compounds are obtained analogously to the methods of preparation explained more fully hereinafter, in particular as described in the experimental section.

romethanesulfonate, methanesulfonate and toluenesulfonate and the like. The reaction is preferably carried out in an inert organic solvent such as DMF, DMSO, acetonitrile, THF, methylene chloride or a mixture of solvents. The reaction usually takes place within 2 to 48 hours. Preferred reaction temperatures are between 0° C. and 150° C.

To obtain a compound of general formula (1-4) according to scheme 1, the alcohol function in compounds of the general formula (1-3) is transferred into a leaving group. Suitable leaving groups (LG) are preferably selected from bromide, chloride, iodide, trifluoroacetate, trifluoromethanesulfonate, methanesulfonate and toluenesulfonate and the like. The methods for preparing the mentioned leaving groups are known to the one skilled in the art and are described in the literature of organic synthesis.

To obtain a compound of general formula (1-5) according to scheme 1, a compound of general formula (1-4) is reacted with an amine $HNR^1R^2$. The amine $HNR^1R^2$ is used in excess (about 2 to 4 mol equivalents based on the compound 1-4). In case of valuable $HNR^1R^2$, a non nucleophilic organic base preferably triethylamine or diisopropyl-ethylamine can be Scheme 1:

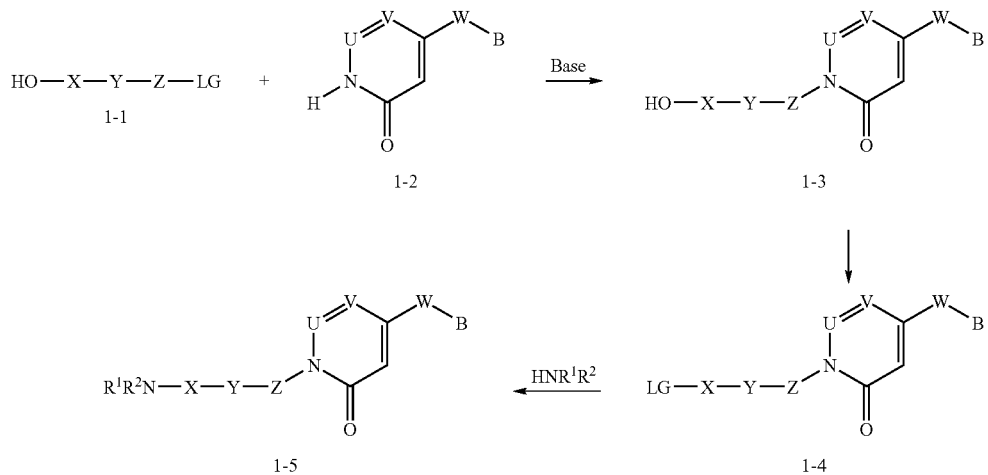

To obtain a compound of general formula (1-3) according to scheme 1, a compound of general formula (1-1) is reacted with a compound of general formula (1-2) in the presence of a base. Suitable bases are particularly inorganic bases such as carbonates, especially cesium carbonate and potassium carbonate. Suitable leaving groups (LG) are preferably selected from bromide, chloride, iodide, trifluoroacetate, trifluoadded, so that only 1.0 equivalent of $HNR^1R^2$ has to be used. The reactions are preferably carried out in an inert organic solvent like DMF, methylene chloride, acetonitrile or THF, or mixtures thereof. DMF is the preferred solvent. The reaction usually takes place within 2 to 48 hours. A preferred temperature range for this reaction is 20° C. to 150° C., preferably 20° C. to 80° C.

Scheme 2:

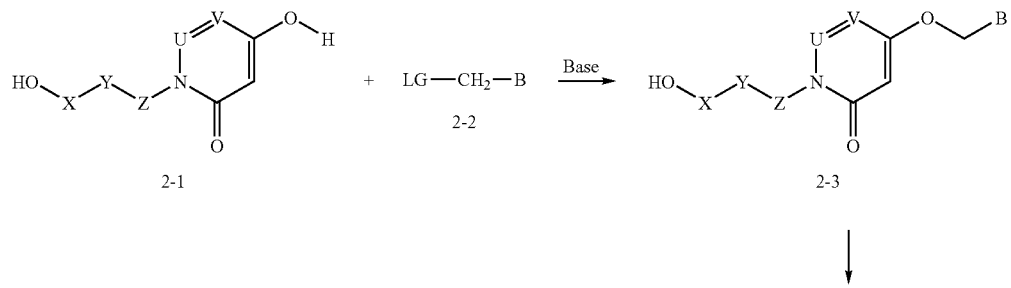

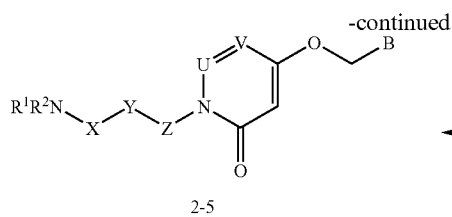 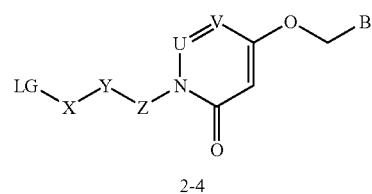

2-5 ← HNR¹R² ← 2-4

To obtain a compound of general formula (2-3) according to scheme 2, a compound of general formula (2-1) is reacted with a compound of general formula (2-2) in the presence of a base. Suitable bases are particularly inorganic bases such as carbonates, especially potassium carbonate. Suitable leaving groups (LG) are preferably selected from bromide, chloride, The reactions are preferably carried out in an inert organic solvent like DMF, methylene chloride, acetonitrile or THF, or mixtures thereof. DMF is the preferred solvent. The reaction usually takes place within 2 to 48 hours. A preferred temperature range for this reaction is 0° C. to 150° C., preferably 20° C. to 80° C.

Scheme 3:

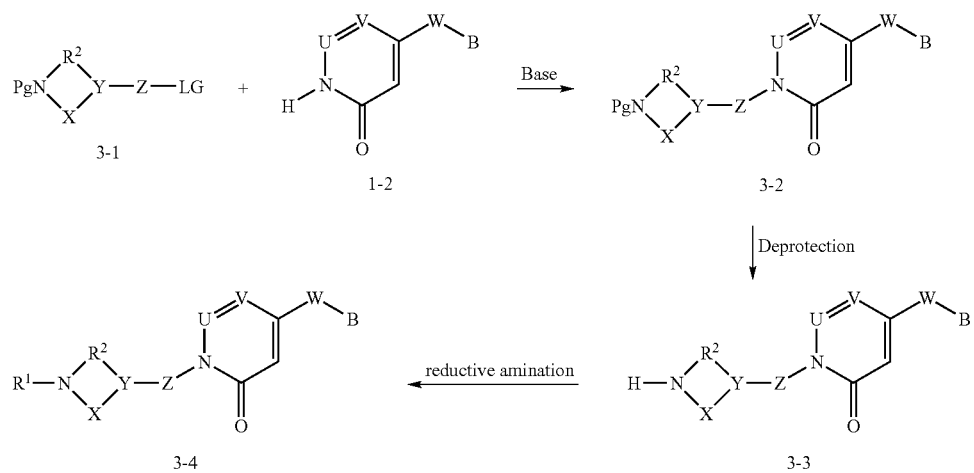

iodide, trifluoroacetate, trifluoromethanesulfonate, methanesulfonate and toluenesulfonate and the like. The reaction is preferably carried out in an inert organic solvent such as DMF, acetonitrile, THF, methylene chloride or a mixture of solvents. DMF is the preferred solvent. The reaction usually takes place within 2 to 48 hours. Preferred reaction temperatures are between −20° C. and 120° C., preferably 0° C. to 60° C.

To obtain a compound of general formula (2-4) according to scheme 2, the alcohol function in compounds of the general formula (2-3) is transferred into a leaving group. Suitable leaving groups (LG) are preferably selected from bromide, chloride, iodide, trifluoroacetate, trifluoromethanesulfonate, methanesulfonate and toluenesulfonate and the like. The methods for preparing the mentioned leaving groups are known to the one skilled in the art and are described in the literature of organic synthesis.

To obtain a compound of general formula (2-5) according to scheme 2, a compound of general formula (2-4) is reacted with an amine HNR¹R². The amine HNR¹R² is used in excess (about 2 to 4 mol equivalents based on the compound 2-4). In case of valuable HNR¹R² a non nucleophilic organic base preferably triethylamine or diisopropyl-ethylamine can be added, so that only 1.0 equivalent of HNR¹R² has to be used.

To obtain a compound of general formula (3-2) according to scheme 3, a compound of general formula (3-1) is reacted with a compound of general formula (1-2) in the presence of a base. Suitable bases are particularly inorganic bases such as carbonates, especially cesium carbonate and potassium carbonate. Suitable leaving groups (LG) are preferably selected from bromide, chloride, iodide, trifluoroacetate, trifluoromethanesulfonate, methanesulfonate and toluenesulfonate and the like. The reaction is preferably carried out in an inert organic solvent such as DMF, DMSO, acetonitrile, THF, methylene chloride or a mixture of solvents. The reaction usually takes place within 2 to 48 hours. Preferred reaction temperatures are between 0° C. and 150° C.

To obtain a compound of general formula (3-3) according to scheme 3, the protecting group (Pg) in compounds of the general formula (3-2) is removed. Suitable Pg are preferably selected from trifluoroacetate, tert-butyloxycarbonyl (BOC) and benzyl and the like. The methods for deprotection are known to the one skilled in the art and are described in the literature of organic synthesis.

To obtain a compound of general formula (3-4) according to scheme 3, a compound of general formula (3-3) is reacted with an aldehyde. The formed imine is reduced with either sodium triacetoxy-borohydride or sodium cyano-borohydride after acidification with acetic acid or pH 5 buffer. The reactions are preferably carried out in an inert organic solvent like THF. The reaction usually takes place within 2 to 24 hours. A preferred temperature range for this reaction is 20° C. to 50° C., preferably approximately 20° C.

Stereoisomeric compounds of formula (1) may chiefly be separated by conventional methods. The diastereomers are separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of formula (I) is reacted with one of the above-mentioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid and in this way the corresponding free compound is obtained in the (+) or (−) form.

The (R) or (S) enantiomer alone or a mixture of two optically active diastereomeric compounds of general formula (I) may also be obtained by performing the syntheses described above with a suitable reaction component in the (R) or (S) configuration.

As already mentioned, the compounds of formula (I) may be converted into the salts thereof, particularly for pharmaceutical use into the physiologically and pharmacologically acceptable salts thereof. These salts may be present on the one hand as physiologically and pharmacologically acceptable acid addition salts of the compounds of formula (I) with inorganic or organic acids. On the other hand, in the case of acidically bound hydrogen, the compound of formula (I) may also be converted by reaction with inorganic bases into physiologically and pharmacologically acceptable salts with alkali or alkaline earth metal cations as counter-ion. The acid addition salts may be prepared, for example, using hydrochloric acid, hydrobromic acid, sulphuric acid, phosphoric acid, methanesulphonic acid, ethanesulphonic acid, toluenesulphonic acid, benzenesulphonic acid, acetic acid, fumaric acid, succinic acid, lactic acid, citric acid, tartaric acid or maleic acid. Moreover, mixtures of the above mentioned acids may be used. To prepare the alkali and alkaline earth metal salts of the compound of formula (I) with acidically bound hydrogen the alkali and alkaline earth metal hydroxides and hydrides are preferably used, while the hydroxides and hydrides of the alkali metals, particularly of sodium and potassium, are preferred and sodium and potassium hydroxide are most preferred.

The compounds according to the present invention, including the physiologically acceptable salts, are effective as antagonists of the MCH receptor, particularly the MCH-1 receptor, and exhibit good affinity in MCH receptor binding studies. Pharmacological test systems for MCH antagonistic properties are described in the following experimental section.

As antagonists of the MCH receptor the compounds according to the invention are advantageously suitable as pharmaceutical active substances for the prevention and/or treatment of symptoms and/or diseases caused by MCH or causally connected with MCH in some other way. Generally the compounds according to the invention have low toxicity, they are well absorbed by oral route and have good intracerebral transitivity, particularly brain accessibility.

Therefore, MCH antagonists which contain at least one compound according to the invention are particularly suitable in mammals, such as for example rats, mice, guinea pigs, hares, dogs, cats, sheep, horses, pigs, cattle, monkeys and humans, for the treatment and/or prevention of symptoms and/or diseases which are caused by MCH or are otherwise causally connected with MCH.

Diseases caused by MCH or otherwise causally connected with MCH are particularly metabolic disorders, such as for example obesity, and eating disorders, such as for example bulimia, including bulimia nervosa. The indication obesity includes in particular exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity, This range of indications also includes cachexia, anorexia and hyperphagia.

Compounds according to the invention may be particularly suitable for reducing hunger, curbing appetite, controlling eating behaviour and/or inducing a feeling of satiation.

In addition, the diseases caused by MCH or otherwise causally connected with MCH also include hyperlipidaemia, cellulitis, fatty accumulation, malignant mastocytosis, systemic mastocytosis, emotional disorders, affectivity disorders, depression, anxiety states, reproductive disorders, sexual disorders, memory disorders, epilepsy, forms of dementia and hormonal disorders.

Compounds according to the invention are also suitable as active substances for the prevention and/or treatment of other illnesses and/or disorders, particularly those which accompany obesity, such as for example diabetes, diabetes mellitus, particularly type II diabetes, hyperglycaemia, particularly chronic hyperglycaemia, complications of diabetes including diabetic retinopathy, diabetic neuropathy, diabetic nephropathy, etc., insulin resistance, pathological glucose tolerance, encephalorrhagia, cardiac insufficiency, cardiovascular diseases, particularly arteriosclerosis and high blood pressure, arthritis and gonitis.

MCH antagonists and formulations according to the invention may advantageously be used in combination with a dietary therapy, such as for example a dietary diabetes treatment, and exercise.

Another range of indications for which the compounds according to the invention are advantageously suitable is the prevention and/or treatment of micturition disorders, such as for example urinary incontinence, hyperactive bladder, urgency, nycturia, enuresis, while the hyperactive bladder and urgency may or may not be connected with benign prostatic hyperplasia.

Generally speaking, the compounds according to the invention are potentially suitable for preventing and/or treating dependencies, such as for example alcohol and/or nicotine dependency, and/or withdrawal symptoms, such as for example weight gain in smokers coming off nicotine. By "dependency" is generally meant here an irresistible urge to take an addictive substance and/or to perform certain actions, particularly in order to either achieve a feeling of wellbeing or to eliminate negative emotions. In particular, the term "dependency" is used here to denote a dependency on an addictive substance. By "withdrawal symptoms" are meant here, in general, symptoms which occur or may occur when addictive substances are withdrawn from patients dependent on one or more such substances. The compounds according to the invention are potentially suitable particularly as active substances for reducing or ending tobacco consumption, for the treatment or prevention of a nicotine dependency and/or for the treatment or prevention of nicotine withdrawal symptoms, for reducing the craving for tobacco and/or nicotine and generally as an anti-smoking agent. The compounds according to the invention may also be useful for preventing or at least reducing the weight gain typically seen when smokers are coming off nicotine. The substances may also be suitable as active substances which prevent or at least reduce the craving for and/or relapse into a dependency on addictive substances. The term addictive substances refers particularly but not exclusively to substances with a psycho-motor activity, such as narcotics or drugs, particularly alcohol, nicotine, cocaine, amphetamine, opiates, benzodiazepines and barbiturates.

The dosage required to achieve such an effect is conveniently, by intravenous or subcutaneous route, 0.001 to 30 mg/kg of body weight, preferably 0.01 to 5 mg/kg of body weight, and by oral or nasal route or by inhalation, 0.01 to 50 mg/kg of body weight, preferably 0.1 to 30 mg/kg of body weight, in each case 1 to 3× daily.

For this purpose, the compounds prepared according to the invention may be formulated, optionally in conjunction with other active substances as described hereinafter, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, lozenges, powders, granules, solutions, emulsions, syrups, aerosols for inhalation, ointments or suppositories.

In addition to pharmaceutical compositions the invention also includes compositions containing at least one compound according to the invention and/or a salt according to the invention optionally together with one or more physiologically acceptable excipients. Such compositions may also be for example foodstuffs which may be solid or liquid, in which the compound according to the invention is incorporated.

For the above mentioned combinations it is possible to use as additional active substances particularly those which for example potentiate the therapeutic effect of an MCH antagonist according to the invention in terms of one of the indications mentioned above and/or which make it possible to reduce the dosage of an MCH antagonist according to the invention. Preferably one or more additional active substances are selected from among active substances for the treatment of diabetes,
active substances for the treatment of diabetic complications,
active substances for the treatment of obesity, preferably other than MCH antagonists,
active substances for the treatment of high blood pressure,
active substances for the treatment of hyperlipidaemia, including arteriosclerosis,
active substances for the treatment of dyslipidaemia, including arteriosclerosis,
active substances for the treatment of arthritis,
active substances for the treatment of anxiety states,
active substances for the treatment of depression.

The above mentioned categories of active substances will now be explained in more detail by means of examples.

Examples of active substances for the treatment of diabetes are insulin sensitisers, insulin secretion accelerators, biguanides, insulins, α-glucosidase inhibitors, β3 adreno-receptor agonists.

Insulin sensitisers include glitazones, particularly pioglitazone and its salts (preferably hydrochloride), troglitazone, rosiglitazone and its salts (preferably maleate), JTT-501, GI-262570, MCC-555, YM-440, DRF-2593, BM-13-1258, KRP-297, R-119702 and GW-1929.

Insulin secretion accelerators include sulphonylureas, such as for example tolbutamide, chloropropamide, tolazamide, acetohexamide, glyclopyramide and its ammonium salts, glibenclamide, gliclazide, glimepiride. Further examples of insulin secretion accelerators are repaglinide, nateglinide, mitiglinide (KAD-1229) and JTT-608.

Biguanides include metformin, buformin and phenformin.

Insulins include those obtained from animals, particularly cattle or pigs, semisynthetic human insulins which are synthesised enzymatically from insulin obtained from animals, human insulin obtained by genetic engineering, e.g. from Escherichi coli or yeasts. Moreover, the term insulin also includes insulin-zinc (containing 0.45 to 0.9 percent by weight of zinc) and protamine-insulin-zinc obtainable from zinc chloride, protamine sulphate and insulin. Insulin may also be obtained from insulin fragments or derivatives (for example INS-1, etc.).

Insulin may also include different kinds, e.g. with regard to the onset time and duration of effect ("ultra immediate action type", "immediate action type", "two phase type", "intermediate type", "prolonged action type", etc.), which are selected depending on the pathological condition of the patient.

α-Glucosidase inhibitors include acarbose, voglibose, miglitol, emiglitate.

$\beta_3$ Adreno receptor agonists include AJ-9677, BMS-196085, SB-226552, AZ40140.

Active substances for the treatment of diabetes other than those mentioned above include ergoset, pramlintide, leptin, BAY-27-9955 as well as glycogen phosphorylase inhibitors, sorbitol dehydrogenase inhibitors, protein tyrosine phosphatase 1B inhibitors, dipeptidyl protease inhibitors, glipazide, glyburide.

Active substances for the treatment of diabetes or diabetic complications furthermore include for example aldose reductase inhibitors, glycation inhibitors and protein kinase C inhibitors, DPPIV blockers, GLP-1 or GLP-2 analogues and SGLT-2 inhibitors.

Aldose reductase inhibitors are for example tolrestat, epalrestat, imirestat, zenarestat, SNK-860, zopolrestat, ARI-50i, AS-3201.

An example of a glycation inhibitor is pimagedine.

Protein Kinase C inhibitors are for example NGF, LY-333531.

DPPIV blockers are for example LAF237 (Novartis), MK431 (Merck) as well as 815541, 823093 and 825964 (all GlaxoSmithkline).

GLP-1 analogues are for example Liraglutide (NN2211) (NovoNordisk), CJC1131 (Conjuchem), Exenatide (Amylin).

SGLT-2 inhibitors are for example AVE-2268 (Aventis) and T-1095 (Tanabe, Johnson&Johnson).

Active substances other than those mentioned above for the treatment of diabetic complications include alprostadil, thiapride hydrochloride, cilostazol, mexiletine hydrochloride, ethyl eicosapentate, memantine, pimagedine (ALT-711).

Active substances for the treatment of obesity, preferably other than MCH antagonists, include lipase inhibitors and anorectics.

A preferred example of a lipase inhibitor is orlistat.

Examples of preferred anorectics are phentermine, mazindol, dexfenfluramine, fluoxetine, sibutramine, baiamine, (S)-sibutramine, SR-141716, NGD-95-1.

Active substances other than those mentioned above for the treatment of obesity include lipstatin.

Moreover, for the purposes of this application, the active substance group of anti-obesity active substances also includes the anorectics, of which the $\beta_3$ agonists, thyromimetic active substances and NPY antagonists should be emphasised. The range of substances which may be considered as preferred anti-obesity or anorectic active substances is indicated by the following additional list, by way of example: phenylpropanolamine, ephedrine, pseudoephedrine, phentermine, a cholecystokinin-A (hereinafter referred to as CCK-A) agonist, a monoamine reuptake inhibitor (such as for example sibutramine), a sympathomimetic active substance, a serotonergic active substance (such as for example dexfenfluramine, fenfluramine, a 5-HT2C agonist such as BVT.933 or APD356, or duloxetine), a dopamine antagonist (such as for example bromocriptine or pramipexol), a melanocyte-stimulating hormone receptor agonist or mimetic, an analogue of melanocyte-stimulating hormone, a cannabinoid receptor antagonist (Rimonabant, ACOMPLIA™), an MCH antagonist, the OB protein (hereinafter referred to as leptin), a leptin analogue, a fatty acid synthase (FAS) antagonist, a leptin receptor agonist, a galanine antagonist, a GI lipase inhibitor or reducer (such as for example orlistat). Other anorectics include bombesin agonists, dehydroepiandrosterone or its analogues, glucocorticoid receptor agonists and antagonists, orexin receptor antagonists, urocortin binding protein antagonists, agonists of the Glucagon-like Peptide-1 receptor, such as for example exendin, AC 2993, CJC-1131, ZP10 or GRT0203Y, DPPIV inhibitors and ciliary neurotrophic factors, such as for example axokines. In this context mention should also be made of the forms of therapy which produce weight loss by increasing the fatty acid oxidation in the peripheral tissue, such as for example inhibitors of acetyl-CoA carboxylase.

Active substances for the treatment of high blood pressure include inhibitors of angiotensin converting enzyme, calcium antagonists, potassium channel openers and angiotensin II antagonists.

Inhibitors of angiotensin converting enzyme include captopril, enalapril, alacepril, delapril (hydrochloride), lisinopril, imidapril, benazepril, cilazapril, temocapril, trandolapril, manidipine (hydrochloride).

Examples of calcium antagonists are nifedipine, amlodipine, efonidipine, nicardipine.

Potassium channel openers include levcromakalim, L-27152, AL0671, NIP-121.

Angiotensin II antagonists include telmisartan, losartan, candesartan cilexetil, valsartan, irbesartan, CS-866, E4177.

Active substances for the treatment of hyperlipidaemia, including arteriosclerosis, include HMG-CoA reductase inhibitors, fibrate compounds.

HMG-CoA reductase inhibitors include pravastatin, simvastatin, lovastatin, atorvastatin, fluvastatin, lipantil, itavastatin, ZD-4522 and their salts.

Fibrate compounds include fenofibrate, bezafibrate, clinofibrate, clofibrate and simfibrate.

Active substances for the treatment of dyslipidaemia, including arteriosclerosis, include e.g. medicaments which raise the HDL level, such as e.g. nicotinic acid and derivatives and preparations thereof, such as e.g. niaspan, as well as agonists of the nicotinic acid receptor.

Active substances for the treatment of arthritis include NSAIDs (non-steroidal antiinflammatory drugs), particularly COX2 inhibitors, such as for example meloxicam or ibuprofen.

Active substances for the treatment of anxiety states include chlordiazepoxide, diazepam, oxozolam, medazepam, cloxazolam, bromazepam, lorazepam, alprazolam, fludiazepam.

Active substances for the treatment of depression include fluoxetine, fluvoxamine, imipramine, paroxetine, sertraline.

The dosage for these active substances is conveniently ⅕ of the lowest normal recommended dose up to ¼ of the normal recommended dose.

In another embodiment the invention also relates to the use of at least one compound according to the invention and/or a salt according to the invention for influencing the eating behaviour of a mammal. This use is particularly based on the fact that compounds according to the invention may be suitable for reducing hunger, curbing appetite, controlling eating behaviour and/or inducing a feeling of satiety. The eating behaviour is advantageously influenced so as to reduce food intake. Therefore, the compounds according to the invention are advantageously used for reducing body weight. Another use according to the invention is the prevention of increases in body weight, for example in people who had previously taken steps to lose weight and are interested in maintaining their lower body weight. A further use may be the prevention of weight gain in a co-medication with a substance generally causing weight gain (such a glitazones). According to this embodiment it is preferably a non-therapeutic use. Such a non-therapeutic use might be a cosmetic use, for example to alter the external appearance, or an application to improve general health. The compounds according to the invention are preferably used non-therapeutically for mammals, particularly humans, not suffering from any diagnosed eating disorders, no diagnosed obesity, bulimia, diabetes and/or no diagnosed micturition disorders, particularly urinary incontinence. Preferably, the compounds according to the invention are suitable for non-therapeutic use in people whose BMI (body mass index), defined as their body weight in kilograms divided by their height (in metres) squared, is below a level of 30, particularly below 25.

Other features and advantages of the present invention will become apparent from the following more detailed examples which illustrate, by way of example, the principles of the invention.

Preliminary Remarks:

As a rule, $^1$H-NMR and/or mass spectra have been obtained for the compounds prepared. The $R_f$ values are determined using ready-made silica gel 60 TLC plates $F_{254}$ (E. Merck, Darmstadt, Item no. 1.05714) without chamber saturation or using ready-made aluminium oxide 60 $F_{254}$ TLC plates (E. Merck, Darmstadt, Item no. 1.05713) without chamber saturation. The ratios given for the eluents relate to units by volume of the solvent in question. The units by volume for NH₃ relate to a concentrated solution of NH₃ in water. Silica gel made by Millipore (MATREX™, 35-70 my) is used for chromatographic purification. Alox (E. Merck, Darmstadt, aluminium oxide 90 standardised, 63-200 μm, Item no. 1.01097.9050) is used for chromatographic purification. Purity data given for compounds are based on ¹H-NMR.

The HPLC data given are measured under the following parameters:

mobile phase A: water:formic acid 99.9:0.1
mobile phase B: acetonitrile:formic acid 99.9:0.1
mobile phase C: water:NH₄OH 99.9:0.1
mobile phase D: acetonitrile NH₄OH 99.9:0.1

| gradient: time in min | % A | % B | flow rate in ml/min |
|---|---|---|---|
| method A: analytical column: Zorbax column (Agilent Technologies), SB (Zorbax stable bond) - C18; 3.5 μm; 4.6 mm × 75 mm; column temperature: RT ||||
| 0.00 | 95.0 | 5.0 | 1.60 |
| 4.50 | 10.0 | 90.0 | 1.60 |
| 5.00 | 10.0 | 90.0 | 1.60 |
| 5.50 | 95.0 | 5.00 | 1.60 |
| method B: analytical column: Zorbax column (Agilent Technologies), Bonus-RP - C14; 3.5 μm; 4.6 mm × 75 mm; column temperature: RT ||||
| 0.00 | 95.0 | 5.0 | 1.60 |
| 4.00 | 50.0 | 50.0 | 1.60 |
| 4.50 | 10.00 | 90.00 | 1.60 |
| 5.00 | 10.00 | 90.00 | 1.60 |
| 5.50 | 95.0 | 5.0 | 1.60 |
| method C: analytical column: Waters Symmetry - C18; 3.5 μm; 4.6 mm × 75 mm; column temperature: RT ||||
| 0.00 | 95.0 | 5.0 | 1.60 |
| 4.00 | 50.0 | 50.0 | 1.60 |
| 4.50 | 10.00 | 90.00 | 1.60 |
| 5.00 | 10.00 | 90.00 | 1.60 |
| 5.50 | 95.0 | 5.0 | 1.60 |
| method D: analytical column: Waters SunFire - C18; 3.5 μm; 4.6 mm × 75 mm; column temperature: RT ||||
| 0.00 | 95.0 | 5.0 | 1.60 |
| 4.00 | 50.0 | 50.0 | 1.60 |
| 4.50 | 10.0 | 90.0 | 1.60 |
| 5.00 | 10.0 | 90.0 | 1.60 |
| 5.50 | 95.0 | 5.0 | 1.60 |
| method E: analytical column: Zorbax column (Agilent Technologies), SB (Zorbax stable bond) - C18; 3.5 μm; 4.6 mm × 75 mm; column temperature: RT ||||
| 0.00 | 95.0 | 5.0 | 1.60 |
| 2.00 | 10.0 | 90.0 | 1.60 |
| 5.00 | 10.0 | 90.0 | 1.60 |
| 5.50 | 95.0 | 5.0 | 1.60 |
| method F: analytical column: Zorbax column (Agilent Technologies), SB (Zorbax stable bond) - C18; 3.5 μm; 4.6 mm × 75 mm; column temperature: RT ||||
| 0.00 | 95.0 | 5.0 | 1.60 |
| 4.00 | 50.0 | 50.0 | 1.60 |
| 4.50 | 10.0 | 90.0 | 1.60 |
| 5.00 | 10.0 | 90.0 | 1.60 |
| 5.50 | 95.0 | 5.0 | 1.60 |
| method G: analytical column: Waters SunFire - C18; 3.5 μm; 4.6 mm × 75 mm; column temperature: RT ||||
| 0.00 | 95.0 | 5.0 | 1.60 |
| 4.50 | 10.0 | 90.0 | 1.60 |
| 5.00 | 10.0 | 90.0 | 1.60 |
| 5.50 | 95.0 | 5.00 | 1.60 |
| method H: analytical column: Waters Symmetry - C18; 3.5 μm; 4.6 mm × 75 mm; column temperature: RT ||||
| 0.00 | 95.0 | 5.0 | 1.60 |
| 4.50 | 10.0 | 90.0 | 1.60 |
| 5.00 | 10.0 | 90.0 | 1.60 |
| 5.50 | 95.0 | 5.00 | 1.60 |
| method I: analytical column: Waters XBridge - C18; 3.5 μm; 4.6 mm × 75 mm; column temperature: RT ||||

| gradient: time in min | % C | % D | flow rate in ml/min |
|---|---|---|---|
| 0.00 | 95.0 | 5.0 | 1.60 |
| 4.50 | 10.0 | 90.0 | 1.60 |
| 5.00 | 10.0 | 90.0 | 1.60 |
| 5.50 | 95.0 | 5.00 | 1.60 |
| method J: analytical column: Zorbax column (Agilent Technologies), SB (Zorbax stable bond) - C18; 1.8 μm; 3.0 mm × 30 mm; column temperature: RT ||||

| gradient: time in min | % A | % B | flow rate in ml/min |
|---|---|---|---|
| 0.00 | 95.0 | 5.0 | 1.60 |
| 0.10 | 95.0 | 5.00 | 1.60 |
| 1.75 | 5.0 | 95.0 | 1.60 |
| 1.90 | 5.0 | 95.0 | 1.60 |
| 1.95 | 95.0 | 5.0 | 1.60 |
| 2.00 | 95.0 | 5.0 | 1.60 |
| method K: analytical column: Waters XBridge - C18; 2.5 μm; 3.0 mm × 30 mm; column temperature: RT ||||

| gradient: time in min | % C | % D | flow rate in ml/min |
|---|---|---|---|
| 0.00 | 95.0 | 5.0 | 1.40 |
| 1.80 | 10.0 | 90.0 | 1.40 |
| 2.00 | 10.0 | 90.0 | 1.40 |
| 2.20 | 95.0 | 5.00 | 1.40 |
| method L: analytical column: Zorbax column (Agilent Technologies), SB (Zorbax stable bond) - C18; 1.8 μm; 3.0 mm × 30 mm; column temperature: RT ||||

| gradient: time in min | % A | % B | flow rate in ml/min |
|---|---|---|---|
| 0.00 | 95.0 | 5.0 | 1.60 |
| 1.00 | 10.0 | 90.0 | 1.60 |
| 2.50 | 10.0 | 90.0 | 1.60 |
| 2.75 | 95.0 | 5.0 | 1.60 |
| method M: analytical column: Waters XBridge - C18; 2.5 μm; 3.0 mm × 30 mm; column temperature: RT ||||

| gradient: time in min | % C | % D | flow rate in ml/min |
|---|---|---|---|
| 0.00 | 95.0 | 5.0 | 1.40 |
| 0.80 | 10.0 | 90.0 | 1.40 |
| 2.00 | 10.0 | 90.0 | 1.40 |
| 2.20 | 95.0 | 5.00 | 1.40 |

The following abbreviations for the eluent mixtures are used hereinafter when giving the $R_f$ values:
(A): silica gel, DCM/MeOH/ammonia (9:1:0.1)
(B): silica gel, DCM/MeOH/ammonia (9.5:0.5:0.05)
(C): silica gel, PE/EtOAc (8:2)
(D) silica gel, DCM/MeOH (9:1)
(E) silica gel, PE/EtOAc (1:1)
(F): silica gel, Cyclohexane/EtOAc (8:2)
(G): silica gel, EtOAc/MeOH/ammonia (8:2:0.2)
(H): silica gel, Chloroform/MeOH/ammonia (9:1:0.1)

(I): silica gel, PE/EtOAc (6:4)
(J): silica gel, Cyclohexane/EtOAc (6:4)

The following abbreviations are used above and hereinafter:
BOC tert-Butylcarbonate
cal. Calculated
CDI 1,1'-Carbonyl-di-imidazole
DCM Dichloromethane
DMAP Dimethyl-pyridin-4-yl-amine
DMF N,N-Dimethylformamide
DMSO Dimethylsulfoxide
EII Electron impact ionisation
ESI Electron spray ionisation
EtOAc Ethyl acetate
h Hour
HCl Hydrochloric acid
HPLC High pressure liquid chromatography
KHSO$_4$ Potassium hydrogen sulfate
MeOH MeOH
min Minutes
Na$_2$CO$_3$ Sodium carbonate
NaHCO$_3$ Sodiumhydrogencarbonate
NH$_4$OH Ammonium hydroxide
PE Petrolether
RT Ambient temperature (approx. 20° C.)
THF Tetrahydrofuran Preparation of Starting Material Preparation 1

[4-(2-iodo-ethyl)-phenyl]-methanol

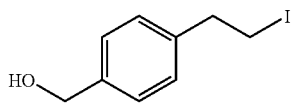

1a [4-(2-Chloro-ethyl)-phenyl]-methanol

To 100 g (525 mmol) 4-(2-chloro-ethyl)-benzoic acid in 1.0 L of THF is added 170 g (1050 mmol) CDI in small portions. The mixture is stirred at 60° C. until the gas evolution ceased. After cooling to RT, the mixture is slowly added into a solution of 39.7 g (1050 mmol) sodium borohydride in ice water and is stirred for 3 h at RT. The solution is acidified with diluted HCL and extracted twice with EtOAc. The organic phase is separated and dried over MgSO$_4$. After evaporation of the solvent, the residue is dissolved in water/EtOAc. The aqueous phase is separated, washed once with EtOAc and the combined organic phase is dried over MgSO$_4$. After evaporation of the solvent the residue is purified by silica gel column chromatography with PE/EtOAc (7:3) as eluent.

Yield: 65.6 g (73% of theory)
ESI Mass spectrum: (M+H)$^+$-H$_2$0=153/155
R$_f$-value: 0.6 (silica gel, mixture A).

1b [4-(2-Iodo-ethyl)-phenyl]-methanol

To 60.0 g (352 mmol) [4-(2-chloro-ethyl)-phenyl]-MeOH (preparation 1a) in 280 mL of acetone is added 105 g (703 mmol) sodium iodide. The reaction mixture is refluxed overnight and cooled to RT. After filtration, the residue is elutriated in DCM, filtered and dried.

Yield: 79.0 g (86% of theory)
Retention time HPLC: 3.9 min (method C).

Preparation 2

4-Hydroxy-1-[2-(4-hydroxymethyl-phenyl)-ethyl]-1H-pyridin-2-one

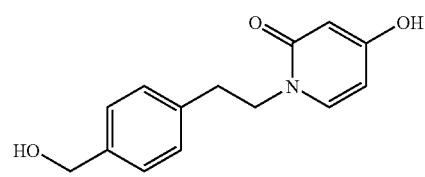

2a 4-Benzyloxy-1-[2-(4-hydroxymethyl-phenyl)-ethyl]-1H-pyridin-2-one

A mixture of 13.0 g (64.6 mmol) 4-benzyloxy-1H-pyridin-2-one, 23.7 g (90.4 mmol) [4-(2-iodoethyl)-phenyl]-methanol (preparation 1b) and 63.1 g (194 mmol) cesium carbonate in 55 mL of DMF is stirred overnight at RT. The reaction mixture is heated to 70° C., filtered through a pad of celite which is washed with hot DMF. The solvent is removed almost completely. After cooling to RT, MeOH is added, the precipitate is filtered, washed with EtOAc and water and is dried in vacuo at 40° C. (fraction A). MeOH is removed in vacuo, the residue is redissolved in DMF and purified by reverse HPLC (Zorbax stable bond, C18; water (0.1% formic acid)/acetonitrile 95:5 to 10:90) to give fraction B, which is combined with fraction A.

Yield: 10.0 g (46% of theory)
ESI Mass spectrum: [M+H]$^+$=336
Retention time HPLC: 3.5 min (method A).

2b 4-Hydroxy-1-[2-(4-hydroxymethyl-phenyl)-ethyl]-1H-pyridin-2-one

To 10.0 g (29.8 mmol) 4-benzyloxy-1-[2-(4-hydroxymethyl-phenyl)-ethyl]-1H-pyridin-2-one (preparation 2a) in 150 mL MeOH is added 1.50 g Rh/C. The reaction mixture is stirred under a hydrogen atmosphere of 3000 hPa at RT for 20 h. 300 mL MeOH is added and the mixture is heated to reflux. The catalyst is removed by filtration and the solvent is removed almost completely. After cooling to RT, the precipitate is collected and dried in vacuo at 40° C.

Yield: 5.70 g (78% of theory)
ESI Mass spectrum: [M+H]$^+$=246
Retention time HPLC: 2.3 min (method A).

Preparation 3

4-Hydroxy-1-[2-(4-pyrrolidin-1-ylmethyl-phenyl)-ethyl]-1H-pyridin-2-one

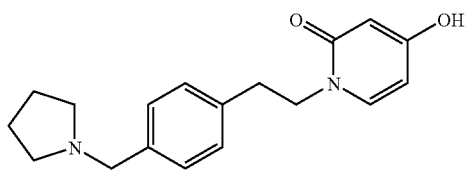

To 1.20 g (3.09 mmol) 4-benzyloxy-1-[2-(4-pyrrolidin-1-ylmethyl-phenyl)-ethyl]-1H-pyridin-2-one (example 1.4) in 80 mL MeOH is added 400 mg Rh/C. The reaction mixture is stirred under a hydrogen atmosphere of 3500 hPa at RT for 11 h. The catalyst is removed by filtration and the solvent is evaporated. The residue is purified by reverse HPLC chromatography (Zorbax stable bond, C18; water (0.1% formic acid)/acetonitrile 95:5 to 10:90).

Yield: 600 mg (65% of theory)
ESI Mass spectrum: $[M+H]^+=299$
Retention time HPLC: 1.9 min (method A).

Preparation 4

1-[2-(4-Bromomethyl-phenyl)-ethyl]-4-hydroxy-1H-pyridin-2-one

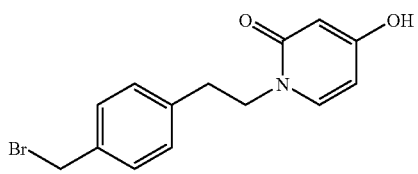

To 2.45 g (10.0 mmol) 4-hydroxy-1-[2-(4-hydroxymethyl-phenyl)-ethyl]-1H-pyridin-2-one (preparation 2.b) in 25 mL DCM is added 470 µL (5.00 mmol) phosphorus tribromide at 0° C. The mixture is stirred overnight at RT and then poured into ice water. The precipitate is collected, washed with DCM and dried.

Yield: 2.10 g (68% of theory)
ESI Mass spectrum: $[M+H]^+=308/310$
$R_f$-value: 0.5 (silica gel, mixture D).

Preparation 5

5-Benzyloxy-2H-pyridazin-3-one

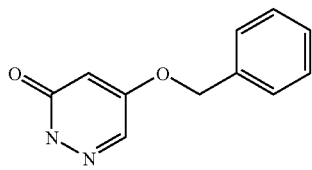

5a 5-Hydroxy-2-(tetrahydro-pyran-2-yl)-2H-pyridazin-3-one

To 14.3 g (62.0 mmol) 4-chloro-5-hydroxy-2-(tetrahydro-pyran-2-yl)-2H-pyridazin-3-one in 200 mL MeOH and 8.71 mL (62.0 mmol) triethylamine is added 5.00 g 10% Pd/C. The reaction mixture is stirred under a hydrogen atmosphere of 1700 hPa at RT for 16 h. The catalyst is removed by filtration and the solvent is evaporated. 200 mL water is added to the residue, the precipitate is collected, washed with water and dried (fraction A, 7.80 g). The aqueous phase is concentrated and the residue is directly added to a reverse HPLC for purification (Waters xbridge; water (0.15% NH$_4$OH)/acetonitril 95:5 to 10:90) to afford fraction B (4.2 g) which is combined with fraction A.

Yield: 12.0 g (99% of theory)
ESI Mass spectrum: $[M-H]^-=195$
Retention time HPLC: 2.4 min (method A).

5b 5-Benzyloxy-2-(tetrahydro-pyran-2-yl)-2H-pyridazin-3-one

To 500 mg (2.55 mmol) 5-hydroxy-2-(tetrahydro-pyran-2-yl)-2H-pyridazin-3-one (preparation 5a) in THF is added at 0° C. subsequently 315 mg (2.80 mmol) potassium-tert-butylate, 47 mg (0.13 mmol) tetra-butylammonium-iodide and 0.45 mL (3.82 mmol) benzylbromide. The reaction mixture is stirred overnight at RT and is diluted with EtOAc and 1M aqueous sodium hydroxide solution. The organic phase is separated, washed with water and dried over MgSO$_4$. After filtration, the solvent is evaporated and the residue is elutriated in tert-butylmethylether. The precipitate is collected and dried.

Yield: 500 mg (69% of theory)
ESI Mass spectrum: $[M+H]^+=287$
Retention time HPLC: 4.0 min (method A).

5c 5-Benzyloxy-2H-pyridazin-3-one

To 500 mg (1.75 mmol) 5-benzyloxy-2-(tetrahydro-pyran-2-yl)-2H-pyridazin-3-one (preparation 5b) in 10 mL MeOH is added 8.73 mL (8.73 mmol) 1M aqueous HCl solution and the reaction mixture is stirred overnight at RT and 10 h at reflux. MeOH is evaporated, to the residual aqueous phase is added saturated aqueous NaHCO$_3$-solution until the solution is basic. The aqueous phase is extracted with EtOAc, the combined organic phase is washed with water, dried over MgSO$_4$, filtered and evaporated to afford the product.

Yield: 200 mg (57% of theory)
ESI Mass spectrum: $[M+H]^+=203$
Retention time HPLC: 3.2 min (method G).

Preparation 6

2,2,2-Trifluoro-1-[7-(2-iodo-ethyl)-1,2,4,5-tetrahydro-3-benzazepin-3-yl]-ethanone

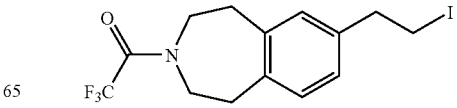

6a 1-[7-(2-Chloro-ethyl)-1,2,4,5-tetrahydro-3-benzazepin-3-yl]-2,2,2-trifluoro-ethanone To 800 mg (2.50 mmol) 1-[7-(2-chloro-acetyl)-1,2,4,5-tetrahydro-3-benzazepin-3-yl]-2,2,2-trifluoro-ethanone in 4.5 mL trifluoro-acetic acid is added at RT 1.59 mL (10.0 mmol) triethyl-silane. The reaction mixture is stirred 2 h at 60° C. and is added into 100 mL water. The aqueous phase is extracted twice with EtOAc, the combined organic phase is washed with water and dried over MgSO$_4$. After filtration and evaporation of the solvent, the residue is purified via chromatography (silica gel; PE:EtOAc 8:2).

Yield: 900 mg (85% purity (contains triethyl-silane), 100% of theory)
ESI Mass spectrum: [M+H]$^+$=306/308
Retention time HPLC: 4.8 min (method A).

6b 2,2,2-Trifluoro-1-[7-(2-iodo-ethyl)-1,2,4,5-tetrahydro-3-benzazepin-3-yl]-ethanone To 800 mg (2.62 mmol) 1-[7-(2-chloro-ethyl)-1,2,4,5-tetrahydro-3-benzazepin-3-yl]-2,2,2-trifluoro-ethanone (preparation 6a) in 40 mL acetone is added 471 mg (3.14 mmol) sodium iodide. The reaction mixture is refluxed overnight, excess sodium iodide is added and the reaction mixture is refluxed additional three days. The solvent is evaporated, the residue is diluted with EtOAc and washed twice with water. The organic phase is dried over MgSO$_4$, filtered and the solvent is evaporated. The residue is purified via reverse HPLC chromatography (Zorbax stable bond; C18; water (0.1% formic acid)/acetonitrile (0.1% formic acid) 95:5 to 10:90).

Yield: 300 mg (29% of theory)
ESI Mass spectrum: [M+H]$^+$=398
Retention time HPLC: 5.1 min (method A).

Preparation 7

7-[2-(Toluene-4-sulfonyloxy)-ethyl]-3,4-dihydro-1H-isoquinoline-2-carboxylic Acid Tert-Butyl Ester

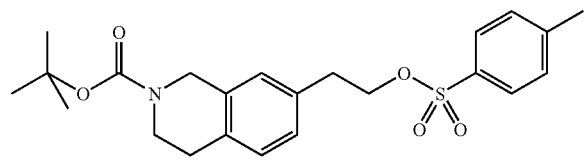

7a 7-Bromo-3,4-dihydro-1H-isoquinoline-2-carboxylic Acid Tert-Butyl Ester

To 10.0 g (40.2 mmol) 7-bromo-1,2,3,4-tetrahydro-isoquinoline hydrochloride in 250 mL DCM and 50 mL (101 mmol) 2M aqueous Na$_2$CO$_3$-solution is added a solution of 9.27 g (42.5 mmol) BOC-anhydride in DCM. The reaction is stirred 1 h at RT and is diluted with 100 mL water. The organic phase is washed with water, dried over MgSO$_4$, filtered and the solvent is evaporated. To the residue is added PE and the mixture is cooled to −30° C. The precipitate is collected, washed with cold PE and dried.

Yield: 10.3 g (82% of theory)
ESI Mass spectrum: [M+H]$^+$=312/314
R$_f$-value: 0.5 (silica gel, mixture C).

7b 7-Iodo-3,4-dihydro-1H-isoquinoline-2-carboxylic Acid Tert-Butyl Ester

To 11.0 g (35.2 mmol) 7-bromo-3,4-dihydro-1H-isoquinoline-2-carboxylic acid tert-butyl ester (preparation 7a) in 35 mL 1,4-1,4-dioxanee is added 692 mg (3.56 mmol) copper (I)-iodide under argon. After flushing with argon, 0.75 mL (7.05 mmol) N,N-dimethylethylen-diamine and 10.6 g (70.5 mmol) sodium-iodide is added at RT. The reaction mixture is stirred 14 h at 110° C., cooled to RT and diluted with 5% aqueous ammonia-solution. The aqueous phase is extracted with EtOAc and the combined organic phase is washed with water, dried over MgSO$_4$. After filtration and evaporation of the solvent, the residue is purified via chromatography (silica gel; Cyclohexane/EtOAc 85/15).

Yield: 10.8 g (purity 75% (contains compound 7a), 78% of theory)
ESI Mass spectrum: [M+H]$^+$=360
R$_f$-value: 0.6 (silica gel, mixture F).

7c 7-(2-Hydroxy-ethyl)-3,4-dihydro-1H-isoquinoline-2-carboxylic Acid Tert-Butyl Ester To 1.80 g (5.00 mmol) 7-iodo-3,4-dihydro-1H-isoquinoline-2-carboxylic acid tert-butyl ester (preparation 7b) in 5.0 mL THF at −20° C. is added 6.34 g (5.50 mmol) of a THF-solution of 14% isopropylmagnesium-chloride*lithiumchloride under argon. The mixture is warmed to 0° C. and stirred 1 h at 0° C. The reaction mixture is cooled to −60° C. and 0.88 g (20.0 mmol) oxirane in 2.0 mL THF is added. The cooling bath is removed and the reaction is warmed to RT. The reaction mixture is poured into 50 mL aqueous ammonium chloride solution and the aqueous phase is extracted with EtOAc. The combined organic phase is washed with water, dried over MgSO$_4$. After filtration and evaporation of the solvent, the residue is purified via reverse HPLC chromatography (Zorbax stable bond, C18; water (0.15% formic acid)/acetonitrile 95:5 to 5:95).

Yield: 800 mg (58% of theory)
ESI Mass spectrum: [M+H]$^+$=278
Retention time HPLC: 2.6 min (method E).

7d 7-[2-(Toluene-4-sulfonyloxy)-ethyl]-3,4-dihydro-1H-isoquinoline-2-carboxylic acid tert-butyl Ester To 800 mg (2.88 mmol) 7-(2-hydroxy-ethyl)-3,4-dihydro-1H-isoquinoline-2-carboxylic acid tert-butyl ester (preparation 7c) in 10 mL DCM is added at 0° C. subsequently 0.34 mL (4.33 mmol) pyridine and 605 mg (3.17 mmol) 4-methyl-benzenesulfonyl chloride in 5.0 mL DCM. The reaction mixture is warmed to RT and is stirred 5 h at RT. Additional 0.34 mL (4.33 mmol) pyridine and 605 mg (3.17 mmol) 4-methyl-benzenesulfonyl chloride in 5.0 mL DCM are added and the mixture is stirred over night. The reaction mixture is poured into ice-water and the organic phase is separated, washed with aqueous KHSO$_4$-solution and aqueous NaHCO$_3$-solution, dried over MgSO$_4$. After evaporation of the solvent, the residue is purified via chromatography (silica gel; cyclohexane/EtOAc 8:2 to 1:1).

Yield: 1.10 g (88% of theory)
ESI Mass spectrum: [M+H]$^+$=432
R$_f$-value: 0.4 (silica gel, method F).

Preparation 8

7-(2-Iodo-ethyl)-3,4-dihydro-1H-isoquinoline-2-carboxylic Acid Tert-Butyl Ester

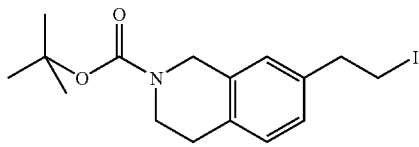

To 1.21 g (4.76 mmol) iodine in 50 mL toluene is added 1.59 g (4.76 mmol) polymer bound triphenyl-phosphane. The mixture is stirred 5 min at RT and then 0.80 mL (9.92 mmol) pyridine and 1.10 g (3.97 mmol) 7-(2-hydroxy-ethyl)-3,4-dihydro-1H-isoquinoline-2-carboxylic acid tert-butyl ester (preparation 7c) is added. The reaction mixture is stirred 5 h at 90° C., is cooled to RT and is filtered. The filtrate is washed with saturated aqueous sodium thiosulfate-solution, brine and dried over MgSO$_4$. After filtration and evaporation of the solvent, the residue is purified via chromatography (silica gel; PE/EtOAc=9:1).

Yield: 470 mg (31% of theory)
ESI Mass spectrum: [M+H]$^+$=388
Retention time HPLC: 4.4 min (method A).

Preparation 9

4-[1-(4-Benzyloxy-2-oxo-2H-pyridin-1-ylmethyl)-vinyl]-benzaldehyde

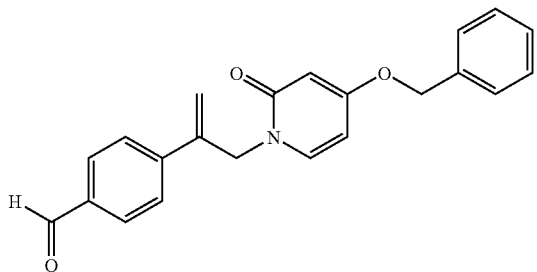

9a 4-Benzyloxy-1-(2-bromo-allyl)-1H-pyridin-2-one

To 6.00 g (29.8 mmol) 4-benzyloxy-1H-pyridin-2-one in 30 mL DMF at 0° C. is added 19.4 g (59.6 mmol) cesium carbonate and after 15 min 11.9 g (59.6 mmol) 2,3-dibromo-propene. The reaction mixture is stirred 2 h at RT and is diluted with EtOAc/MeOH and water. The organic phase is washed with water and is dried over MgSO$_4$. After filtration and evaporation of the solvent, the residue is purified via reverse HPLC chromatography (Waters symmetry, C18; water (0.15% formic acid)/acetonitrile 95:5 to 10:90).

Yield: 6.17 g (65% of theory)
ESI Mass spectrum: [M+H]$^+$=320/322
Retention time HPLC: 4.1 min (method H).

9b 4-[1-(4-Benzyloxy-2-oxo-2H-pyridin-1-ylmethyl)-vinyl]-benzaldehyde

To 6.17 g (19.3 mmol) 4-benzyloxy-1-(2-bromo-allyl)-1H-pyridin-2-one (preparation 9a), 3.76 g (25.1 mmol) 4-formylphenylboronic acid and 1.56 g (1.35 mmol) tetrakis-triphenyl-phosphanepalladium in 150 ml 1,4-1,4-dioxanee and 45 mL MeOH is added 19.3 mL (38.5 mmol) 2M aqueous Na$_2$CO$_3$-solution under a nitrogen atmosphere. The reaction mixture is evacuated three times and flushed with nitrogen. The mixture is refluxed overnight under a nitrogen atmosphere and is diluted with water. The phases are separated and the aqueous phase is extracted with DCM. The combined organic phase is dried over MgSO$_4$, filtered and the solvent is evaporated. To the residue is added MeOH/acetonitrile, the mixture is filtered and purified via reverse HPLC chromatography (Waters symmetry, C18; water (0.15% formic acid)/acetonitrile 95:5 to 10:90).

Yield: 3.70 g (purity 85%, 47% of theory)
ESI Mass spectrum: [M+H]$^+$=346
Retention time HPLC: 4.1 min (method H).

Preparation 10

6-[2-(Toluene-4-sulfonyloxy)-ethyl]-3,4-dihydro-1H-isoquinoline-2-carboxylic Acid Tert-Butyl Ester

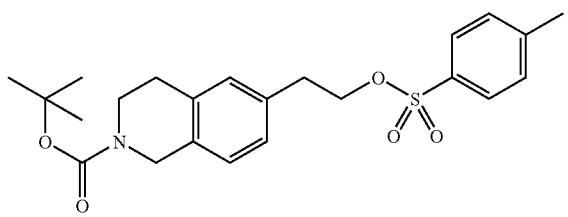

10a 6-Iodo-3,4-dihydro-1H-isoquinoline-2-carboxylic Acid Tert-Butyl Ester

To 13.0 g (41.6 mmol) 6-bromo-3,4-dihydro-1H-isoquinoline-2-carboxylic acid tert-butyl ester in 42 mL 1,4-dioxane is added 817 mg (4.21 mmol) copper(I)-iodide under argon. After flushing with argon, 0.89 mL (8.33 mmol) N,N-dimethylethylen-diamine and 12.5 g (83.3 mmol) sodium iodide is added at RT. The reaction mixture is stirred 14 h at 110° C., is cooled to RT and is diluted with 5% aqueous ammonia-solution. The layers are separated and the aqueous phase is extracted with EtOAc. The combined organic phase is washed with water and is dried over MgSO$_4$, filtered and the solvent is evaporated to give the product.

Yield: 14.0 g (94% of theory)
EII Mass spectrum: [M]$^+$=359
R$_f$-value: 0.8 (silica gel, mixture C).

10b 6-(2-Hydroxy-ethyl)-3,4-dihydro-1H-isoquinoline-2-carboxylic Acid Tert-Butyl Ester 6-(2-Hydroxy-ethyl)-3,4-dihydro-1H-isoquinoline-2-carboxylic acid tert-butyl ester is prepared as example 7c from 8.30 g (23.1 mmol) 6-iodo-3,4-dihydro-1H-isoquinoline-2-carboxylic acid tert-butyl ester (preparation 10a) and 4.07 g (92.4 mmol) oxirane.

Yield: 3.00 g (47% of theory)
R$_f$-value: 0.4 (silica gel, mixture D).

10c 6-[2-(Toluene-4-sulfonyloxy)-ethyl]-3,4-dihydro-1H-isoquinoline-2-carboxylic Acid Tert-Butyl Ester 6-[2-(Toluene-4-sulfonyloxy)-ethyl]-3,4-dihydro-1H-isoquinoline-2-carboxylic acid tert-butyl ester is prepared as example 7d from 1.60 g (5.77 mmol) 6-(2-hydroxy-ethyl)-3,4-dihydro-1H-isoquinoline-2-carboxylic acid tert-butyl ester (preparation 10b) and 1.21 g (6.35 mmol) 4-methyl-benzenesulfonyl chloride.

Yield: 1.30 g (52% of theory)
ESI Mass spectrum: [M+NH$_4$]$^+$=449
R$_f$-value: 0.4 (silica gel, mixture C).

Preparation 11

4-Benzyloxy-1-[2-(5-hydroxymethyl-thiophen-2-yl)-ethyl]-1H-pyridin-2-one

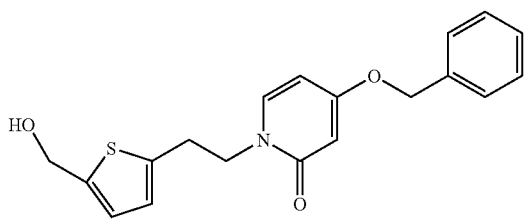

11a 5-(2-Methanesulfonyloxy-ethyl)-thiophene-2-carboxylic Acid Methyl Ester

To a solution of 300 mg (1.61 mmol) 5-(2-hydroxy-ethyl)-thiophene-2-carboxylic acid methyl ester in 10 mL DCM is added 0.90 mL triethylamine (6.44 mmol) and subsequently 312 µL (4.03 mmol) methanesulfonyl chloride at RT. The reaction mixture is stirred 1 h at RT and is diluted with 50 mL DCM. The organic phase is separated, washed three times with water and is dried over MgSO$_4$. After filtration and evaporation of the solvent, the product is afforded.

Yield: 430 mg (101% of theory)
ESI Mass spectrum: [M+H]$^+$=265
Retention time HPLC: 3.5 min (method A).

11b 5-[2-(4-Benzyloxy-2-oxo-2H-pyridin-1-yl)-ethyl]-thiophene-2-carboxylic Acid Methyl Ester To 1.20 g (5.96 mmol) 4-benzyloxy-1H-pyridin-2-one in DMF is added subsequently 3.89 g (11.9 mmol) cesium carbonate and 1.58 g (5.96 mmol) 5-(2-methanesulfonyloxy-ethyl)thiophene-2-carboxylic acid methyl ester (preparation 11a). The reaction mixture is stirred overnight at RT. After filtration, the residue is purified via reverse HPLC chromatography (Zorbax stable bond, C18; water (0.1% formic acid)/acetonitrile (0.1% formic acid) 95:5 to 10:90).

Yield: 540 mg (25% of theory)
ESI Mass spectrum: [M+H]$^+$=370
Retention time HPLC: 4.1 min (method A).

11c 5-[2-(4-Benzyloxy-2-oxo-2H-pyridin-1-yl)-ethyl]-thiophene-2-carboxylic Acid To 540 mg (1.46 mmol) 5-[2-(4-benzyloxy-2-oxo-2H-pyridin-1-yl)-ethyl]-thiophene-2-carboxylic acid methyl ester (preparation 11b) in 8.0 mL MeOH is added 5.5 mL (5.50 mmol) 1M aqueous sodium hydroxide-solution. The reaction is stirred overnight at RT and additional 3.0 mL (3.00 mmol) 1M aqueous sodium hydroxide-solution is added. The reaction mixture is stirred 4 days at RT and the solvent is evaporated. The residue is acidified with 1M aqueous HCl, the precipitate is collected, washed with water and dried.

Yield: 520 mg (100% of theory)
ESI Mass spectrum: [M+H]$^+$=356
Retention time HPLC: 3.5 min (method A).

11d 4-Benzyloxy-1-[2-(5-hydroxymethyl-thiophen-2-yl)-ethyl]-1H-pyridin-2-one To 530 mg (1.49 mmol) 5-[2-(4-benzyloxy-2-oxo-2H-pyridin-1-yl)-ethyl]-thiophene-2-carboxylic acid (preparation 11c) in 15 mL THF is added at RT 266 mg (1.64 mmol) CDI. The reaction mixture is stirred 30 min at 50° C. and is then poured into a solution of 169 mg (4.47 mmol) sodium borohydride in 40 mL water. The mixture is stirred 1 h at RT, diluted with saturated aqueous potassium-hydrogen-sulfate-solution and stirred for another 20 min. The mixture is neutralized with saturated aqueous Na$_2$CO$_3$-solution. The aqueous phase is extracted three times with EtOAc/MeOH. The combined organic phase is dried over MgSO$_4$, filtered and the solvent is evaporated to afford the product.

Yield: 520 mg (102% of theory)
ESI Mass spectrum: [M+H]$^+$=342
Retention time HPLC: 3.5 min (method A).

Preparation 12

Perhydro-azepin-4-ol

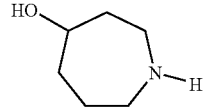

To 2.00 g (13.4 mmol) perhydro-azepin-4-one in 20 mL MeOH is added 200 mg platin(IV)-oxide. The reaction mixture is stirred under a hydrogen atmosphere of 1500 hPa at RT for 22 h. The catalyst is removed by filtration and 7.5 g polymer bound HCO$_3$ (MP resin 100 A) is added. The mixture is stirred 30 min at RT, filtered and the solvent is evaporated to afford the product.

Yield: 1.60 g (104% of theory)
ESI Mass spectrum: [M+H]$^+$=116
R$_f$-value: 0.05 (silica gel, mixture G).

Preparation 13

Perhydro-azepin-3-ol

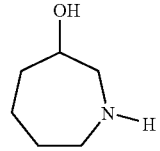

13a Perhydro-azepin-3-one

To 120 g (500 mmol) 1-benzyl-perhydro-azepin-3-one in 800 mL MeOH and 100 mL water is added 12.0 g Pd(II)-O.

The reaction mixture is stirred under a hydrogen atmosphere of 5000 hPa at RT overnight. The solvent is evaporated, the residue is co-evaporated twice with 100 mL toluene. The residue is elutriated with acetone. The precipitate is collected and dried.

Yield: 73.5 g (98% of theory)
Melting point=142° C.
$R_f$-value: 0.55 (silica gel, mixture H).

13b Perhydro-azepin-3-ol

Perhydro-azepin-3-ol is prepared as preparation 12 from 2.00 g (13.4 mmol)) perhydro-azepin-3-one (preparation 13b).

Yield: 1.00 g (65% of theory)
ESI Mass spectrum: $[M+H]^+=116$
$R_f$-value: 0.15 (silica gel, mixture G).

Preparation 14

4-(Benzyl-methyl-amino)-1-[2-(4-bromomethyl-phenyl)-ethyl]-1H-pyridin-2-one

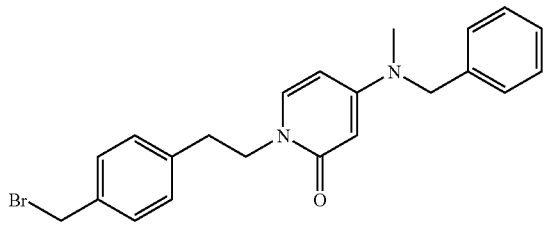

14a Benzyl-methyl-(1-oxy-pyridin-4-yl)-amine

A mixture of 5.00 g (38.6 mmol) 4-chloro-pyridine-1-oxide and 14.9 mL (116 mmol) N-methyl-benzylamine is stirred 4 h at 90° C., is diluted with water/EtOAc and the layers are separated. The organic phase is washed with water and the combined aqueous phase is concentrated in vacuo. The residue is dissolved in MeOH and is purified by HPLC (Zorbax stable bond, C18; water (0.15% formic acid)/acetonitrile 95:5 to 10:90).

Yield: 4.40 g (53% of theory)
ESI Mass spectrum: $[M+H]^+=215$ 14b 4-(Benzyl-methyl-amino)-1H-pyridin-2-one To 4.40 g (20.5 mmol) benzyl-methyl-(1-oxy-pyridin-4-yl)-amine (preparation 14a) is added 58 mL (616 mmol) acetic acid anhydride and the mixture is stirred 5 h at 150° C. The mixture is cooled to RT overnight and the solvent is evaporated. The residue is purified by HPLC (Zorbax stable bond, C18; water (0.15% formic acid)/acetonitrile 95:5 to 10:90).

Yield: 1.53 g (35% of theory)
ESI Mass spectrum: $[M+H]^+=215$
Retention time HPLC: 3.9 min (method F).

14c 4-(Benzyl-methyl-amino)-1-[2-(4-hydroxym-ethyl-phenyl)-ethyl]-1H-pyridin-2-one A mixture of 500 mg (2.33 mmol) 4-(benzyl-methyl-amino)-1H-pyridin-2-one (preparation 14b) and 1.52 g (4.67 mmol) cesium carbonate in 2.3 mL of DMF is stirred 15 min at RT and then 1.22 g (4.67 mmol) [4-(2-iodo-ethyl)-phenyl]-methanol (preparation 1b) is added. The mixture is stirred overnight at RT and the solvent is evaporated. The residue is dissolved in MeOH and is purified by reverse HPLC (Waters symmetry, C18; water (0.15% formic acid)/acetonitrile 95:5 to 10:90).

Yield: 290 mg (26% of theory, 74% purity)
ESI Mass spectrum: $[M+H]^+=349$
Retention time HPLC: 4.4 min (method C).

14d 4-(Benzyl-methyl-amino)-1-[2-(4-bromomethyl-phenyl)-ethyl]-1H-pyridin-2-one

To 280 mg (0.80 mmol, 74% purity) 4-(benzyl-methyl-amino)-1-[2-(4-hydroxymethyl-phenyl)-ethyl]-1H-pyridin-2-one (preparation 14c) in 5.0 mL of DCM is added at 0° C. 53 μL (0.56 mmol) phosphorus tribromide. The mixture is stirred overnight at RT and is diluted with aqueous NaHCO₃-solution and water. The layers are separated and the organic phase is dried over MgSO₄, filtered and the solvent is removed. The residue is used directly without further purification.

Yield: 350 mg (106% of theory)
ESI Mass spectrum: $[M+H]^+=411/413$
Retention time HPLC: 4.2 min (method C).

Preparation 15

4-Benzyloxy-1-[2-(4-bromomethyl-phenyl)-2-oxo-ethyl]-1H-pyridin-2-one

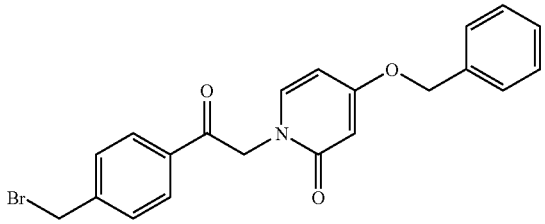

15a 2-Bromo-1-(4-hydroxymethyl-phenyl)-ethanone

To 7.00 g (46.6 mmol) 1-(4-hydroxymethyl-phenyl)-ethanone in 100 mL THF is added 22.5 g (46.6 mmol) tetrabuty-lammonium-tribromide dissolved in MeOH/THF. The reaction mixture is stirred 1 h at RT and the solvent is evaporated. The residue is dissolved with water and tertbutylmethylether. The organic phase is washed eight times with water. The combined organic phase is dried over MgSO₄, filtered and the solvent is evaporated. The residue is elutriated with diisopropylether and the precipitate is collected and dried.

Yield: 8.10 g (76% of theory)
ESI Mass spectrum: $[M+H]^+=229/231$
$R_f$-value: 0.2 (silica gel, mixture 1).

15b 4-Benzyloxy-1-[2-(4-hydroxymethyl-phenyl)-2-oxo-ethyl]-1H-pyridin-2-one

To 3.29 g (16.4 mmol) 4-benzyloxy-1H-pyridin-2-one in 16 mL DMF is added 13.3 g (40.9 mmol) cesium carbonate and the mixture is stirred 15 min at RT. Then 3.75 g (16.4 mmol) 2-bromo-1-(4-hydroxymethyl-phenyl)-ethanone (preparation 15a) is added and is stirred 2 h at RT. Water is added, the precipitate is collected, washed with water and dried.

Yield: 5.30 g (93% of theory)
ESI Mass spectrum: [M+H]$^+$=350
Retention time HPLC: 3.0 min (method A).

15c 4-Benzyloxy-1-[2-(4-bromomethyl-phenyl)-2-oxo-ethyl]-1H-pyridin-2-one

To 3.00 g (8.59 mmol) 4-benzyloxy-1-[2-(4-hydroxymethyl-phenyl)-2-oxo-ethyl]-1H-pyridin-2-one (preparation 15b) in 20 mL of DCM and 20 mL THF is added 0.81 mL (8.59 mmol) phosphorus tribromide at 0° C. The cooling bath is removed and the mixture is stirred 1 h at RT in an ultrasound bath.

The precipitate is collected, washed with diisopropylether and water and is dried.

Yield: 3.40 g (96% of theory)
ESI Mass spectrum: [M+H]$^+$=412/414
Retention time HPLC: 4.0 min (method H).

Preparation 16

4-Benzyloxy-1-[2-(4-bromomethyl-3-fluoro-phenyl)-2-oxo-ethyl]-1H-pyridin-2-one

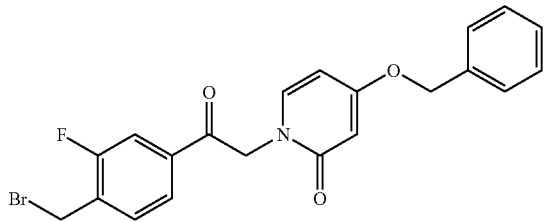

16a (4-Bromo-2-fluoro-benzyloxy)-tert-butyl-dimethyl-silane

To 5.10 g (24.9 mmol) (4-bromo-2-fluoro-phenyl)-methanol in 30 mL DMF is added subsequently 4.06 g (26.1 mmol) tert-butyl-chloro-dimethyl silane, 2.57 g (37.3 mmol) imidazole and 456 mg (3.73 mmol) DMAP. The reaction mixture is stirred overnight at RT and the solvent is evaporated. The residue is diluted with EtOAc, washed five times with water and the combined organic phase is dried over MgSO$_4$, filtered and the solvent is evaporated.

Yield: 7.70 g (97% of theory)
R$_f$-value: 0.9 (silica gel, mixture C).

16b tert-Butyl-(2-fluoro-4-iodo-benzyloxy)-dimethyl-silane

To 7.70 g (24.1 mmol) (4-bromo-2-fluoro-benzyloxy)-tert-butyl-dimethyl-silane (preparation 16a) in 8 mL 1,4-dioxane is added 937 mg (4.82 mmol) Cu(I)-iodide. The reaction mixture is flushed with argon and 7.23 g (48.2 mmol) sodium iodide and 1.03 mL (9.65 mmol) N,N-dimethylethylen-diamine are added. The mixture is stirred at 120° C. for 7 h in a sealed tube. The reaction mixture is diluted at RT with 5% aqueous NH$_3$-solution and the aqueous phase is extracted with EtOAc. The combined organic phase is washed a few times with water, dried over MgSO$_4$, filtered and the solvent is evaporated.

Yield: 7.80 g (88% of theory)
Retention time HPLC: 4.2 min (method E).

16c 4-(tert-Butyl-dimethyl-silanyloxymethyl)-3-fluoro-benzoic Acid Methyl Ester To 3.00 g (8.19 mmol) tert-butyl-(2-fluoro-4-iodo-benzyloxy)-dimethyl-silane (preparation 16b) in 20 mL MeOH and 20 mL DMF is added 455 mg (0.82 mmol) 1,1-bis(diphenylphosphino)ferrocene, 184 mg (0.82 mmol) Pd(II)-acetate and 2.27 mL (16.3 mmol) triethylamine. The reaction mixture is stirred under a CO atmosphere (4000 hPa) at 50° C. for 24 h. The solvent is evaporated, the residue is dissolved in DMF and is purified by HPLC (Zorbax stable bond, C18; water (0.15% formic acid)/acetonitrile 85:5 to 0:100).

Yield: 1.46 g (60% of theory)
Retention time HPLC: 3.8 min (method E).

16d 4-(tert-Butyl-dimethyl-silanyloxymethyl)-3-fluoro-benzoic Acid

To 2.20 g (7.37 mmol) 4-(tert-butyl-dimethyl-silanyloxymethyl)-3-fluoro-benzoic acid methyl ester (preparation 16c) in 30 mL EtOH is added 12 mL 1 M aqueous NaOH-solution. The mixture is stirred 1 h at RT, additional 4 mL 1 M aqueous NaOH-solution are added and the reaction mixture is stirred an additional hour. The solvent is evaporated, the residue is acidified with 1 M aqueous HCl-solution. The precipitate is collected and dried.

Yield: 540 mg (26% of theory)
ESI Mass spectrum: [M−H]$^-$=283
Retention time HPLC: 4.9 min (method A).

16e 1-[4-(tert-Butyl-dimethyl-silanyloxymethyl)-3-fluoro-phenyl]-ethanone

A solution of 540 mg (1.90 mmol) 4-(tert-butyl-dimethyl-silanyloxymethyl)-3-fluoro-benzoic acid (preparation 16d) in 20 mL THF is degassed and cooled to −30° C. 3.56 mL (5.67 mmol) 1.6 M methyl-lithium solution in diethylether is added, the mixture is stirred 2 h at −30° C. and 3.12 mL (24.7 mmol) trimethyl-chloro-silane are added. The mixture is stirred 2 min and is transferred to a pH 7 buffer solution (0° C.). The aqueous phase is extracted with EtOAc and diethylether. The combined organic phase is washed with water, dried over MgSO$_4$, filtered and the solvent is evaporated. The residue is purified by silica gel column chromatography with PE/EtOAc (9:1) as eluent.

Yield: 280 mg (52% of theory)
ESI Mass spectrum: (M+H)$^+$=283
R$_f$-value: 0.5 (silica gel, mixture C).

16f 2-Bromo-1-(3-fluoro-4-hydroxymethyl-phenyl)-ethanone

2-Bromo-1-(3-fluoro-4-hydroxymethyl-phenyl)-ethanone is prepared following preparation 15a from 280 mg (0.99 mmol) 1-[4-(tert-butyl-dimethyl-silanyloxymethyl)-3-fluoro-phenyl]-ethanone (preparation 16e) and 478 mg (0.99 mmol) tetrabutylammonium-tribromide.

Yield: 230 mg (94% of theory)
R$_f$-value: 0.3 (silica gel, mixture J).

16 g 4-Benzyloxy-1-[2-(3-fluoro-4-hydroxymethyl-phenyl)-2-oxo-ethyl]-1H-pyridin-2-one 4-Benzyloxy-1-[2-(3-fluoro-4-hydroxymethyl-phenyl)-2-oxo-ethyl]-1H-pyridin-2-one is prepared following preparation 15b from 193 mg (0.93 mmol) 4-benzyloxy-1H-pyridin-2-one and 230 mg (0.93 mmol) 2-bromo-1-(3-fluoro-4-hydroxymethyl-phenyl)-ethanone (preparation 16f).

Yield: 240 mg (70% of theory)
ESI Mass spectrum: (M+H)$^+$=368
Retention time HPLC: 3.2 min (method A).

16h 4-Benzyloxy-1-[2-(4-bromomethyl-3-fluoro-phenyl)-2-oxo-ethyl]-1H-pyridin-2-one 4-Benzyloxy-1-[2-(4-bromomethyl-3-fluoro-phenyl)-2-oxo-ethyl]-1H-pyridin-2-one is prepared following preparation 15c from 240 mg (0.65 mmol) 4-benzyloxy-1-[2-(3-fluoro-4-hydroxymethyl-phenyl)-2-oxo-ethyl]-1H-pyridin-2-one (preparation 16g) and 0.43 mL (4.57 mmol) phosphorus tribromide.

Yield: 210 mg (75% of theory)
ESI Mass spectrum: (M+H)$^+$=430/432
Retention time HPLC: 2.4 min (method E).

Preparation 17

5-Benzyloxy-2-[2-(4-bromomethyl-phenyl)-2-oxo-ethyl]-2H-pyridazin-3-one

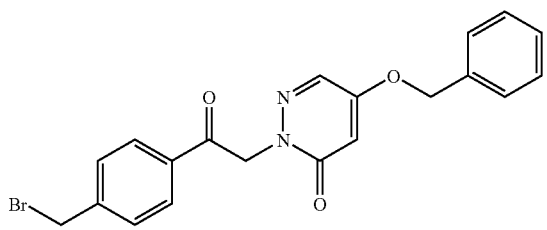

17a 5-Benzyloxy-2-[2-(4-hydroxymethyl-phenyl)-2-oxo-ethyl]-2H-pyridazin-3-one

5-Benzyloxy-2-[2-(4-hydroxymethyl-phenyl)-2-oxo-ethyl]-2H-pyridazin-3-one is prepared following preparation 15b from 5.20 g (25.7 mmol) 5-benzyloxy-2H-pyridazin-3-one (preparation 5c) and 7.70 g (28.6 mmol) 2-bromo-1-(4-hydroxymethyl-phenyl)-ethanone (preparation 15a) using DMSO as solvent.

Yield: 9.40 g (94% of theory)
ESI Mass spectrum: [M+H]$^+$=351
Retention time HPLC: 0.9 min (method L).

17b 5-Benzyloxy-2-[2-(4-bromomethyl-phenyl)-2-oxo-ethyl]-2H-pyridazin-3-one

5-Benzyloxy-2-[2-(4-bromomethyl-phenyl)-2-oxo-ethyl]-2H-pyridazin-3-one is prepared following preparation 15c from 9.40 g (26.8 mmol) 5-benzyloxy-2-[2-(4-hydroxymethyl-phenyl)-2-oxo-ethyl]-2H-pyridazin-3-one (preparation 17a) and 2.52 mL (26.8 mmol) phosphorus tribromide.

Yield: 10.0 g (90% of theory)
ESI Mass spectrum: [M+H]$^+$=413/415
Retention time HPLC: 1.6 min (method J).

Preparation 18

2-[2-(4-Bromomethyl-phenyl)-2-oxo-ethyl]-5-(5-chloro-pyridin-2-ylmethoxy)-2H-pyridazin-3-one

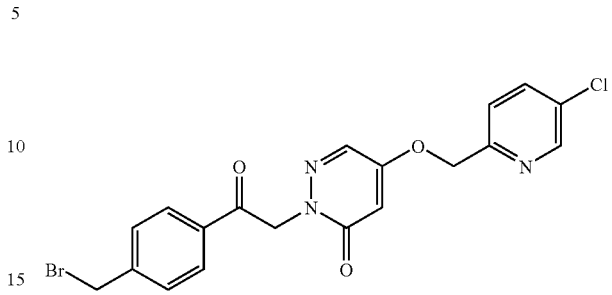

18a 5-(5-Chloro-pyridin-2-ylmethoxy)-2-(tetrahydro-pyran-2-yl)-2H-pyridazin-3-one To 5.00 g (25.5 mmol) 5-hydroxy-2-(tetrahydro-pyran-2-yl)-2H-pyridazin-3-one (see preparation 5a) and 4.03 g (28.0 mmol) (5-chloro-pyridin-2-yl)-methanol in 25 mL THF and 15 mL DCM is added molecular sieve and then 12.7 g (38.2 mmol) of polymer bound triphenylphosphane (3 mmol/g). The reaction mixture is cooled to 0° C. and 7.53 mL (38.2 mmol) diisopropyl azodicarboxylate is added. The mixture is stirred 10 min at 0° C. and 30 min at RT. The reaction mixture is filtered and the solvent is evaporated. The residue is purified via reverse HPLC chromatography (Zorbax stable bond, C18; water (0.1% formic acid)/acetonitrile (0.1% formic acid) 95:5 to 10:90).

Yield: 5.50 g (67% of theory)
ESI Mass spectrum: [M+H]$^+$=322/324
Retention time HPLC: 3.3 min (method A). 18b 5-(5-Chloro-pyridin-2-ylmethoxy)-2H-pyridazin-3-one To 5.50 g (17.1 mmol) 5-(5-chloro-pyridin-2-ylmethoxy)-2-(tetrahydro-pyran-2-yl)-2H-pyridazin-3-one (preparation 18a) in 50 mL MeOH is added 7.1 mL conc. HCl and the reaction mixture is refluxed for 2 h. The solvent is evaporated, the precipitate collected and added to 50 mL of water. The mixture is neutralized with saturated aqueous NaHCO$_3$-solution. The precipitate is collected, washed with water and dried.

Yield: 3.00 g (74% of theory)
ESI Mass spectrum: [M+H]$^+$=238/240
Retention time HPLC: 1.0 min (method J).

18c 5-(5-Chloro-pyridin-2-ylmethoxy)-2-[2-(4-hydroxymethyl-phenyl)-2-oxo-ethyl]-2H-pyridazin-3-one 5-(5-Chloro-pyridin-2-ylmethoxy)-2-[2-(4-hydroxymethyl-phenyl)-2-oxo-ethyl]-2H-pyridazin-3-one is prepared following preparation 15b from 450 mg (1.89 mmol) 5-(5-chloro-pyridin-2-ylmethoxy)-2H-pyridazin-3-one (preparation 18b) and 477 mg (2.08 mmol) 2-bromo-1-(4-hydroxymethyl-phenyl)-ethanone (preparation 15a).

Yield: 650 mg (89% of theory)
ESI Mass spectrum: [M+H]$^+$=386/388
Retention time HPLC: 2.9 min (method A).

18d 2-[2-(4-Bromomethyl-phenyl)-2-oxo-ethyl]-5-(5-chloro-pyridin-2-ylmethoxy)-2H-pyridazin-3-one 2-[2-(4-Bromomethyl-phenyl)-2-oxo-ethyl]-5-(5-chloro-pyridin-2-ylmethoxy)-2H-pyridazin-3-one is prepared following preparation 15c from 650 mg (1.69 mmol) 5-(5-chloro-pyridin-2-ylmethoxy)-2-[2-(4-hydroxymethyl-phenyl)-2-oxo-ethyl]-2H-pyridazin-3-one (preparation 18c) and 0.16 mL (1.69 mmol) phosphorus tribromide.
Yield: 500 mg (66% of theory)
ESI Mass spectrum: (M+H)$^+$=448/450
Retention time HPLC: 2.4 min (method E).

Preparation 19

2-[2-(4-Chloromethyl-phenyl)-2-oxo-ethyl]-5-(5-fluoro-pyridin-2-ylmethoxy)-2H-pyridazin-3-one

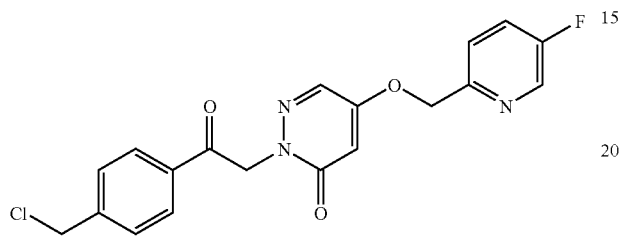

19a 5-(5-Fluoro-pyridin-2-ylmethoxy)-2-(tetrahydro-pyran-2-yl)-2H-pyridazin-3-one 5-(5-Fluoro-pyridin-2-ylmethoxy)-2-(tetrahydro-pyran-2-yl)-2H-pyridazin-3-one is prepared following preparation 18a from 2.40 g (12.2 mmol) 5-hydroxy-2-(tetrahydro-pyran-2-yl)-2H-pyridazin-3-one (see preparation 5a) and 1.56 g (12.2 mmol) (5-fluoro-pyridin-2-yl)-methanol
Yield: 800 mg (21% of theory)
ESI Mass spectrum: (M+H)$^+$=306
Retention time HPLC: 3.0 min (method A).

19b 5-(5-Fluoro-pyridin-2-ylmethoxy)-2H-pyridazin-3-one 5-(5-Fluoro-pyridin-2-ylmethoxy)-2H-pyridazin-3-one is prepared following preparation 18b from 800 mg (2.62 mmol) 5-(5-fluoro-pyridin-2-ylmethoxy)-2-(tetrahydro-pyran-2-yl)-2H-pyridazin-3-one.
Yield: 350 mg (60% of theory)
ESI Mass spectrum: [M+H]$^+$=222
Retention time HPLC: 2.0 min (method A).

19c 5-(5-Fluoro-pyridin-2-ylmethoxy)-2-[2-(4-hydroxymethyl-phenyl)-2-oxo-ethyl]-2H-pyridazin-3-one 5-(5-Fluoro-pyridin-2-ylmethoxy)-2-[2-(4-hydroxymethyl-phenyl)-2-oxo-ethyl]-2H-pyridazin-3-one is prepared following preparation 15b (with acetonitrile as solvent) from 350 mg (1.58 mmol) 5-(5-fluoro-pyridin-2-ylmethoxy)-2H-pyridazin-3-one (preparation 19b) and 399 mg (1.74 mmol) 2-bromo-1-(4-hydroxymethyl-phenyl)-ethanone (preparation 15a).
Yield: 400 mg (68% of theory)
ESI Mass spectrum: [M+H]$^+$=370
Retention time HPLC: 2.7 min (method A).

19d 2-[2-(4-Chloromethyl-phenyl)-2-oxo-ethyl]-5-(5-fluoro-pyridin-2-ylmethoxy)-2H-pyridazin-3-one To 400 mg (1.08 mmol) 5-(5-fluoro-pyridin-2-yl-methoxy)-2-[2-(4-hydroxymethyl-phenyl)-2-oxo-ethyl]-2H-pyridazin-3-one (preparation 19c) in 10 mL DCM is added 0.12 mL (1.62 mmol) thionylchloride at 0° C. The reaction mixture is stirred 2 h at RT and diluted with tert-butylmethylether. The precipitate is collected and dried.
Yield: 350 mg (83% of theory)
ESI Mass spectrum: [M+H]$^+$=388/390
Retention time HPLC: 3.6 min (method A).

Preparation 20

6-Benzyloxy-3-[2-(4-bromomethyl-phenyl)-2-oxo-ethyl]-3H-pyrimidin-4-one

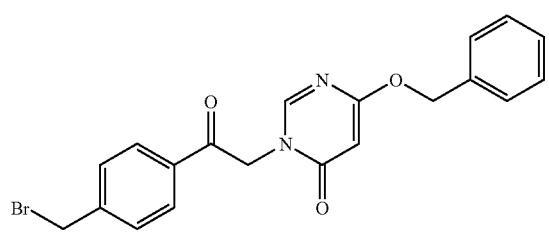

20a 6-Benzyloxy-3-[2-(4-hydroxymethyl-phenyl)-2-oxo-ethyl]-3H-pyrimidin-4-one

6-Benzyloxy-3-[2-(4-hydroxymethyl-phenyl)-2-oxo-ethyl]-3H-pyrimidin-4-one is prepared following preparation 15b from 1.50 g (7.42 mmol) 6-benzyloxy-3H-pyrimidin-4-one and 1.87 g (8.16 mmol) 2-bromo-1-(4-hydroxymethyl-phenyl)-ethanone (preparation 15a).
Yield: 2.5 g (96% of theory)
ESI Mass spectrum: [M+H]$^+$=351
Retention time HPLC: 3.0 min (method A).

20b 6-Benzyloxy-3-[2-(4-bromomethyl-phenyl)-2-oxo-ethyl]-3H-pyrimidin-4-one

6-Benzyloxy-3-[2-(4-bromomethyl-phenyl)-2-oxo-ethyl]-3H-pyrimidin-4-one is prepared following preparation 15c from 2.50 g (7.14 mmol) 6-benzyloxy-3-[2-(4-hydroxymethyl-phenyl)-2-oxo-ethyl]-3H-pyrimidin-4-one (preparation 20a) and 0.67 mL (7.14 mmol) phosphorus tribromide.
Yield: 900 mg (31% of theory)
ESI Mass spectrum: (M+H)$^+$=413/415

Preparation 21

4-Hydroxy-1-{2-[3-(2,2,2-trifluoro-acetyl)-2,3,4,5-tetrahydro-1H-3-benzazepin-7-yl]-ethyl}-1H-pyridin-2-one

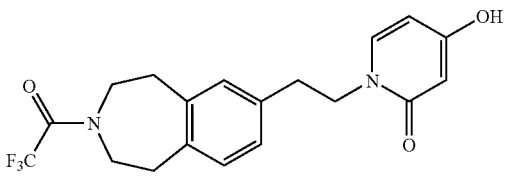

21a 4-Benzyloxy-1-{2-oxo-2-[3-(2,2,2-trifluoro-acetyl)-2,3,4,5-tetrahydro-1H-3-benzazepin-7-yl]-ethyl}-1H-pyridin-2-one To 8.05 g (40.0 mmol) 4-benzyloxy-1H-pyridin-2-one in 50 mL THF is added at 0° C. subsequently 4.94 g (44.0 mmol) potassium tert-butylate, 739 mg (2.00 mmol) tert-butyl ammonium-iodide and 15.3 g (48.0 mmol) 1-[7-(2-chloro-acetyl)-1,2,4,5-tetrahydro-3-benzazepin-3-yl]-2,2,2-trifluoro-ethanone. The reaction mixture is stirred overnight at RT and poured onto 500 mL water. 100 ml tert-butylmethyl-ether is added. The precipitate is collected and dried. The product, which contains 20% 1-[7-(2-chloro-acetyl)-1,2,4,5-tetrahydro-3-benzazepin-3-yl]-2,2,2-trifluoro-ethanone is used without further purification in the next step.

Yield: 16.0 g (66% of theory; 80% purity)
ESI Mass spectrum: [M+H]$^+$=485
Retention time HPLC: 4.3 min (method A).

21b 4-Hydroxy-1-{2-[3-(2,2,2-trifluoro-acetyl)-2,3,4,5-tetrahydro-1H-3-benzazepin-7-yl]-ethyl}-1H-pyridin-2-one To 5.00 g (10.3 mmol) 4-benzyloxy-1-{2-oxo-2-[3-(2,2,2-trifluoro-acetyl)-2,3,4,5-tetrahydro-1H-3-benzazepin-7-yl]-ethyl}-1H-pyridin-2-one (preparation 21a) in 100 mL MeOH and 9.8 mL 1 M aqueous HCl-solution is added 500 mg of 10% Pd/C. The reaction mixture is stirred under a hydrogen atmosphere of 5000 hPa at 50° C. for 18 h. After filtration and evaporation of the solvent, is the residue purified by HPLC (Zorbax stable bond, C18; water (0.15% formic acid)/acetonitrile 95:5 to 5:95).

Yield: 1.90 g (36% of theory; 75% purity)
ESI Mass spectrum: [M+H]$^+$=381
Retention time HPLC: 3.4 min (method A).

Preparation 22.1

4-(4-Fluoro-benzyloxy)-1H-pyridin-2-one

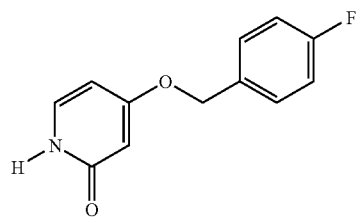

To 1.40 g (7.41 mmol) 1-bromomethyl-4-fluoro-benzene in 20 mL acetonitrile is added 822 mg (7.40 mmol) 2,4-dihydroxy pyridine and 2.05 g (14.8 mmol) potassium carbonate. The reaction mixture is stirred overnight at RT. 5 mL of DMF is added and the reaction is stirred overnight. After filtration and evaporation of the solvent, is the residue purified by HPLC (Zorbax stable bond, C18; water (0.15% formic acid)/acetonitrile 95:5 to 5:95).

Yield: 600 mg (37% of theory)
ESI Mass spectrum: [M+H]$^+$=220
Retention time HPLC: 2.8 min (method A).

The following compounds are prepared as described for preparation 22.1. For the preparation of 22.6 and 22.7 the corresponding chlorides are used as alkylating agents.

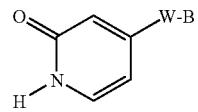

| Preparation | -W-B | Yield (%) | Formula | MS | Retention time HPLC in min (method) |
|---|---|---|---|---|---|
| 22.2 | | 46 | $C_{11}H_9BrN_2O_2$ | 281/283 [M + H]$^+$ | 2.5 (A) |
| 22.3 | | 18 | $C_{10}H_9NO_2S$ | 208 [M + H]+ | 2.5 (A) |
| 22.4 | | 12 | $C_{11}H_{10}N_2O_2$ | 203 [M + H]$^+$ | 1.7 (F) |
| 22.5 | | 43 | $C_{12}H_{10}ClNO_2$ | 236/238 [M + H]$^+$ | 1.1 (K) |

-continued

| Preparation | -W-B | Yield (%) | Formula | MS | Retention time HPLC in min (method) |
|---|---|---|---|---|---|
| 22.6 | 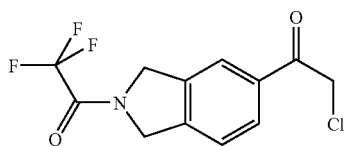 | 37 | $C_{13}H_{13}NO_2$ | 216 $[M + H]^+$ | 1.1 (K) |
| 22.7 | 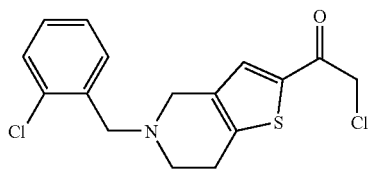 | 24 | $C_{13}H_{13}NO_3$ | 232 $[M + H]^+$ | 1.1 (K) |

Preparation 23

1-[5-(2-Chloro-acetyl)-1,3-dihydro-isoindol-2-yl]-2,2,2-trifluoro-ethanone

To 5.00 g (37.5 mmol) aluminium(III)-chloride in 20 mL 1,2-dichloroethane is added at 0° C. dropwise 2.24 mL (28.1 mmol) 1,3-dichloro-propan-2-one keeping the temperature below 15° C. Then 4.48 g (18.7 mmol) 1-(1,3-dihydro-isoindol-2-yl)-2,2,2-trifluoro-ethanone in 5 mL 1,2-dichloroethane is added dropwise at RT keeping the temperature between 40-45° C. The reaction is stirred for 18 h at RT and is poured onto aqueous HCl-solution. The aqueous phase is extracted twice with DCM, the organic phase is washed with water, dried over MgSO$_4$, filtered and the solvent is evaporated. The residue is elutriated with PE and the precipitate is collected.

Yield: 2.76 g (51% of theory)
ESI Mass spectrum: $[M+H]^+=292/294$
Retention time HPLC: 3.7 min (method H).

Preparation 24

2-Chloro-1-[5-(2-chloro-benzyl)-3a,4,5,6,7,7a-hexahydro-thieno[3,2-c]pyridin-2-yl]-ethanone To 10.0 g (33.3 mmol) 5-(2-chloro-benzyl)-3a,4,5,6,7,7a-hexahydro-thieno[3,2-c]pyridine is added 3.18 mL (40.0 mmol) chloro-acetyl chloride and then 8.88 g (66.6 mmol) aluminium(III)-chloride. The reaction mixture is stirred 1 h at 70° C. and then a water-ice mixture is added followed by DCM. The formed precipitate is collected and dried.

Yield: 9.70 g (77% of theory)
ESI Mass spectrum: $[M+H]^+=340/342/344$
Retention time HPLC: 4.9 min (method J).

Preparation 25

5-(5-Bromo-pyridin-2-ylmethoxy)-2H-pyridazin-3-one

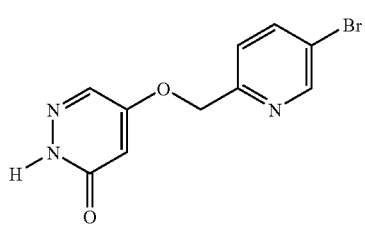

25a 5-(5-Bromo-pyridin-2-ylmethoxy)-2-(tetrahydro-pyran-2-yl)-2H-pyridazin-3-one To 3.29 g (16.7 mmol) 5-hydroxy-2-(tetrahydro-pyran-2-yl)-2H-pyridazin-3-one (preparation 5a) in acetonitrile is added at RT subsequently 4.63 g (33.4 mmol) potassium-carbonate and 4.20 g (16.7 mmol) 5-bromo-2-bromomethyl-pyridine. The reaction mixture is stirred 3 h at RT and 5 mL DMF is added. The reaction mixture is stirred overnight and the solvent is evaporated. To the residue water and tert-butyl-methylether is added. The precipitate is collected and dried.

Yield: 5.30 g (86% of theory)
ESI Mass spectrum: $[M+H]^+=366/368$
Retention time HPLC: 3.7 min (method A).

25b 5-(5-Bromo-pyridin-2-ylmethoxy)-2H-pyridazin-3-one 5-(5-Bromo-pyridin-2-ylmethoxy)-2H-pyridazin-3-one is prepared following preparation 18b from 5.30 g (14.5 mmol) 5-(5-bromo-pyridin-2-ylmethoxy)-2-(tetrahydro-pyran-2-yl)-2H-pyridazin-3-one (preparation 25a).
Yield: 4.20 g (103% of theory)
ESI Mass spectrum: [M+H]$^+$=282/284
Retention time HPLC: 2.8 min (method A).

Preparation 26

5-(4-Fluoro-benzyloxy)-2H-pyridazin-3-one

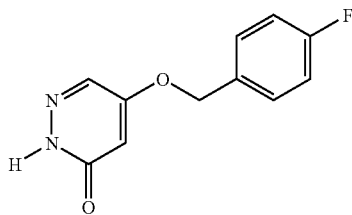

26a 5-(4-Fluoro-benzyloxy)-2-(tetrahydro-pyran-2-yl)-2H-pyridazin-3-one 5-(4-Fluoro-benzyloxy)-2-(tetrahydro-pyran-2-yl)-2H-pyridazin-3-one is prepared following preparation 25a from 8.00 g (40.8 mmol) 5-hydroxy-2-(tetrahydro-pyran-2-yl)-2H-pyridazin-3-one (preparation 5a) and 5.4 mL (44.9 mmol) 1-chloromethyl-4-fluoro-benzene.
Yield: 10.5 g (85% of theory)
ESI Mass spectrum: [M+H]$^+$=305
Retention time HPLC: 3.6 min (method A).

26b 5-(4-Fluoro-benzyloxy)-2H-pyridazin-3-one 5-(4-Fluoro-benzyloxy)-2H-pyridazin-3-one is prepared following preparation 18b from 10.5 g (34.5 mmol) 5-(4-fluoro-benzyloxy)-2-(tetrahydro-pyran-2-yl)-2H-pyridazin-3-one (preparation 26a).
Yield: 7.30 g (96% of theory)
ESI Mass spectrum: [M+H]$^+$=221
Retention time HPLC: 2.7 min (method A).

Preparation 27

5-(Pyridin-2-ylmethoxy)-2H-pyridazin-3-one

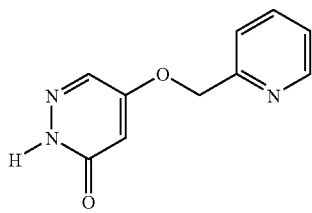

27a 5-(Pyridin-2-ylmethoxy)-2-(tetrahydro-pyran-2-yl)-2H-pyridazin-3-one 5-(Pyridin-2-ylmethoxy)-2-(tetrahydro-pyran-2-yl)-2H-pyridazin-3-one is prepared following preparation 25a from 2.00 g (10.2 mmol) 5-hydroxy-2-(tetrahydro-pyran-2-yl)-2H-pyridazin-3-one (preparation 5a) and 2.58 g (10.2 mmol) 2-bromomethyl-pyridine hydro-bromide.
Yield: 2.40 g (82% of theory)
ESI Mass spectrum: [M+H]$^+$=288
Retention time HPLC: 2.9 min (method A).

27b 5-(Pyridin-2-ylmethoxy)-2H-pyridazin-3-one 5-(Pyridin-2-ylmethoxy)-2H-pyridazin-3-one is prepared following preparation 18b from 2.40 g (8.35 mmol) 5-(pyridin-2-ylmethoxy)-2-(tetrahydro-pyran-2-yl)-2H-pyridazin-3-one (preparation 27a).
Yield: 1.40 g (82% of theory)
ESI Mass spectrum: [M+H]$^+$=204
Retention time HPLC: 1.8 min (method A).

Preparation 28.1

5-Benzyloxy-2-{2-oxo-2-[2-(2,2,2-trifluoro-acetyl)-1,2,3,4-tetrahydro-isoquinolin-7-yl]-ethyl}-2H-pyridazin-3-one

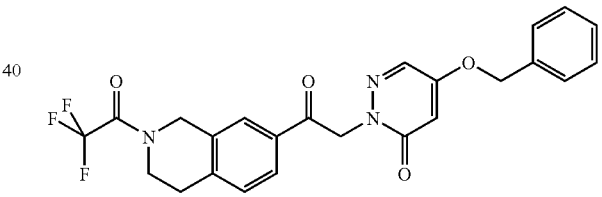

5-Benzyloxy-2-{2-oxo-2-[2-(2,2,2-trifluoro-acetyl)-1,2,3,4-tetrahydro-isoquinolin-7-yl]-ethyl}-2H-pyridazin-3-one is prepared following preparation 15b (DMSO as solvent; purification via HPLC) from 3.00 g (14.8 mmol) 5-benzyloxy-2H-pyridazin-3-one (preparation 5c) and 4.54 g (14.8 mmol) 1-[7-(2-chloro-acetyl)-3,4-dihydro-1H-isoquinolin-2-yl]-2,2,2-trifluoro-ethanone.
Yield: 4.70 g (67% of theory)
ESI Mass spectrum: [M+H]$^+$=472
Retention time HPLC: 4.1 min (method A).

The following compounds are prepared as described for preparation 28.1. For preparation 28.3 DMSO is used as solvent, for preparation 28.2 1-[7-(2-bromo-acetyl)-3,4-dihydro-1H-isoquinolin-2-yl]-2,2,2-trifluoro-ethanone is used as alkylating agent.

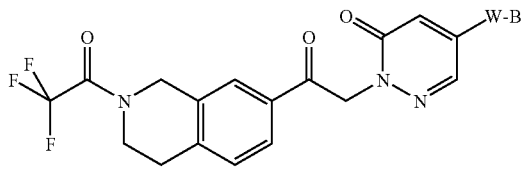

| preparation | -W-B | Starting material | Yield (%) | Formula | MS | Retention time HPLC in min (method) |
|---|---|---|---|---|---|---|
| 28.2 | *-O-CH2-(2-pyridyl) | Preparation 27b | 57 | $C_{23}H_{19}F_3N_4O_4$ | 473 $[M+H]^+$ | 3.7 (A) |
| 28.3 | *-O-CH2-(5-Br-2-pyridyl) | Preparation 25b | 69 | $C_{23}H_{18}BrF_3N_4O_4$ | 551/553 $[M+H]^+$ | 1.8 (K) |
| 28.4 | *-O-CH2-(4-F-phenyl) | Preparation 26b | 90 | $C_{24}H_{19}F_4N_3O_4$ | 490 $[M+H]^+$ | 4.2 (A) |
| 28.5 | *-O-CH2-(5-Cl-2-pyridyl) | Preparation 18b | 19 | $C_{23}H_{18}ClF_3N_4O_4$ | 507/509 $[M+H]^+$ | 3.9 (A) |

Preparation 29

6-[2-(4-Benzyloxy-2-oxo-2H-pyridin-1-yl)-acetyl]-3,4-dihydro-1H-isoquinoline-2-carboxylic Acid Tert-Butyl Ester

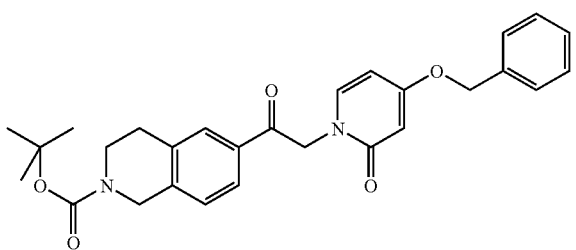

29a 6-(Methoxy-methyl-carbamoyl)-3,4-dihydro-1H-isoquinoline-2-carboxylic Acid Tert-Butyl Ester To 2.00 g (7.21 mmol) 3,4-dihydro-1H-isoquinoline-2,6-dicarboxylic acid 2-tert-butyl ester in 70 mL MeOH is added at RT 844 mg (8.65 mmol) O,N-dimethyl-hydroxylamine and 1.59 mL (14.4 mmol) 4-methyl-morpholine. The mixture is stirred at RT and then 2.10 g (7.57 mmol) 4-(4,6-dimethoxy-1,3,5-triazin-2-yl)-4-methyl-morpholin-4-ium chloride hydrate is added and the mixture is stirred overnight at RT. The residue is directly purified via reverse HPLC chromatography (Waters XBridge, C18; water (0.3% NH4OH)/acetonitrile (0.3% NH4OH) 90:10 to 10:90).

Yield: 2.30 g (100% of theory)
ESI Mass spectrum: $[M+H]^+=321$
Retention time HPLC: 1.7 min (method K).

29b
6-Acetyl-3,4-dihydro-1H-isoquinoline-2-carboxylic Acid Tert-Butyl Ester

To 2.30 g (7.18 mmol) 6-(methoxy-methyl-carbamoyl)-3,4-dihydro-1H-isoquinoline-2-carboxylic acid tert-butyl ester (preparation 29a) in 50 mL THF is added under an argon atmosphere at 0° C. 7.18 mL (21.5 mmol; 3 M solution in diethylether) methylmagnesium bromide. The reaction mixture is stirred 1.5 h at −5° C. and is then transferred into a saturated aqueous ammonium chloride solution. The aqueous phase is extracted three times with tert-butylmethylether, dried over MgSO4, filtered and the solvent is evaporated. The residue is purified by silica gel column chromatography with PE/EtOAc (8:2) as eluent.

Yield: 1.40 g (71% of theory)
ESI Mass spectrum: $[M+H]^+=276$
$R_f$-value: 0.7 (silica gel, mixture E).

29c 6-(2-Bromo-acetyl)-3,4-dihydro-1H-isoquinoline-2-carboxylic Acid Tert-Butyl Ester To 1.40 g (5.09 mmol) 6-acetyl-3,4-dihydro-1H-isoquinoline-2-carboxylic acid tert-butyl ester (preparation 29b) in 20 mL THF is added a solution of 2.45 g (5.09 mmol) tetrabutylammonium-tribromide in MeOH/THF at RT. The reaction mixture is stirred 30 min at RT and the solvent is evaporated. The residue is treated with water and 1 M aqueous HCl-solution and the aqueous phase is extracted with tert-butylmethylether. The organic phase is washed with water and 1 M aqueous HCl-solution, dried over MgSO$_4$, filtered and the solvent is evaporated. The residue is purified by silica gel column chromatography with PE/EtOAc (7:3) as eluent.

Yield: 580 mg (21% of theory)
ESI Mass spectrum: [M+NH$_4$]$^+$=371/373

29d 6-[2-(4-Benzyloxy-2-oxo-2H-pyridin-1-yl)-acetyl]-3,4-dihydro-1H-isoquinoline-2-carboxylic Acid Tert-Butyl Ester 6-[2-(4-Benzyloxy-2-oxo-2H-pyridin-1-yl)-acetyl]-3,4-dihydro-1H-isoquinoline-2-carboxylic acid tert-butyl ester is prepared following preparation 15b (DMSO as solvent; purification via HPLC) from 214 mg (1.06 mmol) 4-benzyloxy-1H-pyridin-2-one and 580 mg (1.06 mmol) 6-(2-bromoacetyl)-3,4-dihydro-1H-isoquinoline-2-carboxylic acid tert-butyl ester (preparation 29c).

Yield: 410 mg (81% of theory)
ESI Mass spectrum: [M+H]$^+$=475
Retention time HPLC: 1.9 min (method K).

Preparation 30

5-Benzyloxy-2-{2-[4-(1-bromo-ethyl)-phenyl]-2-oxo-ethyl}-2H-pyridazin-3-one

30a
2-Bromo-1-[4-(1-hydroxy-ethyl)-phenyl]-ethanone

2-Bromo-1-[4-(1-hydroxy-ethyl)-phenyl]-ethanone is prepared following preparation 29c from 600 mg (3.65 mmol) 1-[4-(1-hydroxy-ethyl)-phenyl]-ethanone.

Yield: 750 mg (84% of theory)
ESI Mass spectrum: [M+H]$^+$=243/245
R$_f$-value: 0.5 (silica gel, mixture E).

30b 5-Benzyloxy-2-{2-[4-(1-hydroxy-ethyl)-phenyl]-2-oxo-ethyl}-2H-pyridazin-3-one 5-Benzyloxy-2-{2-[4-(1-hydroxy-ethyl)-phenyl]-2-oxo-ethyl}-2H-pyridazin-3-one is prepared following preparation 15b (DMSO as solvent) from 624 mg (3.09 mmol) 5-benzyloxy-2H-pyridazin-3-one (preparation 5c) and 750 mg (3.09 mmol) 2-bromo-1-[4-(1-hydroxy-ethyl)phenyl]-ethanone (preparation 30a).

Yield: 920 mg (82% of theory; 72% purity)
ESI Mass spectrum: [M+H]$^+$=365
Retention time HPLC: 1.1 min (method M).

30c 5-Benzyloxy-2-{2-[4-(1-bromo-ethyl)-phenyl]-2-oxo-ethyl}-2H-pyridazin-3-one 5-Benzyloxy-2-{2-[4-(1-bromo-ethyl)-phenyl]-2-oxo-ethyl}-2H-pyridazin-3-one is prepared following example 1.1a from 920 mg (2.53 mmol) 5-benzyloxy-2-{2-[4-(1-hydroxy-ethyl)-phenyl]-2-oxo-ethyl}-2H-pyridazin-3-one (preparation 30b).

Yield: 900 mg (58% of theory; 70% purity)
ESI Mass spectrum: [M+H]$^+$=428/430
Retention time HPLC: 1.6 min (method J).

Preparation 31.1

4-(4-Fluoro-benzyloxy)-1-[2-(4-hydroxymethyl-phenyl)-2-oxo-ethyl]-1H-pyridin-2-one

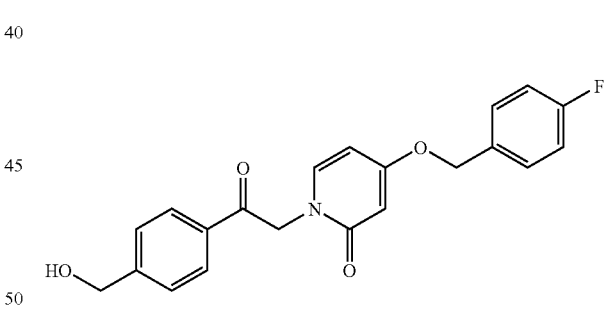

4-(4-Fluoro-benzyloxy)-1-[2-(4-hydroxymethyl-phenyl)-2-oxo-ethyl]-1H-pyridin-2-one is prepared following preparation 15b (DMSO as solvent) from 1.10 g (5.00 mmol) 4-(4-fluoro-benzyloxy)-1H-pyridin-2-one (preparation 22.1) and 1.15 g (5.00 mmol) 2-bromo-1-(4-hydroxymethylphenyl)-ethanone (preparation 15a).

Yield: 1.25 g (68% of theory)
ESI Mass spectrum: [M+H]$^+$=368
Retention time HPLC: 1.6 min (method K).

The following compounds are prepared as described for preparation 31.1.

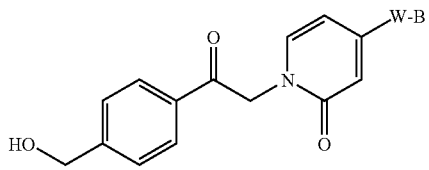

| Preparation | -W-B | Starting material (preparation No.) | Yield (%) | Formula | MS | Retention time HPLC in min (method) |
|---|---|---|---|---|---|---|
| 31.2 | *-O-CH2-C6H4-Cl | 22.5 | 76 | $C_{21}H_{18}ClNO_4$ | 384/386 $[M+H]^+$ | 1.7 (K) |
| 31.3 | *-O-CH2-C6H4-CH3 | 22.6 | 83 | $C_{22}H_{21}NO_4$ | 364 $[M+H]^+$ | 1.6 (K) |
| 31.4 | *-O-CH2-C6H4-OCH3 | 22.7 | 76 | $C_{22}H_{21}NO_5$ | 380 $[M+H]^+$ | 1.5 (K) |

Preparation 32.1

1-[2-(4-Chloromethyl-phenyl)-2-oxo-ethyl]-4-(4-fluoro-benzyloxy)-1H-pyridin-2-one

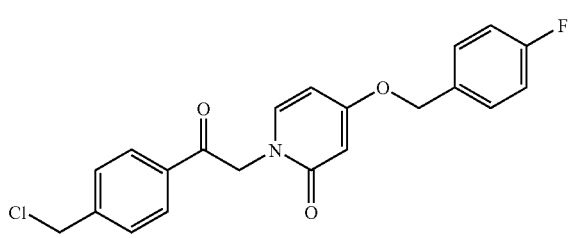

To 1.20 g (3.27 mmol) 4-(4-fluoro-benzyloxy)-1-[2-(4-hydroxymethyl-phenyl)-2-oxo-ethyl]-1H-pyridin-2-one (preparation 31.1) in 20 mL DCM is added 0.29 mL (3.59 mmol) pyridine and 0.26 mL (3.59 mmol) thionylchloride at 0° C. The reaction mixture is stirred 1 h at 0° C., is warmed to RT and is then diluted with water. The organic phase is washed with saturated aqueous $KHSO_4$-solution and then with water, dried over $MgSO_4$, filtered over charcoal and the solvent is evaporated.

Yield: 800 mg (64% of theory)

ESI Mass spectrum: $[M+H]^+=386/388$

Retention time HPLC: 4.2 min (method A).

The following compounds are prepared as described for preparation 32.1.

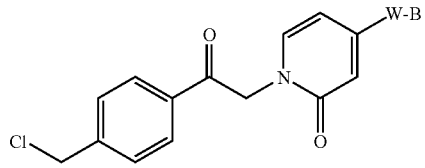

| Preparation | -W-B | Starting material (preparation No.) | Yield (%) | Formula | MS | Retention time HPLC in min (method) |
|---|---|---|---|---|---|---|
| 32.2 | *-O-CH2-C6H4-Cl | 31.2 | 68 | $C_{21}H_{17}Cl_2NO_3$ | 402/404/406 $[M+H]^+$ | 4.5 (A) |
| 32.3 | *-O-CH2-C6H4-CH3 | 31.3 | 39 | $C_{22}H_{20}ClNO_3$ | 382/384 $[M+H]^+$ | 4.4 (A) |
| 32.4 | *-O-CH2-C6H4-OCH3 | 31.4 | 34 | $C_{22}H_{20}ClNO_4$ | 398/400 $[M+H]^+$ | 4.2 (A) |

Preparation of the End Compounds

Example 1.1

4-Benzyloxy-1-{2-[4-(3-hydroxy-piperidin-1-ylmethyl)-phenyl]-ethyl}-1H-pyridin-2-one

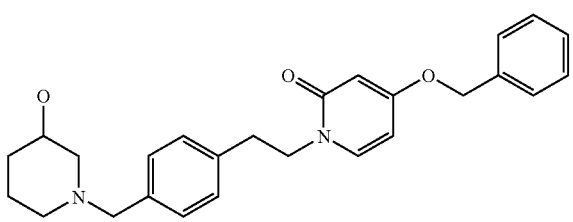

1.1a 4-Benzyloxy-1-[2-(4-bromomethyl-phenyl)-ethyl]-1H-pyridin-2-one

To 3.00 g (8.95 mmol) 4-benzyloxy-1-[2-(4-hydroxymethyl-phenyl)-ethyl]-1H-pyridin-2-one (preparation 2a) in 30 mL of DCM is added 1.26 mL (13.4 mmol) phosphorus tribromide at 0° C. The cooling bath is removed, the mixture is stirred 2 h at RT and is diluted with half saturated aqueous NaHCO$_3$-solution. The layers are separated and the aqueous layer is washed three times with DCM. The combined organic phase is dried over MgSO$_4$, filtered and the solvent is evaporated to afford the product.

Yield: 3.40 g (95% of theory)
ESI Mass spectrum: $[M+H]^+=398/400$
Retention time HPLC: 4.6 min (method A).

1.1b 4-Benzyloxy-1-{2-[4-(3-hydroxy-piperidin-1-ylmethyl)-phenyl]-ethyl}-1H-pyridin-2-one To 100 mg (0.25 mmol) 4-benzyloxy-1-[2-(4-bromomethyl-phenyl)-ethyl]-1H-pyridin-2-one (example 1.1a) in 2.00 mL of DMF is added 76 mg (0.75 mmol) 3-hydroxypiperidine. The reaction mixture is stirred 1 h at RT and is directly purified by HPLC (Zorbax Bonus-RP, C14; water (0.1% formic acid)/acetonitrile (0.1% formic acid) 95:5 to 10:90).

Yield: 78 mg (74% of theory)
ESI Mass spectrum: $[M+H]^+=419$
Retention time HPLC: 2.7 min (method B).

The following examples are prepared as described for Example 1.1b. For example 1.5-1.10 and 1.14-1.30 only 1.5 eq of the corresponding amine and additionally 2.0 eq of N-ethyl-diisopropylamine are used. For example 1.31 to 1.43 2.0 eq of the corresponding amine and 2.0 eq of N-ethyl-diisopropylamine are used.

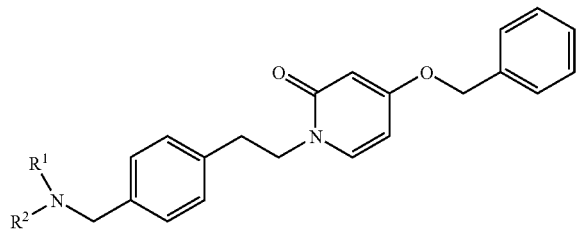
| Example | R¹R²N— | Yield (%) | Formula | MS | Retention time HPLC in min (method) | Rf-Value |
|---|---|---|---|---|---|---|
| 1.2 | (4-hydroxypiperidinyl) | 59 | $C_{26}H_{30}N_2O_3$ | 419 [M + H]⁺ | 2.7 (A) | |
| 1.3 | (4-acetamidopiperidinyl) | 36 | $C_{28}H_{33}N_3O_3$ | 460 [M + H]⁺ | 2.7 (A) | |
| 1.4 | (pyrrolidinyl) | 57 | $C_{25}H_{28}N_2O_2$ | 389 [M + H]⁺ | 2.7 (B) | |
| 1.5 | (4-propanamidopiperidinyl) | 79 | $C_{29}H_{35}N_3O_3$ | 474 [M + H]⁺ | 2.4 (B) | |
| 1.6 | (4-(N-methylacetamido)piperidinyl) | 62 | $C_{29}H_{35}N_3O_3$ | 474 [M + H]⁺ | 2.0 (B) | |
| 1.7 | (3-hydroxyazetidinyl) | 37 | $C_{24}H_{26}N_2O_3$ | 391 [M + H]⁺ | 2.4 (B) | |

-continued

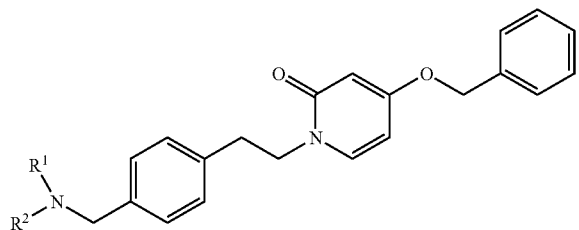

| Example | R¹R²N— | Yield (%) | Formula | MS | Retention time HPLC in min (method) | Rf-Value |
|---|---|---|---|---|---|---|
| 1.8 | (N-methyl-N-(1-piperidin-4-yl)propanamide) | 69 | $C_{30}H_{37}N_3O_3$ | 488 $[M+H]^+$ | 2.1 (B) | |
| 1.9 | (4-methyl-3-oxopiperazin-1-yl) | 76 | $C_{26}H_{29}N_3O_3$ | 432 $[M+H]^+$ | 2.8 (A) | |
| 1.10 | (3-oxopiperazin-1-yl) | 51 | $C_{25}H_{27}N_3O_3$ | 418 $[M+H]^+$ | 2.7 (A) | |
| 1.11 | (2,5-dihydro-1H-pyrrol-1-yl) | 79 | $C_{25}H_{26}N_2O_2$ | 387 $[M+H]^+$ | 2.8 (A) | |
| 1.12 | (N-ethyl-N-methylamino) | 79 | $C_{24}H_{28}N_2O_2$ | 377 $[M+H]^+$ | 2.8 (A) | |
| 1.13 | (N,N-dimethylamino) | 74 | $C_{23}H_{26}N_2O_2$ | 363 $[M+H]^+$ | 2.8 (A) | |
| 1.14 | (morpholin-4-yl) | 80 | $C_{25}H_{28}N_2O_3$ | 405 $[M+H]^+$ | | 0.7 (A) |
| 1.15 | (4-hydroxy-4-methylpiperidin-1-yl) | 79 | $C_{27}H_{32}N_2O_3$ | 433 $[M+H]^+$ | | 0.5 (A) |

-continued
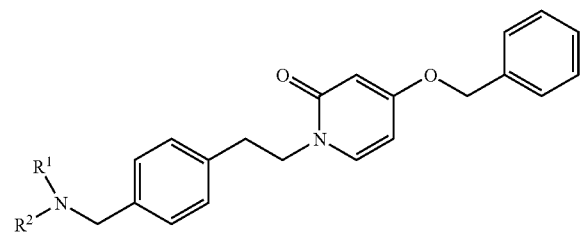
| Example | R¹R²N— | Yield (%) | Formula | MS | Retention time HPLC in min (method) | Rf-Value |
|---|---|---|---|---|---|---|
| 1.16 | (4-piperidinyl-CH₂-O-H) | 78 | $C_{27}H_{32}N_2O_3$ | 433 $[M + H]^+$ | | 0.45 (A) |
| 1.17 | (3-piperidinyl-CH₂-O-H) | 99 | $C_{27}H_{32}N_2O_3$ | 433 $[M + H]^+$ | | 0.45 (B) |
| 1.18 | (2-piperidinyl-CH₂-O-H) | 83 | $C_{27}H_{32}N_2O_3$ | 433 $[M + H]^+$ | | 0.5 (A) |
| 1.19 | (4-methoxypiperidinyl) | 85 | $C_{27}H_{32}N_2O_3$ | 433 $[M + H]^+$ | | 0.55 (A) |
| 1.20 | (3-hydroxypyrrolidinyl) | 82 | $C_{25}H_{28}N_2O_3$ | 405 $[M + H]^+$ | | 0.4 (A) |
| 1.21 | (3-pyrrolidinyl-CH₂-OH) | 68 | $C_{26}H_{30}N_2O_3$ | 419 $[M + H]^+$ | | 0.4 (A) |

-continued
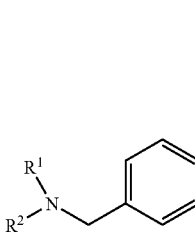
| Example | R¹R²N— | Yield (%) | Formula | MS | Retention time HPLC in min (method) | Rf-Value |
|---|---|---|---|---|---|---|
| 1.22 | 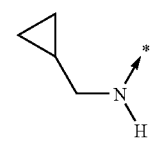 | 80 | $C_{25}H_{27}FN_2O_2$ | 407 $[M+H]^+$ | | 0.6 (A) |
| 1.23 | 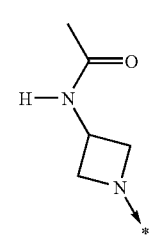 | 22 | $C_{25}H_{28}N_2O_2$ | 389 $[M+H]^+$ | | 0.5 (A) |
| 1.24 | 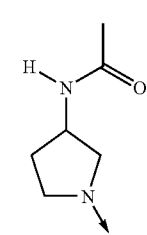 | 47 | $C_{26}H_{29}N_3O_3$ | 432 $[M+H]^+$ | 3.1 (C) | |
| 1.25 | 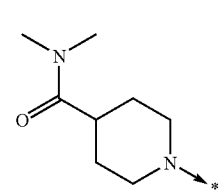 | 88 | $C_{27}H_{31}N_3O_3$ | 446 $[M+H]^+$ | | 0.5 (A) |
| 1.26 | 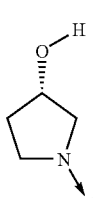 | 75 | $C_{29}H_{35}N_3O_3$ | 474 $[M+H]^+$ | | 0.55 (A) |
| 1.27 |  | 87 | $C_{25}H_{28}N_2O_3$ | 405 $[M+H]^+$ | | 0.4 (A) |

-continued
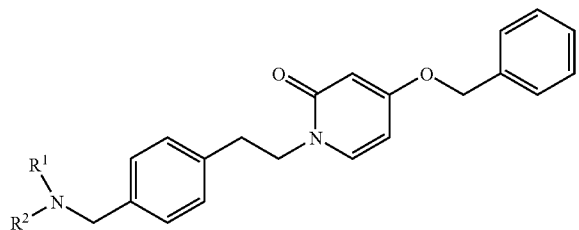
| Example | R¹R²N— | Yield (%) | Formula | MS | Retention time HPLC in min (method) | Rf-Value |
|---|---|---|---|---|---|---|
| 1.28 | | 90 | $C_{26}H_{30}N_2O_3$ | 419 $[M + H]^+$ | | 0.5 (A) |
| 1.29 | | 64 | $C_{26}H_{30}N_2O_3$ | 419 $[M + H]^+$ | | 0.5 (A) |
| 1.30 | | 79 | $C_{27}H_{29}N_3O_2$ | 428 $[M + H]^+$ | 3.2 (C) | |
| 1.31 | | 47 | $C_{27}H_{33}N_3O_2$ | 432 $[M + H]^+$ | 2.4 (C) | |
| 1.32 | | 69 | $C_{27}H_{33}N_3O_2$ | 432 $[M + H]^+$ | 2.4 (C) | |
| 1.33 | | 80 | $C_{27}H_{32}N_2O_3$ | 433 $[M + H]^+$ | 3.1 (C) | |

-continued
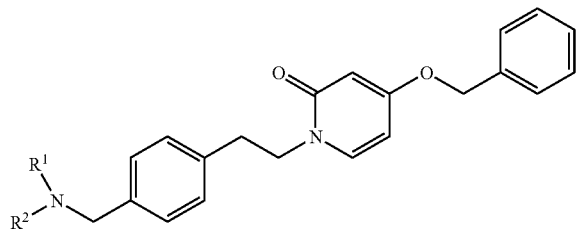
| Example | R¹R²N— | Yield (%) | Formula | MS | Retention time HPLC in min (method) | Rf-Value |
|---|---|---|---|---|---|---|
| 1.34 | 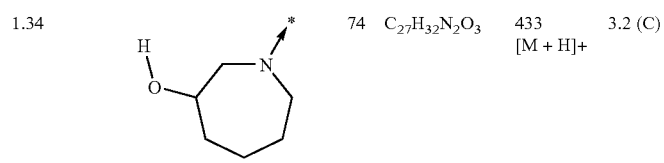 | 74 | $C_{27}H_{32}N_2O_3$ | 433 [M + H]+ | 3.2 (C) | |
| 1.35 | 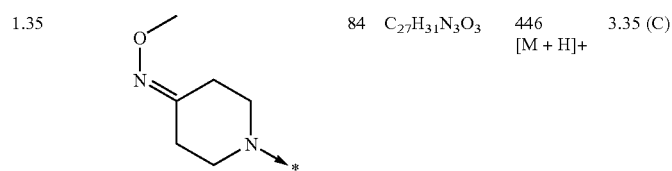 | 84 | $C_{27}H_{31}N_3O_3$ | 446 [M + H]+ | 3.35 (C) | |
| 1.36 | 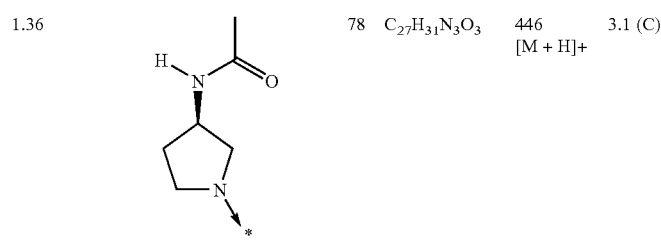 | 78 | $C_{27}H_{31}N_3O_3$ | 446 [M + H]+ | 3.1 (C) | |
| 1.37 | 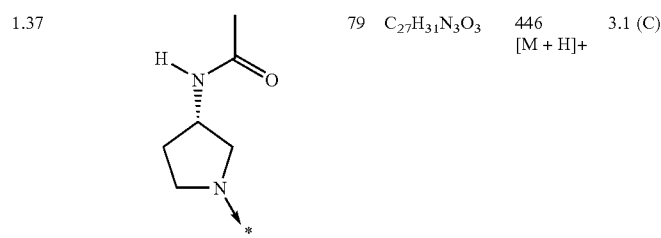 | 79 | $C_{27}H_{31}N_3O_3$ | 446 [M + H]+ | 3.1 (C) | |
| 1.38 | 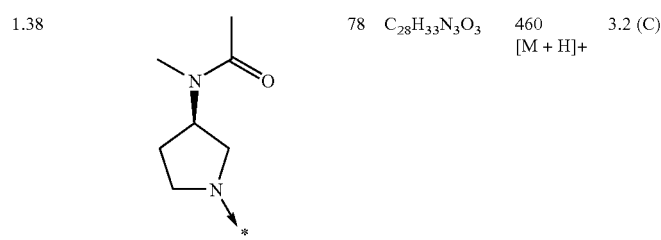 | 78 | $C_{28}H_{33}N_3O_3$ | 460 [M + H]+ | 3.2 (C) | |

-continued
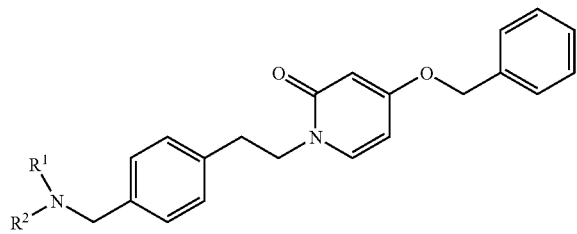
| Example | R¹R²N— | Yield (%) | Formula | MS | Retention time HPLC in min (method) | Rf-Value |
|---|---|---|---|---|---|---|
| 1.39 | | 58 | $C_{28}H_{33}N_3O_3$ | 460 [M + H]+ | 3.1 (D) | |
| 1.40 | | 17 | $C_{26}H_{29}N_3O_3$ | 432 [M + H]+ | 3.1 (C) | |
| 1.41 | | 78 | $C_{27}H_{31}N_3O_3$ | 446 [M + H]+ | 3.1 (C) | |
| 1.42 | | 55 | $C_{26}H_{31}N_3O_2$ | 418 [M + H]+ | 2.9 (C) | |
| 1.43 | | 41 | $C_{25}H_{29}N_3O_2$ | 404 [M + H]+ | 2.7 (C) | |
The following examples are prepared as described for Example 1.1b, followed by BOC-deprotection (BOC deprotection as described for example 24.2; yield given for the BOC-deprotection).

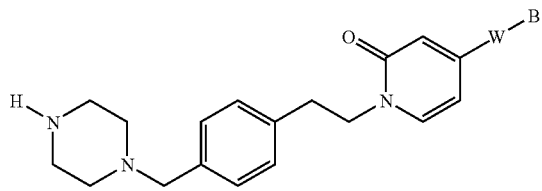

| Example | —W—B | Yield (%) | Formula | MS | Retention time HPLC in min (method) | Rf-Value |
|---|---|---|---|---|---|---|
| 1.44 | (2,4-difluorophenoxymethyl) | 72 | $C_{25}H_{27}F_2N_3O_2$ | 440 $[M+H]^+$ | 2.7 (A) | |
| 1.45 | (4-fluorophenoxymethyl) | 59 | $C_{25}H_{28}FN_3O_2$ | 422 $[M+H]^+$ | 2.3 (A) | |
| 1.46 | (3-fluorophenoxymethyl) | 100 | $C_{25}H_{28}FN_3O_2$ | 422 $[M+H]^+$ | 2.6 (A) | |
| 1.47 | (4-chlorophenoxymethyl) | 57 | $C_{25}H_{28}ClN_3O_2$ | 438/440 $[M+H]^+$ | 2.9 (A) | |
| 1.48 | (2-fluorophenoxymethyl) | 85 | $C_{25}H_{28}FN_3O_2$ | 422 $[M+H]^+$ | 2.6 (A) | |
| 1.49 | (4-bromophenoxymethyl) | 89 | $C_{25}H_{28}BrN_3O_2$ | 482/484 $[M+H]^+$ | 2.9 (A) | |
| 1.50 | (5-bromopyridin-2-yloxymethyl) | 66 | $C_{24}H_{27}BrN_4O_2$ | 483/485 $[M+H]^+$ | 2.5 (A) | |

Example 2.1

N-[1-(4-{2-[2-Oxo-4-(thiophen-2-ylmethoxy)-2H-pyridin-1-yl]-ethyl}-benzyl)-piperidin-4-yl]-acetamide

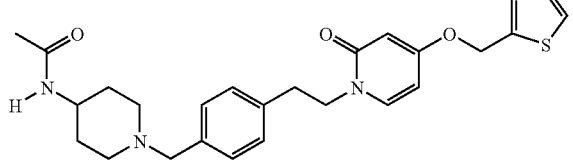

2.1a 1-[2-(4-Hydroxymethyl-phenyl)-ethyl]-4-(thiophen-2-ylmethoxy)-1H-pyridin-2-one To 400 mg (1.63 mmol) 4-hydroxy-1-[2-(4-hydroxymethyl-phenyl)-ethyl]-1H-pyridin-2-one (preparation 2b) and 385 mg (2.00 mmol) methanesulfonic acid thiophen-2-ylmethyl ester in 20 mL DMF is added 451 mg (3.26 mmol) potassium carbonate at RT. The reaction mixture is stirred overnight at RT and is diluted with 60 mL of EtOAc. The organic phase is washed three times with water, dried over MgSO$_4$, filtered and the solvent is evaporated. The residue is purified via reverse HPLC chromatography (Waters symmetry, C18; water (0.1% formic acid)/acetonitrile (0.1% formic acid) 95:5 to 10:90).

Yield: 90 mg (16% of theory)

ESI Mass spectrum: [M+H]$^+$=342

Retention time HPLC: 3.4 min (method A).

2.1b N-[1-(4-{2-[2-Oxo-4-(thiophen-2-ylmethoxy)-2H-pyridin-1-yl]-ethyl}-benzyl)-piperidin-4-yl]-acetamide To 45 mg (0.13 mmol) 1-[2-(4-hydroxymethyl-phenyl)-ethyl]-4-(thiophen-2-ylmethoxy)-1H-pyridin-2-one (example 2.1a) in 3.0 mL DCM is added 55 μL triethylamine (0.40 mmol) and subsequently 20 μL (0.26 mmol) methanesulfonyl chloride at RT. The reaction mixture is stirred 1 h at RT and then 37 mg (0.40 mmol) N-piperidin-4-yl-acetamide is added. The mixture is stirred overnight at RT and is directly added to a reverse HPLC for purification (Zorbax stable bond, C18, 7 μm; water (0.15% formic acid)/acetonitrile 95:5 to 10:90).

Yield: 22 mg (36% of theory)

ESI Mass spectrum: [M+H]$^+$=466

Retention time HPLC: 2.7 min (method A).

Example 2.2

1-[2-(4-Pyrrolidin-1-ylmethyl-phenyl)-ethyl]-4-(thiophen-2-ylmethoxy)-1H-pyridin-2-one

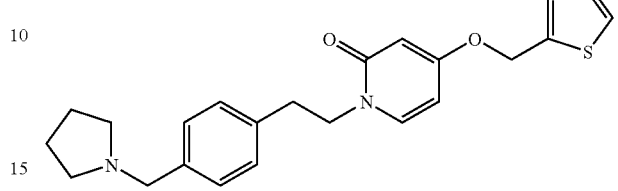

1-[2-(4-Pyrrolidin-1-ylmethyl-phenyl)-ethyl]-4-(thiophen-2-ylmethoxy)-1H-pyridin-2-one is prepared as example 2.1b from 45 mg (mg (0.13 mmol) 1-[2-(4-hydroxymethyl-phenyl)-ethyl]-4-(thiophen-2-ylmethoxy)-1H-pyridin-2-one (example 2.1a) and 22 μL (0.26 mmol) pyrrolidine. The product is purified via reverse HPLC chromatography (Waters X-Bridge; water (0.15% NH$_4$OH)/acetonitrile 95:5 to 10:90 and then Stable bond, C18; water (0.1% formic acid)/acetonitrile (0.1% formic acid) 95:5 to 10:90).

Yield: 8 mg (15% of theory)

ESI Mass spectrum: [M+H]$^+$=395

Retention time HPLC: 2.8 min (method A).

Example 2.3

1-{2-[4-((S)-3-Hydroxy-pyrrolidin-1-ylmethyl)-phenyl]-ethyl}-4-(thiophen-2-ylmethoxy)-1H-pyridin-2-one

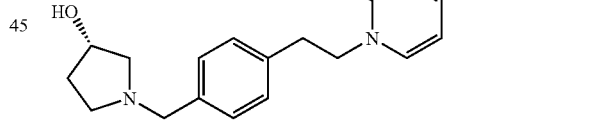

2.3a 1-[2-(4-Bromomethyl-phenyl)-ethyl]-4-(thiophen-2-ylmethoxy)-1H-pyridin-2-one To 480 mg (1.41 mmol) 1-[2-(4-hydroxymethyl-phenyl)-ethyl]-4-(thiophen-2-ylmethoxy)-1H-pyridin-2-one (example 2.1a) in 5.0 mL of DCM is added 67 μL (0.70 mmol) phosphorus tribromide at 0° C. After warming to RT, the mixture is stirred 2 h at RT and is diluted with aqueous 5% NaHCO$_3$-solution. The layers are separated and the aqueous phase is washed with DCM. The combined organic phase is washed with water, dried over MgSO$_4$, filtered and the solvent is evaporated to afford the product.

Yield: 500 mg (88% of theory)

ESI Mass spectrum: [M+H]$^+$=404/406

Retention time HPLC: 2.8 min (method E).

2.3b 1-{2-[4-((S)-3-Hydroxy-pyrrolidin-1-ylmethyl)-phenyl]-ethyl}-4-(thiophen-2-ylmethoxy)-1H-pyridin-2-one To 50 mg (0.12 mmol) 1-[2-(4-bromomethyl-phenyl)-ethyl]-4-(thiophen-2-ylmethoxy)-1H-pyridin-2-one in 5.0 mL DCM is added 23 mg (0.26 mmol) (S)-hydroxy-pyrrolidine at RT. The reaction mixture is stirred overnight at 40° C., diluted with 0.5 mL DMF and is directly added to a reverse HPLC for purification (Zorbax stable bond, C18; water (0.15% formic acid)/acetonitrile 95:5 to 5:95).

Yield: 23 mg (45% of theory)

ESI Mass spectrum: $[M+H]^+ = 411$ $R_f$-value: 0.3 (silica gel, mixture A).

The following examples are prepared as described for Example 2.3b. For the preparation of example 2.6 and 2.9 additional 5.0 eq of triethylamine are used.

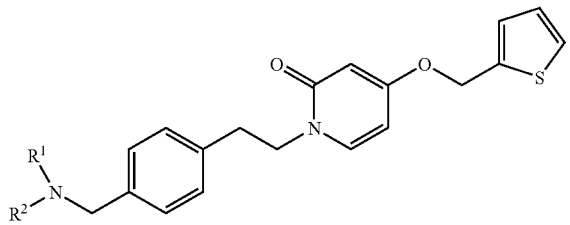

| Example | $R^1R^2N$— | Yield (%) | Formula | MS | Retention time HPLC in min (method) | $R_f$-Value |
|---|---|---|---|---|---|---|
| 2.4 | (3-acetamido-pyrrolidin-1-yl, stereo) | 27 | $C_{25}H_{29}N_3O_3S$ | 452 $[M+H]^+$ | | 0.35 (A) |
| 2.5 | (3-acetamido-pyrrolidin-1-yl, stereo) | 26 | $C_{25}H_{29}N_3O_3S$ | 452 $[M+H]^+$ | | 0.35 (A) |
| 2.6 | (3-acetamido-azetidin-1-yl) | 33 | $C_{24}H_{27}N_3O_3S$ | 438 $[M+H]^+$ | | 0.3 (A) |
| 2.7 | (4-hydroxy-4-methyl-piperidin-1-yl) | 52 | $C_{25}H_{30}N_2O_3S$ | 439 $[M+H]^+$ | | 0.3 (A) |
| 2.8 | (4-hydroxy-piperidin-1-yl) | 51 | $C_{24}H_{28}N_2O_3S$ | 425 $[M+H]^+$ | | 0.3 (A) |

-continued

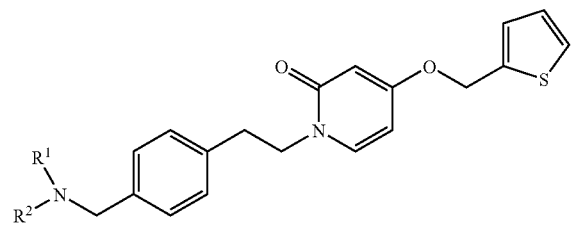

| Example | R¹R²N— | Yield (%) | Formula | MS | Retention time HPLC in min (method) | Rf-Value |
|---|---|---|---|---|---|---|
| 2.9 | H—O-azetidinyl | 24 | $C_{22}H_{24}N_2O_3S$ | 397 $[M + H]^+$ | | 0.3 (A) |
| 2.10 | morpholinyl | 46 | $C_{23}H_{26}N_2O_3S$ | 411 $[M + H]^+$ | 2.8 (A) | |
| 2.11 | dimethylamino | 66 | $C_{21}H_{24}N_2O_2S$ | 369 $[M + H]^+$ | 2.7 (A) | |
| 2.12 | 3-hydroxypyrrolidinyl | 46 | $C_{23}H_{26}N_2O_3S$ | 411 $[M + H]^+$ | 2.7 (A) | |
| 2.13 | N-methyl-N-acetyl-piperidinyl | 56 | $C_{27}H_{33}N_3O_3S$ | 480 $[M + H]^+$ | 2.7 (A) | |

Example 3.1

4-(Pyridin-2-ylmethoxy)-1-[2-(4-pyrrolidin-1-ylm-ethyl-phenyl)-ethyl]-1H-pyridin-2-one

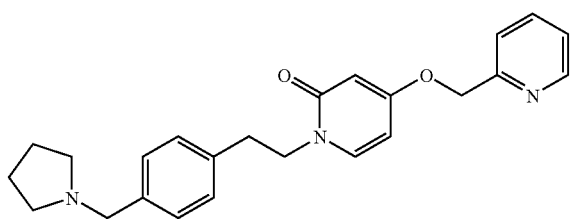

3.1a 1-[2-(4-Hydroxymethyl-phenyl)-ethyl]-4-(pyridin-2-ylmethoxy)-1H-pyridin-2-one To 500 mg (2.04 mmol) 4-hydroxy-1-[2-(4-hydroxymethyl-phenyl)-ethyl]-1H-pyridin-2-one (preparation 2b) in 20 mL DMF is added 0.62 g (2.46 mmol) 2-bromomethyl-pyridine and 0.85 g (6.12 mmol) potassium carbonate. The reaction mixture is stirred overnight at RT and is diluted with 60 mL of EtOAc. The organic phase is washed twice with water, separated, dried over $MgSO_4$ and the solvent is evaporated to afford the product.

Yield: 300 mg (44% of theory)

ESI Mass spectrum: $[M+H]^+=337$

Retention time HPLC: 2.5 min (method A).

3.1b 4-(Pyridin-2-ylmethoxy)-1-[2-(4-pyrrolidin-1-ylmethyl-phenyl)-ethyl]-1H-pyridin-2-one To 150 mg (0.45 mmol) 1-[2-(4-hydroxymethyl-phenyl)-ethyl]-4-(pyridin-2-ylmethoxy)-1H-pyridin-2-one in 5.0 mL DCM is added 186 μL (1.34 mmol) triethylamine and subsequently 69 μL (0.89 mmol) methanesulfonyl chloride at RT. The reaction mixture is stirred 1 h at RT and 74 μL (0.89 mmol) pyrrolidine is added. The mixture is stirred overnight at RT and is directly transferred to a reverse HPLC for purification (Zorbax stable bond, C18; water (0.1% formic acid)/acetonitrile (0.1% formic acid) 95:5 to 10:90).

Yield: 47 mg (27% of theory)
ESI Mass spectrum: [M+H]$^+$=390
Retention time HPLC: 2.2 min (method A).

Example 3.2

N-[1-(4-{2-[2-Oxo-4-(pyridin-2-ylmethoxy)-2H-pyridin-1-yl]-ethyl}-benzyl)-piperidin-4-yl]-acetamide

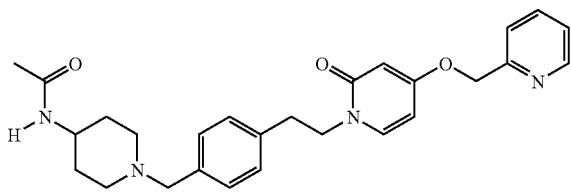

N-[1-(4-{2-[2-Oxo-4-(pyridin-2-ylmethoxy)-2H-pyridin-1-yl]-ethyl}-benzyl)-piperidin-4-yl]-acetamide is prepared as example 3.1b from 150 mg (0.45 mmol) 1-[2-(4-hydroxymethylphenyl)-ethyl]-4-(pyridin-2-ylmethoxy)-1H-pyridin-2-one (example 3.1a) and 127 mg (0.89 mmol) N-piperidin-4-yl-acetamide. The product is purified via reverse HPLC chromatography (Zorbax stable bond, C18; water (0.1% formic acid)/acetonitrile (0.1% formic acid) 95:5 to 10:90).

Yield: 60 mg (29% of theory)
ESI Mass spectrum: [M+H]$^+$=461
Retention time HPLC: 2.1 min (method A).

Example 3.3

1-{2-[4-(4-Hydroxy-4-methyl-piperidin-1-ylmethyl)-phenyl]-ethyl}-4-(pyridin-2-ylmethoxy)-1H-pyridin-2-one

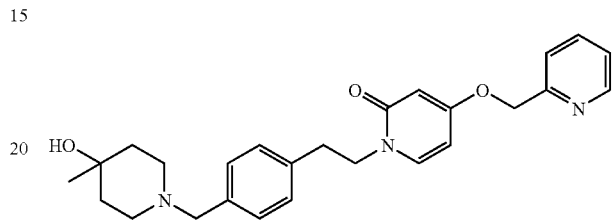

3.3a 1-[2-(4-Bromomethyl-phenyl)-ethyl]-4-(pyridin-2-ylmethoxy)-1H-pyridin-2-one To 1.20 g (3.57 mmol) 1-[2-(4-hydroxymethyl-phenyl)-ethyl]-4-(pyridin-2-ylmethoxy)-1H-pyridin-2-one (example 3.1a) in 25 mL of DCM is added at 0° C. 0.24 mL (2.50 mmol) phosphorus tribromide. After warming to RT, the mixture is stirred 2 h at RT and is diluted with 30 mL tertbutylmethyl-ether. The precipitate is collected and dried.

Yield: 1.90 g (100% of theory)
ESI Mass spectrum: [M+H]$^+$=399/401
Retention time HPLC: 3.8 min (method A).

3.3b 1-{2-[4-(4-Hydroxy-4-methyl-piperidin-1-ylmethyl)-phenyl]-ethyl}-4-(pyridin-2-ylmethoxy)-1H-pyridin-2-one To 140 mg (0.26 mmol) 1-[2-(4-bromomethyl-phenyl)-ethyl]-4-(pyridin-2-ylmethoxy)-1H-pyridin-2-one (example 3.3a) in 1.5 mL DMF is added 61 mg (0.53 mmol) 4-hydroxy-4-methylpiperidine and 0.12 mL (0.66 mmol) N-ethyl-diisopropylamine at RT. The reaction mixture is stirred 2 h at RT and is directly transferred to a reverse HPLC for purification (Waters symmetry, C18; water (0.15% formic acid)/acetonitrile 95:5 to 10:90).

Yield: 55 mg (48% of theory)
ESI Mass spectrum: [M+H]$^+$=434
Retention time HPLC: 2.2 min (method C).

The following examples are prepared as described for example 3.3b. For the preparation of example 3.4 and 3.12-3.15 4.0 eq of amine (as reagent and base) are used.

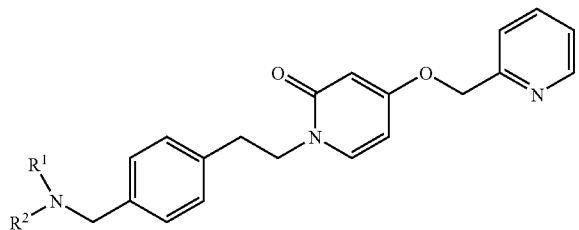
| Example | R¹R²N— | Yield (%) | Formula | MS | Retention time HPLC in min (method) |
|---|---|---|---|---|---|
| 3.4 | morpholine | 45 | $C_{24}H_{27}N_3O_3$ | 406 $[M+H]^+$ | 2.2 (C) |
| 3.5 | 4-hydroxypiperidine | 35 | $C_{25}H_{29}N_3O_3$ | 420 $[M+H]^+$ | 2.1 (C) |
| 3.6 | 3-acetamidoazetidine | 25 | $C_{25}H_{28}N_4O_3$ | 433 $[M+H]^+$ | 2.1 (C) |
| 3.7 | (R)-3-acetamidopyrrolidine | 41 | $C_{26}H_{30}N_4O_3$ | 447 $[M+H]^+$ | 2.2 (C) |
| 3.8 | (S)-3-acetamidopyrrolidine | 46 | $C_{26}H_{30}N_4O_3$ | 447 $[M+H]^+$ | 2.2 (C) |
| 3.9 | (S)-3-hydroxypyrrolidine | 35 | $C_{24}H_{27}N_3O_3$ | 406 $[M+H]^+$ | 2.1 (C) |

-continued
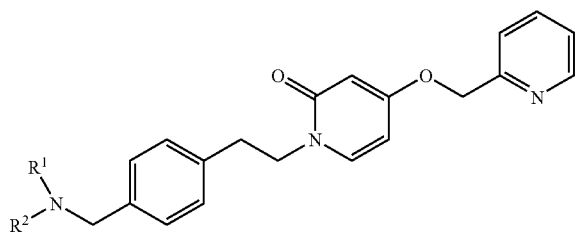
| Example | R¹R²N— | Yield (%) | Formula | MS | Retention time HPLC in min (method) |
|---|---|---|---|---|---|
| 3.10 | (S)-3-hydroxypyrrolidinyl | 36 | $C_{24}H_{27}N_3O_3$ | 406 [M + H]⁺ | 2.1 (C) |
| 3.11 | 3-hydroxyazetidinyl | 17 | $C_{23}H_{25}N_3O_3$ | 392 [M + H]⁺ | 2.1 (C) |
| 3.12 | dimethylamino | 47 | $C_{22}H_{25}N_3O_3$ | 364 [M + H]⁺ | 2.1 (C) |
| 3.13 | N-ethyl-N-methylamino | 29 | $C_{23}H_{27}N_3O_2$ | 378 [M + H]⁺ | 2.2 (C) |
| 3.14 | methylamino | 33 | $C_{21}H_{23}N_3O_2$ | 350 [M + H]⁺ | 2.1 (C) |
| 3.15 | azetidinyl | 39 | $C_{23}H_{25}N_3O_2$ | 376 [M + H]⁺ | 2.2 (C) |
| 3.16 | 4-(N,N-dimethylcarbamoyl)piperidinyl | 59 | $C_{28}H_{34}N_4O_3$ | 475 [M + H]⁺ | 2.3 (C) |

Example 4.1

1-[2-(4-Pyrrolidin-1-ylmethyl-phenyl)-ethyl]-4-(thiophen-3-ylmethoxy)-1H-pyridin-2-one

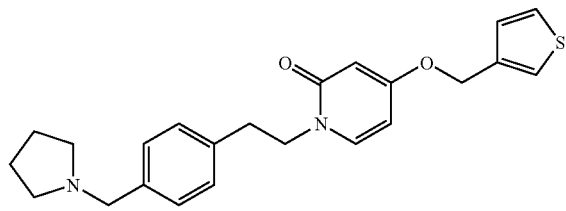

4.1a 1-[2-(4-Hydroxymethyl-phenyl)-ethyl]-4-(thiophen-3-ylmethoxy)-1H-pyridin-2-one To 582 mg (2.37 mmol) 4-hydroxy-1-[2-(4-hydroxymethyl-phenyl)-ethyl]-1H-pyridin-2-one (preparation 2b) in 10 mL DMF is added 0.70 g (3.95 mmol) 3-bromomethyl-thiophene and 1.64 g (11.9 mmol) potassium carbonate. The reaction mixture is stirred overnight at RT, filtered and is directly transferred to a reverse HPLC for purification (Zorbax stable bond C18; water (0.15% formic acid)/acetonitrile 95:5 to 10:90).

Yield: 250 mg (31% of theory)

ESI Mass spectrum: [M+H]$^+$=342

Retention time HPLC: 3.4 min (method A).

4.1b 1-[2-(4-Bromomethyl-phenyl)-ethyl]-4-(thiophen-3-ylmethoxy)-1H-pyridin-2-one To 250 mg (0.73 mmol) 1-[2-(4-hydroxymethyl-phenyl)-ethyl]-4-(pyridin-2-ylmethoxy)-1H-pyridin-2-one (example 4.1a) in 8.0 mL of DCM is added at 0° C. 48 µL (0.51 mmol) phosphorus tribromide. After warming to RT, the mixture is stirred 2 h at RT and is diluted with ice water. The layers are separated, the aqueous phase is extracted three times with DCM/MeOH. The combined organic phase is dried over MgSO$_4$, filtered and the solvent is evaporated to afford the product.

Yield: 300 mg (101% of theory)

ESI Mass spectrum: [M+H]$^+$=404/406

Retention time HPLC: 4.4 min (method A).

4.1c 1-[2-(4-Pyrrolidin-1-ylmethyl-phenyl)-ethyl]-4-(thiophen-3-ylmethoxy)-1H-pyridin-2-one To 150 mg (0.37 mmol) 1-[2-(4-bromomethyl-phenyl)-ethyl]-4-(thiophen-3-ylmethoxy)-1H-pyridin-2-one (example 4.1b) in 1.5 mL acetonitrile is added at RT 122 µL (1.48 mmol) pyrrolidine. The reaction mixture is stirred for 2 h at RT and is directly transferred to a reverse HPLC for purification (Zorbax stable bond, C18; water (0.15% formic acid)/acetonitrile 95:5 to 10:90).

Yield: 62 mg (42% of theory)

ESI Mass spectrum: [M+H]$^+$=395

Retention time HPLC: 2.8 min (method A).

Example 4.2

N-[1-(4-{2-[2-Oxo-4-(thiophen-3-ylmethoxy)-2H-pyridin-1-yl]-ethyl}-benzyl)-piperidin-4-yl]-acetamide

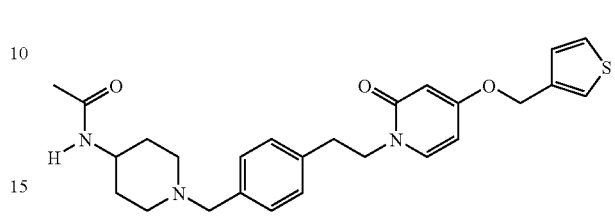

To 30 mg (0.45 mmol) 1-[2-(4-hydroxymethyl-phenyl)-ethyl]-4-(thiophen-3-ylmethoxy)-1H-pyridin-2-one (example 4.1a) in 2.0 mL DCM is added 37 µL triethylamine (0.26 mmol) and subsequently 14 µL (0.18 mmol) methanesulfonyl chloride at RT. The reaction mixture is stirred 1 h at RT and additional 18 µL triethylamine (0.13 mmol) and 7 µL (0.09 mmol) methanesulfonyl chloride is added at RT and the reaction mixture is stirred 1 h at RT. 2.0 mL acetonitrile and 25 mg (0.18 mmol) N-piperidin-4-yl-acetamide are added and the reaction mixture is stirred for 1 h. A precipitate is formed and 1 mL of DMF is added and the reaction mixture is stirred overnight. The sole product formed (HPLC-MS analysis) is 1-[2-(4-chloromethyl-phenyl)-ethyl]-4-(thiophen-3-ylmethoxy)-1H-pyridin-2-one. The reaction mixture is diluted with EtOAc, washed twice with water and is dried over MgSO$_4$. After filtration, the solvent is evaporated and 30 mg (95% yield) of 1-[2-(4-chloromethyl-phenyl)-ethyl]-4-(thiophen-3-ylmethoxy)-1H-pyridin-2-one is isolated. To 30 mg (0.09 mmol) 1-[2-(4-chloromethyl-phenyl)-ethyl]-4-(thiophen-3-ylmethoxy)-1H-pyridin-2-one in 2.0 mL DMF is added 26 mg (0.18 mmol) N-piperidin-4-yl-acetamide and 37 mg (0.27 mmol) potassium carbonate at RT. The reaction mixture is stirred overnight at RT, filtered and is directly transferred to a reverse HPLC for purification (Zorbax stable bond, C18; water (0.15% formic acid)/acetonitrile 95:5 to 10:90).

Yield: 9 mg (22% of theory)

ESI Mass spectrum: [M+H]$^+$=466

Retention time HPLC: 2.7 min (method A).

Example 5.1

4-(Furan-3-ylmethoxy)-1-[2-(4-pyrrolidin-1-ylmethyl-phenyl)-ethyl]-1H-pyridin-2-one

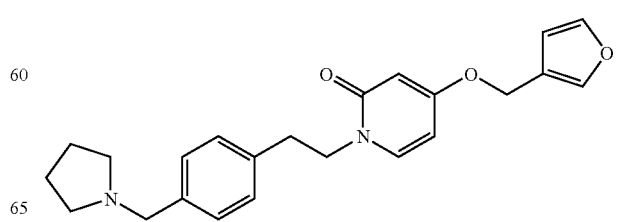

5.1a 4-(Furan-3-ylmethoxy)-1-[2-(4-hydroxymethyl-phenyl)-ethyl]-1H-pyridin-2-one To 582 mg (2.37 mmol) 4-hydroxy-1-[2-(4-hydroxymethyl-phenyl)-ethyl]-1H-pyridin-2-one (preparation 2b) in 10 mL DMF is added 0.76 g (4.74 mmol) 3-bromomethyl-furan and 0.98 g (7.12 mmol) potassium carbonate. The reaction mixture is stirred overnight at RT, filtered and is directly transferred to a reverse HPLC for purification (Zorbax stable bond C18; water (0.15% formic acid)/acetonitrile 95:5 to 10:90).
Yield: 220 mg (29% of theory)
ESI Mass spectrum: [M+H]$^+$=326
Retention time HPLC: 3.2 min (method A).

5.1b 1-[2-(4-Bromomethyl-phenyl)-ethyl]-4-(furan-3-ylmethoxy)-1H-pyridin-2-one To 220 mg (0.68 mmol) 4-(furan-3-ylmethoxy)-1-[2-(4-hydroxymethyl-phenyl)-ethyl]-1H-pyridin-2-one (example 5.1a) in 8.0 mL of DCM is added at 0° C. 44 µL (0.47 mmol) phosphorus tribromide. After warming to RT, the mixture is stirred 2 h at RT and is diluted with ice water. The layers are separated, the aqueous phase is extracted three times with DCM/MeOH. The combined organic phase is dried over MgSO$_4$, filtered and the solvent is evaporated to afford the product.
Yield: 300 mg (purity: 85%; 97% of theory)
ESI Mass spectrum: [M+H]$^+$=388/390
Retention time HPLC: 4.3 min (method A).

5.1c 4-(Furan-3-ylmethoxy)-1-[2-(4-pyrrolidin-1-ylmethyl-phenyl)-ethyl]-1H-pyridin-2-one To 150 mg (85% purity, 0.33 mmol) 1-[2-(4-bromomethyl-phenyl)-ethyl]-4-(furan-3-ylmethoxy)-1H-pyridin-2-one (example 5.1b) in 1.5 mL DCM is added 108 µL (1.31 mmol) pyrrolidine at RT. The reaction mixture is stirred for 2 h at RT and is directly transferred to a reverse HPLC for purification (Zorbax stable bond, C18; water (0.15% formic acid)/acetonitrile 95:5 to 10:90).
Yield: 76 mg (61% of theory)
ESI Mass spectrum: [M+H]$^+$=379
Retention time HPLC: 2.6 min (method A).

Example 5.2

N-[1-(4-{2-[4-(Furan-3-ylmethoxy)-2-oxo-2H-pyridin-1-yl]-ethyl}-benzyl)-piperidin-4-yl]-acetamide

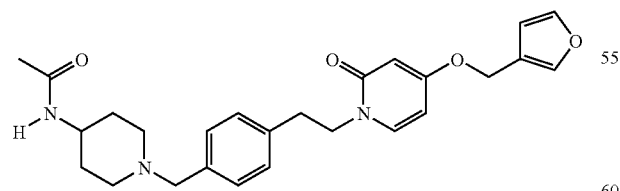

N-[1-(4-{2-[4-(Furan-3-ylmethoxy)-2-oxo-2H-pyridin-1-yl]-ethyl}-benzyl)-piperidin-4-yl]-acetamide is prepared as example 5.1c from 150 mg (85% purity, 0.33 mmol) 1-[2-(4-bromomethylphenyl)-ethyl]-4-(furan-3-ylmethoxy)-1H-pyridin-2-one (example 5.1b) and 187 mg (1.31 mmol) N-piperidin-4-yl-acetamide.

Yield: 115 mg (78% of theory)
ESI Mass spectrum: [M+H]$^+$=450
Retention time HPLC: 2.4 min (method A).

Example 6.1

4-(Furan-2-ylmethoxy)-1-[2-(4-pyrrolidin-1-ylmethyl-phenyl)-ethyl]-1H-pyridin-2-one

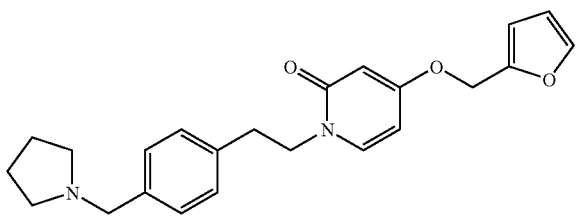

6.1a 4-(Furan-2-ylmethoxy)-1-[2-(4-hydroxymethyl-phenyl)-ethyl]-1H-pyridin-2-one To 491 mg (2.00 mmol) 4-hydroxy-1-[2-(4-hydroxymethyl-phenyl)-ethyl]-1H-pyridin-2-one (preparation 2b) in 20 mL DMF is added 0.35 g (2.00 mmol) methanesulfonic acid furan-2-ylmethyl ester and 0.83 g (6.00 mmol) potassium carbonate. The reaction mixture is stirred overnight at RT, filtered and is directly transferred to a reverse HPLC for purification (Zorbax stable bond C18; water (0.15% formic acid)/acetonitrile 95:5 to 10:90).
Yield: 80 mg (12% of theory)
ESI Mass spectrum: [M+H]$^+$=326
Retention time HPLC: 3.2 min (method A).

6.1b 1-[2-(4-Bromomethyl-phenyl)-ethyl]-4-(furan-2-ylmethoxy)-1H-pyridin-2-one To 80 mg (0.25 mmol) 4-(furan-2-ylmethoxy)-1-[2-(4-hydroxymethyl-phenyl)-ethyl]-1H-pyridin-2-one (example 6.1a) in 3.0 mL of DCM is added at 0° C. 35 µL (0.37 mmol) phosphorus tribromide. After warming to RT, the mixture is stirred 2 h at RT and is diluted with half saturated aqueous NaHCO$_3$-solution. The layers are separated, the aqueous phase is extracted three times with DCM/MeOH. The combined organic phase is dried over MgSO$_4$, filtered and the solvent is evaporated to afford the product.
Yield: 100 mg (105% of theory)
ESI Mass spectrum: [M+H]$^+$=388/390
Retention time HPLC: 4.2 min (method A).

6.1c 4-(Furan-2-ylmethoxy)-1-[2-(4-pyrrolidin-1-ylmethyl-phenyl)-ethyl]-1H-pyridin-2-one To 50 mg (0.13 mmol) 1-[2-(4-bromomethyl-phenyl)-ethyl]-4-(furan-2-ylmethoxy)-1H-pyridin-2-one in 1.5 mL DMF is added 42 µL (0.52 mmol) pyrrolidine at RT. The reaction mixture is stirred for 2 h at RT and is directly added to a reverse HPLC for purification (Zorbax stable bond, C18; water (0.15% formic acid)/acetonitrile 95:5 to 10:90).
Yield: 31 mg (64% of theory)
ESI Mass spectrum: [M+H]$^+$=379
Retention time HPLC: 2.6 min (method A).

Example 6.2

N-[1-(4-{2-[4-(Furan-2-ylmethoxy)-2-oxo-2H-pyridin-1-yl]-ethyl}-benzyl)-piperidin-4-yl]-acetamide

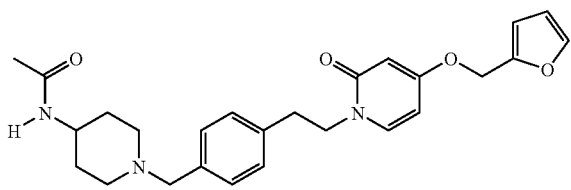

N-[1-(4-{2-[4-(Furan-2-ylmethoxy)-2-oxo-2H-pyridin-1-yl]-ethyl}-benzyl)-piperidin-4-yl]-acetamide is prepared as example 6.1c from 50 mg (0.13 mmol) 1-[2-(4-bromomethyl-phenyl)-ethyl]-4-(furan-2-ylmethoxy)-1H-pyridin-2-one (example 6.1b) and 73 mg (0.52 mmol) N-piperidin-4-yl-acetamide.

Yield: 32 mg (55% of theory)
ESI Mass spectrum: [M+H]$^+$=450
Retention time HPLC: 2.5 min (method A).

Example 7.1

4-(4-Fluoro-benzyloxy)-1-[2-(4-pyrrolidin-1-ylmethyl-phenyl)-ethyl]-1H-pyridin-2-one

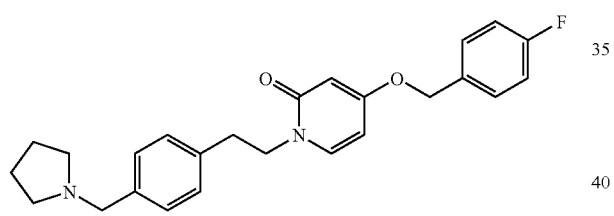

7.1a 4-(4-Fluoro-benzyloxy)-1-[2-(4-hydroxymethyl-phenyl)-ethyl]-1H-pyridin-2-one To 400 mg (1.63 mmol) 4-hydroxy-1-[2-(4-hydroxymethyl-phenyl)-ethyl]-1H-pyridin-2-one (preparation 2b) in 30 mL acetonitrile is added 0.22 mL (1.79 mmol) 1-bromomethyl-4-fluoro-benzene and 0.45 g (3.26 mmol) potassium carbonate. The reaction mixture is stirred overnight at RT. 5.0 mL DMF is added and the reaction mixture is stirred additional 24 h at RT. The reaction mixture is diluted with 60 mL of EtOAc and is washed twice with water. The organic phase is dried over MgSO$_4$, filtered and the solvent is evaporated. The residue is purified via reverse HPLC chromatography (Waters symmetry C18; water (0.15% formic acid)/acetonitrile 95:5 to 10:90).

Yield: 300 mg (52% of theory)
ESI Mass spectrum: [M+H]$^+$=354
Retention time HPLC: 3.6 min (method A).

7.1b 1-[2-(4-Bromomethyl-phenyl)-ethyl]-4-(4-fluoro-benzyloxy)-1H-pyridin-2-one To 300 mg (0.85 mmol) 4-(4-fluoro-benzyloxy)-1-[2-(4-hydroxymethyl-phenyl)-ethyl]-1H-pyridin-2-one (example 7.1a) in 5.0 mL of DCM is added 120 μL (1.27 mmol) phosphorus tribromide. The mixture is stirred 2 h at RT and is diluted with half saturated aqueous NaHCO$_3$-solution. The layers are separated and the aqueous phase is extracted three times with DCM. The combined organic phase is dried over MgSO$_4$, filtered and the solvent is evaporated to afford the product.

Yield: 250 mg (71% of theory)
ESI Mass spectrum: [M+H]$^+$=416/418
Retention time HPLC: 4.6 min (method A).

7.1c 4-(4-Fluoro-benzyloxy)-1-[2-(4-pyrrolidin-1-ylmethyl-phenyl)-ethyl]-1H-pyridin-2-one To 80 mg (0.19 mmol) 1-[2-(4-bromomethyl-phenyl)-ethyl]-4-(4-fluoro-benzyloxy)-1H-pyridin-2-one (example 7.1b) in 1.5 mL DMF is added at RT 63 μL (0.77 mmol) pyrrolidine. The reaction mixture is stirred overnight at RT and is directly transferred to a reverse HPLC for purification (Waters symmetry, C18; water (0.15% formic acid)/acetonitrile 95:5 to 10:90).

Yield: 52 mg (67% of theory)
ESI Mass spectrum: [M+H]$^+$=407
Retention time HPLC: 3.0 min (method A).

Example 7.2

N-[1-(4-{2-[4-(4-Fluoro-benzyloxy)-2-oxo-2H-pyridin-1-yl]-ethyl}-benzyl)-piperidin-4-yl]-acetamide

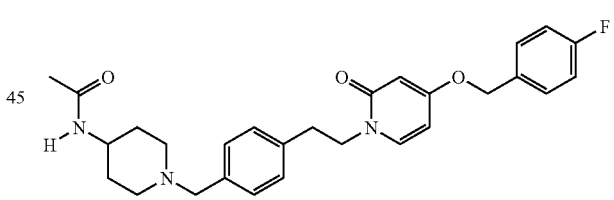

N-[1-(4-{2-[4-(4-Fluoro-benzyloxy)-2-oxo-2H-pyridin-1-yl]-ethyl}-benzyl)-piperidin-4-yl]-acetamide is prepared as example 7.1c from 80 mg (0.19 mmol) 1-[2-(4-bromomethyl-phenyl)ethyl]-4-(4-fluoro-benzyloxy)-1H-pyridin-2-one (example 7.1b), 41 mg (0.29 mmol) N-piperidin-4-yl-acetamide and 70 μL (0.40 mmol) N-ethyl-diisopropylamine as base.

Yield: 56 mg (61% of theory)
ESI Mass spectrum: [M+H]$^+$=478
Retention time HPLC: 2.8 min (method A).

Example 8.1

4-(3-Fluoro-benzyloxy)-1-[2-(4-pyrrolidin-1-ylm-ethyl-phenyl)-ethyl]-1H-pyridin-2-one

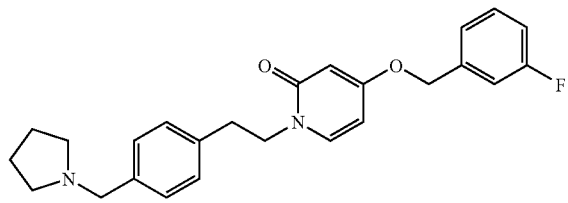

8.1a 4-(3-Fluoro-benzyloxy)-1-[2-(4-hydroxym-ethyl-phenyl)-ethyl]-1H-pyridin-2-one To 400 mg (1.63 mmol) 4-hydroxy-1-[2-(4-hydroxym-ethyl-phenyl)-ethyl]-1H-pyridin-2-one (preparation 2b) in 20 mL DMF is added 339 mg (1.79 mmol) 1-bromomethyl-3-fluoro-benzene and 0.45 g (3.26 mmol) potassium carbonate. The reaction mixture is stirred overnight at RT, diluted with 60 mL of EtOAc and is washed twice with water. The combined organic phase is dried over MgSO$_4$, filtered and the solvent is evaporated. The residue is purified via reverse HPLC chromatography (Waters symmetry C18; water (0.15% formic acid)/acetonitrile 95:5 to 10:90).

Yield: 250 mg (43% of theory)
ESI Mass spectrum: [M+H]$^+$=354
Retention time HPLC: 3.6 min (method A).

8.1b 1-[2-(4-Bromomethyl-phenyl)-ethyl]-4-(3-fluoro-benzyloxy)-1H-pyridin-2-one To 250 mg (0.71 mmol) 4-(3-fluoro-benzyloxy)-1-[2-(4-hydroxymethyl-phenyl)-ethyl]-1H-pyridin-2-one (example 8.1a) in 4.0 mL of DCM is added 100 μL (1.06 mmol) phosphorus tribromide. The mixture is stirred 2 h at RT and is diluted with half saturated aqueous NaHCO$_3$-solution. The layers are separated and the aqueous phase is extracted three times with DCM. The organic phase is dried over MgSO$_4$, filtered and the solvent is evaporated to afford the product.

Yield: 250 mg (85% of theory)
ESI Mass spectrum: [M+H]$^+$=416/418
Retention time HPLC: 2.9 min (method E).

8.1c 4-(3-Fluoro-benzyloxy)-1-[2-(4-pyrrolidin-1-ylmethyl-phenyl)-ethyl]-1H-pyridin-2-one To 120 mg (0.29 mmol) 1-[2-(4-bromomethyl-phenyl)-ethyl]-4-(3-fluoro-benzyloxy)-1H-pyridin-2-one (example 8.1b) in 2.0 mL DMF is added at RT 95 μL (1.15 mmol) pyrrolidine. The reaction mixture is stirred overnight at RT and is directly transferred to a reverse HPLC for purification (Waters symmetry; water (0.15% formic acid)/acetonitrile 95:5 to 10:90).

Yield: 48 mg (41% of theory)
ESI Mass spectrum: [M+H]$^+$=407
Retention time HPLC: 2.9 min (method A).

Example 8.2

N-[1-(4-{2-[4-(3-Fluoro-benzyloxy)-2-oxo-2H-pyridin-1-yl]-ethyl}-benzyl)-piperidin-4-yl]-acetamide

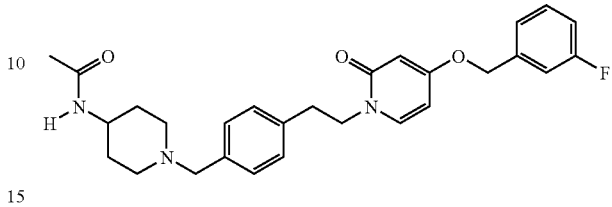

N-[1-(4-{2-[4-(3-Fluoro-benzyloxy)-2-oxo-2H-pyridin-1-yl]-ethyl}-benzyl)-piperidin-4-yl]-acetamide is prepared as example 8.1c from 120 mg (0.29 mmol) 1-[2-(4-bromomethyl-phenyl)ethyl]-4-(3-fluoro-benzyloxy)-1H-pyridin-2-one (example 8.1b), 61 mg (0.43 mmol) N-piperidin-4-yl-acetamide and 126 μL (0.72 mmol) N-ethyl-diisopropylamine as base.

Yield: 95 mg (69% of theory)
ESI Mass spectrum: [M+H]$^+$=478
Retention time HPLC: 2.7 min (method A).

Example 9.1

4-(2-Fluoro-benzyloxy)-1-[2-(4-pyrrolidin-1-ylm-ethyl-phenyl)-ethyl]-1H-pyridin-2-one

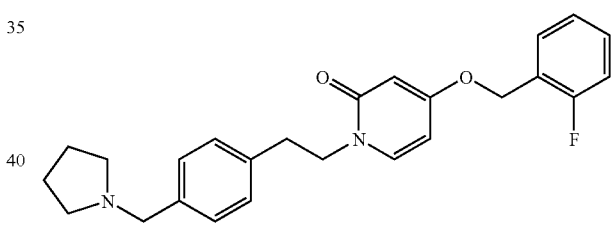

9.1a 4-(2-Fluoro-benzyloxy)-1-[2-(4-hydroxym-ethyl-phenyl)-ethyl]-1H-pyridin-2-one To 400 mg (1.63 mmol) 4-hydroxy-1-[2-(4-hydroxym-ethyl-phenyl)-ethyl]-1H-pyridin-2-one (preparation 2b) in 20 mL DMF is added 216 μL (1.79 mmol) 1-bromomethyl-2-fluoro-benzene and 0.45 g (3.26 mmol) potassium carbonate. The reaction mixture is stirred overnight at RT, diluted with 60 mL of EtOAc and is washed twice with water. The combined organic phase is dried over MgSO$_4$, filtered and the solvent is evaporated. The residue is purified via reverse HPLC chromatography (Waters symmetry C18; water (0.15% formic acid)/acetonitrile 95:5 to 10:90).

Yield: 250 mg (43% of theory)
ESI Mass spectrum: [M+H]$^+$=354
Retention time HPLC: 3.5 min (method A).

9.1b 1-[2-(4-Bromomethyl-phenyl)-ethyl]-4-(2-fluoro-benzyloxy)-1H-pyridin-2-one To 250 mg (0.71 mmol) 4-(2-fluoro-benzyloxy)-1-[2-(4-hydroxymethyl-phenyl)-ethyl]-1H-pyridin-2-one (example 9.1a) in 4.0 mL of DCM is added 100 µL (1.06 mmol) phosphorus tribromide. The mixture is stirred 2 h at RT and is diluted with half saturated aqueous NaHCO$_3$-solution. The layers are separated and the aqueous phase is extracted three times with DCM. The combined organic phase is dried over MgSO$_4$, filtered and the solvent is evaporated to afford the product.

Yield: 200 mg (68% of theory)

ESI Mass spectrum: [M+H]$^+$=416/418

Retention time HPLC: 2.9 min (method E).

9.1c 4-(2-Fluoro-benzyloxy)-1-[2-(4-pyrrolidin-1-ylmethyl-phenyl)-ethyl]-1H-pyridin-2-one To 80 mg (0.19 mmol) 1-[2-(4-Bromomethyl-phenyl)-ethyl]-4-(2-fluoro-benzyloxy)-1H-pyridin-2-one (example 9.1b) in 1.5 mL DMF is added at RT 63 µL (0.77 mmol) pyrrolidine. The reaction mixture is stirred overnight at RT and is directly transferred to a reverse HPLC for purification (Zorbax stable bond, C18; water (0.15% formic acid)/acetonitrile 95:5 to 10:90).

Yield: 69 mg (88% of theory)

ESI Mass spectrum: [M+H]$^+$=407

Retention time HPLC: 2.8 min (method A).

Example 9.2

N-[1-(4-{2-[4-(2-Fluoro-benzyloxy)-2-oxo-2H-pyridin-1-yl]-ethyl}-benzyl)-piperidin-4-yl]-acetamide

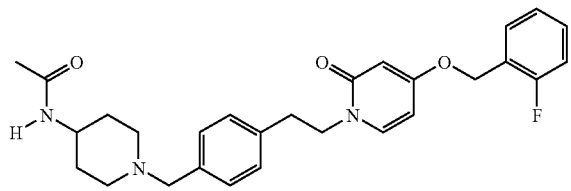

N-[1-(4-{2-[4-(2-Fluoro-benzyloxy)-2-oxo-2H-pyridin-1-yl]-ethyl}-benzyl)-piperidin-4-yl]-acetamide is prepared as example 9.1c from 80 mg (0.19 mmol) 1-[2-(4-bromomethyl-phenyl)ethyl]-4-(2-fluoro-benzyloxy)-1H-pyridin-2-one (example 9.1b), 41 mg (0.29 mmol) N-piperidin-4-yl-acetamide and 84 µL (0.48 mmol) N-ethyl-diisopropylamine as base.

Yield: 77 mg (84% of theory)

ESI Mass spectrum: [M+H]$^+$=478

Retention time HPLC: 2.7 min (method A).

Example 10.1

4-(Pyridin-4-ylmethoxy)-1-[2-(4-pyrrolidin-1-ylmethyl-phenyl)-ethyl]-1H-pyridin-2-one

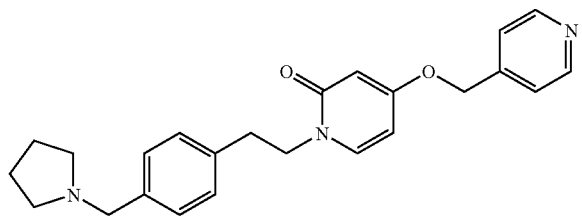

10.1a 1-[2-(4-Hydroxymethyl-phenyl)-ethyl]-4-(pyridin-4-ylmethoxy)-1H-pyridin-2-one To 400 mg (1.63 mmol) 4-hydroxy-1-[2-(4-hydroxymethyl-phenyl)-ethyl]-1H-pyridin-2-one (preparation 2b) in 20 mL DMF is added 0.45 g (1.79 mmol) 4-bromomethyl-pyridine and 0.68 g (4.89 mmol) potassium carbonate. The reaction mixture is stirred overnight at RT, diluted with 60 mL of EtOAc and is washed twice with water. The organic phase is dried over MgSO$_4$, filtered and the solvent is evaporated. The residue is purified via reverse HPLC chromatography (Waters symmetry C18; water (0.15% formic acid)/acetonitrile 95:5 to 10:90).

Yield: 50 mg (9% of theory)

ESI Mass spectrum: [M+H]$^+$=337

Retention time HPLC: 2.1 min (method A).

10.1b 4-(Pyridin-4-ylmethoxy)-1-[2-(4-pyrrolidin-1-ylmethyl-phenyl)-ethyl]-1H-pyridin-2-one To 45 mg (0.13 mmol) 1-[2-(4-hydroxymethyl-phenyl)-ethyl]-4-(pyridin-4-ylmethoxy)-1H-pyridin-2-one (example 10.1a) in 3.0 mL DCM is added at RT 56 µL (0.40 mmol) triethylamine and subsequently 21 µL (0.27 mmol) methanesulfonyl chloride. The reaction mixture is stirred 1 h at RT. Additional 56 µL triethylamine (0.40 mmol) and subsequently 21 µL (0.27 mmol) methanesulfonyl chloride are added at RT and the reaction mixture is stirred for additional 1.5 h. Then 22 µL (0.27 mmol) pyrrolidine is added. The mixture is stirred overnight at RT, diluted with 50 mL DCM and is washed four times with water. The organic phase is dried over MgSO$_4$, filtered and the solvent is evaporated. The residue is purified via chromatography (silica gel; DCM/MeOH/NH$_4$OH 9:1:0.1 to 8:2:0.2).

Yield: 23 mg (44% of theory)

ESI Mass spectrum: [M+H]$^+$=390

Retention time HPLC: 2.0 min (method F).

Example 10.2

N-[1-(4-{2-[2-Oxo-4-(pyridin-4-ylmethoxy)-2H-pyridin-1-yl]-ethyl}-benzyl)-piperidin-4-yl]-acetamide

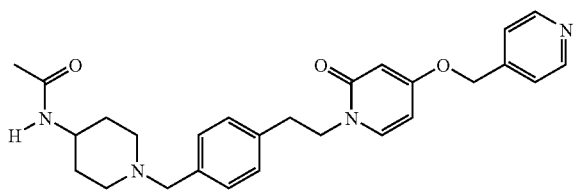

N-[1-(4-{2-[2-Oxo-4-(pyridin-4-ylmethoxy)-2H-pyridin-1-yl]-ethyl}-benzyl)-piperidin-4-yl]-acetamide is prepared as example 10.1b from 80 mg (0.24 mmol) 1-[2-(4-hydroxymethylphenyl)-ethyl]-4-(pyridin-4-ylmethoxy)-1H-pyridin-2-one (example 10.1a), 101 mg (0.71 mmol) N-piperidin-4-yl-acetamide, 99 μL triethylamine (0.71 mmol) and subsequently 37 μL (0.48 mmol) methanesulfonyl chloride. The product is purified via reverse HPLC chromatography (Zorbax stable bond, C18; water (0.1% formic acid)/acetonitrile (0.1% formic acid) 95:5 to 10:90).

Yield: 61 mg (56% of theory)
ESI Mass spectrum: [M+H]$^+$=461
Retention time HPLC: 2.0 min (method F).

Example 11.1

4-(Pyridin-3-ylmethoxy)-1-[2-(4-pyrrolidin-1-ylmethyl-phenyl)-ethyl]-1H-pyridin-2-one

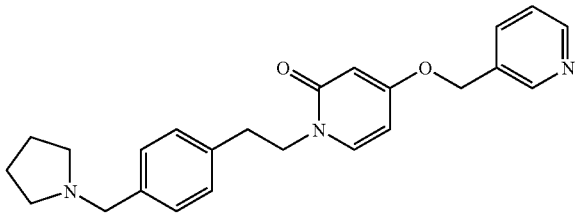

11.1a 1-[2-(4-Hydroxymethyl-phenyl)-ethyl]-4-(pyridin-3-ylmethoxy)-1H-pyridin-2-one To 500 mg (2.04 mmol) 4-hydroxy-1-[2-(4-hydroxymethyl-phenyl)-ethyl]-1H-pyridin-2-one (preparation 2b) in 20 mL DMF is added 0.62 g (2.45 mmol) 3-bromomethyl-pyridine and 0.85 g (6.12 mmol) potassium carbonate. The reaction mixture is stirred overnight at RT, diluted with 60 mL of EtOAc and is washed twice with water. The organic phase is dried over MgSO$_4$, filtered and the solvent is evaporated. The residue is purified via reverse HPLC chromatography (Zorbax stable bond, C18; water (0.15% formic acid)/acetonitrile 95:5 to 10:90).

Yield: 50 mg (7% of theory)
ESI Mass spectrum: [M+H]$^+$=337
Retention time HPLC: 2.2 min (method A).

11.1b 4-(Pyridin-3-ylmethoxy)-1-[2-(4-pyrrolidin-1-ylmethyl-phenyl)-ethyl]-1H-pyridin-2-one To 50 mg (0.15 mmol) 1-[2-(4-hydroxymethyl-phenyl)-ethyl]-4-(pyridin-3-ylmethoxy)-1H-pyridin-2-one (example 11.1a) in 3.0 mL DCM is added 62 μL triethylamine (0.45 mmol) and subsequently 23 μL (0.30 mmol) methanesulfonyl chloride at RT. The reaction mixture is stirred 1 h at RT, and then 25 μL (0.30 mmol) pyrrolidine is added. The mixture is stirred additional 2 h at RT and is directly transferred to a reverse HPLC for purification (Zorbax stable bond, C18; water (0.15% formic acid)/acetonitrile 95:5 to 10:90).

Yield: 13 mg (22% of theory)
ESI Mass spectrum: [M+H]$^+$=390
Retention time HPLC: 2.2 min (method F).

Example 12.1

4-(5-Bromo-pyridin-2-ylmethoxy)-1-[2-(4-pyrrolidin-1-ylmethyl-phenyl)-ethyl]-1H-pyridin-2-one

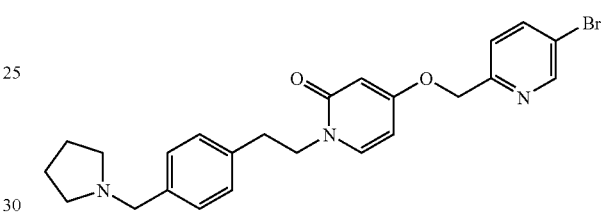

12.1a 4-(5-Bromo-pyridin-2-ylmethoxy)-1-[2-(4-hydroxymethyl-phenyl)-ethyl]-1H-pyridin-2-one To 1.23 g (5.00 mmol) 4-hydroxy-1-[2-(4-hydroxymethyl-phenyl)-ethyl]-1H-pyridin-2-one (preparation 2b) in 8.0 mL DMF is added 1.26 g (5.00 mmol) 5-bromo-2-bromomethyl-pyridine and 2.07 g (15.0 mmol) potassium carbonate. The reaction mixture is stirred overnight at RT, diluted with 80 mL of water, the formed precipitate is collected and dissolved in DMF. The solution is directly transferred to a reverse HPLC for purification (Zorbax stable bond, C18; water (0.15% formic acid)/acetonitrile 95:5 to 10:90).

Yield: 450 mg (22% of theory)
ESI Mass spectrum: [M+H]$^+$=415/417
Retention time HPLC: 3.3 min (method A).

12.1b 1-[2-(4-Bromomethyl-phenyl)-ethyl]-4-(5-bromo-pyridin-2-ylmethoxy)-1H-pyridin-2-one To 150 mg (0.36 mmol) 4-(5-bromo-pyridin-2-ylmethoxy)-1-[2-(4-hydroxymethyl-phenyl)-ethyl]-1H-pyridin-2-one (example 12.1a) in 8.0 mL of DCM is added at 0° C. 27 μL (0.29 mmol) phosphorus tribromide. The mixture is stirred 2 h at RT and the formed precipitate is collected. The product is washed with tert-butylmethylether and dried.

Yield: 180 mg (104% of theory)
ESI Mass spectrum: [M+H]$^+$=477/479/481
Retention time HPLC: 4.5 min (method A).

12.1c 4-(5-Bromo-pyridin-2-ylmethoxy)-1-[2-(4-pyrrolidin-1-ylmethyl-phenyl)-ethyl]-1H-pyridin-2-one To 90 mg (0.19 mmol) 1-[2-(4-bromomethyl-phenyl)-ethyl]-4-(5-bromo-pyridin-2-ylmethoxy)-1H-pyridin-2-one (example 12.1b) in 2.0 mL acetonitrile is added at RT 63 µL (0.75 mmol) pyrrolidine. The reaction mixture is stirred for 2 h at RT and is directly transferred to a reverse HPLC for purification (Waters symmetry, C18; water (0.15% formic acid)/acetonitrile 95:5 to 10:90).

Yield: 39 mg (44% of theory)
ESI Mass spectrum: [M+H]$^+$=468/470
Retention time HPLC: 3.0 min (method C).

Example 12.2

N-[1-(4-{2-[4-(5-Bromo-pyridin-2-ylmethoxy)-2-oxo-2H-pyridin-1-yl]-ethyl}-benzyl)-piperidin-4-yl]-acetamide

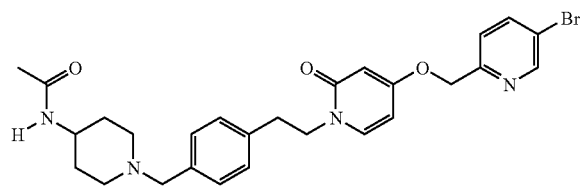

N-[1-(4-{2-[4-(5-Bromo-pyridin-2-ylmethoxy)-2-oxo-2H-pyridin-1-yl]-ethyl}-benzyl)-piperidin-4-yl]-acetamide is prepared as example 12.1c from 75 mg (0.16 mmol) 1-[2-(4-bromomethyl-phenyl)-ethyl]-4-(5-bromo-pyridin-2-ylmethoxy)-1H-pyridin-2-one (example 12.1b) and 89 mg (0.63 mmol) N-piperidin-4-yl-acetamide.

Yield: 37 mg (44% of theory)
ESI Mass spectrum: [M+H]$^+$=539/541
Retention time HPLC: 2.6 min (method C).

Example 13.1

4-(5-Methyl-pyridin-2-ylmethoxy)-1-[2-(4-pyrrolidin-1-ylmethyl-phenyl)-ethyl]-1H-pyridin-2-one

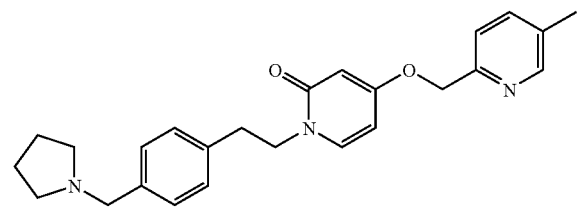

13.1a 1-[2-(4-Hydroxymethyl-phenyl)-ethyl]-4-(5-methyl-pyridin-2-ylmethoxy)-1H-pyridin-2-one To 300 mg (0.72 mmol) 4-(5-bromo-pyridin-2-ylmethoxy)-1-[2-(4-hydroxymethyl-phenyl)-ethyl]-1H-pyridin-2-one (example 12.1a) is added 25 mg (0.04 mmol) bis(triphenylphosphan)palladium(II)-chloride, 1.08 mL (2.17 mmol) 2 M aqueous Na$_2$CO$_3$-solution and a solution of 65 mg (1.08 mmol) methyl-boronic acid in 10 mL 1,4-dioxane/5 mL MeOH. The reaction mixture is refluxed for 48 h. The solvent is evaporated and the residue is dissolved in water/DCM. The layers are separated and the aqueous phase is extracted with DCM. The combined organic phase is dried over MgSO$_4$, filtered and the solvent is evaporated. The residue is purified via reverse HPLC chromatography (Waters symmetry, C18; water (0.15% formic acid)/acetonitrile 95:5 to 10:90).

Yield: 100 mg (40% of theory)
ESI Mass spectrum: [M+H]$^+$=351
Retention time HPLC: 3.2 min (method C).

13.1b 1-[2-(4-Bromomethyl-phenyl)-ethyl]-4-(5-methyl-pyridin-2-ylmethoxy)-1H-pyridin-2-one To 100 mg (0.29 mmol) 1-[2-(4-hydroxymethyl-phenyl)-ethyl]-4-(5-methyl-pyridin-2-ylmethoxy)-1H-pyridin-2-one (example 13.1a) in 5.0 mL of DCM is added 21 µL (0.23 mmol) phosphorus tribromide. The mixture is stirred 2 h at RT, diluted with DCM/MeOH and extracted twice with water. The organic phase is dried over MgSO$_4$, filtered and the solvent is evaporated to afford the product.

Yield: 110 mg (93% of theory)
ESI Mass spectrum: [M+H]$^+$=413/415
Retention time HPLC: 3.9 min (method A).

13.1c 4-(5-Methyl-pyridin-2-ylmethoxy)-1-[2-(4-pyrrolidin-1-ylmethyl-phenyl)-ethyl]-1H-pyridin-2-one To 55 mg (0.13 mmol) 1-[2-(4-bromomethyl-phenyl)-ethyl]-4-(5-methyl-pyridin-2-ylmethoxy)-1H-pyridin-2-one (example 13.1b) in 1.5 mL DMF is added at RT 44 µL (0.53 mmol) pyrrolidine. The reaction mixture is stirred for 2 h at RT and is directly transferred to a reverse HPLC for purification (Waters SunFire, C18; water (0.15% formic acid)/acetonitrile 95:5 to 10:90).

Yield: 28 mg (52% of theory)
ESI Mass spectrum: [M+H]$^+$=404
Retention time HPLC: 2.3 min (method D).

Example 13.2

N-[1-(4-{2-[4-(5-Methyl-pyridin-2-ylmethoxy)-2-oxo-2H-pyridin-1-yl]-ethyl}-benzyl)-piperidin-4-yl]-acetamide

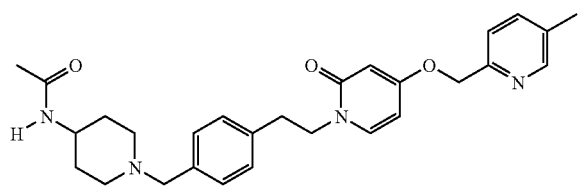

N-[1-(4-{2-[4-(5-Methyl-pyridin-2-ylmethoxy)-2-oxo-2H-pyridin-1-yl]-ethyl}-benzyl)-piperidin-4-yl]-acetamide is prepared as example 13.1c from 55 mg (0.13 mmol) 1-[2-(4-bromomethyl-phenyl)-ethyl]-4-(5-methyl-pyridin-2-ylmethoxy)-1H-pyridin-2-one (example 13.1b) and 76 mg (0.53 mmol) N-piperidin-4-yl-acetamide.

Yield: 30 mg (48% of theory)
ESI Mass spectrum: [M+H]$^+$=475
Retention time HPLC: 2.2 min (method D).

Example 14.1

4-(3-Methyl-pyridin-2-ylmethoxy)-1-[2-(4-pyrrolidin-1-ylmethyl-phenyl)-ethyl]-1H-pyridin-2-one

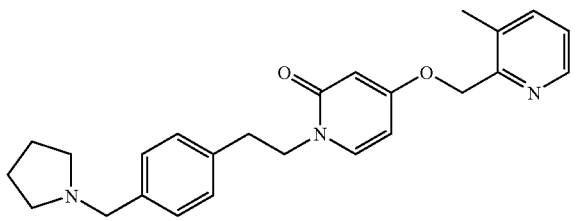

14.1a 1-[2-(4-Hydroxymethyl-phenyl)-ethyl]-4-(3-methyl-pyridin-2-ylmethoxy)-1H-pyridin-2-one To 500 mg (2.04 mmol) 4-hydroxy-1-[2-(4-hydroxymethyl-phenyl)-ethyl]-1H-pyridin-2-one (preparation 2b) in 10 mL DMF is added 472 mg (2.65 mmol) 2-chloromethyl-3-methyl-pyridine and 845 mg (6.12 mmol) potassium carbonate. The reaction mixture is stirred overnight at RT, filtered and directly transferred to a reverse HPLC for purification (Zorbax stable bond, C18; water (0.15% formic acid)/acetonitrile 95:5 to 10:90).

Yield: 350 mg (49% of theory)
ESI Mass spectrum: [M+H]$^+$=351
Retention time HPLC: 2.3 min (method A).

14.1b 1-[2-(4-Bromomethyl-phenyl)-ethyl]-4-(3-methyl-pyridin-2-ylmethoxy)-1H-pyridin-2-one To 280 mg (0.80 mmol) 1-[2-(4-hydroxymethyl-phenyl)-ethyl]-4-(3-methyl-pyridin-2-ylmethoxy)-1H-pyridin-2-one (example 14.1a) in 8.0 mL of DCM is added 75 μL (0.80 mmol) phosphorus tribromide. The mixture is stirred 2 h at RT and tert-butylmethylether is added. The formed precipitate is collected, washed with tert-butylmethylether and dried.

Yield: 370 mg (112% of theory)
ESI Mass spectrum: [M+H]$^+$=413/415
Retention time HPLC: 3.4 min (method A).

14.1c 4-(3-Methyl-pyridin-2-ylmethoxy)-1-[2-(4-pyrrolidin-1-ylmethyl-phenyl)-ethyl]-1H-pyridin-2-one To 100 mg (0.24 mmol) 1-[2-(4-bromomethyl-phenyl)-ethyl]-4-(3-methyl-pyridin-2-ylmethoxy)-1H-pyridin-2-one (example 14.1b) in 1.5 mL DMF is added 79 μL (0.97 mmol) pyrrolidine at RT. The reaction mixture is stirred for 2 h at RT and is directly transferred to a reverse HPLC for purification (Zorbax stable bond, C18; water (0.15% formic acid)/acetonitrile 95:5 to 10:90).

Yield: 28 mg (29% of theory)
ESI Mass spectrum: [M+H]$^+$=404
Retention time HPLC: 2.0 min (method A).

Example 14.2

N-[1-(4-{2-[4-(3-Methyl-pyridin-2-ylmethoxy)-2-oxo-2H-pyridin-1-yl]-ethyl}-benzyl)-piperidin-4-yl]-acetamide

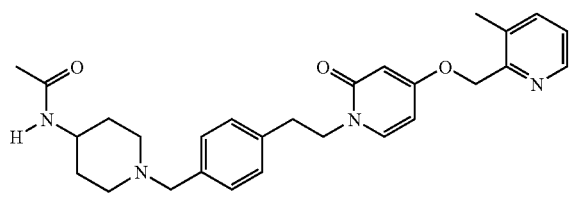

N-[1-(4-{2-[4-(3-Methyl-pyridin-2-ylmethoxy)-2-oxo-2H-pyridin-1-yl]-ethyl}-benzyl)-piperidin-4-yl]-acetamide is prepared as example 14.1c from 100 mg (0.24 mmol) 1-[2-(4-bromomethyl-phenyl)-ethyl]-4-(3-methyl-pyridin-2-ylmethoxy)-1H-pyridin-2-one (example 14.1b) and 138 mg (0.97 mmol) N-piperidin-4-yl-acetamide.

Yield: 45 mg (39% of theory)
ESI Mass spectrum: [M+H]$^+$=475
Retention time HPLC: 2.0 min (method A).

Example 15.1

4-(Pyridazin-3-ylmethoxy)-1-[2-(4-pyrrolidin-1-ylmethyl-phenyl)-ethyl]-1H-pyridin-2-one

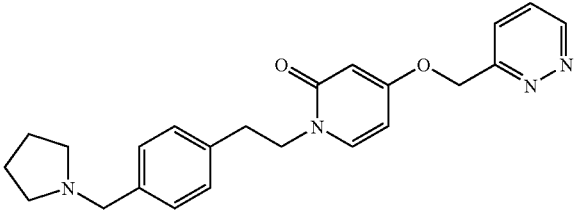

15.1a 1-[2-(4-Hydroxymethyl-phenyl)-ethyl]-4-(pyridazin-3-ylmethoxy)-1H-pyridin-2-one To 491 mg (2.00 mmol) 4-hydroxy-1-[2-(4-hydroxymethyl-phenyl)-ethyl]-1H-pyridin-2-one (preparation 2b) in 20 mL DMF is added 386 mg (3.00 mmol) 3-chloromethyl-pyridazine and 829 mg (6.00 mmol) potassium carbonate. The reaction mixture is stirred overnight at RT, diluted with water and the layers are separated. The aqueous phase is extracted twice with DCM and the combined organic phase is washed twice with water, dried over MgSO$_4$, filtered and the solvent is evaporated. The residue is purified via reverse HPLC chromatography (Zorbax stable bond, C18; water (0.15% formic acid)/acetonitrile 95:5 to 10:90).

Yield: 240 mg (36% of theory)
ESI Mass spectrum: [M+H]$^+$=338
Retention time HPLC: 2.5 min (method A).

15.1b 1-[2-(4-Bromomethyl-phenyl)-ethyl]-4-(pyridazin-3-ylmethoxy)-1H-pyridin-2-one To 240 mg (0.71 mmol) 1-[2-(4-hydroxymethyl-phenyl)-ethyl]-4-(pyridazin-3-ylmethoxy)-1H-pyridin-2-one (example 15.1a) in 5.0 mL of DCM is added at 0° C. 47 μL (0.50 mmol) phosphorus tribromide. The mixture is warmed to RT, stirred 2 h at RT and is diluted with 30 mL tertbutylmethylether. The formed precipitate is collected and dried.

Yield: 230 mg (81% of theory)
ESI Mass spectrum: [M+H]$^+$=400/402
Retention time HPLC: 3.6 min (method A).

15.1c 4-(Pyridazin-3-ylmethoxy)-1-[2-(4-pyrrolidin-1-ylmethyl-phenyl)-ethyl]-1H-pyridin-2-one To 110 mg (0.28 mmol) 1-[2-(4-bromomethyl-phenyl)-ethyl]-4-(pyridazin-3-ylmethoxy)-1H-pyridin-2-one (example 15.1b) in 1.5 mL DMF is added 92 μL (1.10 mmol) pyrrolidine at RT. The reaction mixture is stirred for 2 h at RT and is directly transferred to a reverse HPLC for purification (Waters symmetry, C18; water (0.15% formic acid)/acetonitrile 95:5 to 10:90).

Yield: 18 mg (17% of theory)
ESI Mass spectrum: [M+H]$^+$=391
Retention time HPLC: 2.1 min (method C).

Example 15.2

N-[1-(4-{2-[2-Oxo-4-(pyridazin-3-ylmethoxy)-2H-pyridin-1-yl]-ethyl}-benzyl)-piperidin-4-yl]-acetamide

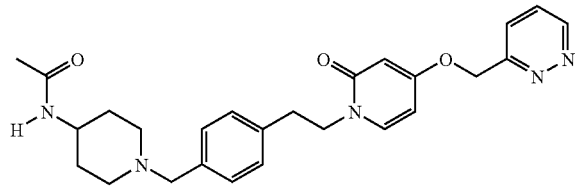

N-[1-(4-{2-[2-Oxo-4-(pyridazin-3-ylmethoxy)-2H-pyridin-1-yl]-ethyl}-benzyl)-piperidin-4-yl]-acetamide is prepared as example 15.1c from 110 mg (0.28 mmol) 1-[2-(4-bromomethylphenyl)-ethyl]-4-(pyridazin-3-ylmethoxy)-1H-pyridin-2-one (example 15.1b) and 156 mg (1.10 mmol) N-piperidin-4-yl-acetamide.

Yield: 19 mg (15% of theory)
ESI Mass spectrum: [M+H]$^+$=462
Retention time HPLC: 2.1 min (method C).

Example 16.1

4-Phenoxy-1-[2-(4-pyrrolidin-1-ylmethyl-phenyl)-ethyl]-1H-pyridin-2-one

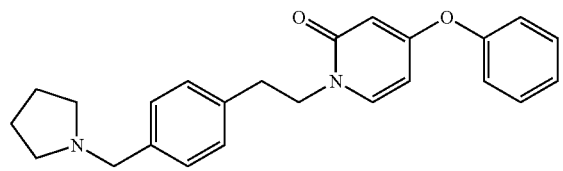

To 100 mg (0.34 mmol) 4-hydroxy-1-[2-(4-pyrrolidin-1-ylmethyl-phenyl)-ethyl]-1H-pyridin-2-one (preparation 3) in 2.0 mL 1,4-dioxane is added 43 mg (0.39) potassium-tert-butylate and the mixture is stirred 30 min at RT. 77 μL (0.34 mmol) iodo-benzene and 21 mg (0.34 mmol) Cu-powder are added and the reaction mixture is stirred 5 h at 125° C. A few drops formic acid are added and after filtration the mixture is purified via HPLC chromatography (Zorbax stable bond, C18; water (0.15% formic acid)/acetonitrile 95:5 to 5:95)

Yield: 31 mg (25% of theory)
ESI Mass spectrum: [M+H]$^+$=375
Retention time HPLC: 2.9 min (method A).

Example 16.2

N-(1-{4-[2-(2-Oxo-4-phenoxy-2H-pyridin-1-yl)-ethyl]-benzyl}-piperidin-4-yl)-acetamide

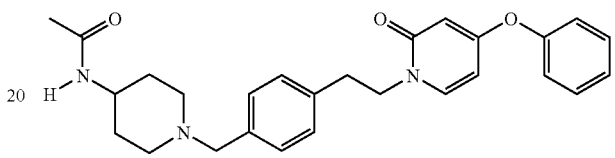

16.2a 1-[2-(4-Hydroxymethyl-phenyl)-ethyl]-4-phenoxy-1H-pyridin-2-one

To 1.87 g (10.0 mmol) 4-phenoxy-1H-pyridin-2-one in 10 mL DMF is added at 0° C. 6.52 g (20.0 mmol) cesium carbonate and after 15 min 3.93 g (15 mmol) [4-(2-iodo-ethyl)-phenyl]-methanol (preparation 1b) is added. The reaction mixture is stirred overnight at RT and is diluted with EtOAc, water and a few drops of MeOH. The layers are separated, the organic phase is washed with water, dried over MgSO$_4$, filtered and the solvent is evaporated. The residue is dissolved in MeOH/DMF and is purified via HPLC chromatography (Zorbax stable bond, C18; water (0.15% formic acid)/acetonitrile 95:5 to 10:90).

Yield: 2.3 g (72% of theory)
ESI Mass spectrum: [M+H]$^+$=322
Retention time HPLC: 2.4 min (method E).

16.2b 1-[2-(4-Bromomethyl-phenyl)-ethyl]-4-phenoxy-1H-pyridin-2-one

To 1.50 g (4.67 mmol) 1-[2-(4-hydroxymethyl-phenyl)-ethyl]-4-phenoxy-1H-pyridin-2-one (example 16.2a) in 15 mL of DCM is added at 0° C. 222 μL (2.33 mmol) phosphorus tribromide. The mixture is stirred 2 h at RT and is added to aqueous 5% NaHCO$_3$-solution. The layers are separated, the aqueous phase is extracted with DCM and the combined organic phase is washed with water, dried over MgSO$_4$, filtered and the solvent is evaporated to afford the product.

Yield: 1.42 g (79% of theory)
ESI Mass spectrum: [M+H]$^+$=384/386
R$_f$-value: 0.80 (silica gel, mixture C).

16.2c N-(1-{4-[2-(2-Oxo-4-phenoxy-2H-pyridin-1-yl)-ethyl]-benzyl}-piperidin-4-yl)-acetamide To 100 mg (0.26 mmol) 1-[2-(4-bromomethyl-phenyl)-ethyl]-4-phenoxy-1H-pyridin-2-one (example 16.2b) in 1.0 mL DMF is added at RT 148 mg (1.04 mmol) N-piperidin-4-yl-acetamide. The reaction mixture is stirred for 2 h at 50° C., filtered and is directly transferred to a reverse HPLC for purification (Waters symmetry; water (0.15% formic acid)/acetonitrile 95:5 to 5:95).

Yield: 84 mg (72% of theory)
ESI Mass spectrum: [M+H]$^+$=446
Retention time HPLC: 2.6 min (method A).

Example 16.3

1-{2-[4-(4-Hydroxy-piperidin-1-ylmethyl)-phenyl]-ethyl}-4-phenoxy-1H-pyridin-2-one

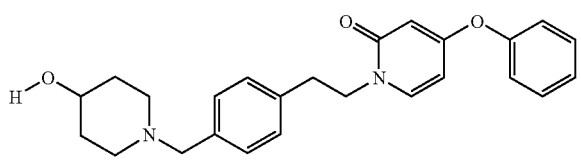

1-{2-[4-(4-Hydroxy-piperidin-1-ylmethyl)-phenyl]-ethyl}-4-phenoxy-1H-pyridin-2-one is prepared as example 16.2c from 100 mg (0.26 mmol) 1-[2-(4-bromomethyl-phenyl)-ethyl]-4-phenoxy-1H-pyridin-2-one (example 16.2b) and 105 mg (1.04 mmol) 4-hydroxy-piperidine.
Yield: 35 mg (33% of theory)
ESI Mass spectrum: [M+H]$^+$=405
Retention time HPLC: 3.4 min (method F).

Example 17.1

1-(4-{2-[2-Oxo-4-(thiophen-2-ylmethoxy)-2H-pyridin-1-yl]-ethyl}-benzyl)-piperidine-4-carboxylic Acid Dimethylamide

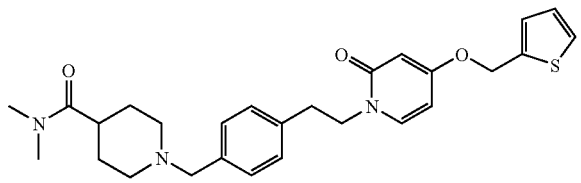

17.1a 1-{4-[2-(4-Hydroxy-2-oxo-2H-pyridin-1-yl)-ethyl]-benzyl}-piperidine-4-carboxylic Acid Dimethylamide To 500 mg (1.62 mmol) 1-[2-(4-bromomethyl-phenyl)-ethyl]-4-hydroxy-1H-pyridin-2-one (preparation 4) in 2.5 mL DMF is added at RT 482 mg (1.79) piperidine-4-carboxylic acid dimethylamide and 0.46 mL (3.25 mmol) triethylamine. The mixture is stirred overnight at RT and after filtration is purified via HPLC chromatography (Zorbax stable bond, C18; water (0.15% formic acid)/acetonitrile 95:5 to 5:95).
Yield: 200 mg (32% of theory)
ESI Mass spectrum: [M+H]$^+$=384

17.1b 1-(4-{2-[2-Oxo-4-(thiophen-2-ylmethoxy)-2H-pyridin-1-yl]-ethyl}-benzyl)-piperidine-4-carboxylic Acid Dimethylamide To 50 mg (0.13 mmol) 1-{4-[2-(4-hydroxy-2-oxo-2H-pyridin-1-yl)-ethyl]-benzyl}-piperidine-4-carboxylic acid dimethylamide (example 17.1a) in 2.0 mL DMF is added 130 µL (1 M solution in 1,4-dioxane, 0.13 mmol) 2-bromomethyl-thiophene and 45 mg (0.33 mmol) potassium carbonate at 0° C. The reaction mixture is stirred overnight at RT, filtered and the solvent is evaporated. The residue is dissolved in 2.5 mL of DMF and is purified via reverse HPLC chromatography (Waters symmetry, C18, 7 µm; water (0.15% formic acid)/acetonitrile 95:5 to 5:95).
Yield: 16 mg (26% of theory)
ESI Mass spectrum: [M+H]$^+$=480
Retention time HPLC: 2.8 min (method A).

The following examples are prepared as described in Example 17.1b.

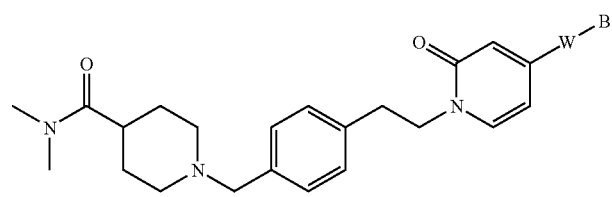

| Example | —W—B | Yield (%) | Formula | MS | Retention time HPLC in min (method) |
|---|---|---|---|---|---|
| 17.2 | *—O—CH$_2$—(3-F-phenyl) | 31 | C$_{29}$H$_{34}$FN$_3$O$_3$ | 492 [M + H]$^+$ | 2.9 (A) |

-continued

| Example | —W—B | Yield (%) | Formula | MS | Retention time HPLC in min (method) |
|---|---|---|---|---|---|
| 17.3 | *~O~C6H4~F (4-fluorobenzyloxy) | 30 | C29H34FN3O3 | 492 [M + H]+ | 2.9 (A) |
| 17.4 | *~O~CH2-(3-thienyl) | 32 | C27H33N3O3S | 480 [M + H]+ | 2.5 (H) |

Example 18.1

4-Phenethyl-1-[2-(4-pyrrolidin-1-ylmethyl-phenyl)-ethyl]-1H-pyridin-2-one

18.1a 1-[2-(4-Hydroxymethyl-phenyl)-ethyl]-4-phenethyl-1H-pyridin-2-one

To 200 mg (1.01 mmol) 4-phenethyl-1H-pyridin-2-one in 1.0 mL DMF is added at 0° C. 650 mg (2.01 mmol) cesium carbonate and the mixture is stirred 15 min at 0° C. Then 0.53 g (2.01 mmol) [4-(2-iodo-ethyl)-phenyl]-methanol (preparation 1b) is added, the mixture is warmed to RT and is stirred overnight at RT. The reaction mixture is diluted with EtOAc, water and a few drops of MeOH, the layers are separated and the organic phase is washed with water, dried over MgSO4, filtered and the solvent is evaporated. The residue is dissolved in MeOH/DMF and is purified via HPLC chromatography (Zorbax stable bond, C18; water (0.15% formic acid)/acetonitrile 95:5 to 10:90).

Yield: 150 mg (45% of theory)
ESI Mass spectrum: [M+H]+=334
Retention time HPLC: 2.8 min (method A).

18.1b 1-[2-(4-Bromomethyl-phenyl)-ethyl]-4-phenethyl-1H-pyridin-2-one

To 150 mg (0.45 mmol) 1-[2-(4-hydroxymethyl-phenyl)-ethyl]-4-phenethyl-1H-pyridin-2-one (example 18.1a) in 2.0 mL of DCM is added at 0° C. 21 μL (0.23 mmol) phosphorus tribromide. The mixture is stirred 2 h at RT and is then added to aqueous 5% NaHCO3-solution. The layers are separated, the aqueous phase is extracted with DCM. The combined organic phase is washed with water, dried over MgSO4, filtered and the solvent is evaporated to afford the product.

Yield: 120 mg (67% of theory)
Rf-value: 0.9 (silica gel, mixture E).

18.1c 4-Phenethyl-1-[2-(4-pyrrolidin-1-ylmethyl-phenyl)-ethyl]-1H-pyridin-2-one To 85 mg (0.21 mmol) 1-[2-(4-bromomethyl-phenyl)-ethyl]-4-phenethyl-1H-pyridin-2-one (example 18.1b) in 1.0 mL DMF is added 36 μL (0.43 mmol) pyrrolidine at RT. The reaction mixture is stirred overnight at RT, filtered and directly transferred to a reverse HPLC for purification (Zorbax stable bond, C18; water (0.15% formic acid)/acetonitrile 95:5 to 10:90).

Yield: 14 mg (17% of theory)
ESI Mass spectrum: [M+H]+=387
Retention time HPLC: 2.3 min (method A).

Example 19.1

4-Benzyloxy-1-[2-(4-methylaminomethyl-phenyl)-ethyl]-1H-pyridin-2-one

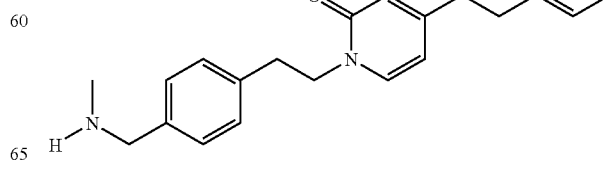

19.1a {4-[2-(4-Benzyloxy-2-oxo-2H-pyridin-1-yl)-ethyl]-benzyl}-methyl-carbamic Acid Tert-Butyl Ester To 49 mg (0.38 mmol) methyl-carbamic acid tert-butyl ester in 4.0 mL THF is added at RT 48 mg (0.43 mmol) potassium-tert-butylate. The reaction mixture is stirred 20 min at RT and then 100 mg (0.25 mmol) 4-benzyloxy-1-[2-(4-bromomethyl-phenyl)-ethyl]-1H-pyridin-2-one (example 1.1a) is added. The mixture is stirred additional 1 h at RT and is diluted with EtOAc and water. The layers are separated and the organic phase is washed with water, dried over MgSO$_4$, filtered and the solvent is evaporated to afford the product.

Yield: 100 mg (89% of theory)
ESI Mass spectrum: [M+H]$^+$=449
Retention time HPLC: 5.0 min (method G).

19.1b 4-Benzyloxy-1-[2-(4-methylaminomethyl-phenyl)-ethyl]-1H-pyridin-2-one

To 100 mg (0.22 mmol) {4-[2-(4-benzyloxy-2-oxo-2H-pyridin-1-yl)-ethyl]-benzyl}-methyl-carbamic acid tert-butyl ester (example 19.1a) in DCM is added at RT 0.70 mL trifluoro-acetic acid. The reaction mixture is stirred 2 h at RT, neutralized with aqueous saturated NaHCO$_3$-solution and is diluted with water and DCM. The layers are separated, the aqueous phase is extracted twice with DCM. The combined organic phase is dried over MgSO$_4$, filtered and the solvent is evaporated. The residue is purified via reverse HPLC chromatography (Waters symmetry, C18; water (0.1% formic acid)/acetonitrile (0.1% formic acid) 95:5 to 10:90).

Yield: 48 mg (62% of theory)
ESI Mass spectrum: [M+H]$^+$=349
Retention time HPLC: 2.8 min (method A).

Example 20.1

N-(1-{4-[2-(4-Benzyloxy-6-oxo-6H-pyrimidin-1-yl)-ethyl]-benzyl}-piperidin-4-yl)-acetamide

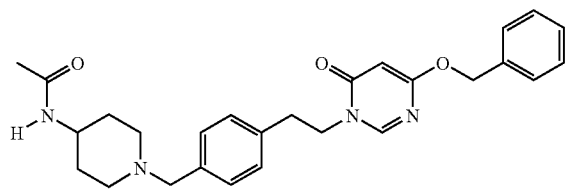

20.1a 6-Benzyloxy-3-[2-(4-hydroxymethyl-phenyl)-ethyl]-3H-pyrimidin-4-one

To 3.00 g (14.8 mmol) 6-benzyloxy-3H-pyrimidin-4-one in 15 mL DMF is added 2.66 g (15.6 mmol) [4-(2-chloro-ethyl)-phenyl]-methanol (preparation 1b) and 5.13 g (37.1 mmol) potassium carbonate. The reaction mixture is stirred 3 h at 100° C., filtered and the solvent is evaporated. The residue is put on silica gel and is purified by chromatography (silica gel; PE/EtOAc 1:1 to 2.5:7.5)

Yield: 1.77 g (36% of theory)
ESI Mass spectrum: [M+H]$^+$=337
Retention time HPLC: 2.3 min (method E).

20.1b 6-Benzyloxy-3-[2-(4-bromomethyl-phenyl)-ethyl]-3H-pyrimidin-4-one

To 200 mg (0.60 mmol) 6-benzyloxy-3-[2-(4-hydroxymethyl-phenyl)-ethyl]-3H-pyrimidin-4-one (example 20.1a) in 2.0 mL of DCM is added at 0° C. 29 μL (0.30 mmol) phosphorus tribromide. The mixture is stirred 2 h at RT and is then added to 5% aqueous NaHCO$_3$-solution. The layers are separated, the aqueous phase is extracted with DCM and the organic phase is washed with water. The combined organic phase is dried over MgSO$_4$, filtered and the solvent is evaporated to afford the product.

Yield: 240 mg (100% of theory)
ESI Mass spectrum: [M+H]$^+$=399/401
R$_f$-value: 0.4 (silica gel, mixture E).

20.1c N-(1-{4-[2-(4-Benzyloxy-6-oxo-6H-pyrimidin-1-yl)-ethyl]-benzyl}-piperidin-4-yl)-acetamide To 100 mg (0.25 mmol) 6-benzyloxy-3-[2-(4-bromomethyl-phenyl)-ethyl]-3H-pyrimidin-4-one (example 20.1b) in 1.0 mL DCM is added 71 mg (0.50 mmol) N-piperidin-4-yl-acetamide at RT. The reaction mixture is refluxed for 2 h and the solvent is evaporated. The residue is dissolved in DMF and a few drops of formic acid and is transferred to a reverse HPLC for purification (Waters symmetry, C18; water (0.15% formic acid)/acetonitrile 95:5 to 5:95).

Yield: 75 mg (65% of theory)
ESI Mass spectrum: [M+H]$^+$=461
Retention time HPLC: 2.2 min (method G).

The following examples are prepared as described in Example 20.1c (in all cases 4.0 eq. of amine are used; for 20.5 and 20.11 excess of amine is condensed into the reaction mixture). For the preparation of example 20.3-20.12 DMF is used as solvent at 50° C. and the reaction mixture is filtered upon completion and the residue is directly transferred to reverse HPLC purification. Example 20.16 is synthesized in a two step protocol (alkylation with piperazine-1-carboxylic acid tert-butyl ester then BOC deprotection as described for example 24.2; yield given for the BOC-deprotection).

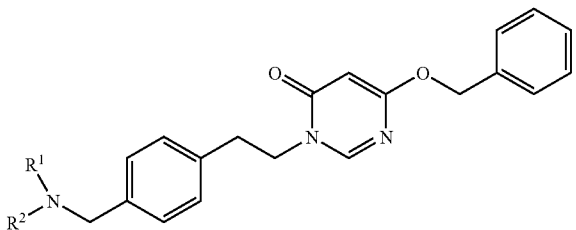
| Example | R¹R²N— | Yield (%) | Formula | MS | Retention time HPLC in min (method) |
|---|---|---|---|---|---|
| 20.2 | pyrrolidin-1-yl | 31 | $C_{24}H_{27}N_3O_2$ | 390 $[M+H]^+$ | 2.3 (G) |
| 20.3 | (3S)-3-hydroxypyrrolidin-1-yl | 46 | $C_{24}H_{27}N_3O_3$ | 406 $[M+H]^+$ | 2.4 (H) |
| 20.4 | (3R)-3-hydroxypyrrolidin-1-yl | 30 | $C_{24}H_{27}N_3O_3$ | 406 $[M+H]^+$ | 2.4 (H) |
| 20.5 | dimethylamino | 24 | $C_{22}H_{25}N_3O_3$ | 364 $[M+H]^+$ | 2.4 (H) |
| 20.6 | 3-hydroxyazetidin-1-yl | 20 | $C_{23}H_{25}N_3O_3$ | 392 $[M+H]^+$ | 2.4 (H) |
| 20.7 | cyclopropylmethylamino | 21 | $C_{24}H_{27}N_3O_3$ | 390 $[M+H]^+$ | — |
| 20.8 | morpholin-4-yl | 39 | $C_{24}H_{27}N_3O_3$ | 406 $[M+H]^+$ | 2.4 (H) |
| 20.9 | 4-methoxypiperidin-1-yl | 34 | $C_{26}H_{31}N_3O_3$ | 434 $[M+H]^+$ | 2.5 (H) |

-continued
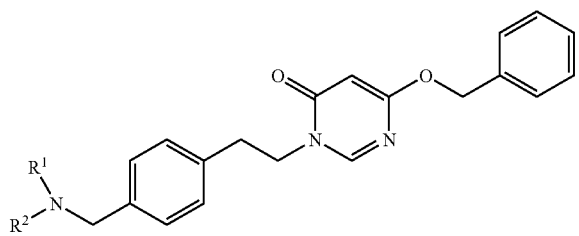
| Example | R¹R²N— | Yield (%) | Formula | MS | Retention time HPLC in min (method) |
|---|---|---|---|---|---|
| 20.10 | (4-hydroxymethyl-piperidin-1-yl) | 46 | $C_{26}H_{31}N_3O_3$ | 434 $[M+H]^+$ | 2.4 (H) |
| 20.11 | methylamino | 5 | $C_{21}H_{23}N_3O_2$ | 350 $[M+H]^+$ | 2.4 (H) |
| 20.12 | (4-hydroxy-piperidin-1-yl) | 33 | $C_{25}H_{29}N_3O_3$ | 420 $[M+H]^+$ | 2.3 (H) |
| 20.13 | (4-acetyl-piperazin-1-yl) | 72 | $C_{26}H_{30}N_4O_3$ | 447 $[M+H]+$ | 2.9 (C) |
| 20.14 | (4-formyl-piperazin-1-yl) | 63 | $C_{25}H_{28}N_4O_3$ | 433 $[M+H]+$ | 2.9 (C) |
| 20.15 | (4-methyl-piperazin-1-yl) | 71 | $C_{25}H_{30}N_4O_2$ | 419 $[M+H]+$ | 2.7 (C) |
| 20.16 | piperazin-1-yl | 62 | $C_{24}H_{28}N_4O_2$ | 405 $[M+H]+$ | 2.5 (C) |

Example 21.1

N-(1-{4-[2-(4-Benzyloxy-6-oxo-6H-pyridazin-1-yl)-ethyl]-benzyl}-piperidin-4-yl)-acetamide

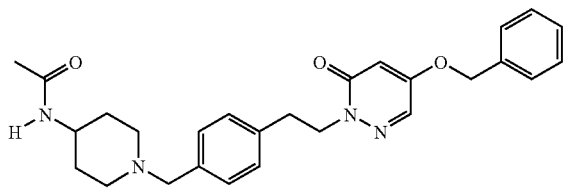

21.1a 5-Benzyloxy-2-[2-(4-hydroxymethyl-phenyl)-ethyl]-2H-pyridazin-3-one

To 200 mg (0.99 mmol) 5-benzyloxy-2H-pyridazin-3-one (preparation 5) in 1.0 mL DMF is added 645 mg (1.98 mmol) cesium carbonate and the mixture is stirred 15 min at RT. Then 518 mg (1.98 mmol) [4-(2-iodo-ethyl)-phenyl]-methanol (preparation 1b) is added and the reaction mixture is stirred overnight. The mixture is diluted with EtOAc, a few drops of MeOH and water. The layers are separated, the organic phase is washed with water, dried over MgSO$_4$, filtered and the solvent is evaporated. The precipitate is elutriated in acetone and the product is collected by filtration and dried.

Yield: 240 mg (72% of theory)
ESI Mass spectrum: [M+H]$^+$=337
Retention time HPLC: 3.7 min (method A).

21.1b 5-Benzyloxy-2-[2-(4-bromomethyl-phenyl)-ethyl]-2H-pyridazin-3-one

To 240 mg (0.71 mmol) 5-benzyloxy-2-[2-(4-hydroxymethyl-phenyl)-ethyl]-2H-pyridazin-3-one (example 21.1a) in 2.0 mL of DCM is added at 0° C. 134 µL (1.43 mmol) phosphorus tribromide. The mixture is stirred 4 h at RT, cooled to 0° C. and aqueous saturated NaHCO$_3$-solution is added until pH >7. The layers are separated, the aqueous phase is extracted with DCM and the combined organic phase is washed with water, dried over MgSO$_4$, filtered and the solvent is evaporated.

Yield: 250 mg (88% of theory)
ESI Mass spectrum: [M+H]$^+$=399/401

21.1c N-(1-{4-[2-(4-Benzyloxy-6-oxo-6H-pyridazin-1-yl)-ethyl]-benzyl}-piperidin-4-yl)-acet-amide To 125 mg (0.31 mmol) 5-benzyloxy-2-[2-(4-bromomethyl-phenyl)-ethyl]-2H-pyridazin-3-one (example 21.1b) in 2.0 mL DMF is added at RT 89 mg (0.63 mmol) N-piperidin-4-yl-acetamide and 109 µL (0.63 mmol) N-ethyl-diisopropylamine. The reaction mixture is stirred 1 h at RT and is directly transferred to reverse HPLC purification (Waters symmetry, C18; water (0.15% formic acid)/acetonitrile 95:5 to 5:95).

Yield: 107 mg (74% of theory)
ESI Mass spectrum: [M+H]$^+$=461
Retention time HPLC: 3.2 min (method C).

The following examples are prepared as described in example 21.1c. For the preparation of examples 21.2, 21.3, 21.10 and 21.11 4.0 eq. of amine is used (no additional N-ethyl-diisopropylamine added in these cases). Example 21.15 is synthesized in a two step protocol (alkylation with piperazine-1-carboxylic acid tert-butyl ester then BOC deprotection as described for example 24.2; yield given for the BOC-deprotection).

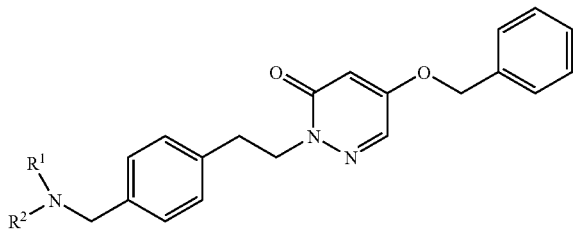

| Example | R$^1$R$^2$N— | Yield (%) | Formula | MS | Retention time HPLC in min (method) |
|---|---|---|---|---|---|
| 21.2 | (pyrrolidinyl) | 78 | C$_{24}$H$_{27}$N$_3$O$_2$ | 390 [M + H]$^+$ | 3.4 (C) |
| 21.3 | (morpholinyl) | 66 | C$_{24}$H$_{27}$N$_3$O$_3$ | 406 [M + H]$^+$ | 3.3 (C) |

-continued

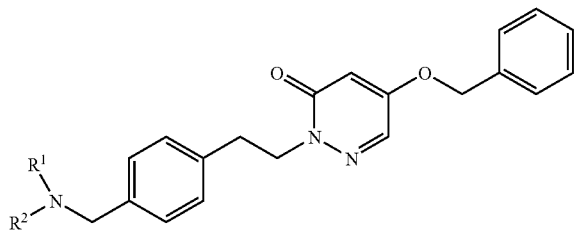

| Example | R¹R²N— | Yield (%) | Formula | MS | Retention time HPLC in min (method) |
|---|---|---|---|---|---|
| 21.4 | HO-(4-methyl-piperidin-1-yl)* | 44 | $C_{26}H_{31}N_3O_3$ | 434 $[M + H]^+$ | 3.3 (C) |
| 21.5 | HO-(piperidin-1-yl)* | 62 | $C_{25}H_{29}N_3O_3$ | 420 $[M + H]^+$ | 3.3 (C) |
| 21.6 | (acetamido-pyrrolidin-1-yl)* | 54 | $C_{26}H_{30}N_4O_3$ | 447 $[M + H]^+$ | 3.3 (C) |
| 21.7 | (3-hydroxy-pyrrolidin-1-yl)* | 49 | $C_{24}H_{27}N_3O_3$ | 406 $[M + H]^+$ | 3.2 (C) |
| 21.8 | (3-hydroxy-azetidin-1-yl)* | 43 | $C_{23}H_{25}N_3O_3$ | 392 $[M + H]^+$ | 3.3 (C) |
| 21.9 | (3-acetamido-azetidin-1-yl)* | 42 | $C_{25}H_{28}N_4O_3$ | 433 $[M + H]^+$ | 3.3 (C) |
| 21.10 | (N-ethyl-N-methyl-amino)* | 61 | $C_{23}H_{27}N_3O_2$ | 378 $[M + H]^+$ | 3.4 (C) |
| 21.11 | (cyclopropylmethyl-amino)* | 43 | $C_{24}H_{27}N_3O_2$ | 390 $[M + H]^+$ | 3.5 (C) |

-continued
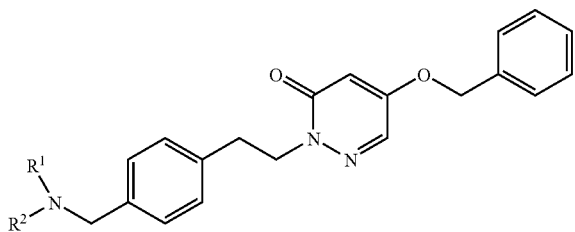
| Example | R¹R²N— | Yield (%) | Formula | MS | Retention time HPLC in min (method) |
|---|---|---|---|---|---|
| 21.12 | 4-methylpiperazinyl | 69 | $C_{25}H_{30}N_4O_2$ | 419 [M + H]+ | 2.9 (A) |
| 21.13 | 4-formylpiperazinyl | 48 | $C_{25}H_{28}N_4O_3$ | 433 [M + H]+ | 3.2 (C) |
| 21.14 | 4-acetylpiperazinyl | 43 | $C_{26}H_{30}N_4O_3$ | 447 [M + H]+ | 3.0 (C) |
| 21.15 | piperazinyl | 70 | $C_{24}H_{28}N_4O_2$ | 405 [M + H]+ | 2.7 (A) |
| 21.16 | piperidinyl | 86 | $C_{25}H_{29}N_3O_2$ | 404 [M + H]+ | 3.3 (A) |
| 21.17 | thiomorpholinyl | 87 | $C_{24}H_{27}N_3O_2S$ | 422 [M + H]+ | 3.3 (A) |
| 21.18 | 4-(cyclopropanecarbonylamino)piperidinyl | 82 | $C_{29}H_{34}N_4O_3$ | 487 [M + H]+ | 3.2 (A) |
| 21.19 | azetidinyl | 79 | $C_{23}H_{25}N_3O_2$ | 376 [M + H]+ | 3.1 (A) |

-continued

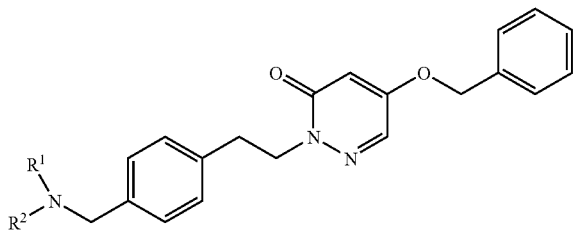

| Example | R¹R²N— | Yield (%) | Formula | MS | Retention time HPLC in min (method) |
|---|---|---|---|---|---|
| 21.20 | (3-acetamido-pyrrolidin-1-yl) | 86 | $C_{26}H_{30}N_4O_3$ | 447 [M + H]+ | 2.8 (C) |
| 21.21 | (3-hydroxy-pyrrolidin-1-yl) | 89 | $C_{24}H_{27}N_3O_3$ | 406 [M + H]⁺ | 2.8 (C) |
| 21.22 | (4-trifluoroacetamido-piperidin-1-yl) | 62 | $C_{27}H_{29}F_3N_4O_3$ | 515 [M + H]+ | 3.3 (C) |

Example 22.1

4-Benzyloxy-1-{2-oxo-2-[3-(2,2,2-trifluoro-acetyl)-2,3,4,5-tetrahydro-1H-3-benzazepin-7-yl]-ethyl}-1H-pyridin-2-one

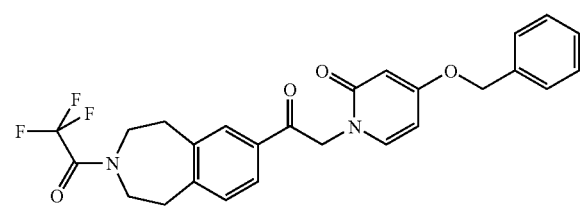

To 1.00 g (4.97 mmol) 4-benzyloxy-1H-pyridin-2-one in THF at 0° C. is added subsequently 613 mg (5.47 mmol) potassium-tert-butylate, 92 mg (0.25 mmol) tetra-butylammonium-iodide and 2.38 g (7.46 mmol) 1-[7-(2-chloro-acetyl)-1,2,4,5-tetrahydro-3-benzazepin-3-yl]-2,2,2-trifluoro-ethanone. The reaction mixture is stirred overnight at RT and the solvent is evaporated. The residue is taken up in DCM and aqueous 2M sodium hydroxide solution. The layers are separated, the organic phase is washed with water, dried over MgSO₄, filtered and the solvent is evaporated. The residue is purified via chromatography (silica gel; DCM/MeOH 95:5) and then via reverse HPLC purification (Zorbax stable bond, C18; water (0.15% formic acid)/acetonitrile 95:5 to 5:95).

Yield: 1.30 g (54% of theory)
ESI Mass spectrum: [M+H]⁺=485
Retention time HPLC: 4.3 min (method A).

Example 22.2

4-Benzyloxy-1-{2-hydroxy-2-[3-(2,2,2-trifluoro-acetyl)-2,3,4,5-tetrahydro-1H-3-benzazepin-7-yl]-ethyl}-1H-pyridin-2-one

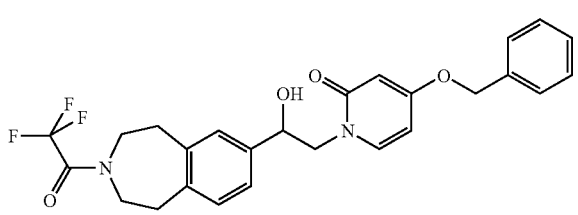

To 1.20 g (2.48 mmol) 4-benzyloxy-1-{2-oxo-2-[3-(2,2,2-trifluoro-acetyl)-2,3,4,5-tetrahydro-1H-3-benzazepin-7-yl]-ethyl}-1H-pyridin-2-one (example 22.1) in 10 mL MeOH is added 94 mg (2.48 mmol) sodium-borohydride and the mixture is stirred 2 h at RT. The solvent is evaporated, the residue is taken up in EtOAc and water. The layers are separated, the organic phase is dried over MgSO$_4$, filtered and the solvent is evaporated. The residue is purified via chromatography (silica gel; EE/MeOH 8:2).

Yield: 460 mg (38% of theory)
ESI Mass spectrum: [M+H]$^+$=487
Retention time HPLC: 4.2 min (method A).

Example 22.3

4-Benzyloxy-1-[2-oxo-2-(2,3,4,5-tetrahydro-1H-3-benzazepin-7-yl)-ethyl]-1H-pyridin-2-one

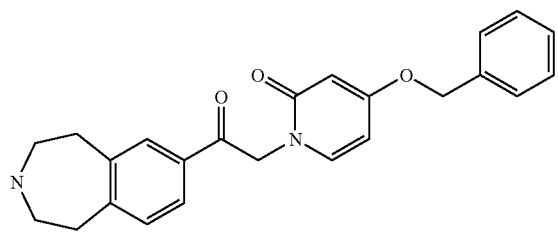

To 100 mg (0.21 mmol) 4-benzyloxy-1-{2-oxo-2-[3-(2,2,2-trifluoro-acetyl)-2,3,4,5-tetrahydro-1H-3-benzazepin-7-yl]-ethyl}-1H-pyridin-2-one (example 22.1) in 5.0 mL MeOH is added 0.41 mL (0.41 mmol) aqueous 1 M sodium hydroxide solution. The reaction mixture is stirred 2 h at RT. The solvent is evaporated, the residue is dissolved in DMF and purified via reverse HPLC chromatography (Zorbax stable bond, C18; water (0.15% formic acid)/acetonitrile 95:5 to 5:95).

Yield: 52 mg (65% of theory)
ESI Mass spectrum: [M+H]$^+$=389
Retention time HPLC: 2.75 min (method A).

Example 22.4

4-Benzyloxy-1-[2-hydroxy-2-(2,3,4,5-tetrahydro-1H-3-benzazepin-7-yl)-ethyl]-1H-pyridin-2-one

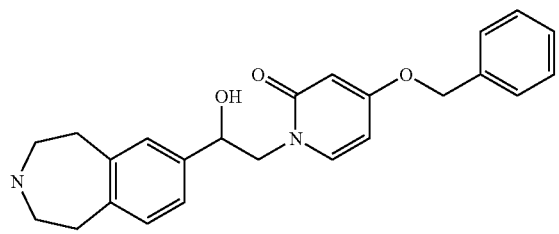

To 100 mg (0.21 mmol) 4-benzyloxy-1-{2-hydroxy-2-[3-(2,2,2-trifluoro-acetyl)-2,3,4,5-tetrahydro-1H-3-benzazepin-7-yl]-ethyl}-1H-pyridin-2-one (example 22.2) in 5.0 mL MeOH is added 0.41 mL (0.41 mmol) aqueous 1 M sodium hydroxide solution. The reaction mixture is stirred 2 h at RT. The solvent is evaporated, the residue is dissolved in DMF and purified via reverse HPLC chromatography (Zorbax stable bond, C18; water (0.15% formic acid)/acetonitrile 95:5 to 5:95).

Yield: 38 mg (47% of theory)
ESI Mass spectrum: [M+H]$^+$=391
Retention time HPLC: 2.65 min (method A).

Example 22.5

4-Benzyloxy-1-[2-(3-methyl-2,3,4,5-tetrahydro-1H-3-benzazepin-7-yl)-2-oxo-ethyl]-1H-pyridin-2-one

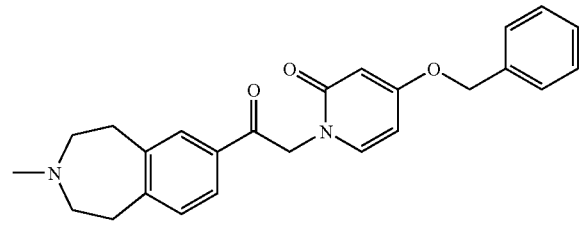

To 2.00 g (5.15 mmol) 4-benzyloxy-1-[2-oxo-2-(2,3,4,5-tetrahydro-1H-3-benzazepin-7-yl)-ethyl]-1H-pyridin-2-one (preparation 22.3) in 20 mL THF is added 0.41 mL (5.51 mmol) aqueous 37% formaldehyde solution. The mixture is acidified (pH 4-5) with acetic acid and then 1.27 g (5.97 mmol) sodium triacetoxy-borohydride is added. The reaction mixture is stirred overnight at RT, diluted with aqueous saturated NaHCO$_3$-solution until pH 7 and THF is evaporated. The residue is diluted with EtOAc, the layers are separated and the organic phase is concentrated. The residue is elutriated in tert-butylmethylether and is collected by filtration. The residue is dissolved in DMF and purified via reverse HPLC chromatography (Waters symmetry, C18; water (0.15% formic acid)/acetonitrile 95:5 to 5:95).

Yield: 1.13 g (55% of theory)
ESI Mass spectrum: [M+H]$^+$=403
Retention time HPLC: 2.5 min (method H).

Example 23.1

4-Benzyloxy-1-{2-[3-(2,2,2-trifluoro-acetyl)-2,3,4,5-tetrahydro-1H-3-benzazepin-7-yl]-ethyl}-1H-pyridin-2-one

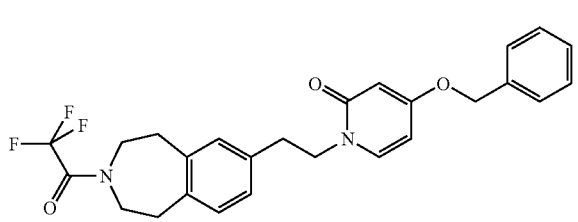

To 152 mg (0.76 mmol) 4-benzyloxy-1H-pyridin-2-one in THF at 0° C. is added subsequently 492 mg (1.51 mmol) cesium carbonate, 14 mg (0.08 mmol) tetra-butylammonium-iodide and 300 mg (0.76 mmol) 2,2,2-trifluoro-1-[7-(2-iodo-ethyl)-1,2,4,5-tetrahydro-3-benzazepin-3-yl]-ethanone (preparation 6b). The reaction mixture is stirred overnight at RT, diluted with DMF and filtered. The residue is purified via reverse HPLC chromatography (Zorbax stable bond, C18; water (0.1% formic acid)/acetonitrile (0.1% formic acid) 95:5 to 5:95).

Yield: 100 mg (28% of theory)
ESI Mass spectrum: $[M+H]^+=471$
Retention time HPLC: 4.6 min (method A).

Example 23.2

4-Benzyloxy-1-[2-(2,3,4,5-tetrahydro-1H-3-benzazepin-7-yl)-ethyl]-1H-pyridin-2-one

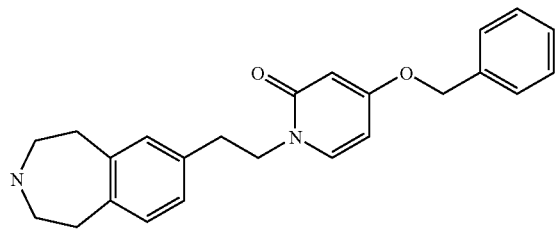

To 200 mg (0.43 mmol) 4-benzyloxy-1-{2-[3-(2,2,2-trifluoro-acetyl)-2,3,4,5-tetrahydro-1H-3-benzazepin-7-yl]-ethyl}-1H-pyridin-2-one (example 23.1) in 5.0 mL MeOH is added 0.85 mL (0.85 mmol) aqueous 1 M sodium hydroxide solution. The reaction mixture is stirred 2 h at RT. The solvent is evaporated, the residue is taken up in water and is extracted twice with DCM/MeOH. The combined organic phase is dried over MgSO₄, filtered and the solvent is evaporated to afford the product.

Yield: 150 mg (94% of theory)
ESI Mass spectrum: $[M+H]^+=375$
Retention time HPLC: 2.9 min (method A).

Example 23.3

4-Benzyloxy-1-[2-(3-methyl-2,3,4,5-tetrahydro-1H-3-benzazepin-7-yl)-ethyl]-1H-pyridin-2-one

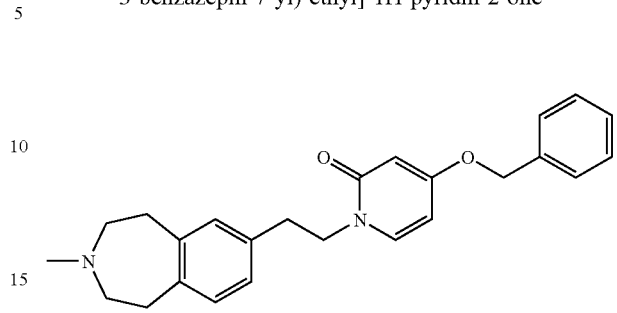

To 100 mg (0.27 mmol) 4-benzyloxy-1-[2-(2,3,4,5-tetrahydro-1H-3-benzazepin-7-yl)-ethyl]-1H-pyridin-2-one (preparation 23.2) in 5.0 mL THF is added 43 μL (0.53 mmol) aqueous 37% formaldehyde solution. The mixture is acidified with acetic acid and then 62 mg (0.29 mmol) sodium triac-etoxy-borohydride is added. The reaction mixture is stirred 3 h at RT and is diluted with aqueous saturated NaHCO₃-solution. The mixture is stirred additional 1 h at RT, the layers are separated and the aqueous phase is extracted three times with DCM/MeOH. The combined organic phase is dried over MgSO₄, filtered and the solvent is evaporated to afford the product.

Yield: 76 mg (73% of theory)
ESI Mass spectrum: $[M+H]^+=389$
Retention time HPLC: 2.9 min (method A).

Example 23.4

4-(Pyridin-2-ylmethoxy)-1-{2-[3-(2,2,2-trifluoro-acetyl)-2,3,4,5-tetrahydro-1H-3-benzazepin-7-yl]-ethyl}-1H-pyridin-2-one

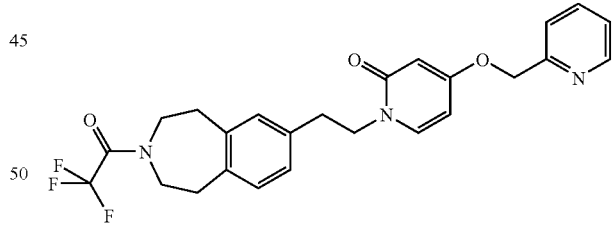

To 200 mg (0.53 mmol) 4-hydroxy-1-{2-[3-(2,2,2-trifluoro-acetyl)-2,3,4,5-tetrahydro-1H-3-benzazepin-7-yl]-ethyl}-1H-pyridin-2-one (preparation 21b) in DMF is added 145 mg (1.05 mmol) potassium carbonate and the mixture is stirred 10 min at RT before 133 mg (0.53 mmol) 2-(bromom-ethyl)-pyridine hydro-bromide is added. The reaction mixture is stirred 5 h at RT and is directly purified via reverse HPLC chromatography (Zorbax stable bond, C18; water (0.1% formic acid)/acetonitrile (0.1% formic acid) 95:5 to 5:95).

Yield: 80 mg (32% of theory)
ESI Mass spectrum: $[M+H]^+=472$
Retention time HPLC: 2.6 min (method E).

The following compounds are prepared as described for example 23.4.

aqueous phase is extracted with DCM, dried over Na$_2$SO$_4$ and the solvent is evaporated. The residue is purified via reverse

| Example | —W—B | Yield (%) | Formula | MS | Retention time HPLC in min (method) |
|---|---|---|---|---|---|
| 23.5 | * —O—CH$_2$—(2-thienyl) | 32 | C$_{24}$H$_{23}$F$_3$N$_2$O$_3$S | 477 [M + H]$^+$ | 2.8 (E) |
| 23.6 | * —O—CH$_2$—(3-thienyl) | 32 | C$_{24}$H$_{23}$F$_3$N$_2$O$_3$S | 477 [M + H]$^+$ | 2.8 (E) |
| 23.7 | * —O—CH$_2$—(4-F-phenyl) | 29 | C$_{26}$H$_{24}$F$_4$N$_2$O$_3$ | 489 [M + H]$^+$ | 4.5 (A) |
| 23.8 | * —O—CH$_2$—(5-Br-pyridin-2-yl) | 41 | C$_{25}$H$_{23}$BrF$_3$N$_3$O$_3$ | 550/552 [M + H]$^+$ | 4.4 (A) |

Example 23.9

4-(5-Methyl-pyridin-2-ylmethoxy)-1-{2-[3-(2,2,2-trifluoro-acetyl)-2,3,4,5-tetrahydro-1H-3-benzazepin-7-yl]-ethyl}-1H-pyridin-2-one To 320 mg (0.84 mmol) 4-hydroxy-1-{2-[3-(2,2,2-trifluoro-acetyl)-2,3,4,5-tetrahydro-1H-3-benzazepin-7-yl]-ethyl}-1H-pyridin-2-one (preparation 21b) in 25 mL DCM is added 129 mg (1.05 mmol) (5-methyl-pyridin-2-yl)-methanol and 221 mg (0.84 mmol) triphenylphosphane. The reaction mixture is cooled to 0° C. and 174 μL (0.84 mmol) diisopropyl azodicarboxylate is added. The reaction mixture is stirred 16 h at RT and then additional 221 mg (0.84 mmol) triphenylphosphane and 174 μL (0.84 mmol) diisopropyl azodicarboxylate is added. The mixture is stirred 2 h at RT, the solvent is evaporated and to the residue water is added. The HPLC chromatography (Zorbax stable bond, C18; water (0.1% formic acid)/acetonitrile (0.1% formic acid) 95:5 to 5:95).

Yield: 240 mg (59% of theory)

ESI Mass spectrum: [M+H]$^+$=486

Retention time HPLC: 3.9 min (method A).

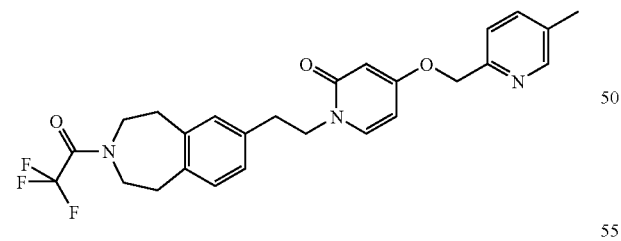

Example 23.10

4-(5-Fluoro-pyridin-2-ylmethoxy)-1-[2-(2,3,4,5-tetrahydro-1H-3-benzazepin-7-yl)-ethyl]-1H-pyridin-2-one

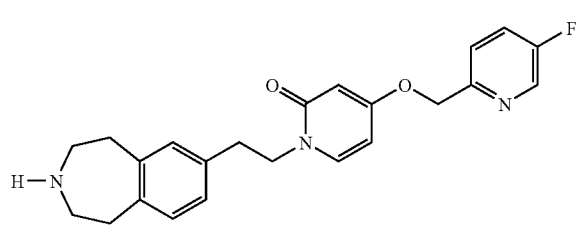

23.10a 4-(5-Fluoro-pyridin-2-ylmethoxy)-1-{2-[3-(2,2,2-trifluoro-acetyl)-2,3,4,5-tetrahydro-1H-3-benzazepin-7-yl]-ethyl}-1H-pyridin-2-one 4-(5-Fluoro-pyridin-2-ylmethoxy)-1-{2-[3-(2,2,2-trifluoro-acetyl)-2,3,4,5-tetrahydro-1H-3-benzazepin-7-yl]-ethyl}-1H-pyridin-2-one is prepared following example 23.9 from 500 mg (1.32 mmol) 4-hydroxy-1-{2-[3-(2,2,2-trifluoro-acetyl)-2,3,4,5-tetrahydro-1H-3-benzazepin-7-yl]-ethyl}-1H-pyridin-2-one (preparation 21b) and 251 mg (1.97 mmol) (5-fluoro-pyridin-2-yl)-methanol.

Yield: 380 mg (59% of theory)
ESI Mass spectrum: [M+H]⁺=490
Retention time HPLC: 4.1 min (method A).

23.10b 4-(5-Fluoro-pyridin-2-ylmethoxy)-1-[2-(2,3,4,5-tetrahydro-1H-3-benzazepin-7-yl)-ethyl]-1H-pyridin-2-one To 350 mg (0.72 mmol) 4-(5-fluoro-pyridin-2-ylmethoxy)-1-{2-[3-(2,2,2-trifluoro-acetyl)-2,3,4,5-tetrahydro-1H-3-benzazepin-7-yl]-ethyl}-1H-pyridin-2-one (preparation 23.10a) in 10 mL MeOH is added 1.1 mL (1.10 mmol) 1 M aqueous NaOH-solution. The reaction mixture is stirred overnight at RT. After filtration is the residue purified via reverse HPLC chromatography (Waters Xbridge; water (0.3% NH₄OH)/acetonitrile (0.3% NH₄OH) 95:5 to 5:95).

Yield: 240 mg (85% of theory)
ESI Mass spectrum: [M+H]⁺=394
Retention time HPLC: 2.6 min (method A).

The following compounds are prepared as described for example 23.10b

Example 23.14

4-(4-Fluoro-benzyloxy)-1-[2-(2,3,4,5-tetrahydro-1H-3-benzazepin-7-yl)-ethyl]-1H-pyridin-2-one

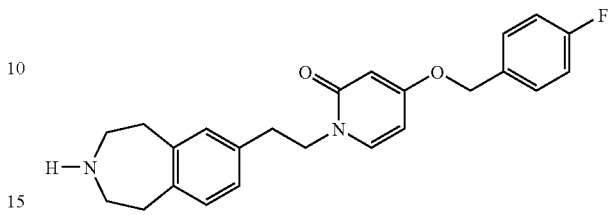

To 1.05 g (3.42 mmol) 1-[7-(2-chloro-ethyl)-1,2,4,5-tetrahydro-3-benzazepin-3-yl]-2,2,2-trifluoro-ethanone in 5 mL DMF is added at 0° C. cesium carbonate and after 15 min 600 mg (2.74 mmol) 4-(4-fluoro-benzyloxy)-1H-pyridin-2-one (preparation 22.1). The reaction mixture is stirred overnight at RT and is then added to 50 mL 1 M aqueous NaOH-solution. The mixture is stirred 2 h at RT. The aqueous phase is extracted with tert-butylmethylether. The combined organic phase is dried over MgSO₄, filtered and the solvent is evaporated. The residue is purified via reverse HPLC chromatography (Zorbax stable bond, C18; water (0.15% formic acid)/acetonitrile (0.15% formic acid) 95:5 to 5:95).

Yield: 220 mg (21% of theory)
ESI Mass spectrum: [M+H]⁺=393
Retention time HPLC: 3.3 min (method A).

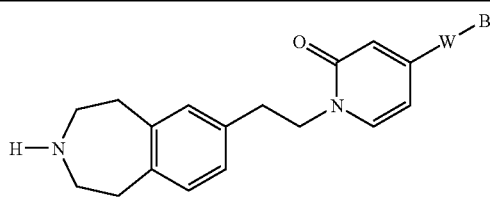

| Example | —W—B | Yield (%) | Formula | MS | Retention time HPLC in min (method) |
|---|---|---|---|---|---|
| 23.11 | ![5-methylpyridin-2-ylmethoxy] | 75 | C₂₄H₂₇N₃O₂ | 390 [M + H]⁺ | 2.3 (A) |
| 23.12 | ![thiophen-3-ylmethoxy] | 70 | C₂₂H₂₄N₂O₂S | 381 [M + H]⁺ | 3.6 (K) |
| 23.13 | ![pyridin-2-ylmethoxy] | 71 | C₂₃H₂₅N₃O₂ | 376 [M + H]⁺ | 3.0 (K) |

The following examples are prepared as described for example 23.14

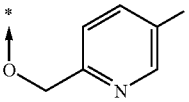

| Example | —W—B | Yield (%) | Formula | MS | Retention time HPLC in min (method) |
|---|---|---|---|---|---|
| 23.15 | 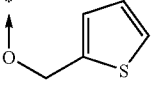 | 17 | C₂₃H₂₄BrN₃O₂ | 454/456 [M + H]⁺ | 3.1 (A) |
| 23.16 | 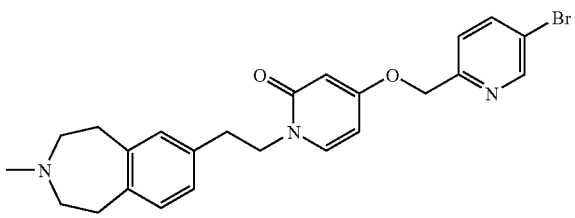 | 25 | C₂₂H₂₄N₂O₂S | 381 [M + H]⁺ | 3.1 (A) |

Example 23.17

4-(5-Bromo-pyridin-2-ylmethoxy)-1-[2-(3-methyl-2,3,4,5-tetrahydro-1H-3-benzazepin-7-yl)-ethyl]-1H-pyridin-2-one To 60 mg (0.13 mmol) 4-(5-bromo-pyridin-2-ylmethoxy)-1-[2-(2,3,4,5-tetrahydro-1H-3-benzazepin-7-yl)-ethyl]-1H-pyridin-2-one (example 23.15) in 5.0 mL THF is added 43 µL (0.53 mmol) aqueous 37% formaldehyde solution and 56 mg (0.26 mmol) sodium triacetoxy-borohydride. The mixture is acidified with pH 5 buffer solution and is stirred 48 h at RT. After filtration is the residue purified via reverse HPLC chromatography (Waters Xbridge; water (0.30% NH₄OH)/acetonitrile (0.30% NH₄OH) 95:5 to 5:95).

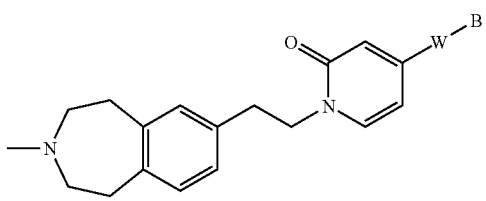

Yield: 55 mg (89% of theory)

ESI Mass spectrum: [M+H]⁺=468/470

Retention time HPLC: 2.9 min (method A).

The following compounds are prepared as described for example 23.17.

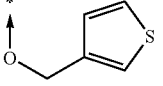

| Example | —W—B | Yield (%) | Starting material see example | Formula | MS | Retention time HPLC in min (method) |
|---|---|---|---|---|---|---|
| 23.18 | * (thiophene-CH₂-O-) | 85 | 23.12 | C₂₃H₂₆N₂O₂S | 395 [M + H]⁺ | 3.0 (A) |

-continued

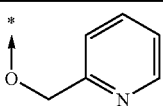

| Example | —W—B | Yield (%) | Starting material see example | Formula | MS | Retention time HPLC in min (method) |
|---|---|---|---|---|---|---|
| 23.19 | 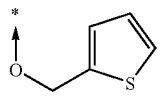 | 88 | 23.13 | $C_{24}H_{27}N_3O_2$ | 390 $[M + H]^+$ | 2.3 (A) |
| 23.20 | 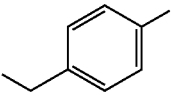 | 85 | 23.16 | $C_{23}H_{26}N_2O_2S$ | 395 $[M + H]^+$ | 2.9 (A) |
| 23.21 | 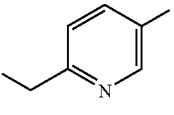 | 63 | 23.14 | $C_{25}H_{27}FN_2O_2$ | 407 $[M + H]^+$ | 3.1 (A) |
| 23.22 | 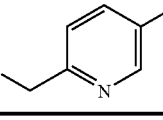 | 31 | 23.10 | $C_{24}H_{26}FN_3O_2$ | 408 $[M + H]^+$ | 2.6 (A) |
| 23.23 | | 97 | 23.11 | $C_{25}H_{29}N_3O_2$ | 404 $[M + H]+$ | 2.4 (A) |

Example 24.1

7-[2-(4-Benzyloxy-2-oxo-2H-pyridin-1-yl)-ethyl]-3,4-dihydro-1H-isoquinoline-2-carboxylic Acid Tert-Butyl Ester

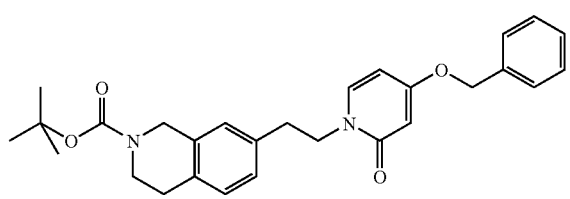

To 450 mg (2.24 mmol) 4-benzyloxy-1H-pyridin-2-one in 2.2 mL DMF at 0° C. is added 1.46 g (4.47 mmol) cesium carbonate and after 15 min 1.00 g (2.32 mmol) 7-[2-(toluene-4-sulfonyloxy)ethyl]-3,4-dihydro-1H-isoquinoline-2-carboxylic acid tert-butyl ester (preparation 7). The reaction mixture is stirred overnight at RT, filtered and is directly transferred to reverse HPLC chromatography (Zorbax stable bond, C18; water (0.15% formic acid)/acetonitrile 95:5 to 5:95).

Yield: 400 mg (39% of theory)
ESI Mass spectrum: $[M+H]^+=461$
Retention time HPLC: 3.1 min (method E).

Example 24.2

4-Benzyloxy-1-[2-(1,2,3,4-tetrahydro-isoquinolin-7-yl)-ethyl]-1H-pyridin-2-one

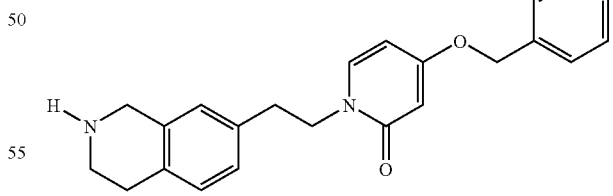

To 400 mg (0.87 mmol) 7-[2-(4-benzyloxy-2-oxo-2H-pyridin-1-yl)-ethyl]-3,4-dihydro-1H-isoquinoline-2-carboxylic acid tert-butyl ester (example 24.1) in 5.0 mL DCM is added at RT 0.5 mL trifluoroacetic acid. The reaction mixture is stirred overnight at RT and is neutralized with aqueous 5% NaHCO₃-solution. The layers are separated, the organic phase is washed with water, dried over MgSO₄, filtered and the solvent is evaporated. The residue is elutriated in tertbutylmethyether, the precipitate is collected and dried.

Yield: 250 mg (80% of theory)
ESI Mass spectrum: [M+H]$^+$=361
Retention time HPLC: 2.8 min (method A).

Example 24.3

4-Benzyloxy-1-[2-(2-methyl-1,2,3,4-tetrahydro-isoquinolin-7-yl)-ethyl]-1H-pyridin-2-one

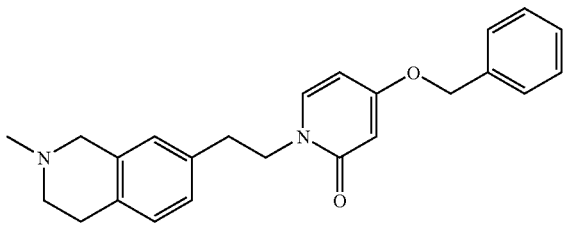

To 150 mg (0.42 mmol) 4-benzyloxy-1-[2-(1,2,3,4-tetrahydro-isoquinolin-7-yl)-ethyl]-1H-pyridin-2-one (example 24.2) in 5.0 mL THF is added 68 µL (0.83 mmol) aqueous 37% formaldehyde solution. The mixture is acidified with 3 drops of acetic acid and then 97 mg (0.46 mmol) sodium triacetoxy-borohydride is added. The reaction mixture is stirred 2 h at RT and additional 68 µL (0.83 mmol) aqueous 37% formaldehyde solution and 97 mg (0.46 mmol) sodium triacetoxy-borohydride are added. The reaction mixture is stirred overnight and additional 68 µL (0.83 mmol) aqueous 37% formaldehyde solution and 97 mg (0.46 mmol) sodium triacetoxy-borohydride is added and the reaction mixture is stirred additional 48 h at RT. The mixture is poured into aqueous 10% Na$_2$CO$_3$-solution, the layers are separated and the aqueous phase is extracted with DCM. The combined organic phase is washed a few times with water, dried over MgSO$_4$, filtered and the solvent is evaporated. The residue is purified via reverse HPLC chromatography (Zorbax stable bond, C18; water (0.15% formic acid)/acetonitrile 95:5 to 5:95).

Yield: 50 mg (32% of theory)
ESI Mass spectrum: [M+H]$^+$=375
Retention time HPLC: 2.8 min (method A).

Example 24.4

4-(Pyridin-2-ylmethoxy)-1-[2-(1,2,3,4-tetrahydro-isoquinolin-7-yl)-ethyl]-1H-pyridin-2-one

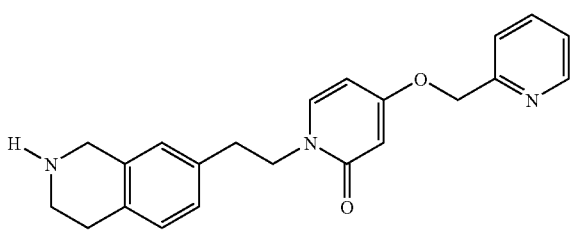

24.4a 7-{2-[2-Oxo-4-(pyridin-2-ylmethoxy)-2H-pyridin-1-yl]-ethyl}-3,4-dihydro-1H-isoquinoline-2-carboxylic Acid Tert-Butyl Ester 7-{2-[2-Oxo-4-(pyridin-2-ylmethoxy)-2H-pyridin-1-yl]-ethyl}-3,4-dihydro-1H-isoquinoline-2-carboxylic acid tert-butyl ester is prepared following example 24.1 from 530 mg (2.23 mmol) 4-(pyridin-2-ylmethoxy)-1H-pyridin-2-one (preparation 22.4) and 1.06 g (2.45 mmol) 7-[2-(toluene-4-sulfonyloxy)-ethyl]-3,4-dihydro-1H-isoquinoline-2-carboxylic acid tert-butyl ester (preparation 7).

Yield: 230 mg (22% of theory)
ESI Mass spectrum: [M+H]$^+$=462
Retention time HPLC: 3.9 min (method A).

24.4b 4-(Pyridin-2-ylmethoxy)-1-[2-(1,2,3,4-tetrahydro-isoquinolin-7-yl)-ethyl]-1H-pyridin-2-one 4-(Pyridin-2-ylmethoxy)-1-[2-(1,2,3,4-tetrahydro-isoquinolin-7-yl)-ethyl]-1H-pyridin-2-one is prepared following example 24.2 from 230 mg (0.50 mmol) 7-{2-[2-oxo-4-(pyridin-2-ylmethoxy)-2H-pyridin-1-yl]-ethyl}-3,4-dihydro-1H-isoquinoline-2-carboxylic acid tert-butyl ester (example 24.4a).

Yield: 172 mg (96% of theory)
ESI Mass spectrum: [M+H]$^+$=362
Retention time HPLC: 1.8 min (method A).

Example 24.5

4-(5-Bromo-pyridin-2-ylmethoxy)-1-[2-(1,2,3,4-tetrahydro-isoquinolin-7-yl)-ethyl]-1H-pyridin-2-one

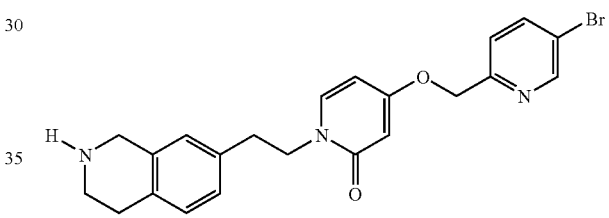

24.5a 7-{2-[4-(5-Bromo-pyridin-2-ylmethoxy)-2-oxo-2H-pyridin-1-yl]-ethyl}-3,4-dihydro-1H-isoquinoline-2-carboxylic Acid Tert-Butyl Ester 7-{2-[4-(5-Bromo-pyridin-2-ylmethoxy)-2-oxo-2H-pyridin-1-yl]-ethyl}-3,4-dihydro-1H-isoquinoline-2-carboxylic acid tert-butyl ester is prepared following example 24.1 from 562 mg (2.00 mmol) 4-(5-bromo-pyridin-2-ylmethoxy)-1H-pyridin-2-one (preparation 22.2) and 863 mg (2.00 mmol) 7-[2-(toluene-4-sulfonyloxy)-ethyl]-3,4-dihydro-1H-isoquinoline-2-carboxylic acid tert-butyl ester (preparation 7).

Yield: 550 mg (51% of theory)
ESI Mass spectrum: [M+H]$^+$=540/542
Retention time HPLC: 4.6 min (method A).

24.5b 4-(5-Bromo-pyridin-2-ylmethoxy)-1-[2-(1,2,3,4-tetrahydro-isoquinolin-7-yl)-ethyl]-1H-pyridin-2-one 4-(5-Bromo-pyridin-2-ylmethoxy)-1-[2-(1,2,3,4-tetrahydro-isoquinolin-7-yl)-ethyl]-1H-pyridin-2-one is prepared following example 24.2 from 550 mg (1.02 mmol) 7-{2-[4-(5-bromo-pyridin-2-ylmethoxy)-2-oxo-2H-pyridin-1-yl]-ethyl}-3,4-dihydro-1H-isoquinoline-2-carboxylic acid tert-butyl ester (example 24.5a).

Yield: 230 mg (51% of theory)
ESI Mass spectrum: [M+H]$^+$=440/442
Retention time HPLC: 2.3 min (method A).

Example 24.6

4-(5-Bromo-pyridin-2-ylmethoxy)-1-[2-(2-methyl-1,2,3,4-tetrahydro-isoquinolin-7-yl)-ethyl]-1H-pyridin-2-one

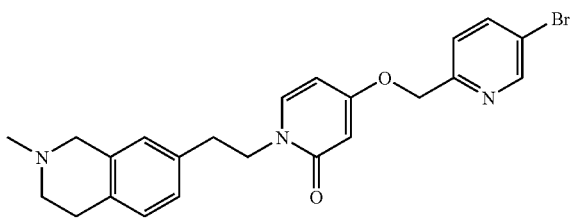

4-(5-Bromo-pyridin-2-ylmethoxy)-1-[2-(2-methyl-1,2,3,4-tetrahydro-isoquinolin-7-yl)-ethyl]-1H-pyridin-2-one is prepared following example 24.3 from 110 mg (0.25 mmol) 4-(5-bromo-pyridin-2-ylmethoxy)-1-[2-(1,2,3,4-tetrahydro-isoquinolin-7-yl)-ethyl]-1H-pyridin-2-one (example 24.5b).
Yield: 50 mg (44% of theory)
ESI Mass spectrum: [M+H]$^+$=454/456
Retention time HPLC: 2.8 min (method A).

Example 25.1

5-Benzyloxy-2-[2-(1,2,3,4-tetrahydro-isoquinolin-7-yl)-ethyl]-2H-pyridazin-3-one

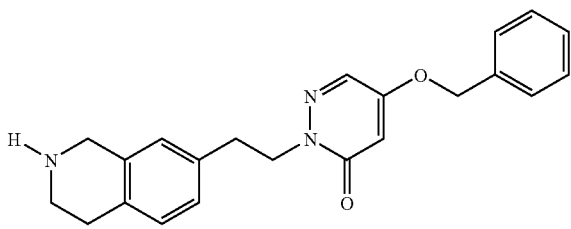

25.1a 7-[2-(4-Benzyloxy-6-oxo-6H-pyridazin-1-yl)-ethyl]-3,4-dihydro-1H-isoquinoline-2-carboxylic Acid Tert-Butyl Ester To 245 mg (1.21 mmol) 5-benzyloxy-2H-pyridazin-3-one (preparation 5c) in 1.2 mL DMF is added 791 mg (2.43 mmol) cesium carbonate and after 15 min 470 mg (1.21 mmol) 7-(2-iodoethyl)-3,4-dihydro-1H-isoquinoline-2-carboxylic acid tert-butyl ester (preparation 8). The reaction mixture is stirred overnight at RT and the precipitate is removed by filtration. The solvent is evaporated, the residue is dissolved in DMF and purified via reverse HPLC chromatography (Waters symmetry, C18; water (0.15% formic acid)/acetonitrile 95:5 to 10:90).
Yield: 40 mg (7% of theory)
ESI Mass spectrum: [M+H]$^+$=462
Retention time HPLC: 3.3 min (method E).

25.1b 5-Benzyloxy-2-[2-(1,2,3,4-tetrahydro-isoquinolin-7-yl)-ethyl]-2H-pyridazin-3-one To 30 mg (0.06 mmol) 7-[2-(4-benzyloxy-6-oxo-6H-pyridazin-1-yl)-ethyl]-3,4-dihydro-1H-isoquinoline-2-carboxylic acid tert-butyl ester (example 25.1a) in 2.0 mL DCM is added 50 μL trifluoroacetic acid at RT. The solvent is evaporated and the residue is purified via reverse HPLC chromatography (Waters SunFire, C18; water (0.1% formic acid)/acetonitrile (0.1% formic acid) 95:5 to 10:90).
Yield: 12 mg (51% of theory)
ESI Mass spectrum: [M+H]$^+$=362
Retention time HPLC: 3.2 min (method D).

Example 25.2

5-Benzyloxy-2-[2-(2-methyl-1,2,3,4-tetrahydro-isoquinolin-7-yl)-ethyl]-2H-pyridazin-3-one

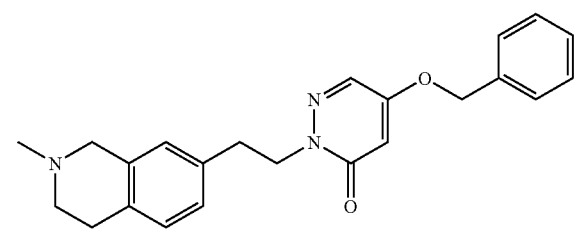

To 90 mg (0.25 mmol) 5-benzyloxy-2-[2-(1,2,3,4-tetrahydro-isoquinolin-7-yl)-ethyl]-2H-pyridazin-3-one (example 25.1) in 2.0 mL THF is added 28 μL (0.37 mmol) aqueous 37% formaldehyde solution. The mixture is acidified with 2 drops of acetic acid and then 79 mg (0.37 mmol) sodium triacetoxy-borohydride is added. The reaction mixture is stirred 2 h at RT and is poured into aqueous 10% Na$_2$CO$_3$-solution, the layers are separated and the aqueous phase is extracted with EtOAc. The combined organic phase is washed with water, dried over MgSO$_4$, filtered and the solvent is evaporated. The residue is dissolved in DMF and is purified via reverse HPLC chromatography (Waters symmetry, C18; water (0.15% formic acid)/acetonitrile 95:5 to 5:95).
Yield: 63 mg (67% of theory)
ESI Mass spectrum: [M+H]$^+$=376
Retention time HPLC: 2.6 min (method H).

Example 26.1

4-Benzyloxy-1-[2-(4-pyrrolidin-1-ylmethyl-phenyl)-allyl]-1H-pyridin-2-one

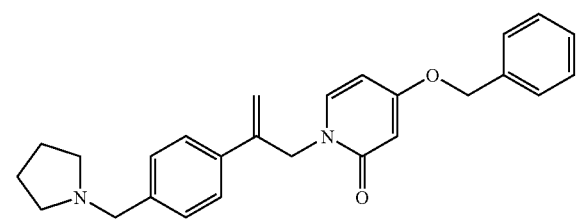

To 242 μL (2.90 mmol) pyrrolidine in 10 mL THF is added 500 mg (1.45 mmol) 4-[1-(4-benzyloxy-2-oxo-2H-pyridin-1-ylmethyl)-vinyl]-benzaldehyde (preparation 9b). The mixture is acidified with 3 drops of acetic acid and then 614 mg (2.90 mmol) sodium triacetoxy-borohydride is added. The reaction mixture is stirred overnight at RT and is poured into aqueous 10% Na$_2$CO$_3$-solution, the layers are separated and the aqueous phase is extracted with DCM. The combined organic phase is washed a few times with water, dried over MgSO$_4$, filtered and the solvent is evaporated. The residue is purified via reverse HPLC chromatography (Zorbax stable bond, C18; water (0.15% formic acid)/acetonitrile 95:5 to 5:95).

Yield: 500 mg (86% of theory)
ESI Mass spectrum: [M+H]$^+$=401
Retention time HPLC: 2.6 min (method A).

The following examples are prepared as described in Example 26.1. For the preparation of example 26.7 additional 2.0 eq of triethylamine as base are used.

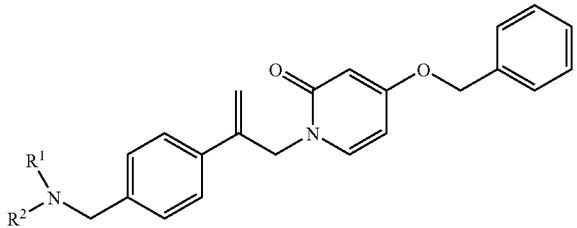

| Example | R$^1$R$^2$N— | Yield (%) | Formula | MS | Retention time HPLC in min (method) |
|---|---|---|---|---|---|
| 26.2 | | 34 | C$_{29}$H$_{33}$N$_3$O$_3$ | 472 [M + H]$^+$ | 2.9 (A) |
| 26.3 | | 86 | C$_{26}$H$_{28}$N$_2$O$_3$ | 417 [M + H]$^+$ | 3.4 (C) |
| 26.4 | | 47 | C$_{28}$H$_{32}$N$_2$O$_3$ | 445 [M + H]$^+$ | 3.4 (C) |
| 26.5 | | 53 | C$_{27}$H$_{30}$N$_2$O$_3$ | 431 [M + H]$^+$ | 2.8 (A) |
| 26.6 | | 44 | C$_{25}$H$_{28}$N$_2$O$_2$ | 389 [M + H]$^+$ | 3.5 (C) |
| 26.7 | | 18 | C$_{25}$H$_{26}$N$_2$O$_3$ | 403 [M + H]$^+$ | 3.4 (C) |

Example 27.1

6-[2-(4-Benzyloxy-2-oxo-2H-pyridin-1-yl)-ethyl]-3,4-dihydro-1H-isoquinoline-2-carboxylic Acid Tert-Butyl Ester

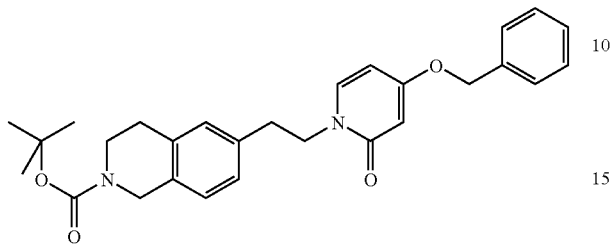

6-[2-(4-Benzyloxy-2-oxo-2H-pyridin-1-yl)-ethyl]-3,4-dihydro-1H-isoquinoline-2-carboxylic acid tert-butyl ester is prepared as example 24.1 from 604 mg (3.00 mmol) 4-benzyloxy-1H-pyridin-2-one and 1.30 g (3.01 mmol) 6-[2-(toluene-4-sulfonyloxy)-ethyl]-3,4-dihydro-1H-isoquinoline-2-carboxylic acid tert-butyl ester (preparation 10c).
Yield: 590 mg (43% of theory)
ESI Mass spectrum: [M+H]$^+$=461
Retention time HPLC: 3.1 min (method E).

Example 27.2

4-Benzyloxy-1-[2-(1,2,3,4-tetrahydro-isoquinolin-6-yl)-ethyl]-1H-pyridin-2-one

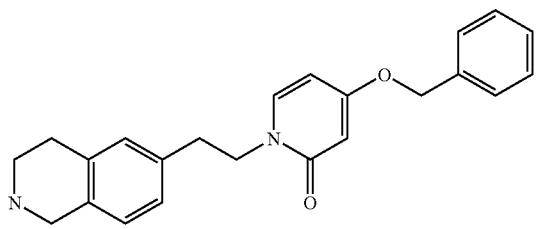

4-Benzyloxy-1-[2-(1,2,3,4-tetrahydro-isoquinolin-6-yl)-ethyl]-1H-pyridin-2-one is prepared as example 24.2 from 461 mg (1.00 mmol) 6-[2-(4-benzyloxy-2-oxo-2H-pyridin-1-yl)-ethyl]-3,4-dihydro-1H-isoquinoline-2-carboxylic acid tert-butyl ester (example 27.1).
Yield: 330 mg (92% of theory)
ESI Mass spectrum: [M+H]$^+$=361
Retention time HPLC: 2.8 min (method A).

Example 27.3

4-Benzyloxy-1-[2-(2-methyl-1,2,3,4-tetrahydro-isoquinolin-6-yl)-ethyl]-1H-pyridin-2-one

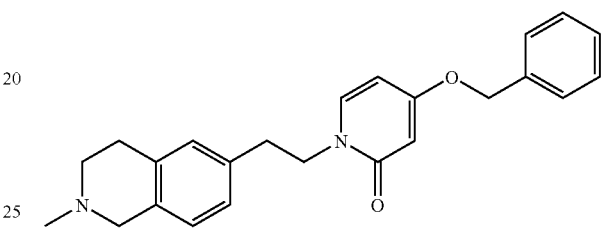

To 170 mg (0.47 mmol) 4-benzyloxy-1-[2-(1,2,3,4-tetrahydro-isoquinolin-6-yl)-ethyl]-1H-pyridin-2-one (example 27.2) in 5.0 mL THF is added 57 µL (0.71 mmol) aqueous 37% formaldehyde solution. The mixture is acidified with 3 drops of acetic acid and then 150 mg (0.71 mmol) sodium triacetoxy-borohydride is added. The reaction mixture is stirred 2 h at RT, poured into aqueous 10% Na$_2$CO$_3$-solution and the layers are separated. The aqueous phase is extracted with tert-butylmethylether, the combined organic phase is washed a few times with water, dried over MgSO$_4$, filtered and the solvent is evaporated to afford the product.
Yield: 130 mg (74% of theory)
ESI Mass spectrum: [M+H]$^+$=375
Retention time HPLC: 2.8 min (method A).

The following compounds are prepared as described for example 27.1 (first step, alkylation) followed by example 27.2 (second step, deprotection).
yield 1: alkylation step; yield 2: deprotection step;

| Example | —W—B | Yield 1 (%) | Yield 2 (%) | Pyridon Starting material see preparation | Formula | MS | Retention time HPLC in min (method) |
|---|---|---|---|---|---|---|---|
| 27.4 | 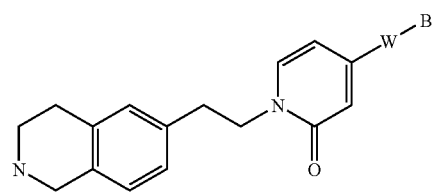 | 26 | 62 | 22.4 | C$_{22}$H$_{23}$N$_3$O$_2$ | 362 [M + H]$^+$ | 2.1 (A) |

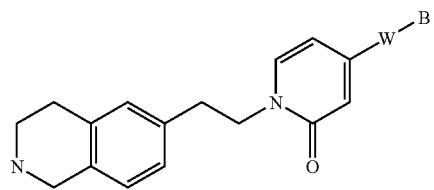

| Example | —W—B | Yield 1 (%) | Yield 2 (%) | Pyridon Starting material see preparation | Formula | MS | Retention time HPLC in min (method) |
|---|---|---|---|---|---|---|---|
| 27.5 | ![structure with Br-pyridyl-CH2-O-*] | 38 | 66 | 22.2 | C₂₂H₂₂BrN₃O₂ | 440/442 [M + H]⁺ | 2.7 (A) |

Example 27.6

4-(5-Bromo-pyridin-2-ylmethoxy)-1-[2-(2-methyl-1,2,3,4-tetrahydro-isoquinolin-6-yl)-ethyl]-1H-pyridin-2-one

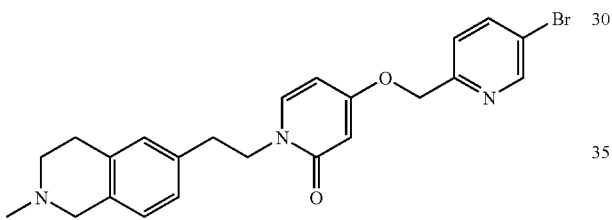

4-(5-Bromo-pyridin-2-ylmethoxy)-1-[2-(2-methyl-1,2,3,4-tetrahydro-isoquinolin-6-yl)-ethyl]-1H-pyridin-2-one is prepared following example 27.3 from 50 mg (0.11 mmol) 4-(5-bromo-pyridin-2-ylmethoxy)-1-[2-(1,2,3,4-tetrahydro-isoquinolin-6-yl)-ethyl]-1H-pyridin-2-one (example 27.5b).

Yield: 27 mg (52% of theory)
ESI Mass spectrum: [M+H]⁺=454/456
Retention time HPLC: 2.7 min (method A).

Example 28.1

4-Benzyloxy-1-[2-(5-pyrrolidin-1-ylmethyl-thiophen-2-yl)-ethyl]-1H-pyridin-2-one

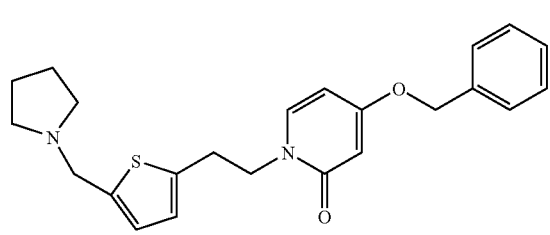

To 200 mg (0.59 mmol) 4-benzyloxy-1-[2-(5-hydroxymethyl-thiophen-2-yl)-ethyl]-1H-pyridin-2-one (preparation 11d) in 8.0 mL DCM is added 245 μL (1.76 mmol) triethylamine and subsequently 91 μL (1.17 mmol) methanesulfonyl chloride at RT. The reaction mixture is stirred 1 h at RT and 98 μL (1.17 mmol) pyrrolidine is added. The mixture is stirred overnight at RT and is directly transferred to a reverse HPLC for purification (Zorbax stable bond, C18; water (0.1% formic acid)/acetonitrile (0.1% formic acid) 95:5 to 10:90).

Yield: 48 mg (21% of theory)
ESI Mass spectrum: [M+H]⁺=395
Retention time HPLC: 2.8 min (method A).

Example 28.2

N-(1-{5-[2-(4-Benzyloxy-2-oxo-2H-pyridin-1-yl)-ethyl]-thiophen-2-ylmethyl}-piperidin-4-yl)-acetamide

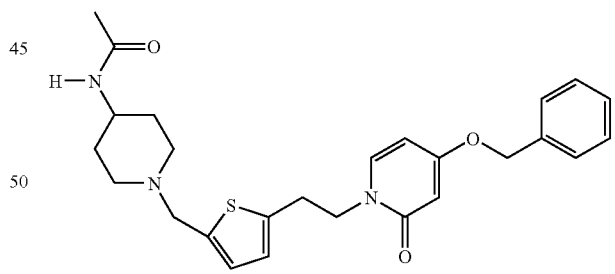

N-(1-{5-[2-(4-Benzyloxy-2-oxo-2H-pyridin-1-yl)-ethyl]-thiophen-2-ylmethyl}-piperidin-4-yl)acetamide is prepared as example 28.1 from 70 mg (0.21 mmol) 4-benzyloxy-1-[2-(5-hydroxymethyl-thiophen-2-yl)-ethyl]-1H-pyridin-2-one (preparation 11d) and 58 mg (0.41 mmol) N-piperidin-4-yl-acetamide.

Yield: 23 mg (24% of theory)
ESI Mass spectrum: [M+H]⁺=466
Retention time HPLC: 2.7 min (method A).

Example 29.1

4-Benzyloxy-1-[2-oxo-2-(4-pyrrolidin-1-ylmethyl-phenyl)-ethyl]-1H-pyridin-2-one

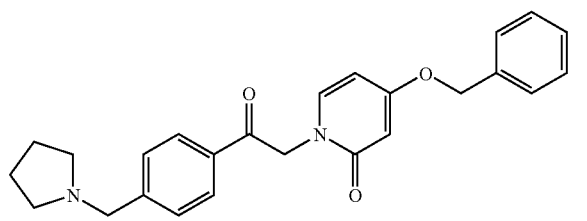

To 200 mg (0.50 mmol) 4-benzyloxy-1-[2-(4-pyrrolidin-1-ylmethyl-phenyl)-allyl]-1H-pyridin-2-one (example 26.1) in 6.0 mL acetonitrile is added at RT subsequently a solution of 4 mg (0.02 mmol) ruthenium(III)-trichloride hydrate in 1.0 mL water and then 214 mg (1.00 mmol) sodium metaperiodate in small portions. The reaction mixture is stirred 4 h at RT and is diluted with aqueous 10% sodium thiosulfate solution. The layers are separated and the aqueous phase is extracted with DCM. The combined organic phase is dried over MgSO$_4$, filtered and the solvent is evaporated. The residue is purified via reverse HPLC chromatography (Waters xbridge; water (15% NH$_4$OH)/acetonitrile (15% NH$_4$OH) 95:5 to 5:95).

Yield: 55 mg (27% of theory)

ESI Mass spectrum: [M+H]$^+$=403

Retention time HPLC: 3.1 min (method A).

Example 29.2

N-(1-{4-[2-(4-Benzyloxy-2-oxo-2H-pyridin-1-yl)-acetyl]-benzyl}-piperidin-4-yl)-acetamide

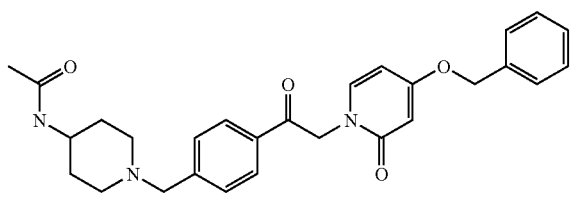

N-(1-{4-[2-(4-Benzyloxy-2-oxo-2H-pyridin-1-yl)-acetyl]-benzyl}-piperidin-4-yl)-acetamide is prepared as example 29.1 from 200 mg (0.42 mmol) N-(1-{4-[1-(4-benzyloxy-2-oxo-2H-pyridin-1-ylmethyl)-vinyl]-benzyl}-piperidin-4-yl)-acetamide (example 26.2).

Yield: 46 mg (23% of theory)

ESI Mass spectrum: [M+H]$^+$=474

Retention time HPLC: 2.8 min (method A).

Example 29.3

4-Benzyloxy-1-{2-[4-(4-hydroxy-piperidin-1-ylmethyl)-phenyl]-2-oxo-ethyl}-1H-pyridin-2-one

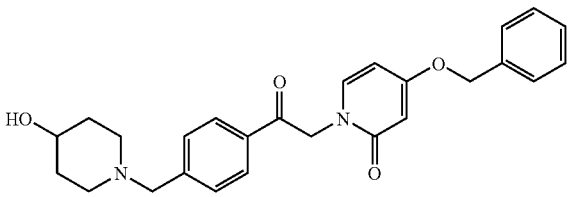

To 400 mg (0.97 mmol) 4-benzyloxy-1-[2-(4-bromomethyl-phenyl)-2-oxo-ethyl]-1H-pyridin-2-one (preparation 15c) in 5.0 mL of DMF is added 393 mg (3.88 mmol) 4-hydroxypiperidine. The reaction mixture is stirred 1 h at RT and is directly purified by HPLC (Waters Symmetry, C18; water (0.1% formic acid)/acetonitrile (0.1% formic acid) 95:5 to 0:100).

Yield: 268 mg (64% of theory)

ESI Mass spectrum: [M+H]$^+$=433

Retention time HPLC: 2.1 min (method H).

The following compounds are prepared as described for example 29.3.

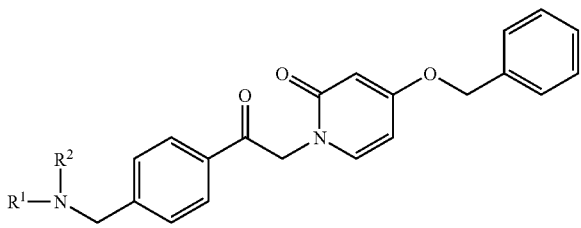

| Example | R¹R²N— | Yield (%) | Formula | MS | Retention time HPLC in min (method) |
|---|---|---|---|---|---|
| 29.4 | HO-[4-hydroxypiperidinyl] | 59 | $C_{27}H_{30}N_2O_4$ | 447 [M + H]$^+$ | 1.6 (K) |
| 29.5 | morpholinyl | 26 | $C_{25}H_{26}N_2O_4$ | 419 [M + H]$^+$ | 2.8 (C) |
| 29.6 | N-methyl,ethyl | 67 | $C_{24}H_{26}N_2O_3$ | 391 [M + H]$^+$ | 2.2 (H) |
| 29.7 | 4-methylpiperazinyl | 51 | $C_{26}H_{29}N_3O_3$ | 432 [M + H]$^+$ | 1.5 (K) |
| 29.8 | N,N-dimethyl | 36 | $C_{23}H_{24}N_2O_3$ | 377 [M + H]$^+$ | 2.6 (J) |
| 29.9 | N,N-diethyl | 22 | $C_{25}H_{28}N_2O_3$ | 405 [M + H]$^+$ | 1.8 (K) |
| 29.10 | N-propyl | 32 | $C_{23}H_{24}N_2O_3$ | 377 [M + H]$^+$ | 1.6 (K) |
| 29.11 | (3S)-3-hydroxypyrrolidinyl | 22 | $C_{25}H_{26}N_2O_4$ | 419 [M + H]$^+$ | 1.6 (K) |
| 29.12 | cyclopropylmethylamino | 31 | $C_{25}H_{26}N_2O_3$ | 403 [M + H]+ | 1.7 (K) |
| 29.13 | 3-hydroxyazetidinyl | 47 | $C_{24}H_{24}N_2O_4$ | 405 [M + H]+ | 2.1 (H) |

-continued

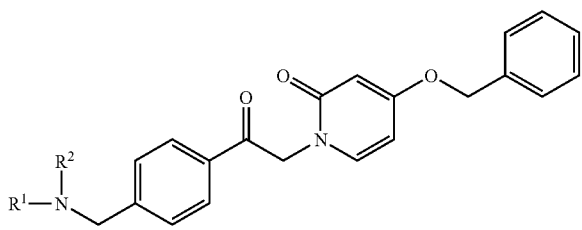

| Example | R¹R²N— | Yield (%) | Formula | MS | Retention time HPLC in min (method) |
|---|---|---|---|---|---|
| 29.14 | cyclopropylmethyl-N(Me)– | 36 | $C_{26}H_{28}N_2O_3$ | 417 [M + H]+ | 1.8 (K) |
| 29.15 | H–N(Me)(iPr)– | 16 | $C_{22}H_{22}N_2O_3$ | 363 [M + H]+ | 1.6 (K) |
| 29.16 | 3-hydroxy-3-methyl-8-azabicyclo | 35 | $C_{29}H_{32}N_2O_4$ | 473 [M + H]+ | 1.7 (K) |
| 29.17 | 4-hydroxy-4-isopropyl-piperidinyl | 31 | $C_{29}H_{34}N_2O_4$ | 475 [M + H]+ | 1.7 (K) |
| 29.18 | 4-hydroxy-4-ethyl-piperidinyl | 40 | $C_{28}H_{32}N_2O_4$ | 461 [M + H]+ | 1.6 (K) |

Example 30.1

4-(Benzyl-methyl-amino)-1-[2-(4-pyrrolidin-1-ylmethyl-phenyl)-ethyl]-1H-pyridin-2-one

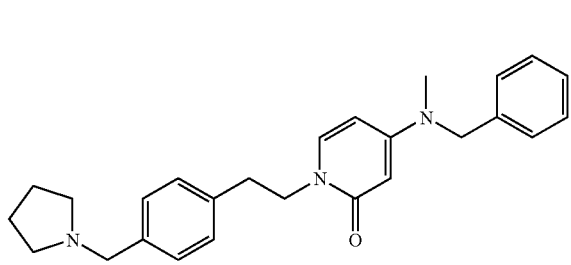

To 150 mg (0.37 mmol) 4-(benzyl-methyl-amino)-1-[2-(4-bromomethyl-phenyl)-ethyl]-1H-pyridin-2-one (preparation 14d) in 2.0 mL DMF is added 152 μL (1.82 mmol) pyrrolidine at RT. The reaction mixture is stirred for 1 h at RT and is directly transferred to a reverse HPLC for purification (Waters symmetry, C18; water (0.15% formic acid)/acetonitrile 95:5 to 10:90).

Yield: 95 mg (65% of theory)
ESI Mass spectrum: [M+H]⁺=402
Retention time HPLC: 3.0 min (method C).

Example 30.2

N-[1-(4-{2-[4-(Benzyl-methyl-amino)-2-oxo-2H-pyridin-1-yl]-ethyl}-benzyl)-piperidin-4-yl]-acetamide

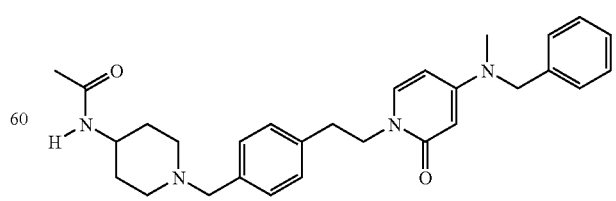

N-[1-(4-{2-[4-(Benzyl-methyl-amino)-2-oxo-2H-pyridin-1-yl]-ethyl}-benzyl)-piperidin-4-yl]-acetamide is prepared as example 30.1 from 150 mg (0.37 mmol) 4-(benzylmethyl-amino)-1-[2-(4-bromomethyl-phenyl)-ethyl]-1H-pyridin-2-one (preparation 14d) and 259 mg (1.82 mmol) N-piperidin-4-yl-acetamide.

Yield: 80 mg (46% of theory)
ESI Mass spectrum: [M+H]$^+$=473
Retention time HPLC: 2.9 min (method C).

Example 31.1

4-Benzyloxy-1-{2-[3-fluoro-4-(4-hydroxy-4-methyl-piperidin-1-ylmethyl)-phenyl]-2-oxo-ethyl}-1H-pyridin-2-one

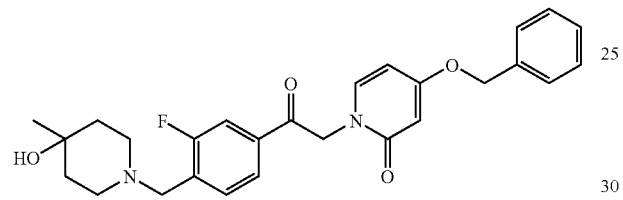

4-Benzyloxy-1-{2-[3-fluoro-4-(4-hydroxy-4-methyl-piperidin-1-ylmethyl)-phenyl]-2-oxo-ethyl}-1H-pyridin-2-one is prepared as example 1.1b from 105 mg (0.24 mmol) 4-benzyloxy-1-[2-(4-bromomethyl-3-fluoro-phenyl)-2-oxo-ethyl]-1H-pyridin-2-one (preparation 16 h) and 84 mg (0.73 mmol) 4-hydroxy-4 methyl-piperidine.

Yield: 70 mg (62% of theory)
ESI Mass spectrum: [M+H]$^+$=465
Retention time HPLC: 2.9 min (method C).

Example 31.2

4-Benzyloxy-1-[2-(3-fluoro-4-pyrrolidin-1-ylmethyl-phenyl)-2-oxo-ethyl]-1H-pyridin-2-one

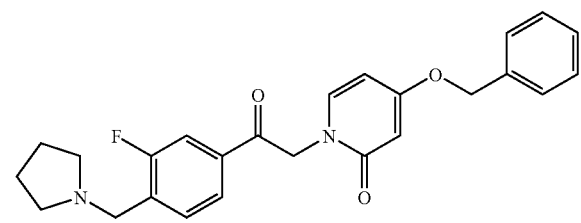

4-Benzyloxy-1-[2-(3-fluoro-4-pyrrolidin-1-ylmethyl-phenyl)-2-oxo-ethyl]-1H-pyridin-2-one is prepared as example 1.1b from 105 mg (0.24 mmol) 4-benzyloxy-1-[2-(4-bromomethyl-3-fluoro-phenyl)-2-oxo-ethyl]-1H-pyridin-2-one (preparation 16h) and 0.06 mL (0.73 mmol) pyrrolidine.

Yield: 49 mg (48% of theory)
ESI Mass spectrum: [M+H]$^+$=421
Retention time HPLC: 2.9 min (method C).

Example 32.1

5-Benzyloxy-2-[2-(4-morpholin-4-ylmethyl-phenyl)-2-oxo-ethyl]-2H-pyridazin-3-one

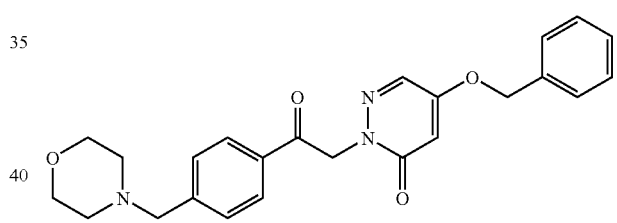

5-Benzyloxy-2-[2-(4-morpholin-4-ylmethyl-phenyl)-2-oxo-ethyl]-2H-pyridazin-3-one is prepared as example 1.1b from 90 mg (0.22 mmol) 5-benzyloxy-2-[2-(4-bromomethyl-phenyl)-2-oxo-ethyl]-2H-pyridazin-3-one (preparation 17b) and 76 μL (0.87 mmol) morpholine.

Yield: 64 mg (70% of theory)
ESI Mass spectrum: [M+H]$^+$=420
Retention time HPLC: 2.6 min (method A).

The following compounds are prepared as described for example 32.1. For example 32.5 3.0 eq. of the corresponding amine and 4.0 eq. of N-ethyl-diisopropylamine are used.

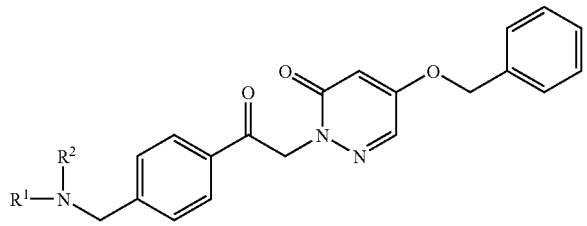

| Example | R¹R²N— | Yield (%) | Formula | MS | Retention time HPLC in min (method) |
|---|---|---|---|---|---|
| 32.2 | HO-piperidine | 76 | $C_{25}H_{27}N_3O_4$ | 434 $[M + H]^+$ | 1.6 (K) |
| 32.3 | 4-methyl-4-hydroxypiperidine | 51 | $C_{26}H_{29}N_3O_4$ | 448 $[M + H]^+$ | 1.6 (A) |
| 32.4 | N-methyl-N-ethyl | 82 | $C_{23}H_{25}N_3O_3$ | 392 $[M + H]^+$ | 2.1 (H) |
| 32.5 | 3-hydroxyazetidine | 68 | $C_{23}H_{23}N_3O_4$ | 406 $[M + H]^+$ | 2.5 (A) |
| 32.6 | pyrrolidine | 84 | $C_{24}H_{25}N_3O_3$ | 404 $[M + H]+$ | 2.7 (A) |
| 32.7 | N,N-dimethyl | 80 | $C_{22}H_{23}N_3O_3$ | 378 $[M + H]+$ | 2.1 (H) |
| 32.8 | cyclopropylmethylamino | 56 | $C_{24}H_{25}N_3O_3$ | 404 $[M + H]+$ | 1.1 (J) |
| 32.9 | piperazine | 93 | $C_{24}H_{26}N_4O_3$ | 419 $[M + H]+$ | 2.5 (A) |
| 32.10 | 4-methylpiperazine | 72 | $C_{25}H_{28}N_4O_3$ | 433 $[M + H]+$ | 1.1 (J) |

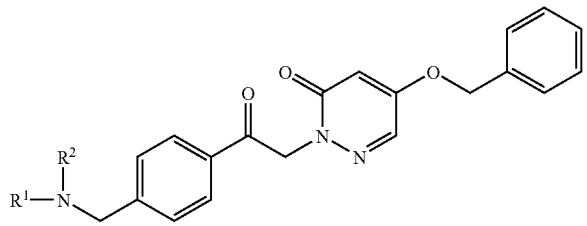

| Example | R¹R²N— | Yield (%) | Formula | MS | Retention time HPLC in min (method) |
|---|---|---|---|---|---|
| 32.11 | | 34 | $C_{27}H_{27}F_3N_4O_4$ | 529 [M + H]+ | 3.2 (C) |
| 32.12 | | 25 | $C_{25}H_{27}N_3O_4$ | 434 [M + H]+ | 2.6 (J) |
| 32.13 | | 29 | $C_{24}H_{25}N_3O_4$ | 420 [M + H]+ | 2.5 (A) |
| 32.14 | | 33 | $C_{24}H_{25}N_3O_4$ | 420 [M + H]+ | 2.5 (A) |

Example 33.1

5-(5-Fluoro-pyridin-2-ylmethoxy)-2-[2-oxo-2-(4-piperidin-1-ylmethyl-phenyl)-ethyl]-2H-pyridazin-3-one

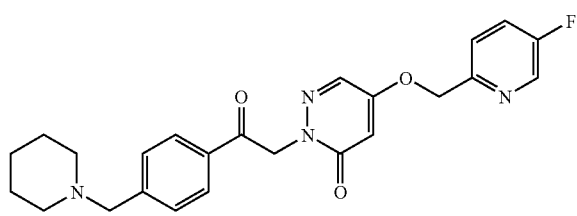

To 70 mg (0.14 mmol) 2-[2-(4-chloromethyl-phenyl)-2-oxo-ethyl]-5-(5-fluoro-pyridin-2-ylmethoxy)-2H-pyridazin-3-one (preparation 19d) in 2.00 mL of DMF is added 71 µL (0.72 mmol) piperidine. The reaction mixture is stirred overnight at RT and is directly purified by HPLC (Zorbax stable bond, C18; water (0.1% formic acid)/acetonitrile (0.1% formic acid) 95:5 to 0:100).

Yield: 31 mg (49% of theory)

ESI Mass spectrum: [M+H]⁺=437

Retention time HPLC: 2.2 min (method A).

The following examples are prepared as described for example 33.1 (Starting materials: either preparation 18d or 19d depending on substituent X). For example 33.6-33.10 3.0 eq of the corresponding amine are used.

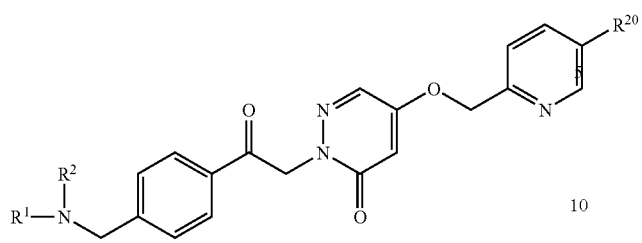

| Example | R¹R²N— | R²⁰ | Yield (%) | Formula | MS | Retention time HPLC in min (method) |
|---|---|---|---|---|---|---|
| 33.2 | pyrrolidinyl | F | 38 | $C_{23}H_{23}FN_4O_3$ | 423 [M + H]⁺ | 2.8 (F) |
| 33.3 | N,N-diethylamino | F | 41 | $C_{23}H_{25}FN_4O_3$ | 425 [M + H]⁺ | 2.9 (F) |
| 33.4 | N-ethyl-N-methylamino | F | 46 | $C_{22}H_{23}FN_4O_3$ | 411 [M + H]⁺ | 2.8 (F) |
| 33.5 | N,N-dimethylamino | F | 51 | $C_{21}H_{21}FN_4O_3$ | 397 [M + H]⁺ | 2.0 (A) |
| 33.6 | N,N-diethylamino | Cl | 37 | $C_{23}H_{25}ClN_4O_3$ | 441/443 [M + H]⁺ | 2.3 (C) |
| 33.7 | N,N-dimethylamino | Cl | 4 | $C_{21}H_{21}ClN_4O_3$ | 413/415 [M + H]⁺ | 2.5 (C) |
| 33.8 | pyrrolidinyl | Cl | 31 | $C_{23}H_{23}ClN_4O_3$ | 439/441 [M + H]⁺ | 2.6 (C) |
| 33.9 | N-ethyl-N-methylamino | Cl | 32 | $C_{22}H_{23}ClN_4O_3$ | 427/429 [M + H]⁺ | 2.6 (C) |
| 33.10 | piperidinyl | Cl | 25 | $C_{24}H_{25}ClN_4O_3$ | 453/455 [M + H]+ | 2.7 (C) |

Example 34.1

6-Benzyloxy-3-[2-oxo-2-(4-pyrrolidin-1-ylmethyl-phenyl)-ethyl]-3H-pyrimidin-4-one

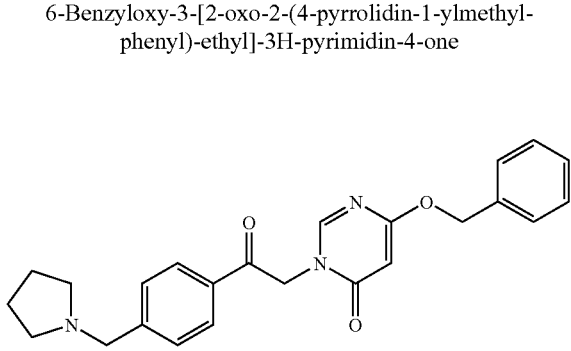

To 52 mg (0.13 mmol) 6-benzyloxy-3-[2-(4-bromomethyl-phenyl)-2-oxo-ethyl]-3H-pyrimidin-4-one (preparation 20b) in 2.00 mL of DMF is added 42 µL (0.50 mmol) pyrrolidine. The reaction mixture is stirred 30 min at RT and is directly purified by HPLC (Waters Xbridge; water (0.1% formic acid)/acetonitrile (0.1% formic acid) 95:5 to 0:100).

Yield: 33 mg (65% of theory)
ESI Mass spectrum: $[M+H]^+=404$
Retention time HPLC: 1.7 min (method K).

The following examples are prepared as described for example 34.1. For example 34.10 the BOC protected amine is used, followed by deprotection of the BOC group with TFA (yield for deprotection given).

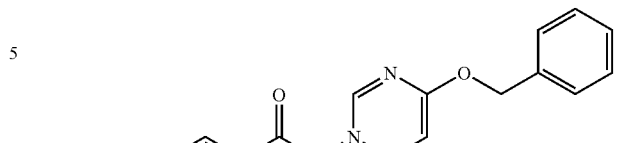

| Example | $R^1R^2N-$ | Yield (%) | Formula | MS | Retention time HPLC in min (method) |
|---|---|---|---|---|---|
| 34.2 | (3-hydroxypyrrolidin-1-yl) | 19 | $C_{24}H_{25}N_3O_4$ | 420 [M + H]$^+$ | 1.5 (K) |
| 34.3 | (piperidin-1-yl) | 50 | $C_{25}H_{27}N_3O_3$ | 418 [M + H]$^+$ | 1.8 (K) |
| 34.4 | (4-hydroxypiperidin-1-yl) | 46 | $C_{25}H_{27}N_3O_4$ | 434 [M + H]$^+$ | 1.5 (K) |
| 34.5 | (4-hydroxy-4-methylpiperidin-1-yl) | 48 | $C_{26}H_{29}N_3O_4$ | 448 [M + H]$^+$ | 1.5 (K) |
| 34.6 | (4-methylpiperazin-1-yl) | 51 | $C_{25}H_{28}N_4O_3$ | 433 [M + H]$^+$ | 1.5 (K) |
| 34.7 | (N-ethyl-N-methylamino) | 39 | $C_{23}H_{25}N_3O_3$ | 392 [M + H]$^+$ | 1.7 (K) |
| 34.8 | (cyclopropylmethylamino) | 41 | $C_{24}H_{25}N_3O_3$ | 404 [M + H]$^+$ | 1.7 (K) |
| 34.9 | (1-hydroxycyclopropylmethylamino) | 25 | $C_{24}H_{25}N_3O_4$ | 420 [M + H]$^+$ | 1.5 (K) |
| 34.10 | (piperazin-1-yl) | 57 | $C_{24}H_{26}N_4O_3$ | 419 [M + H]$^+$ | 1.5 (K) |

Example 35.1

4-Benzyloxy-1-[2-oxo-2-(1,2,3,4-tetrahydro-isoquinolin-7-yl)-ethyl]-1H-pyridin-2-one

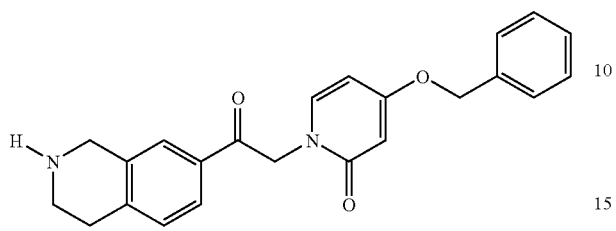

35.1a 4-Benzyloxy-1-{2-oxo-2-[2-(2,2,2-trifluoro-acetyl)-1,2,3,4-tetrahydro-isoquinolin-7-yl]-ethyl}-1H-pyridin-2-one To 600 mg (2.98 mmol) 4-benzyloxy-1H-pyridin-2-one in 6 mL THF is added at 0° C. 368 mg (3.28 mmol) potassium tert-butylate and 55 mg (0.15 mmol) tert-butylammonium iodide. After 5 min 1.00 g (3.28 mmol) 1-[7-(2-chloro-acetyl)-3,4-dihydro-1H-isoquinolin-2-yl]-2,2,2-trifluoro-ethanone is added. After 2 h additional 600 mg (1.97 mmol) 1-[7-(2-chloro-acetyl)-3,4-dihydro-1H-isoquinolin-2-yl]-2,2,2-trifluoro-ethanone is added and the mixture is stirred an additional hour. The reaction mixture is diluted with EtOAc and the organic phase is washed with water, filtered, dried over $MgSO_4$ and the solvent is evaporated. The residue is purified via reverse HPLC chromatography (Zorbax stable bond; water (0.15% formic acid)/acetonitrile (0.15% formic acid) 95:5 to 5:95).

Yield: 600 mg (43% of theory)

ESI Mass spectrum: $[M+H]^+=471$

Retention time HPLC: 3.9 min (method A).

35.1b 4-Benzyloxy-1-[2-oxo-2-(1,2,3,4-tetrahydro-isoquinolin-7-yl)-ethyl]-1H-pyridin-2-one 4-Benzyloxy-1-[2-oxo-2-(1,2,3,4-tetrahydro-isoquinolin-7-yl)-ethyl]-1H-pyridin-2-one is prepared following example 22.3 from 600 mg (1.28 mmol) 4-benzyloxy-1-{2-oxo-2-[2-(2,2,2-trifluoroacetyl)-1,2,3,4-tetrahydro-isoquinolin-7-yl]-ethyl}-1H-pyridin-2-one (example 35.1a).

Yield: 220 mg (46% of theory)

ESI Mass spectrum: $[M+H]^+=375$

Retention time HPLC: 2.5 min (method A).

The following examples are prepared as described for example 35.1a (first step, alkylation) followed by example 35.1b (second step, deprotection). For example 35.2 and 35.4 potassium tert-butylate and tert-butylammonium iodide are substituted by cesium carbonate. For example 35.2 acetonitrile is used in the alkylation step acetonitrile is used as the solvent and in 35.4 DMSO.

yield 1: alkylation step; yield 2: deprotection step;

| Example | —W—B | Yield 1 (%) | Yield 2 (%) | Pyridon Starting material see preparation | Formula | MS | Retention time HPLC in min (method) |
|---|---|---|---|---|---|---|---|
| 35.2 | *—O—CH₂—(pyridyl)—Br | 10 | 26 | 22.2 | $C_{22}H_{20}BrN_3O_3$ | 454/456 $[M+H]^+$ | 2.3 (A) |
| 35.3 | *—O—CH₂—(pyridyl) | 12 | 77 | 22.4 | $C_{22}H_{21}N_3O_3$ | 376 $[M+H]^+$ | 2.0 (A) |
| 35.4 | *—O—CH₂—(phenyl)—F | 58 | 94 | 22.1 | $C_{23}H_{21}FN_2O_3$ | 393 $[M+H]^+$ | 2.5 (A) |

The following examples are prepared as described for example 23.17.

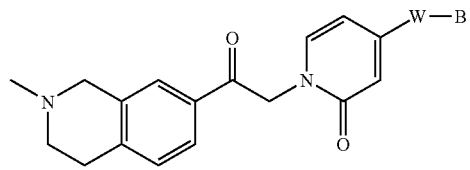

| Example | —W—B | Yield (%) | Pyridon Starting material see preparation | Formula | MS | Retention time HPLC in min (method) |
|---|---|---|---|---|---|---|
| 36.1 | *–O–CH₂–C₆H₅ | 72 | 35.1 | C₂₄H₂₄N₂O₃ | 389 [M + H]⁺ | 4.3 (A) |
| 36.2 | *–O–CH₂–C₆H₄–F | 29 | 35.4 | C₂₄H₂₃FN₂O₃ | 407 [M + H]⁺ | 1.7 (K) |
| 36.3 | *–O–CH₂–(pyridyl-Br) | 61 | 35.2 | C₂₃H₂₂BrN₃O₃ | 468/470 [M + H]⁺ | 1.1 (J) |

Example 37.1

4-Benzyloxy-1-[2-(2,3-dihydro-1H-isoindol-5-yl)-2-oxo-ethyl]-1H-pyridin-2-one

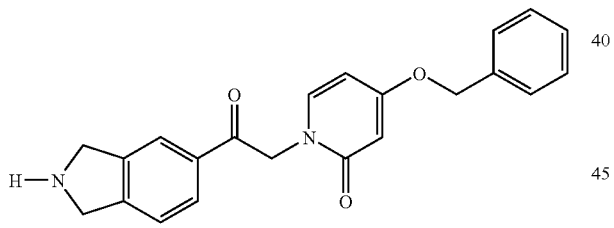

37.1a 4-Benzyloxy-1-{2-oxo-2-[2-(2,2,2-trifluoro-acetyl)-2,3-dihydro-1H-isoindol-5-yl]-ethyl}-1H-pyridin-2-one 4-Benzyloxy-1-{2-oxo-2-[2-(2,2,2-trifluoro-acetyl)-2,3-dihydro-1H-isoindol-5-yl]-ethyl}-1H-pyridin-2-one is prepared following preparation 15b from 1.50 g (7.45 mmol) 4-benzyloxy-1H-pyridin-2-one and 2.28 g (7.83 mmol) 1-[5-(2-chloro-acetyl)-1,3-dihydro-isoindol-2-yl]-2,2,2-trifluoro-ethanone (see preparation 23) in DMSO as solvent.
Yield: 2.10 g (62% of theory)
ESI Mass spectrum: [M+H]⁺=457
Retention time HPLC: 1.7 min (method K).

37.1b 4-Benzyloxy-1-[2-(2,3-dihydro-1H-isoindol-5-yl)-2-oxo-ethyl]-1H-pyridin-2-one 4-Benzyloxy-1-[2-(2,3-dihydro-1H-isoindol-5-yl)-2-oxo-ethyl]-1H-pyridin-2-one is prepared following example 22.3 from 2.10 g (4.60 mmol) 4-benzyloxy-1-{2-oxo-2-[2-(2,2,2-trifluoroacetyl)-2,3-dihydro-1H-isoindol-5-yl]-ethyl}-1H-pyridin-2-one (example 37.1a).
Yield: 1.50 g (91% of theory)
ESI Mass spectrum: [M+H]⁺=361
Retention time HPLC: 1.5 min (method K).

Example 37.2

4-Benzyloxy-1-[2-(2-methyl-2,3-dihydro-1H-isoindol-5-yl)-2-oxo-ethyl]-1H-pyridin-2-one 4-Benzyloxy-1-[2-(2-methyl-2,3-dihydro-1H-isoindol-5-yl)-2-oxo-ethyl]-1H-pyridin-2-one is prepared following example 23.17 from 900 mg (2.50 mmol) 4-benzyloxy-1-[2-(2,3-dihydro-1H-isoindol-5-yl)-2-oxo-ethyl]-1H-pyridin-2-one (example 37.1b).
Yield: 300 mg (32% of theory)
ESI Mass spectrum: [M+H]⁺=375
Retention time HPLC: 1.9 min (method K).

Example 38.1

4-Benzyloxy-1-[2-oxo-2-(4,5,6,7-tetrahydro-thieno[3,2-c]pyridin-2-yl)-ethyl]-1H-pyridin-2-one

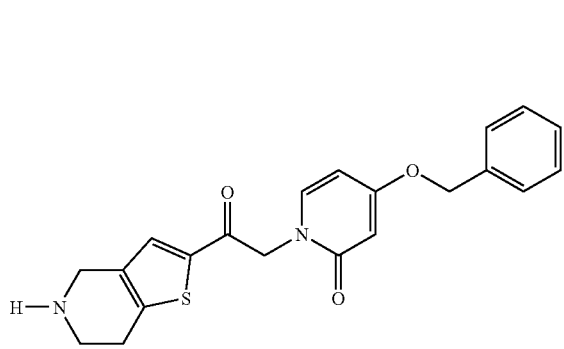

38.1a 4-Benzyloxy-1-{2-[5-(2-chloro-benzyl)-4,5,6,7-tetrahydro-thieno[3,2-c]pyridin-2-yl]-2-oxoethyl}-1H-pyridin-2-one 4-Benzyloxy-1-{2-[5-(2-chloro-benzyl)-4,5,6,7-tetrahydro-thieno[3,2-c]pyridin-2-yl]-2-oxo-ethyl}-1H-pyridin-2-one is prepared following preparation 15b (in DMSO as solvent) from 500 mg (2.49 mmol) 4-benzyloxy-1H-pyridin-2-one and 936 mg (2.49 mmol) 2-chloro-1-[5-(2-chloro-benzyl)-3a,4,5,6,7,7a-hexahydro-thieno[3,2-c]pyridin-2-yl]-ethanone (preparation 24).

Yield: 1.10 g (88% of theory)

ESI Mass spectrum: [M+H]$^+$=505/507

Retention time HPLC: 2.0 min (method K).

38.1b 4-Benzyloxy-1-[2-oxo-2-(4,5,6,7-tetrahydro-thieno[3,2-c]pyridin-2-yl)-ethyl]-1H-pyridin-2-one To 1.10 g (2.18 mmol) 4-benzyloxy-1-{2-[5-(2-chloro-benzyl)-4,5,6,7-tetrahydro-thieno[3,2-c]pyridin-2-yl]-2-oxo-ethyl}-1H-pyridin-2-one (example 38.1a) in 20 mL DCM is added at 0° C. 0.29 mL (2.61 mL) chloro-formic acid 1-chloro-ethyl ester. The reaction mixture is stirred 60 h at RT. Additional 0.29 mL (2.61 mL) chloro-formic acid 1-chloro-ethyl ester is added and the mixture is stirred overnight. Additional 0.29 mL (2.61 mL) chloro-formic acid 1-chloro-ethyl ester is added and the reaction mixture is refluxed overnight. The solvent is removed, to the residue 30 mL of methanol are added and the reaction mixture is refluxed for 30 min. After cooling to RT, the precipitate is collected after cooling the mixture to RT, washed with cold methanol and dried.

Yield: 260 mg (29% of theory)

ESI Mass spectrum: [M+H]$^+$=381

Retention time HPLC: 1.1 min (method M).

Example 38.2

4-Benzyloxy-1-[2-(5-methyl-4,5,6,7-tetrahydro-thieno[3,2-c]pyridin-2-yl)-2-oxo-ethyl]-1H-pyridin-2-one

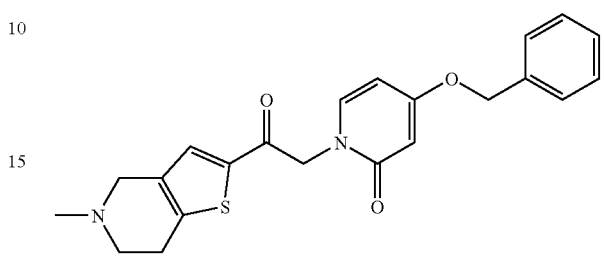

4-Benzyloxy-1-[2-(5-methyl-4,5,6,7-tetrahydro-thieno[3,2-c]pyridin-2-yl)-2-oxo-ethyl]-1H-pyridin-2-one is prepared following example 23.17 from 170 mg (0.45 mmol) 4-benzyloxy-1-[2-oxo-2-(4,5,6,7-tetrahydro-thieno[3,2-c]pyridin-2-yl)-ethyl]-1H-pyridin-2-one (example 38.1b).

Yield: 76 mg (43% of theory)

ESI Mass spectrum: [M+H]$^+$=395

Retention time HPLC: 1.6 min (method K).

Example 39.1

4-(5-Bromo-pyridin-2-ylmethoxy)-1-[2-hydroxy-2-(1,2,3,4-tetrahydro-isoquinolin-7-yl)-ethyl]-1H-pyridin-2-one

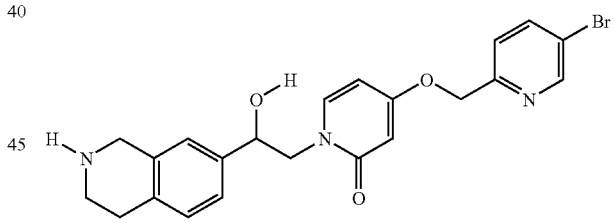

39.1a 4-(5-Bromo-pyridin-2-ylmethoxy)-1-{2-oxo-2-[2-(2,2,2-trifluoro-acetyl)-1,2,3,4-tetrahydro-isoquinolin-7-yl]-ethyl}-1H-pyridin-2-one 4-(5-Bromo-pyridin-2-ylmethoxy)-1-{2-oxo-2-[2-(2,2,2-trifluoro-acetyl)-1,2,3,4-tetrahydro-isoquinolin-7-yl]-ethyl}-1H-pyridin-2-one is prepared following preparation 15b (in acetonitrile as solvent) from 3.50 g (12.5 mmol) 4-(5-bromo-pyridin-2-ylmethoxy)-1H-pyridin-2-one (preparation 22.2) and 3.81 g (12.5 mmol) 1-[7-(2-chloro-acetyl)-3,4-dihydro-1H-isoquinolin-2-yl]-2,2,2-trifluoro-ethanone.

Yield: 700 mg (10% of theory)

ESI Mass spectrum: [M+H]$^+$=550/552

Retention time HPLC: 3.7 min (method A).

39.1b 4-(5-Bromo-pyridin-2-ylmethoxy)-1-{2-hydroxy-2-[2-(2,2,2-trifluoro-acetyl)-1,2,3,4-tetrahydro-isoquinolin-7-yl]-ethyl}-1H-pyridin-2-one 4-(5-Bromo-pyridin-2-ylmethoxy)-1-{2-hydroxy-2-[2-(2,2,2-trifluoro-acetyl)-1,2,3,4-tetrahydro-isoquinolin-7-yl]-ethyl}-1H-pyridin-2-one is prepared following example 22.2 from 260 mg (0.47 mmol) 4-(5-bromo-pyridin-2-ylmethoxy)-1-{2-oxo-2-[2-(2,2,2-trifluoro-acetyl)-1,2,3,4-tetrahydro-isoquinolin-7-yl]-ethyl}-1H-pyridin-2-one (example 39.1a).

Yield: 40 mg (15% of theory)
ESI Mass spectrum: [M+H]$^+$=552/554
Retention time HPLC: 4.0 min (method A).

39.1c 4-(5-Bromo-pyridin-2-ylmethoxy)-1-[2-hydroxy-2-(1,2,3,4-tetrahydro-isoquinolin-7-yl)ethyl]-1H-pyridin-2-one 4-(5-Bromo-pyridin-2-ylmethoxy)-1-[2-hydroxy-2-(1,2,3,4-tetrahydro-isoquinolin-7-yl)-ethyl]-1H-pyridin-2-one is prepared following example 22.3 from 70 mg (0.13 mmol) 4-(5-bromo-pyridin-2-ylmethoxy)-1-{2-hydroxy-2-[2-(2,2,2-trifluoro-acetyl)-1,2,3,4-tetrahydro-isoquinolin-7-yl]-ethyl}-1H-pyridin-2-one (example 39.1b).

Yield: 70 mg (quantitative)
ESI Mass spectrum: [M+H]$^+$=456/458
Retention time HPLC: 2.1 min (method A).

Example 39.2

4-(5-Bromo-pyridin-2-ylmethoxy)-1-[2-hydroxy-2-(2-methyl-1,2,3,4-tetrahydro-isoquinolin-7-yl)ethyl]-1H-pyridin-2-one

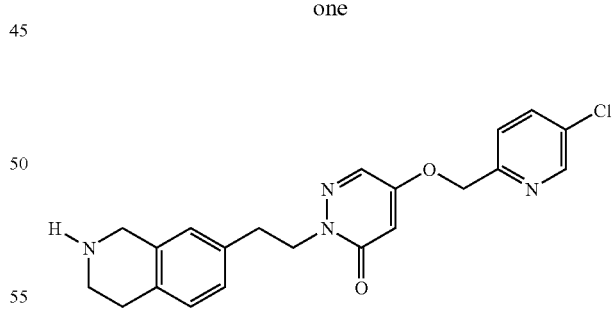

4-(5-Bromo-pyridin-2-ylmethoxy)-1-[2-hydroxy-2-(2-methyl-1,2,3,4-tetrahydro-isoquinolin-7-yl)ethyl]-1H-pyridin-2-one is prepared following example 23.17 from 160 mg (0.35 mmol) 4-(5-bromo-pyridin-2-ylmethoxy)-1-[2-hydroxy-2-(1,2,3,4-tetrahydro-isoquinolin-7-yl)-ethyl]-1H-pyridin-2-one (example 39.1c).

Yield: 120 mg (73% of theory)
ESI Mass spectrum: [M+H]$^+$=470/472
Retention time HPLC: 2.2 min (method A).

Example 39.3

4-(5-Bromo-pyridin-2-ylmethoxy)-1-[2-fluoro-2-(2-methyl-1,2,3,4-tetrahydro-isoquinolin-7-yl)ethyl]-1H-pyridin-2-one

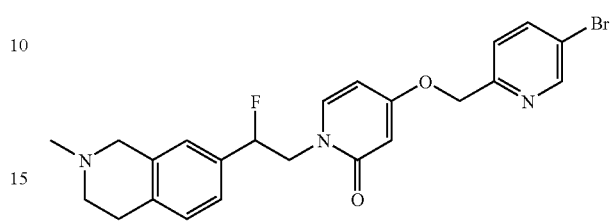

To 70 mg (0.15 mmol) 4-(5-bromo-pyridin-2-ylmethoxy)-1-[2-hydroxy-2-(2-methyl-1,2,3,4-tetrahydro-isoquinolin-7-yl)-ethyl]-1H-pyridin-2-one (example 39.2) in 3 mL DCM is added at −72° C. 36 μL (0.19 mmol) (bis(2-methoxyethyl)amino)-sulfurtrifluoride ("New Dast"). The reaction is stirred at −78° C. and is warmed to RT overnight. The reaction mixture is coolded down to −78° C. and additional 36 μL (0.19 mmol) (bis(2-methoxyethyl)amino)-sulfurtrifluoride is added. The reaction is stirred 30 min at −78° C. and is warmed to RT. The mixture is diluted with aqueous NaHCO$_3$-solution, the aqueous phase is washed three times with EtOAc and dried over MgSO$_4$.

The solvent is evaporated and the residue is purified via reverse HPLC chromatography (Zorbax stable bond; water (0.1% formic acid)/acetonitrile (0.1% formic acid) 95:5 to 5:95).

Yield: 3 mg (4% of theory)
ESI Mass spectrum: [M+H]$^+$=472/474
Retention time HPLC: 2.6 min (method A).

Example 40.1

5-(5-Chloro-pyridin-2-ylmethoxy)-2-[2-(1,2,3,4-tetrahydro-isoquinolin-7-yl)-ethyl]-2H-pyridazin-3-one

40.1a 7-{2-[4-(5-Chloro-pyridin-2-ylmethoxy)-6-oxo-6H-pyridazin-1-yl]-ethyl}-3,4-dihydro-1H-isoquinoline-2-carboxylic Acid Tert-Butyl Ester 7-{2-[4-(5-Chloro-pyridin-2-ylmethoxy)-6-oxo-6H-pyridazin-1-yl]-ethyl}-3,4-dihydro-1H-isoquinoline-2-carboxylic acid tert-butyl ester is prepared following preparation 15b from 1.20 g (5.05 mmol) 5-(5-chloro-pyridin-2-ylmethoxy)-2H-pyridazin-3-one (preparation 18b) and 2.62 g (6.06 mmol) 7-[2-(toluene-4-sulfonyloxy)-ethyl]-3,4-dihydro-1H-isoquinoline-2-carboxylic acid tert-butyl ester (preparation 7).

Yield: 2.50 g (100% of theory)
ESI Mass spectrum: [M+H]$^+$=497/499
Retention time HPLC: 2.8 min (method E).

40.1b 5-(5-Chloro-pyridin-2-ylmethoxy)-2-[2-(1,2,3,4-tetrahydro-isoquinolin-7-yl)-ethyl]-2H-pyridazin-3-one 5-(5-Chloro-pyridin-2-ylmethoxy)-2-[2-(1,2,3,4-tetrahydro-isoquinolin-7-yl)-ethyl]-2H-pyridazin-3-one is prepared following example 24.2 from 2.50 g (5.03 mmol) 7-{2-[4-(5-chloro-pyridin-2-ylmethoxy)-6-oxo-6H-pyridazin-1-yl]-ethyl}-3,4-dihydro-1H-isoquinoline-2-carboxylic acid tert-butyl ester (example 40.1a) (purification via reversed HPLC chromatography).

Yield: 1.20 g (60% of theory)
ESI Mass spectrum: [M+H]$^+$=397/399
Retention time HPLC: 2.4 min (method A).

Example 40.2

5-(5-Bromo-pyridin-2-ylmethoxy)-2-[2-(1,2,3,4-tetrahydro-isoquinolin-7-yl)-ethyl]-2H-pyridazin-3-one

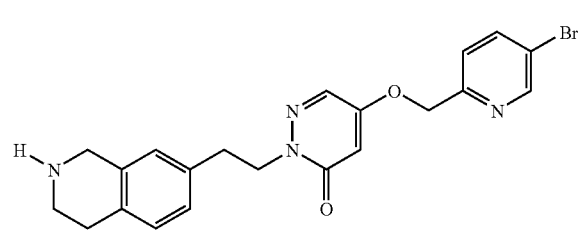

40.2a 7-{2-[4-(5-Bromo-pyridin-2-ylmethoxy)-6-oxo-6H-pyridazin-1-yl]-ethyl}-3,4-dihydro-1H-isoquinoline-2-carboxylic Acid Tert-Butyl Ester 7-{2-[4-(5-Bromo-pyridin-2-ylmethoxy)-6-oxo-6H-pyridazin-1-yl]-ethyl}-3,4-dihydro-1H-isoquinoline-2-carboxylic acid tert-butyl ester is prepared following preparation 15b from 1.13 g (4.00 mmol) 5-(5-bromo-pyridin-2-ylmethoxy)-2H-pyridazin-3-one (preparation 25b) and 1.73 g (4.00 mmol) 7-[2-(toluene-4-sulfonyloxy)-ethyl]-3,4-dihydro-1H-isoquinoline-2-carboxylic acid tert-butyl ester (preparation 7).

Yield: 1.40 g (65% of theory)
ESI Mass spectrum: [M+H]$^+$=541/543
Retention time HPLC: 2.9 min (method E).

40.2b 5-(5-Bromo-pyridin-2-ylmethoxy)-2-[2-(1,2,3,4-tetrahydro-isoquinolin-7-yl)-ethyl]-2H-pyridazin-3-one 5-(5-Bromo-pyridin-2-ylmethoxy)-2-[2-(1,2,3,4-tetrahydro-isoquinolin-7-yl)-ethyl]-2H-pyridazin-3-one is prepared following example 24.2 from 1.40 g (2.59 mmol) 7-{2-[4-(5-bromo-pyridin-2-ylmethoxy)-6-oxo-6H-pyridazin-1-yl]-ethyl}-3,4-dihydro-1H-isoquinoline-2-carboxylic acid tert-butyl ester (example 40.2a) (purification via reversed HPLC chromatography).

Yield: 0.90 g (79% of theory)
ESI Mass spectrum: [M+H]$^+$=441/443
Retention time HPLC: 2.7 min (method F).

Example 40.3

5-(5-Chloro-pyridin-2-ylmethoxy)-2-[2-(2-methyl-1,2,3,4-tetrahydro-isoquinolin-7-yl)-ethyl]-2H-pyridazin-3-one

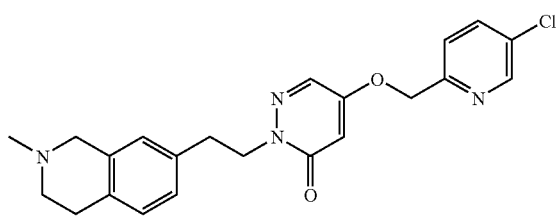

5-(5-Chloro-pyridin-2-ylmethoxy)-2-[2-(2-methyl-1,2,3,4-tetrahydro-isoquinolin-7-yl)-ethyl]-2H-pyridazin-3-one is prepared following example 23.17 from 75 mg (0.19 mmol) 5-(5-chloropyridin-2-ylmethoxy)-2-[2-(1,2,3,4-tetrahydro-isoquinolin-7-yl)-ethyl]-2H-pyridazin-3-one (example 40.1b).

Yield: 46 mg (59% of theory)
ESI Mass spectrum: [M+H]$^+$=411/413
Retention time HPLC: 2.9 min (method A).

Example 40.4

5-(5-Bromo-pyridin-2-ylmethoxy)-2-[2-(2-methyl-1,2,3,4-tetrahydro-isoquinolin-7-yl)-ethyl]-2H-pyridazin-3-one

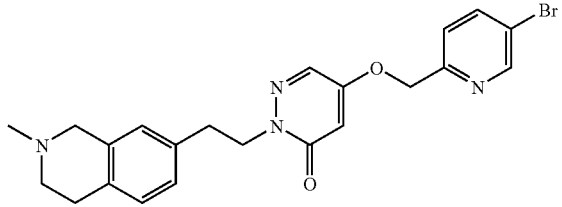

5-(5-Bromo-pyridin-2-ylmethoxy)-2-[2-(2-methyl-1,2,3,4-tetrahydro-isoquinolin-7-yl)-ethyl]-2H-pyridazin-3-one is prepared following example 23.17 from 500 mg (1.13 mmol) 5-(5-bromo-pyridin-2-ylmethoxy)-2-[2-(1,2,3,4-tetrahydro-isoquinolin-7-yl)-ethyl]-2H-pyridazin-3-one (example 40.2b).

Yield: 290 mg (56% of theory)
ESI Mass spectrum: [M+H]$^+$=455/457
Retention time HPLC: 2.5 min (method A).

Example 41.1

5-Benzyloxy-2-[2-oxo-2-(1,2,3,4-tetrahydro-iso-quinolin-7-yl)-ethyl]-2H-pyridazin-3-one

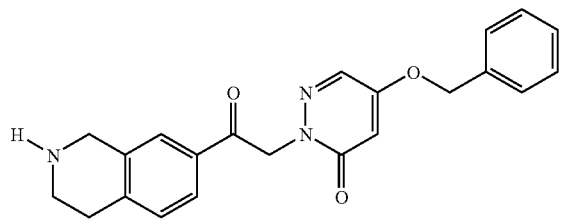

5-Benzyloxy-2-[2-oxo-2-(1,2,3,4-tetrahydro-isoquinolin-7-yl)-ethyl]-2H-pyridazin-3-one is prepared following example 22.3 from 4.70 g (9.97 mmol) 5-benzyloxy-2-{2-oxo-2-[2-(2,2,2-trifluoro-acetyl)-1,2,3,4-tetrahydro-iso-quinolin-7-yl]-ethyl}-2H-pyridazin-3-one (preparation 28.1).

Yield: 3.40 g (91% of theory)
ESI Mass spectrum: [M+H]$^+$=376
Retention time HPLC: 2.5 min (method A).

The following examples are prepared as described for example 41.1.

Example 42.1

5-Benzyloxy-2-[2-(2-methyl-1,2,3,4-tetrahydro-iso-quinolin-7-yl)-2-oxo-ethyl]-2H-pyridazin-3-one

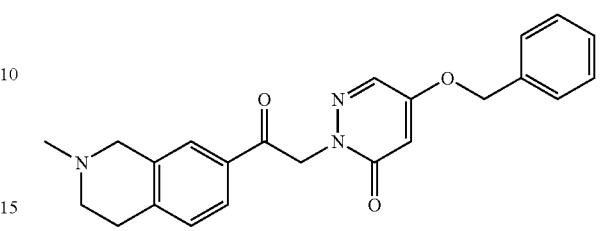

5-Benzyloxy-2-[2-(2-methyl-1,2,3,4-tetrahydro-iso-quinolin-7-yl)-2-oxo-ethyl]-2H-pyridazin-3-one is prepared following example 23.17 from 130 mg (0.35 mmol) 5-benzyloxy-2-[2-oxo-2-(1,2,3,4-tetrahydro-isoquinolin-7-yl)-ethyl]-2H-pyridazin-3-one (example 41.1).

Yield: 52 mg (39% of theory)
ESI Mass spectrum: [M+H]$^+$=390
Retention time HPLC: 3.0 min (method A).

The following examples are prepared as described for example 42.1.

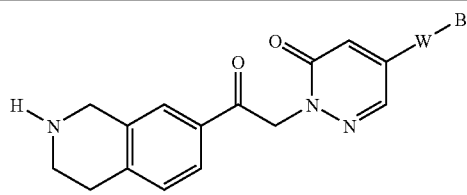

| example | —W—B | Starting material | Yield (%) | Formula | MS | Retention time HPLC in min (method) |
|---|---|---|---|---|---|---|
| 41.2 | *–O–CH₂–(2-pyridyl) | Preparation 28.2 | 40 | C$_{21}$H$_{20}$N$_4$O$_3$ | 377 [M + H]$^+$ | 2.2 (A) |
| 41.3 | *–O–CH₂–(5-bromo-2-pyridyl) | Preparation 28.3 | 76 | C$_{21}$H$_{19}$BrN$_4$O$_3$ | 455/457 [M + H]$^+$ | 1.5 (K) |
| 41.4 | *–O–CH₂–(4-fluorophenyl) | Preparation 28.4 | 87 | C$_{22}$H$_{20}$FN$_3$O$_3$ | 394 [M + H]$^+$ | 2.6 (A) |
| 41.5 | *–O–CH₂–(5-chloro-2-pyridyl) | Preparation 28.5 | 58 | C$_{21}$H$_{19}$ClN$_4$O$_3$ | 411/413 [M + H]$^+$ | 2.3 (A) |

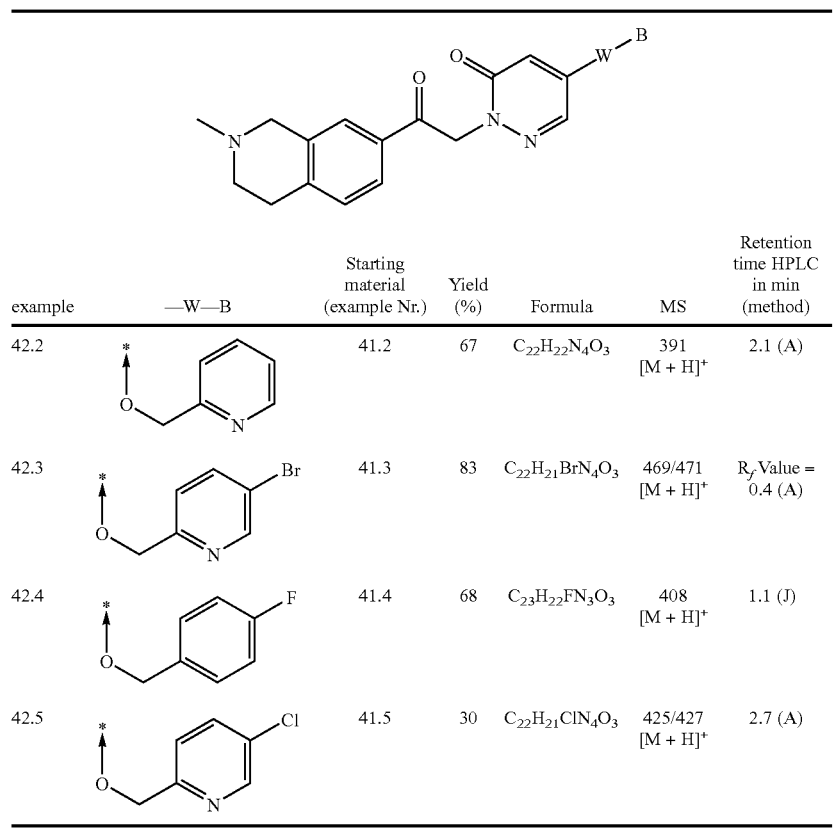

| example | —W—B | Starting material (example Nr.) | Yield (%) | Formula | MS | Retention time HPLC in min (method) |
|---|---|---|---|---|---|---|
| 42.2 | *-O-CH₂-(2-pyridyl) | 41.2 | 67 | $C_{22}H_{22}N_4O_3$ | 391 $[M + H]^+$ | 2.1 (A) |
| 42.3 | *-O-CH₂-(5-Br-2-pyridyl) | 41.3 | 83 | $C_{22}H_{21}BrN_4O_3$ | 469/471 $[M + H]^+$ | $R_f$ Value = 0.4 (A) |
| 42.4 | *-O-CH₂-(4-F-phenyl) | 41.4 | 68 | $C_{23}H_{22}FN_3O_3$ | 408 $[M + H]^+$ | 1.1 (J) |
| 42.5 | *-O-CH₂-(5-Cl-2-pyridyl) | 41.5 | 30 | $C_{22}H_{21}ClN_4O_3$ | 425/427 $[M + H]^+$ | 2.7 (A) |

Example 43.1

5-Benzyloxy-2-[2-(2,3-dihydro-1H-isoindol-5-yl)-2-oxo-ethyl]-2H-pyridazin-3-one

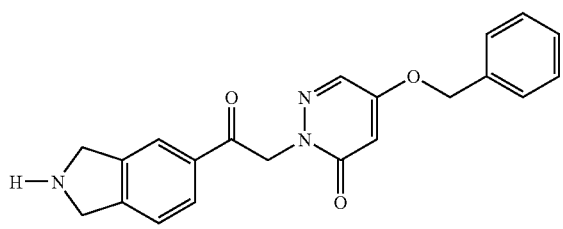

43.1a 5-Benzyloxy-2-{2-oxo-2-[2-(2,2,2-trifluoro-acetyl)-2,3-dihydro-1H-isoindol-5-yl]-ethyl}-2H-pyridazin-3-one 5-Benzyloxy-2-{2-oxo-2-[2-(2,2,2-trifluoro-acetyl)-2,3-dihydro-1H-iso indol-5-yl]-ethyl}-2H-pyridazin-3-one is prepared following preparation 15b from 1.38 g (6.80 mmol) 5-benzyloxy-2H-pyridazin-3-one (preparation 5c) and 2.08 g (7.14 mmol) 1-[5-(2-chloro-acetyl)-1,3-dihydroisoindol-2-yl]-2,2,2-trifluoro-ethanone (see preparation 23) in DMSO as solvent (purification via reversed HPLC chromatography).

Yield: 1.90 g (61% of theory)
ESI Mass spectrum: $[M+H]^+=458$
Retention time HPLC: 1.8 min (method K).

43.1b 5-Benzyloxy-2-[2-(2,3-dihydro-1H-isoindol-5-yl)-2-oxo-ethyl]-2H-pyridazin-3-one 5-Benzyloxy-2-[2-(2,3-dihydro-1H-isoindol-5-yl)-2-oxo-ethyl]-2H-pyridazin-3-one is prepared following example 22.3 from 1.90 g (4.15 mmol) 5-benzyloxy-2-{2-oxo-2-[2-(2,2,2-trifluoroacetyl)-2,3-dihydro-1H-isoindol-5-yl]-ethyl}-2H-pyridazin-3-one (example 43.1a).

Yield: 0.80 g (53% of theory)
ESI Mass spectrum: $[M+H]^+=362$
Retention time HPLC: 1.6 min (method K).

Example 43.2

5-Benzyloxy-2-[2-(2-methyl-2,3-dihydro-1H-isoindol-5-yl)-2-oxo-ethyl]-2H-pyridazin-3-one

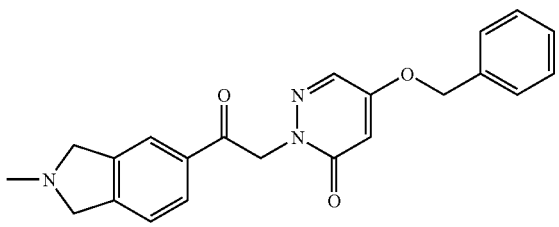

5-Benzyloxy-2-[2-(2-methyl-2,3-dihydro-1H-isoindol-5-yl)-2-oxo-ethyl]-2H-pyridazin-3-one is prepared following example 23.17 from 70 mg (0.19 mmol) 5-benzyloxy-2-[2-(2,3-dihydro-1H-isoindol-5-yl)-2-oxo-ethyl]-2H-pyridazin-3-one (example 43.1b).

Yield: 10 mg (14% of theory)
ESI Mass spectrum: [M+H]$^+$=376
Retention time HPLC: 3.4 min (method J).

Example 44.1

5-Benzyloxy-2-[2-oxo-2-(4,5,6,7-tetrahydro-thieno[3,2-c]pyridin-2-yl)-ethyl]-2H-pyridazin-3-one

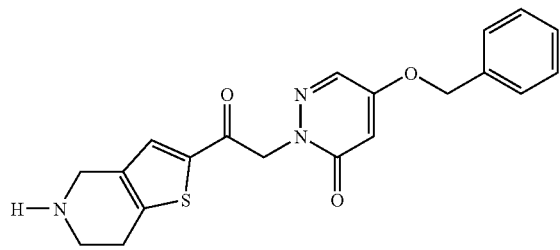

44.1a 5-Benzyloxy-2-{2-[5-(2-chloro-benzyl)-4,5,6,7-tetrahydro-thieno[3,2-c]pyridin-2-yl]-2-oxoethyl}-2H-pyridazin-3-one Hydrochloride 5-Benzyloxy-2-{2-[5-(2-chloro-benzyl)-4,5,6,7-tetrahydro-thieno[3,2-c]pyridin-2-yl]-2-oxo-ethyl}-2H-pyridazin-3-one is prepared following preparation 15b (in DMSO as solvent; purification via reversed HPLC chromatography) from 500 mg (2.47 mmol) 5-benzyloxy-2H-pyridazin-3-one (preparation 5c) and 1.03 g (2.72 mmol) 2-chloro-1-[5-(2-chloro-benzyl)-3a,4,5,6,7,7a-hexahydro-thieno[3,2-c]pyridin-2-yl]-ethanone (preparation 24).

Yield: 350 mg (28% of theory)
ESI Mass spectrum: [M+H]$^+$=506/508
Retention time HPLC: 2.7 min (method H).

44.1b 5-Benzyloxy-2-[2-oxo-2-(4,5,6,7-tetrahydro-thieno[3,2-c]pyridin-2-yl)-ethyl]-2H-pyridazin-3-one hydrochloride 5-Benzyloxy-2-[2-oxo-2-(4,5,6,7-tetrahydro-thieno[3,2-c]pyridin-2-yl)-ethyl]-2H-pyridazin-3-one hydrochloride is prepared following example 38.1b from 300 mg (0.59 mmol) 5-benzyloxy-2-{2-[5-(2-chloro-benzyl)-4,5,6,7-tetrahydro-thieno[3,2-c]pyridin-2-yl]-2-oxo-ethyl}-2H-pyridazin-3-one (example 44.1a).

Yield: 200 mg (81% of theory)
ESI Mass spectrum: [M+H]$^+$=382
Retention time HPLC: 3.4 min (method J).

Example 44.2

5-Benzyloxy-2-[2-(5-methyl-4,5,6,7-tetrahydro-thieno[3,2-c]pyridin-2-yl)-2-oxo-ethyl]-2H-pyridazin-3-one

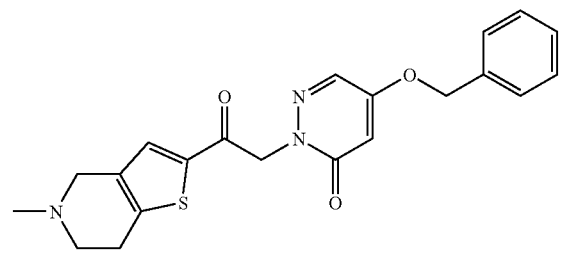

5-Benzyloxy-2-[2-(5-methyl-4,5,6,7-tetrahydro-thieno[3,2-c]pyridin-2-yl)-2-oxo-ethyl]-2H-pyridazin-3-one is prepared following example 23.17 from 130 mg (0.31 mmol) 5-benzyloxy-2-[2-oxo-2-(4,5,6,7-tetrahydro-thieno[3,2-c]pyridin-2-yl)-ethyl]-2H-pyridazin-3-one hydrochloride (example 44.1b).

Yield: 80 mg (65% of theory)
ESI Mass spectrum: [M+H]$^+$=396
Retention time HPLC: 3.6 min (method J).

Example 45.1

6-Benzyloxy-3-[2-oxo-2-(1,2,3,4-tetrahydro-isoquinolin-7-yl)-ethyl]-3H-pyrimidin-4-one

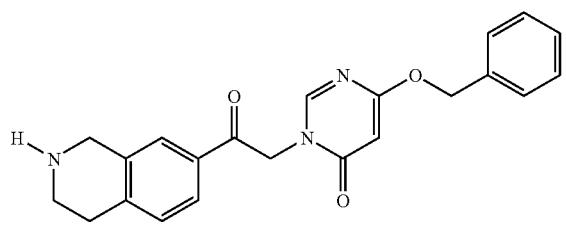

45.1a 6-Benzyloxy-3-{2-oxo-2-[2-(2,2,2-trifluoro-acetyl)-1,2,3,4-tetrahydro-isoquinolin-7-yl]-ethyl}-3H-pyrimidin-4-one 6-Benzyloxy-3-{2-oxo-2-[2-(2,2,2-trifluoro-acetyl)-1,2,3,4-tetrahydro-isoquinolin-7-yl]-ethyl}-3H-pyrimidin-4-one is prepared following preparation 15b from 850 mg (4.20 mmol) 6-benzyloxy-3H-pyrimidin-4-one and 1.35 g (4.41 mmol) 1-[7-(2-chloro-acetyl)-3,4-dihydro-1H-isoquinolin-2-yl]-2,2,2-trifluoro-ethanone in acetonitrile as solvent (purification via reversed HPLC chromatography).

Yield: 850 mg (43% of theory)
ESI Mass spectrum: [M+H]$^+$=472
Retention time HPLC: 1.5 min (method J).

45.1b 6-Benzyloxy-3-[2-oxo-2-(1,2,3,4-tetrahydro-isoquinolin-7-yl)-ethyl]-3H-pyrimidin-4-one 6-Benzyloxy-3-[2-oxo-2-(1,2,3,4-tetrahydro-isoquinolin-7-yl)-ethyl]-3H-pyrimidin-4-one is prepared following example 22.3 from 800 mg (1.70 mmol) 6-benzyloxy-3-{2-oxo-2-[2-(2,2,2-trifluoro-acetyl)-1,2,3,4-tetrahydro-isoquinolin-7-yl]-ethyl}-3H-pyrimidin-4-one (example 45.1a).
Yield: 400 mg (63% of theory)
ESI Mass spectrum: [M+H]$^+$=376
Retention time HPLC: 3.3 min (method J).

Example 45.2

6-Benzyloxy-3-[2-(2-methyl-1,2,3,4-tetrahydro-isoquinolin-7-yl)-2-oxo-ethyl]-3H-pyrimidin-4-one

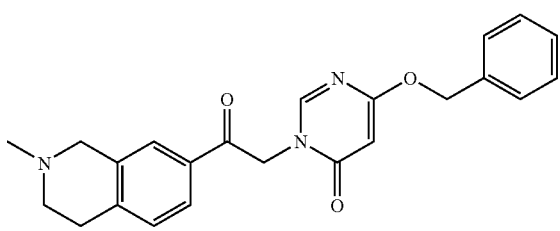

6-Benzyloxy-3-[2-(2-methyl-1,2,3,4-tetrahydro-isoquinolin-7-yl)-2-oxo-ethyl]-3H-pyrimidin-4-one is prepared following example 23.17 from 110 mg (0.29 mmol) 6-benzyloxy-3-[2-oxo-2-(1,2,3,4-tetrahydro-isoquinolin-7-yl)-ethyl]-3H-pyrimidin-4-one (example 45.1b).
Yield: 50 mg (44% of theory)
ESI Mass spectrum: [M+H]$^+$=390
Retention time HPLC: 3.5 min (method J).

Example 46.1

4-Benzyloxy-1-[2-oxo-2-(1,2,3,4-tetrahydro-isoquinolin-6-yl)-ethyl]-1H-pyridin-2-one

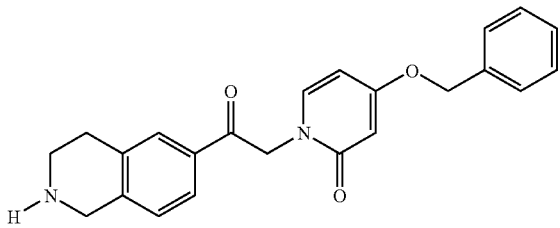

4-Benzyloxy-1-[2-oxo-2-(1,2,3,4-tetrahydro-isoquinolin-6-yl)-ethyl]-1H-pyridin-2-one is prepared following example 24.2 from 410 mg (0.86 mmol) 6-[2-(4-benzyloxy-2-oxo-2H-pyridin-1-yl)acetyl]-3,4-dihydro-1H-isoquinoline-2-carboxylic acid tert-butyl ester (preparation 29d).
Yield: 250 mg (77% of theory)
ESI Mass spectrum: [M+H]$^+$=375
Retention time HPLC: 1.5 min (method K).

Example 46.2

4-Benzyloxy-1-[2-(2-methyl-1,2,3,4-tetrahydro-isoquinolin-6-yl)-2-oxo-ethyl]-1H-pyridin-2-one

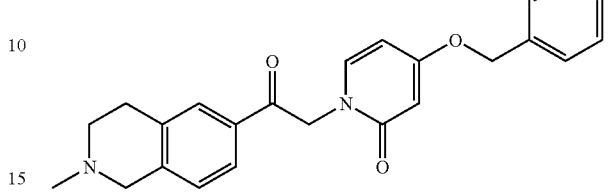

4-Benzyloxy-1-[2-(2-methyl-1,2,3,4-tetrahydro-isoquinolin-6-yl)-2-oxo-ethyl]-1H-pyridin-2-one is prepared following example 23.17 from 200 mg (0.53 mmol) 4-benzyloxy-1-[2-oxo-2-(1,2,3,4-tetrahydro-isoquinolin-6-yl)-ethyl]-1H-pyridin-2-one (example 46.1).
Yield: 129 mg (62% of theory)
ESI Mass spectrum: [M+H]$^+$=389
Retention time HPLC: 1.6 min (method K).

Example 47.1

5-Benzyloxy-2-{2-oxo-2-[4-(1-piperazin-1-yl-ethyl)-phenyl]-ethyl}-2H-pyridazin-3-one

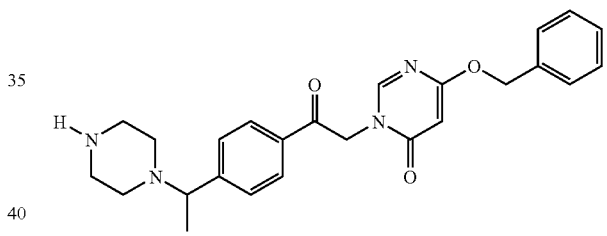

47.1a 4-(1-{4-[2-(4-Benzyloxy-6-oxo-6H-pyridazin-1-yl)-acetyl]-phenyl}-ethyl)-piperazine-1-carboxylic Acid Tert-Butyl Ester 4-(1-{4-[2-(4-Benzyloxy-6-oxo-6H-pyridazin-1-yl)-acetyl]-phenyl}-ethyl)-piperazine-1-carboxylic acid tert-butyl ester is prepared following example 1.1b from 200 mg (0.47 mmol) 5-benzyloxy-2-{2-[4-(1-bromo-ethyl)-phenyl]-2-oxo-ethyl}-2H-pyridazin-3-one (preparation 30c) and 262 mg (1.40 mmol) piperazine-1-carboxylic acid tert-butyl ester.
Yield: 130 mg (52% of theory)
Retention time HPLC: 2.0 min (method K).

47.1b 5-Benzyloxy-2-{2-oxo-2-[4-(1-piperazin-1-yl-ethyl)-phenyl]-ethyl}-2H-pyridazin-3-one 5-Benzyloxy-2-{2-oxo-2-[4-(1-piperazin-1-yl-ethyl)-phenyl]-ethyl}-2H-pyridazin-3-one is prepared following example 24.2 from 130 mg (0.24 mmol) 4-(1-{4-[2-(4-benzyloxy-6-oxo-6H-pyridazin-1-yl)-acetyl]-phenyl}-ethyl)-piperazine-1-carboxylic acid tert-butyl ester (example 47.1a).
Yield: 99 mg (94% of theory)
ESI Mass spectrum: [M+H]$^+$=433
Retention time HPLC: 1.2 min (method M).

The following examples are prepared from 5-benzyloxy-2-{2-[4-(1-bromo-ethyl)-phenyl]-2-oxoethyl}-2H-pyridazin-3-one (preparation 30c) as described for example 1.1b (4.0 eq. amine are used).

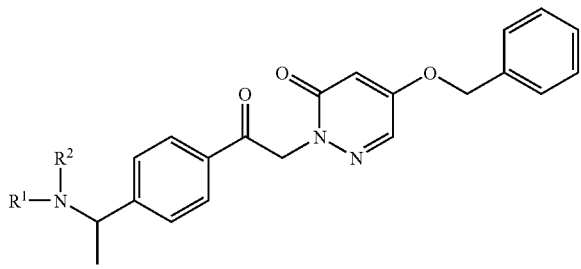

| Example | $R^1R^2N-$ | Yield (%) | Formula | MS | Retention time HPLC in min (method) |
|---|---|---|---|---|---|
| 47.2 | (S)-3-hydroxypyrrolidin-1-yl | 63 | $C_{25}H_{27}N_3O_4$ | 434 $[M + H]^+$ | 1.6 (K) |
| 47.3 | 4-hydroxypiperidin-1-yl | 63 | $C_{26}H_{29}N_3O_4$ | 448 $[M + H]^+$ | 1.6 (K) |
| 47.4 | 4-hydroxy-4-methylpiperidin-1-yl | 59 | $C_{27}H_{31}N_3O_4$ | 462 $[M + H]^+$ | 1.7 (K) |
| 47.5 | 4-methylpiperazin-1-yl | 67 | $C_{26}H_{30}N_4O_3$ | 447 $[M + H]^+$ | 1.7 (K) |
| 47.6 | N-ethyl-N-methylamino | 64 | $C_{24}H_{27}N_3O_3$ | 406 $[M + H]^+$ | 1.8 (K) |

Example 48.1

4-(4-Fluoro-benzyloxy)-1-{2-[4-(4-methyl-piperazin-1-ylmethyl)-phenyl]-2-oxo-ethyl}-1H-pyridin-2-one

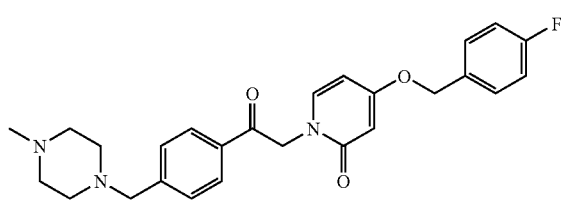

4-(4-Fluoro-benzyloxy)-1-{2-[4-(4-methyl-piperazin-1-ylmethyl)-phenyl]-2-oxo-ethyl}-1H-pyridin-2-one is prepared following example 1.1b from 100 mg (0.26 mmol) 1-[2-(4-chloromethylphenyl)-2-oxo-ethyl]-4-(4-fluoro-benzyloxy)-1H-pyridin-2-one (preparation 32.1) and 65 mg (0.65 mmol) N-methylpiperazine.

Yield: 85 mg (73% of theory)
ESI Mass spectrum: [M+H]$^+$=450
Retention time HPLC: 1.6 min (method K).

The following compounds are prepared as described for example 48.1.

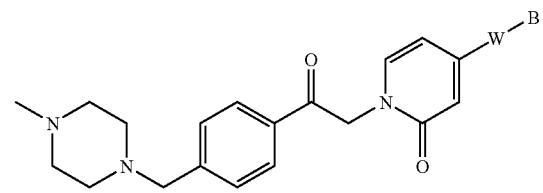

| Example | —W—B | Starting material (preparation Nr.) | Yield (%) | Formula | MS | Retention time HPLC in min (method) |
|---|---|---|---|---|---|---|
| 48.2 | *—O—CH₂—C₆H₄—Cl (4-Cl) | 32.2 | 61 | $C_{26}H_{28}ClN_3O_3$ | 466/468 [M + H]$^+$ | 1.6 (K) |
| 48.3 | *—O—CH₂—C₆H₄—CH₃ (4-Me) | 32.3 | 67 | $C_{27}H_{31}N_3O_3$ | 446 [M + H]$^+$ | 1.6 (K) |
| 48.4 | *—O—CH₂—C₆H₄—OMe (4-OMe) | 32.4 | 26 | $C_{27}H_{31}N_3O_4$ | 462 [M + H]$^+$ | 1.5 (K) |

The following compounds are prepared as described for example 48.1 (4.0 eq. of amine are used).

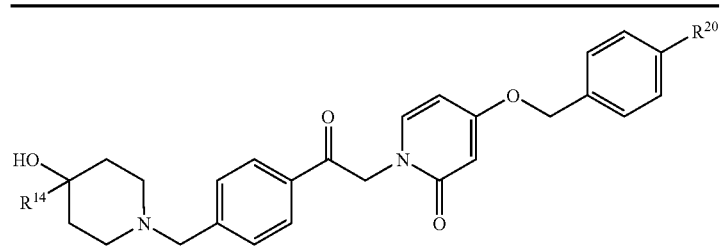

| Example | R$^{14}$ | R$^{20}$ | Starting material (preparation Nr.) | Yield (%) | Formula | MS | Retention time HPLC in min (method) |
|---|---|---|---|---|---|---|---|
| 48.5 | Me | OMe | 32.4 | 67 | $C_{28}H_{32}N_2O_5$ | 477 [M + H]$^+$ | 1.6 (K) |

-continued

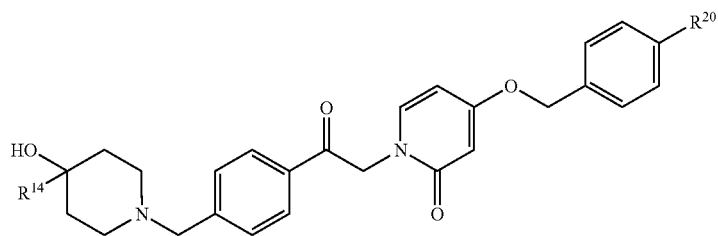

| Example | $R^{14}$ | $R^{20}$ | Starting material (preparation Nr.) | Yield (%) | Formula | MS | Retention time HPLC in min (method) |
|---|---|---|---|---|---|---|---|
| 48.6 | H | OMe | 32.4 | 56 | $C_{27}H_{30}N_2O_5$ | 463 $[M+H]^+$ | 1.6 (K) |
| 48.7 | Me | F | 32.1 | 65 | $C_{27}H_{29}FN_2O_4$ | 465 $[M+H]^+$ | 1.6 (K) |
| 48.8 | H | F | 32.1 | 31 | $C_{26}H_{27}FN_2O_4$ | 451 $[M+H]^+$ | 1.6 (K) |
| 48.9 | Me | Cl | 32.2 | 82 | $C_{27}H_{29}ClN_2O_4$ | 481/483 $[M+H]^+$ | 1.7 (K) |
| 48.10 | H | Cl | 32.2 | 44 | $C_{26}H_{27}ClN_2O_4$ | 467/469 $[M+H]^+$ | 1.7 (K) |

The following examples (49.1-49.42) are prepared following the above described procedures:

| Example | Structure | MS | Retention time HPLC in min (method) |
|---|---|---|---|
| 49.1 | 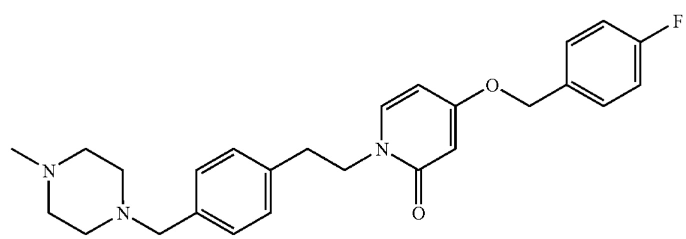 | 436 $[M+H]^+$ | 2.6 (C) |
| 49.2 | 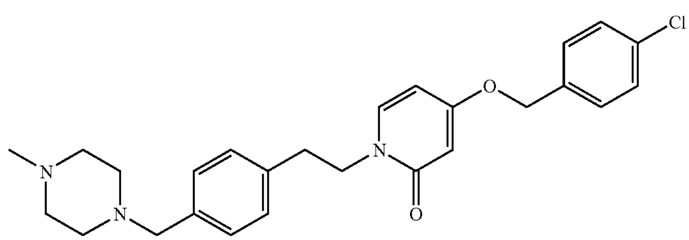 | 452/454 $[M+H]+$ | 2.9 (C) |
| 49.3 | 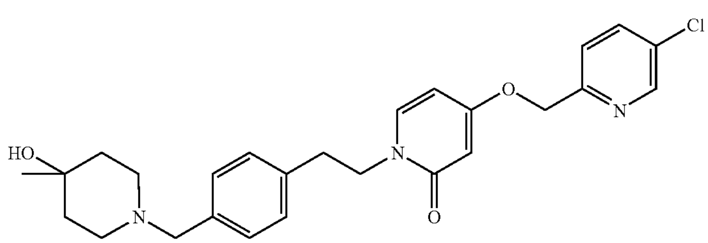 | 468/470 $[M+H]+$ | 2.4 (C) |

| Example | Structure | MS | Retention time HPLC in min (method) |
|---|---|---|---|
| 49.4 | 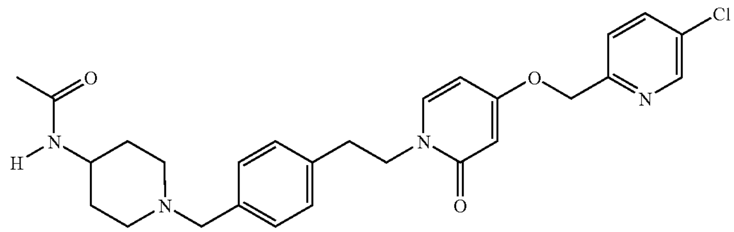 | 495/497 [M + H]+ | 2.3 (A) |
| 49.5 | 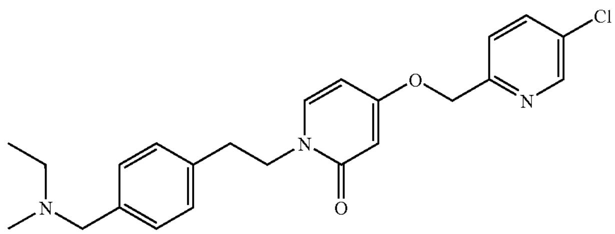 | 412/414 [M + H]+ | 2.8 (A) |
| 49.6 | 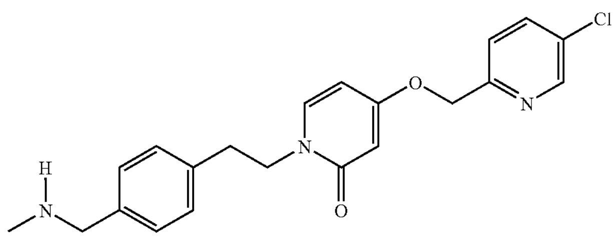 | 384/386 [M + H]+ | 2.7 (A) |
| 49.7 | 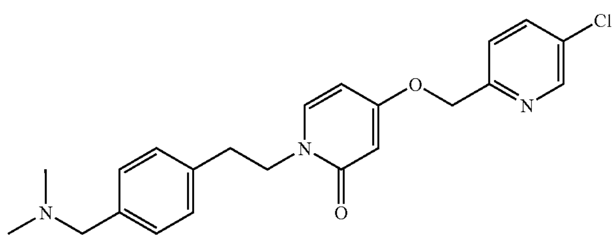 | 398/400 [M + H]+ | 2.7 (A) |
| 49.8 | 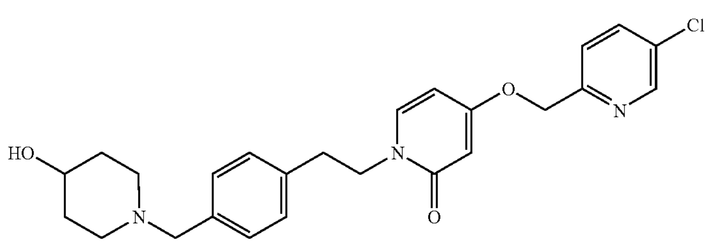 | 454/456 [M + H]+ | 2.6 (A) |
| 49.9 | 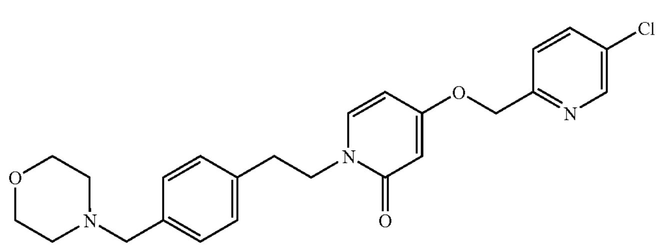 | 440/442 [M + H]+ | 2.7 (A) |

-continued

| Example | Structure | MS | Retention time HPLC in min (method) |
|---|---|---|---|
| 49.10 | 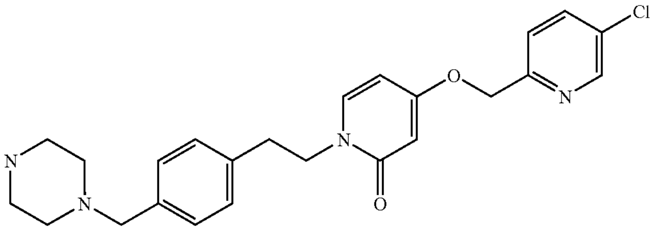 | 439/441 [M + H]+ | 2.4 (A) |
| 49.11 | 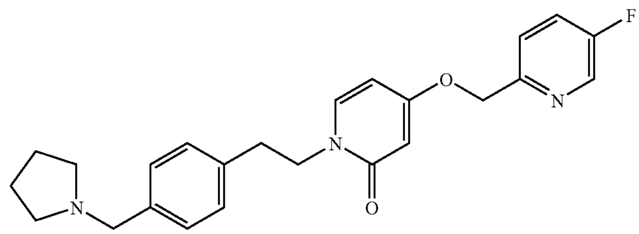 | 408 [M + H]+ | 4.8 (I) |
| 49.12 | 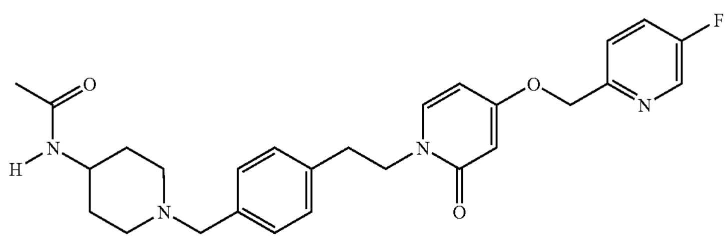 | 479 [M + H]+ | 5.2 (I) |
| 49.13 | 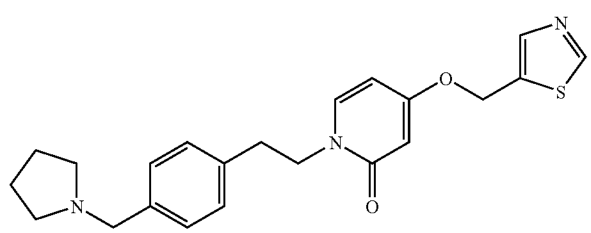 | 396 [M + H]+ | 2.4 (A) |
| 49.14 | 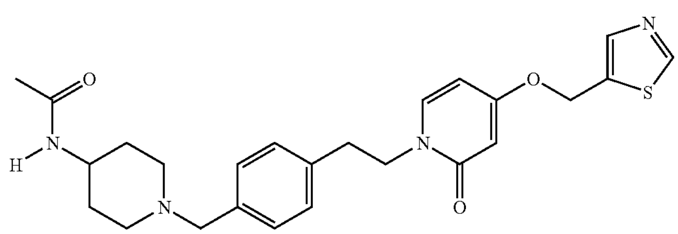 | 467 [M + H]+ | 2.2 (A) |
| 49.15 | 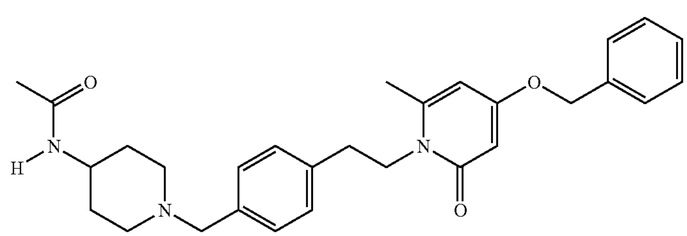 | 474 [M + H]+ | 2.4 (D) |

-continued

| Example | Structure | MS | Retention time HPLC in min (method) |
|---|---|---|---|
| 49.16 | 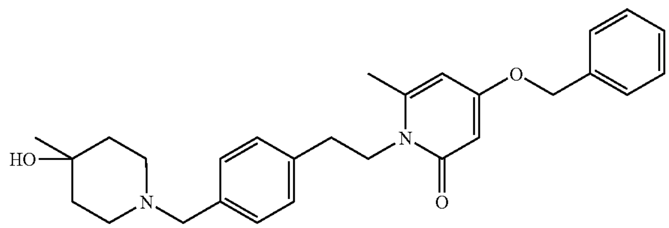 | 447 [M + H]+ | 2.7 (A) |
| 49.17 | 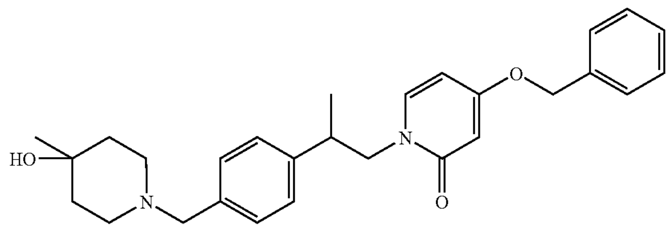 | 447 [M + H]+ | 3.1 (D) |
| 49.18 | 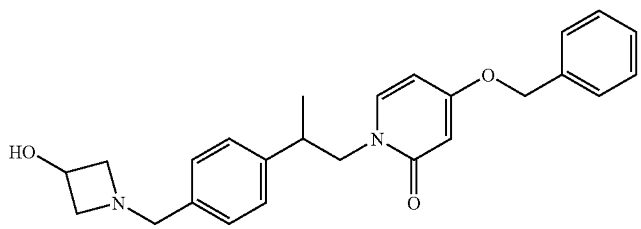 | 405 [M + H]+ | 3.8 (F) |
| 49.19 | 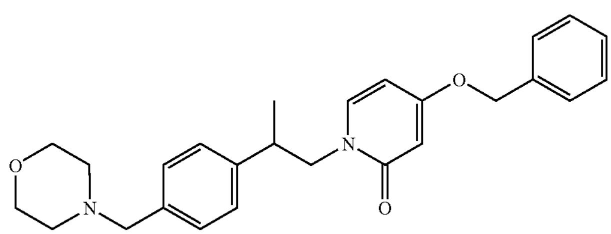 | 419 [M + H]+ | 3.0 (D) |
| 49.20 | 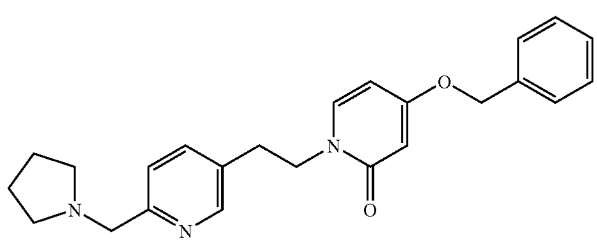 | 390 [M + H]+ | TLC 0.25 (A) |
| 49.21 | 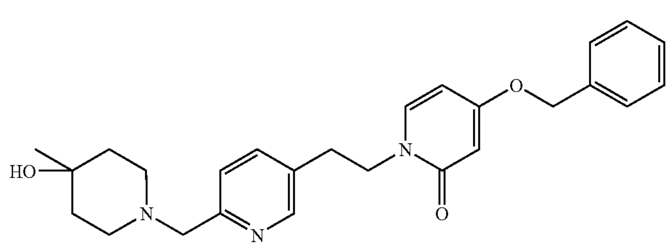 | 434 [M + H]+ | 2.6 (C) |

-continued

| Example | Structure | MS | Retention time HPLC in min (method) |
|---|---|---|---|
| 49.22 | 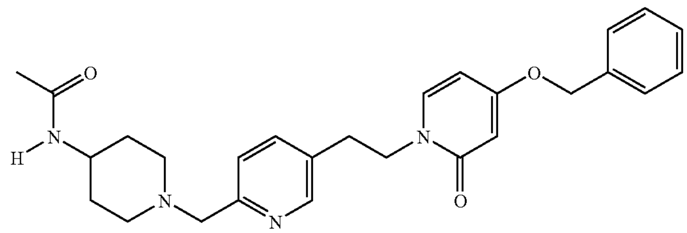 | 461 [M + H]+ | 2.5 (C) |
| 49.23 | 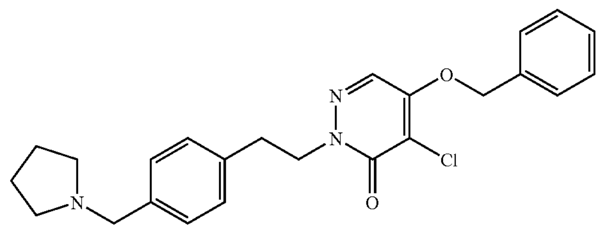 | 424/426 [M + H]+ | 3.3 (A) |
| 49.24 | 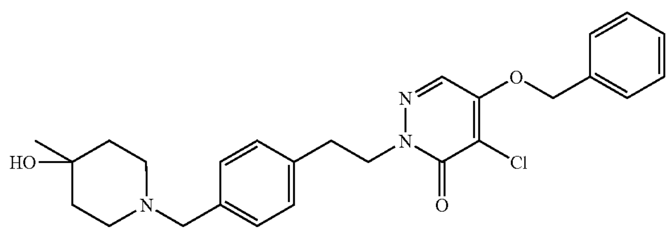 | 468/470 [M + H]+ | 3.2 (A) |
| 49.25 | 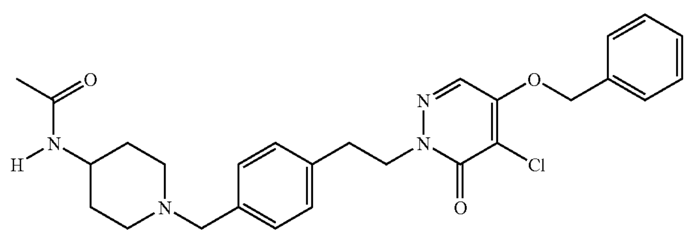 | 495/497 [M + H]+ | 3.1 (A) |
| 40.26 | 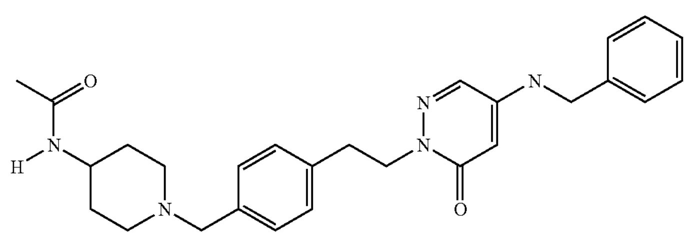 | 460 [M + H]+ | 1.0 (J) |
| 49.27 | 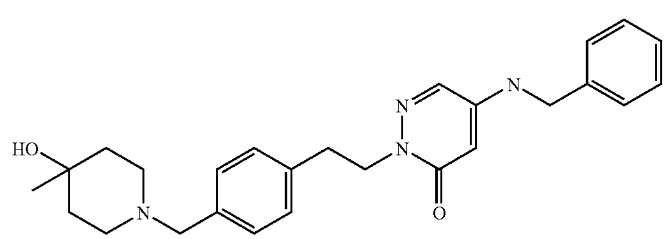 | 433 [M + H]+ | 1.0 (J) |

-continued

| Example | Structure | MS | Retention time HPLC in min (method) |
|---|---|---|---|
| 49.28 | 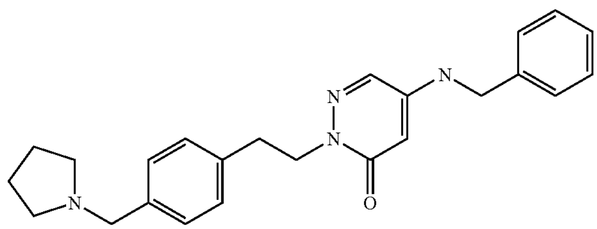 | 389 [M + H]+ | TLC 0.50 (A) |
| 49.29 | 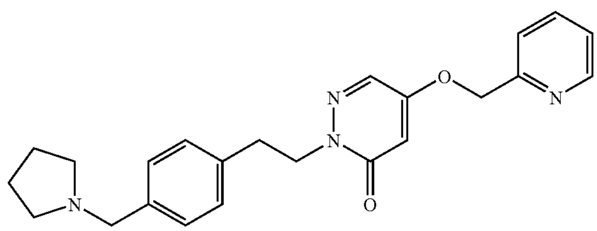 | 391 [M + H]+ | 2.1 (C) |
| 49.30 | 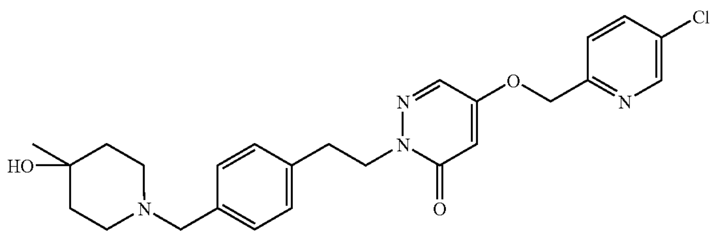 | 469/471 [M + H]+ | 2.5 (A) |
| 49.31 | 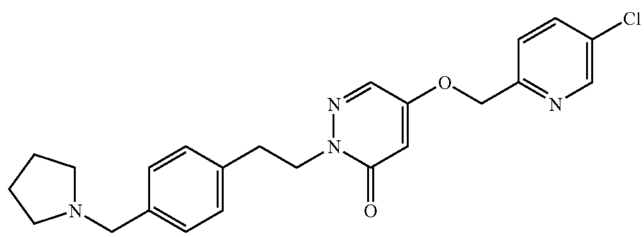 | 425/427 [M + H]+ | 2.6 (A) |
| 49.32 | 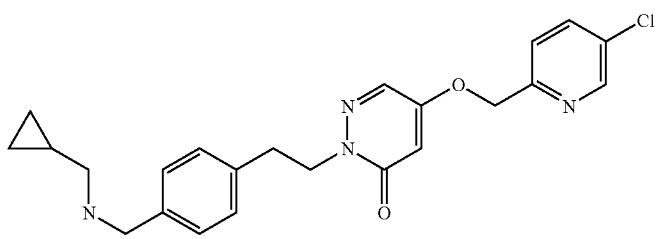 | 425/427 [M + H]+ | 3.1 (A) |
| 49.33 | 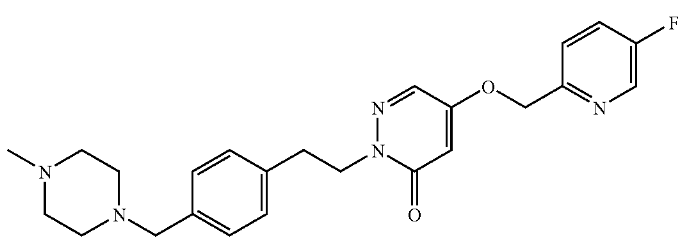 | 438 [M + H]+ | 2.1 (C) |

-continued

| Example | Structure | MS | Retention time HPLC in min (method) |
|---|---|---|---|
| 49.34 | 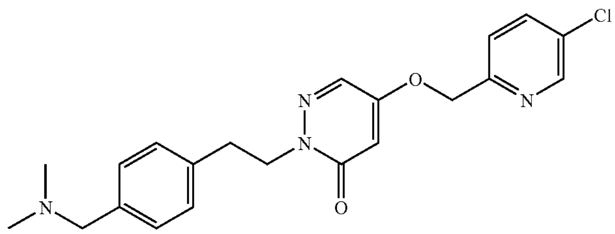 | 399/401 [M + H]+ | 1.1 (J) |
| 49.35 | 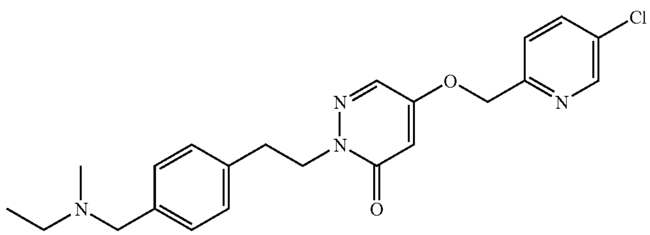 | 413/415 [M + H]+ | 2.4 (A) |
| 49.36 | 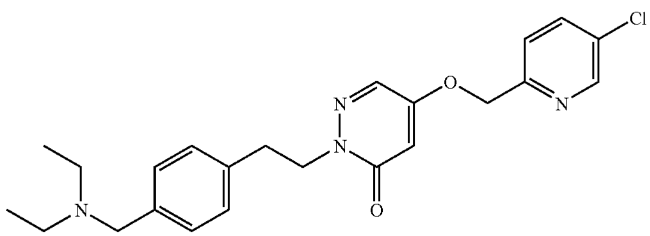 | 427/429 [M + H]+ | 2.5 (A) |
| 49.37 | 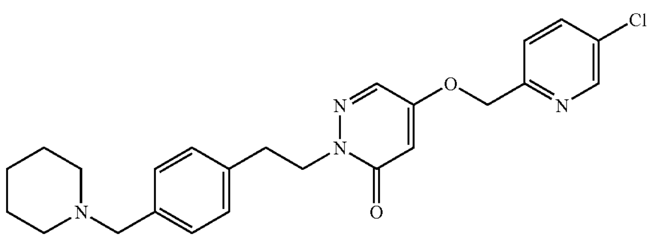 | 439/441 [M + H]+ | 1.1 (J) |
| 49.38 | 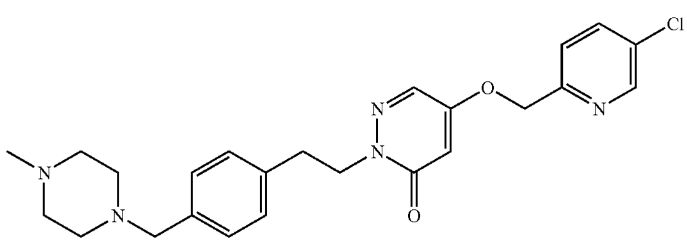 | 454/456 [M + H]+ | 2.4 (C) |
| 49.39 | 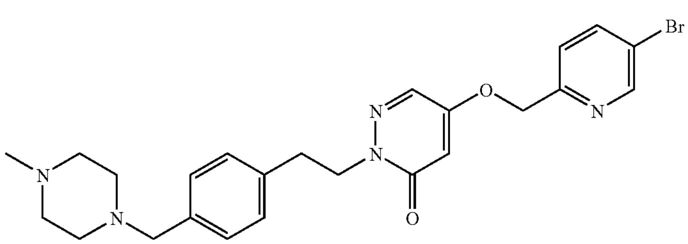 | 498/500 [M + H]+ | 2.3 (A) |

-continued

| Example | Structure | MS | Retention time HPLC in min (method) |
|---------|-----------|-----|-------------------------------------|
| 49.40 | 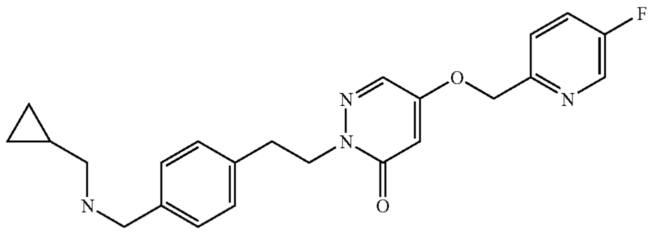 | 408 [M + H]+ | 2.9 (D) |
| 49.41 | 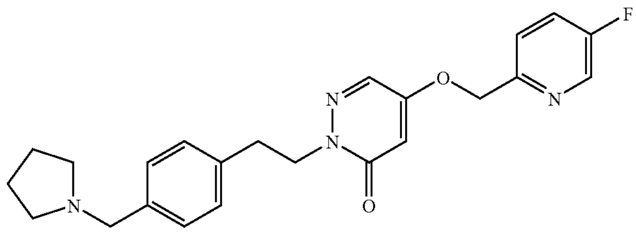 | 409 [M + H]+ | 2.8 (A) |
| 49.42 | 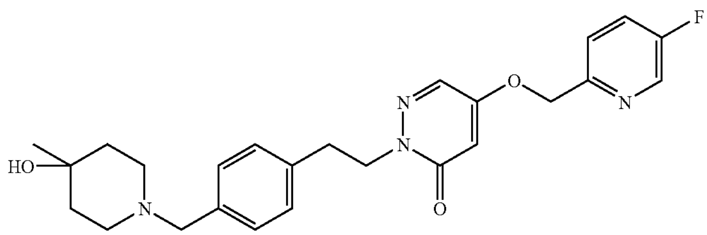 | 453 [M + H]+ | 2.7 (A) |

The following examples can be prepared following the above described procedures:

| Example | Structure |
|---------|-----------|
| 50.1 | 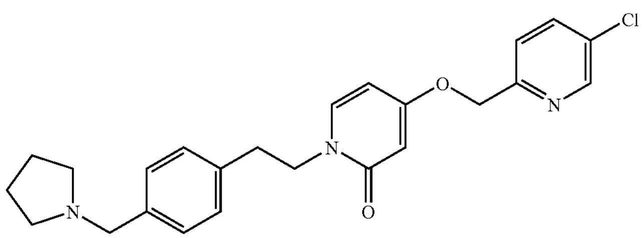 |
| 50.2 | 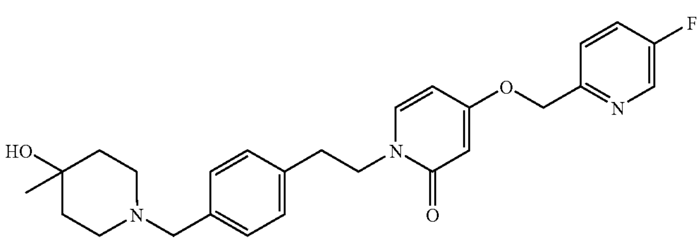 |

| Example | Structure |
|---|---|
| 50.3 | 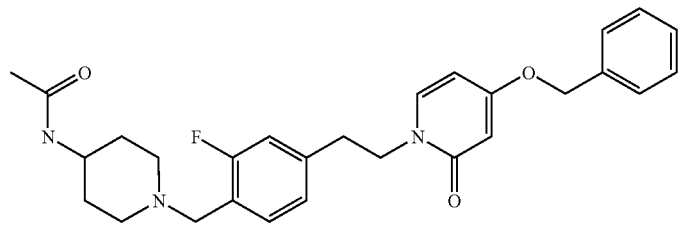 |
| 50.4 | 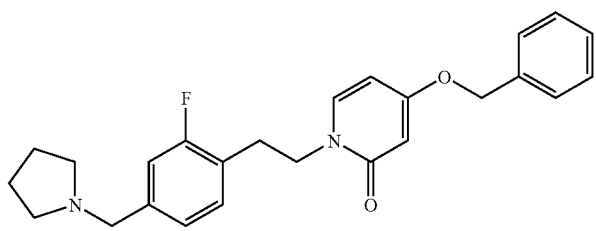 |
| 50.5 | 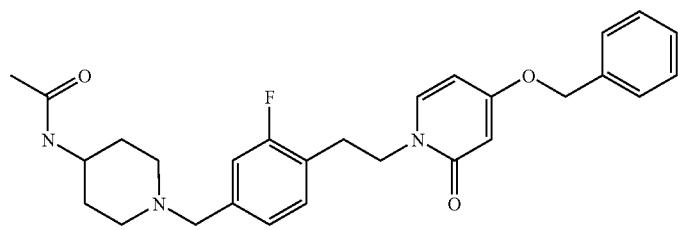 |
| 50.6 | 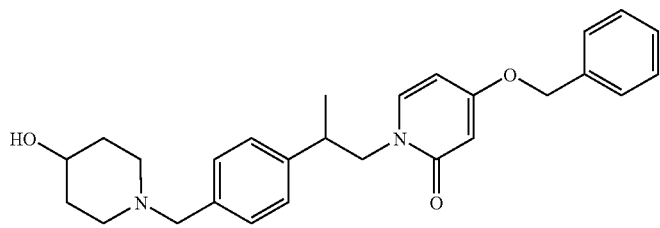 |
| 50.7 | 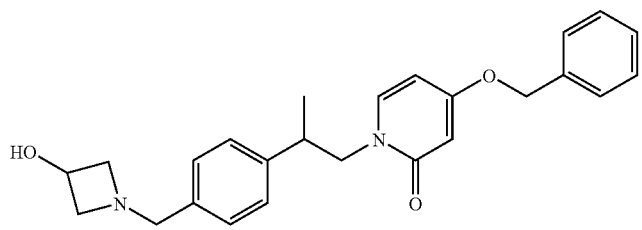 |
| 50.8 | 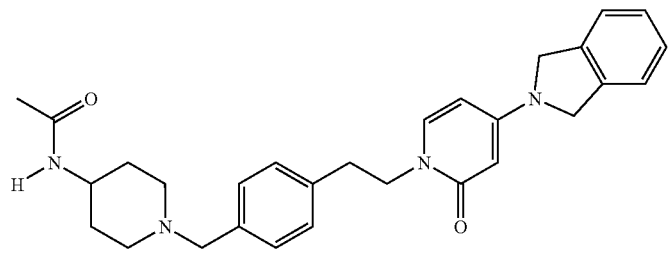 |

| Example | Structure |
|---|---|
| 50.9 | 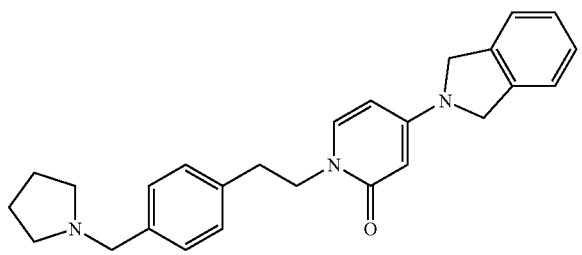 |
| 50.10 | 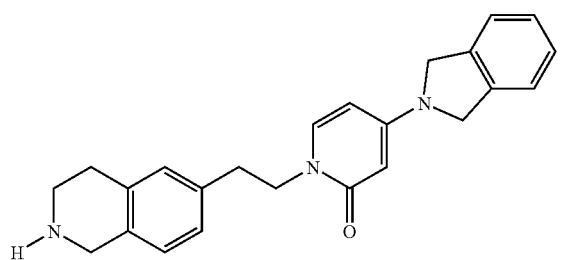 |
| 50.11 | 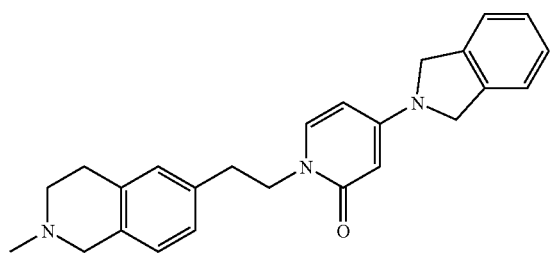 |
| 50.12 | 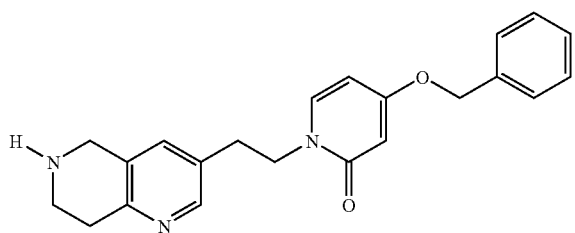 |
| 50.13 | 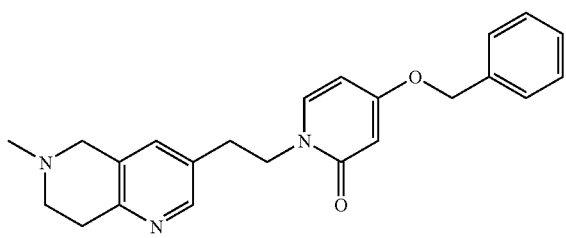 |
| 50.14 | 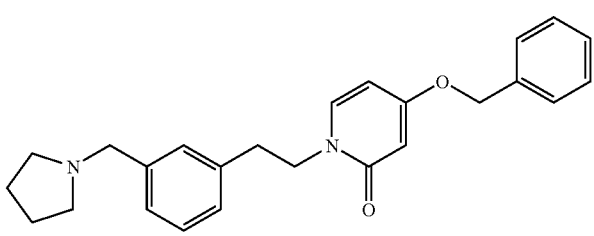 |

| Example | Structure |
|---|---|
| 50.15 | 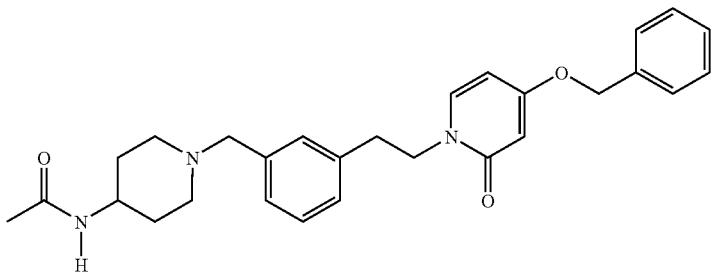 |
| 50.16 | 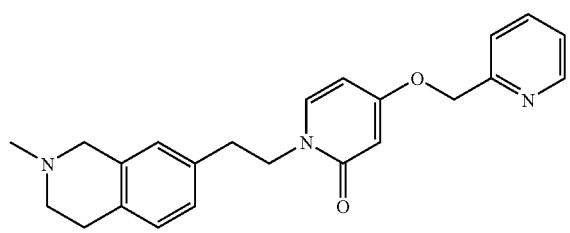 |
| 50.17 | 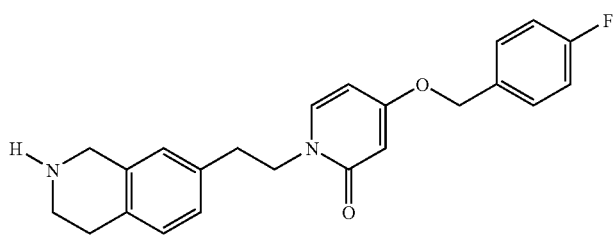 |
| 50.18 | 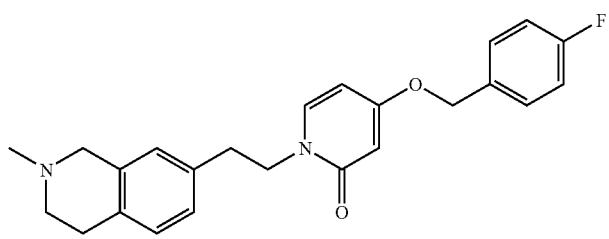 |
| 50.19 | 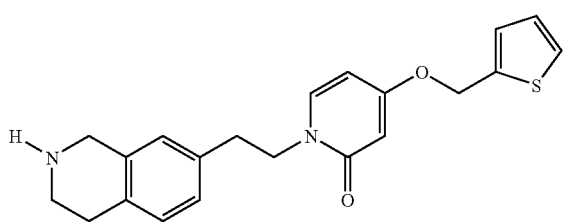 |
| 50.20 | 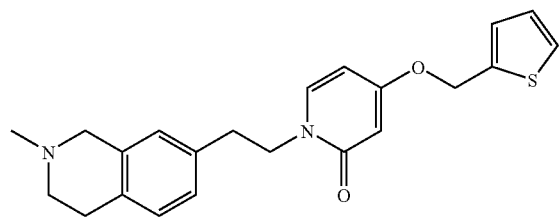 |

| Example | Structure |
|---|---|
| 50.21 | 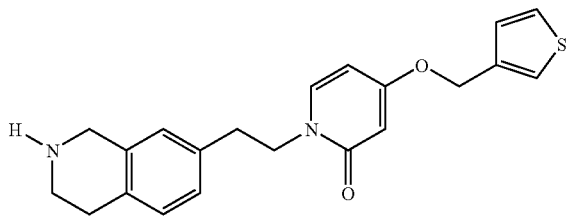 |
| 50.22 | 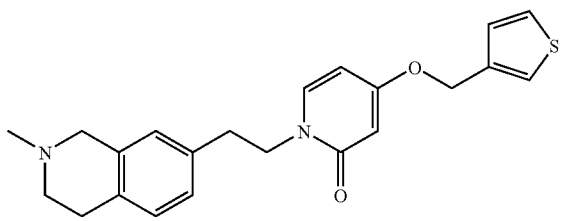 |
| 50.23 | 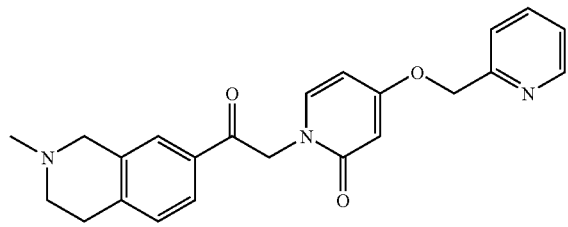 |
| 50.24 | 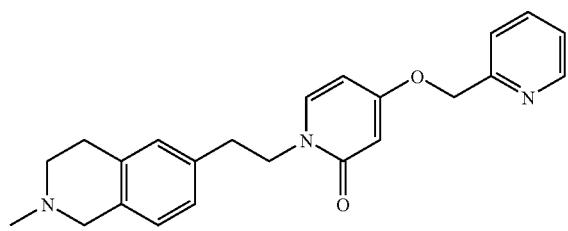 |

Some test methods for determining an MCH-receptor antagonistic activity will now be described. In addition, other test methods known to the skilled man may be used, e.g. by inhibiting the MCH-receptor-mediated inhibition of cAMP production, as described by Hoogduijn M et al. in "Melanin-concentrating hormone and its receptor are expressed and functional in human skin", Biochem. Biophys. Res Commun. 296 (2002) 698-701 and by biosensory measurement of the binding of MCH to the MCH receptor in the presence of antagonistic substances by plasmon resonance, as described by Karlsson OP and Lofas S. in "Flow-Mediated On-Surface Reconstitution of G-Protein Coupled Receptors for Applications in Surface Plasmon Resonance Biosensors", Anal. Biochem. 300 (2002), 132-138. Other methods of testing antagonistic activity to MCH receptors are contained in the references and patent documents mentioned hereinbefore, and the description of the test methods used is hereby incorporated in this application.

| MCH-1 receptor binding test | |
|---|---|
| Method: | MCH binding to hMCH-1R transfected cells |
| Species: | Human |
| Test cell: | hMCH-1R stably transfected into CHO/Galpha16 cells |
| Results: | IC50 values |

Membranes from CHO/Galpha16 cells stably transfected with human hMCH-1R are resuspended using a syringe (needle 0.6×25 mm) and diluted in test buffer (50 mM HEPES, 10 mM $MgCl_2$, 2 mM EGTA, pH 7.00; 0.1% bovine serum albumin (protease-free), 0.021% bacitracin, 1 μg/ml aprotinin, 1 μg/ml leupeptin and 1 μM phosphoramidone) to a concentration of 5 to 15 μg/ml.

200 microlitres of this membrane fraction (contains 1 to 3 μg of protein) are incubated for 60 minutes at ambient temperature with 100 pM of $^{125}$I-tyrosyl melanin concentrating hormone ($^{125}$I-MCH commercially obtainable from NEN) and increasing concentrations of the test compound in a final volume of 250 microlitres. After the incubation the reaction is filtered using a cell harvester through 0.5% PEI treated fibreglass filters (GF/B, Unifilter Packard). The membranebound radioactivity retained on the filter is then determined after the addition of scintillator substance (Packard Microscint 20) in a measuring device (TopCount of Packard). The non-specific binding is defined as bound radioactivity in the presence of 1 micromolar MCH during the incubation period.

The analysis of the concentration binding curve is carried out on the assumption of one receptor binding site.

Standard:

Non-labelled MCH competes with labelled $^{125}$I-MCH for the receptor binding with an IC50 value of between 0.06 and 0.15 nM.

The KD value of the radioligand is 0.156 nM.

| MCH-1 receptor-coupled $Ca^{2+}$ mobilisation test | |
|---|---|
| Method: | Calcium mobilisation test with human MCH (FLIPR$^{384}$) |
| Species: | Human |
| Test cells: | CHO/Galpha 16 cells stably transfected with hMCH-R1 |
| Results: | 1st measurement:: % stimulation of the reference (MCH $10^{-6}$M) |
| | 2nd measurement: pKB value |
| Reagents: | HBSS(10x) (GIBCO) |
| | HEPES buffer (1M) (GIBCO) |
| | Pluronic F-127 (Molecular Probes) |
| | Fluo-4 (Molecular Probes) |
| | Probenecid (Sigma) |
| | MCH (Bachem) |
| | bovine serum albumin (protease-free) (Serva) |
| | DMSO (Serva) |
| | Ham's F12 (BioWhittaker) |
| | FCS (BioWhittaker) |
| | L-Glutamine (GIBCO) |
| | Hygromycin B (GIBCO) |
| | PENStrep (BioWhittaker) |
| | Zeocin (Invitrogen) |

Clonal CHO/Galpha16 hMCH-R1 cells are cultivated in Ham's F12 cell culture medium (with L-glutamine; BioWhittaker; Cat. No.: BE12-615F). This contains per 500 ml 10% FCS, 1% PENStrep, 5 ml L-glutamine (200 mM stock solution), 3 ml hygromycin B (50 mg/ml in PBS) and 1.25 ml zeocin (100 μg/ml stock solution). One day before the experiment the cells are plated on a 384-well microtitre plate (black-walled with a transparent base, made by Costar) in a density of 2500 cells per cavity and cultivated in the above medium overnight at 37° C., 5% $CO_2$ and 95% relative humidity. On the day of the experiment the cells are incubated with cell culture medium to which 2 mM Fluo-4 and 4.6 mM Probenicid have been added, at 37° C. for 45 minutes. After charging with fluorescent dye the cells are washed four times with Hanks buffer solution (1×HBSS, 20 mM HEPES), which has been combined with 0.07% Probenicid. The test substances are diluted in Hanks buffer solution, combined with 2.5% DMSO. The background fluorescence of non-stimulated cells is measured in the presence of substance in the 384-well microtitre plate five minutes after the last washing step in the FLIPR$^{384}$ apparatus (Molecular Devices; excitation wavelength: 488 nm; emission wavelength: bandpass 510 to 570 nm). To stimulate the cells MCH is diluted in Hanks buffer with 0.1% BSA, pipetted into the 384-well cell culture plate 35 minutes after the last washing step and the MCH-stimulated fluorescence is then measured in the FLIPR$^{384}$ apparatus.

Data Analysis:

1st measurement: The cellular $Ca^{2+}$ mobilisation is measured as the peak of the relative fluorescence minus the background and is expressed as the percentage of the maximum signal of the reference (MCH $10^{-6}$M). This measurement serves to identify any possible agonistic effect of a test substance.

2nd measurement: The cellular $Ca^{2+}$ mobilisation is measured as the peak of the relative fluorescence minus the background and is expressed as the percentage of the maximum signal of the reference (MCH $10^{-6}$M, signal is standardised to 100%). The EC50 values of the MCH dosage activity curve with and without test substance (defined concentration) are determined graphically by the GraphPad Prism 2.01 curve program. MCH antagonists cause the MCH stimulation curve to shift to the right in the graph plotted.

The inhibition is expressed as a pKB value:

$$pKB = \log(EC_{50(testsubstance+MCH)}/EC_{50(MCH)} - 1) - \log c_{(testsubstance)}$$

The compounds according to the invention, including their salts, exhibit an MCH-receptor antagonistic activity in the tests mentioned above. Using the MCH-1 receptor binding test described above an antagonistic activity is obtained for representative compounds of the present invention in a dosage range from about $10^{-10}$ to $10^{-5}$ M, particularly from $10^{-9}$ to $10^{-6}$ M.

In order to illustrate that compounds according to the invention with different structural elements possess a good to very good MCH-1 receptor antagonistic activity, the IC50 values of the compounds depicted in the following table are provided. It is noted that the compounds are selected in view of their different structural elements by way of example without any intent to highlight any specific compound.

| Compound according to Example no. | IC50 value |
|---|---|
| 4.2 | 8 nM |
| 6.1 | 13 nM |
| 21.2 | 3 nM |
| 22.1 | 51 nM |
| 23.2 | 7 nM |
| 23.16 | 12 nM |
| 23.23 | 40 nM |
| 27.2 | 8 nM |
| 28.1 | 26 nM |
| 29.3 | 16 nM |
| 29.4 | 16 nM |
| 29.11 | 14 nM |
| 29.13 | 18 nM |
| 32.2 | 12 nM |
| 32.3 | 9 nM |
| 32.8 | 6 nM |
| 32.10 | 23 nM |
| 33.8 | 19 nM |
| 34.3 | 16 nM |
| 35.2 | 15 nM |
| 36.1 | 18 nM |
| 37.2 | 33 nM |
| 39.1 | 34 nM |
| 41.1 | 17 nM |
| 41.3 | 17 nM |
| 42.1 | 14 nM |
| 42.3 | 18 nM |
| 44.2 | 20 nM |
| 46.2 | 21 nM |
| 47.5 | 27 nM |

Some examples of formulations will be described hereinafter, wherein the term "active substance" denotes one or more compounds according to the invention, including their salts. In the case of one of the combinations with one or more active substances described, the term "active substance" also includes the additional active substances.

Example A

Capsules for Powder Inhalation Containing 1 mg Active Substance

| Composition: 1 capsule for powder inhalation contains: | |
| --- | --- |
| active substance | 1.0 mg |
| lactose | 20.0 mg |
| hard gelatine capsules | 50.0 mg |
| | 71.0 mg |

Method of Preparation:

The active substance is ground to the particle size required for inhalation. The ground active substance is homogeneously mixed with the lactose. The mixture is packed into hard gelatine capsules.

Example B

Inhalable Solution for Respimat® Containing 1 mg Active Substance

| Composition: 1 spray contains: | |
| --- | --- |
| active substance | 1.0 mg |
| benzalkonium chloride | 0.002 mg |
| disodium edetate | 0.0075 mg |
| purified water ad | 15.0 µl |

Method of Preparation:

The active substance and benzalkonium chloride are dissolved in water and packed into Respimat® cartridges.

Example C

Inhalable Solution for Nebulisers Containing 1 mg Active Substance

| Composition: 1 vial contains: | |
| --- | --- |
| active substance | 0.1 g |
| sodium chloride | 0.18 g |
| benzalkonium chloride | 0.002 g |
| purified water ad | 20.0 ml |

Method of Preparation:

The active substance, sodium chloride and benzalkonium chloride are dissolved in water.

Example D

Propellant Type Metered Dose Aerosol Containing 1 mg Active Substance

| Composition: 1 spray contains: | |
| --- | --- |
| active substance | 1.0 mg |
| lecithin | 0.1% |
| propellant gas ad | 50.0 µl |

Method of Preparation:

The micronised active substance is homogeneously suspended in the mixture of lecithin and propellant gas. The suspension is transferred into a pressurised container with a metering valve.

Example E

Nasal Spray Containing 1 mg Active Substance

| Composition: | |
| --- | --- |
| active substance | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active substance and the excipients are dissolved in water and transferred into a corresponding container.

Example F

Injectable Solution Containing 5 mg of Active Substance Per 5 ml

| Composition: | |
| --- | --- |
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (Wfl); human serum albumin is added; active ingredient

Example G

Injectable Solution Containing 100 mg of Active Substance Per 20 ml

| Composition: | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

Example H

Lyophilisate Containing 10 mg of Active Substance

| Composition: | |
|---|---|
| Active substance | 10 mg |
| Mannitol | 300 mg |
| human serum albumin | 20 mg |

Preparation:

Mannitol is dissolved in water for injections (Wfl); human serum albumin is added; active ingredient is dissolved with heating; made up to specified volume with Wfl; transferred into vials; freeze-dried.

| Solvent for lyophilisate: | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (Wfl); transferred into ampoules.

Example I

Tablets Containing 20 mg of Active Substance

| Composition: | |
|---|---|
| active substance | 20 mg |
| lactose | 120 mg |
| maize starch | 40 mg |
| magnesium stearate | 2 mg |
| Povidone K 25 | 18 mg |

Preparation:

Active substance, lactose and maize starch are homogeneously mixed; granulated with an aqueous solution of Povidone; mixed with magnesium stearate; compressed in a tablet press; weight of tablet 200 mg.

Example J

Capsules Containing 20 mg Active Substance

| Composition: | |
|---|---|
| active substance | 20 mg |
| maize starch | 80 mg |
| highly dispersed silica | 5 mg |
| magnesium stearate | 2.5 mg |

Preparation:

Active substance, maize starch and silica are homogeneously mixed; mixed with magnesium stearate; the mixture is packed into size 3 hard gelatine capsules in a capsule filling machine.

Example K

Suppositories Containing 50 mg of Active Substance

| Composition: | |
|---|---|
| active substance | 50 mg |
| hard fat (Adeps solidus) q.s. ad | 1700 mg |

Preparation:

Hard fat is melted at about 38° C.; ground active substance is homogeneously dispersed in the molten hard fat; after cooling to about 35° C. it is poured into chilled moulds.

Example L

Injectable Solution Containing 10 mg of Active Substance Per 1 ml

| Composition: | |
|---|---|
| active substance | 10 mg |
| mannitol | 50 mg |
| human serum albumin | 10 mg |
| water for injections ad | 1 ml |

Preparation:

Mannitol is dissolved in water for injections (Wfl); human serum albumin is added; active ingredient is dissolved with heating; made up to specified volume with Wfl; transferred into ampoules under nitrogen gas.

What is claimed is:

1. A compound of formula I

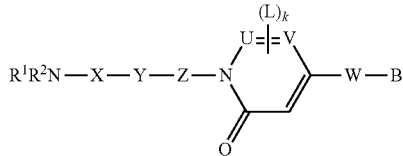

wherein $R^1$, $R^2$ independently of one another denote H, $C_{1-8}$-alkyl or $C_{3-7}$-cycloalkyl, while the alkyl or cycloalkyl group may be mono- or polysubstituted by identical or different groups $R^{11}$; or $R^2$ denotes a —$CH_2$— or —$CH_2$—$CH_2$ bridge which is linked to the group Y, and $R^1$ is defined as hereinbefore or denotes a group selected from $C_{1-4}$-alkyl-CO—, $C_{1-4}$-alkyl-O—CO—, ($C_{1-4}$-alkyl)NH—CO— or ($C_{1-4}$-alkyl)$_2$N—CO— wherein alkyl-groups may be mono- or polyfluorinated; or $R^1$ and $R^2$ form alkylene bridge such that $R^1R^2$N— denotes a group which is selected from azetidine, pyrrolidine, piperidine, azepan, 2,5-dihydro-1H-pyrrole, 1,2,3,6-tetrahydro-pyridine, 2,3,4,7-tetrahydro-1H-azepine, 2,3,6,7-tetrahydro-1H-azepine, piperazine in which the free imine function is substituted by $R^{13}$, piperidin-4-one, morpholine, thiomorpholine, 4-$C_{1-4}$-alkoxy-imino-piperidin-1-yl and 4-hydroxy-imino-piperidin-1-yl, while in the case when $R^1$ and $R^2$ form an alkylene bridge in the alkylene bridge one or more H atoms may be replaced by identical or different groups $R^{14}$, and X denotes a $C_{1-3}$-alkylene bridge, which may comprise one, two or three identical or different C1-4-alkyl substituents; and Y denotes a group characterized by a subformula selected from

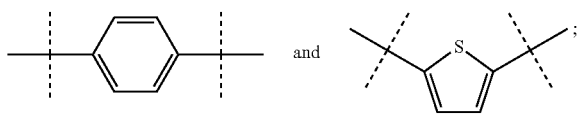

which may be mono substituted by substituent $R^{20}$

Z denotes —$CH_2$—$CH_2$— or —$C(=O)$—$CH_2$—;

U, V one of the groups U, V denotes N and the other of U, V denotes CH; and

L independently of each other denotes halogen, cyano or $C_{1-3}$-alkyl; and k denotes 0, 1 or 2;

W is selected from the group consisting of —$CH_2$—O— and —O—$CH_2$—;

B is selected from the group consisting of phenyl, pyridyl, pyridazinyl, pyrazinyl, pyrimidinyl, pyrrolyl, pyrazolyl, imidazolyl, triazolyl, tetrazolyl, furyl, thiophenyl and thiazolyl; each of which may be mono- or polysubstituted by identical or different substituents $R^{20}$; and $R^{11}$ denotes halogen, $C_{1-6}$-alkyl, $R^{15}$—O—, $R^{15}$—O—CO—, $R^{15}$—CO—O—, cyano, $R^{16}R^{17}$N—, $R^{18}R^{19}$N—CO— or $C_{3-7}$-cycloalkyl, while in the above-mentioned groups one or more C atoms may be substituted independently of one another by substituents selected from F;

$R^{13}$ has one of the meanings given for $R^{17}$ or denotes formyl;

$R^{14}$ denotes halogen, cyano, $C_{1-6}$-alkyl, $R^{15}$—O—, $R^{15}$—O—CO—, $R^{15}$—CO—, $R^{15}$—CO—O—, $R^{16}R^{17}$N—, HCO—NR$^{15}$—, $R^{18}R^{19}$N—CO—, $R^{18}R^{19}$N—CO—NH—, $R^{15}$—O—$C_{1-3}$-alkyl, $R^{15}$—O—CO—$C_{1-3}$-alkyl-, $R^{15}$—SO$_2$—NH—, $R^{15}$—SO$_2$—N($C_{1-3}$-alkyl)-, $R^{15}$—O—CO—NH—$C_{1-3}$-alkyl-, $R^{15}$—SO$_2$—NH—$C_{1-3}$-alkyl-, $R^{15}$—CO—O—$C_{1-3}$-alkyl-, $R^{15}$—CO—O—$C_{1-3}$-alkyl-, $R^{16}R^{17}$N—$C_{1-3}$-alkyl-, $R^{18}R^{19}$N—CO—$C_{1-3}$-alkyl-, $R^{15}$ denotes H, $C_{1-4}$-alkyl, $C_{3-7}$-cycloalkyl, $C_{3-7}$-cycloalkyl-$C_{1-3}$-alkyl, $R^{16}$ denotes H, $C_{1-6}$-alkyl, $C_{3-7}$-cycloalkyl, ω-hydroxy-$C_{2-3}$-alkyl, ω-($C_{1-4}$-alkoxy)-$C_{2-3}$-alkyl, amino-$C_{2-6}$-alkyl, $C_{1-4}$-alkyl-amino-$C_{2-6}$-alkyl, di-($C_{1-4}$-alkyl)-amino-$C_{2-6}$-alkyl, $R^{17}$ has one of the meanings given for $R^{16}$ or denotes $C_{1-4}$-alkylcarbonyl, $C_{1-4}$-alkoxycarbonyl;

$R^{18}$, $R^{19}$ independently of one another denote H or $C_{1-6}$-alkyl wherein $R^{18}$, $R^{19}$ may be linked to form a $C_{3-6}$-alkylene bridge;

$R^{20}$ denotes halogen, hydroxy, cyano, nitro, $C_{1-6}$-alkyl, hydroxy-$C_{1-3}$-alkyl, or $C_{1-4}$-alkoxy; and while in the above-mentioned groups and radicals, particularly in L, W, X, Z, $R^N$, $R^{11}$, $R^{13}$ to $R^{20}$, in each case one or more C atoms may additionally be mono- or polysubstituted by F and/or in each case one or two C atoms independently of one another may additionally be monosubstituted by Cl or Br and/or in each case one or more phenyl rings may additionally comprise independently of one another one, two or three substituents selected from the group F, Cl, Br, I, cyano, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)-amino, acetylamino, aminocarbonyl, difluoromethoxy, trifluoromethoxy, amino-$C_{1-3}$-alkyl, $C_{1-3}$-alkylamino-$C_{1-3}$-alkyl- and di-($C_{1-3}$-alkyl)-amino-$C_{1-3}$-alkyl and/or may be monosubstituted by nitro, and a tautomer thereof, a diastereomer thereof, an enantiomer thereof, a mixture of any such forms or a salt thereof.

2. The compound according to claim 1, characterised in that the groups $R^1$, $R^2$ are selected independently of one another from the group comprising H, $C_{1-4}$-alkyl, $C_{3-7}$-cycloalkyl-$C_{1-3}$-alkyl, hydroxy-$C_{1-4}$-alkyl, $C_{3-7}$-cycloalkyl, hydroxy-$C_{3-7}$cycloalkyl, dihydroxy-$C_{3-6}$-alkyl, $C_{1-4}$-alkoxy-$C_{2-3}$-alkyl, hydroxy-$C_{1-4}$-alkoxy-$C_{2-3}$-alkyl, $C_{1-4}$-alkoxy-$C_{1-4}$-alkoxy-$C_{2-3}$-alkyl, while an alkyl, cycloalkyl or cycloalkyl-alkyl group may additionally be mono- or disubstituted by hydroxy and/or hydroxy-$C_{1-3}$-alkyl, and/or mono- or polysubstituted by F or $C_{1-3}$-alkyl and/or monosubstituted by CF$_3$, Br, Cl or CN.

3. The compound according to claim 1, characterised in that $R^1$ and $R^2$ together with the N atom to which they are bound form a heterocyclic group which is selected from the meanings azetidine, pyrrolidine, piperidine, piperazine in which the free imine function is substituted by $R^{13}$, and morpholine;

while one or more H atoms may be replaced by identical or different groups $R^{14}$, and the groups $R^{13}$, $R^{14}$ and the group Cy are defined as in claim 1.

4. The compound according to claim 1, characterised in that the subformula

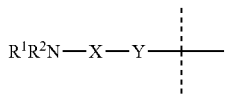

is selected from the group consisting of

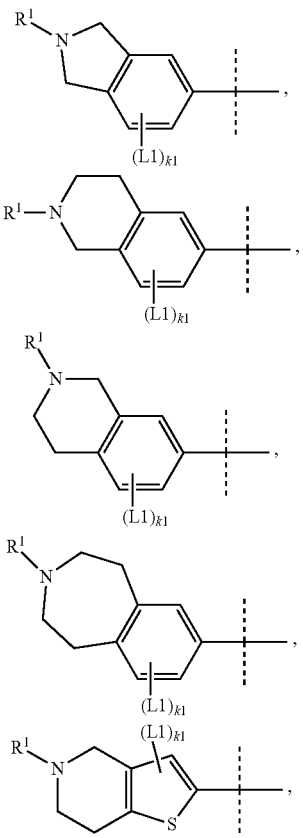

wherein $R^1$ denotes H, $C_{1-4}$alkyl or $C_{1-4}$-alkyl-carbonyl, wherein alkyl may be mono- or polyfluorinated, L1 is defined as $R^{20}$ and k1 denotes 0 or 1.

5. The compound according to claim 1, characterised in that X denotes a —CH₂—, —CH₂—CH₂— or —CH₂CH₂CH₂— bridging group, wherein one or two hydrogen atoms may be replaced by identical or different $C_{1-3}$-alkyl-groups.

6. The compound according to claim 1, characterised in that the group Y denotes

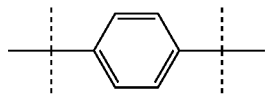

which may be mono substituted by substituent $R^{20}$.

7. The compound according to claim 1, characterised in that the group Z denotes —C(=O)—CH₂—.

8. The Compound according to claim 1, characterised in that the group W denotes —O—CH₂.

9. The compound according to claim 1, characterised in that the group B is selected from the group consisting of phenyl and pyridyl, wherein said group B may be mono- or polysubstituted by identical or different substituents $R^{20}$.

10. The physiologically acceptable salt of the compound according to claim 1.

11. A pharmaceutical composition comprising a compound according to claim 1 or its salt, together with one or more inert carriers or diluents.

12. A compound selected from the group consisting of
5-Benzyloxy-2-{2-[4-(3-hydroxy-3-methyl-pyrrolidin-1-ylmethyl)-phenyl]-2-oxo-ethyl}-2H-pyridazin-3-one,
5-Benzyloxy-2-{2-[4-((R)-3-hydroxy-pyrrolidin-1-ylmethyl)-phenyl]-2-oxo-ethyl}-2H-pyridazin-3-on,
5-Benzyloxy-2-{2-[4-(4-hydroxy-piperidin-1-ylmethyl)-phenyl]-2-oxo-ethyl}-2H-pyridazin-3-one,
5-(5-Chloro-pyridin-2-ylmethoxy)-2-[2-oxo-2-(4-piperidin-1-ylmethyl-phenyl)-ethyl]-2H-pyridazin-3-one,
6-Benzyloxy-3-{2-[4-(4-hydroxy-4-methyl-piperidin-1-ylmethyl)-phenyl]-2-oxo-ethyl}-3H-pyrimidin-4-one,
5-Benzyloxy-2-[2-oxo-2-(1,2,3,4-tetrahydro-isoquinolin-7-yl)-ethyl]-2H-pyridazin-3-one,
5-(5-Bromo-pyridin-2-ylmethoxy)-2-[2-oxo-2-(1,2,3,4-tetrahydro-isoquinolin-7-yl)-ethyl]-2H-pyridazin-3-one,
5-(5-Bromo-pyridin-2-ylmethoxy)-2-[2-(2-methyl-1,2,3,4-tetrahydro-isoquinolin-7-yl)-2-oxo-ethyl]-2H-pyridazin-3-one,
5-Benzyloxy-2-[2-(2,3-dihydro-1H-isoindol-5-yl)-2-oxo-ethyl]-2H-pyridazin-3-one, and
5-Benzyloxy-2-[2-(2-methyl-2,3-dihydro-1H-isoindol-5-yl)-2-oxo-ethyl]-2H-pyridazin-3-one.

* * * * *